(12) United States Patent
Bobrowicz et al.

(10) Patent No.: US 9,139,632 B2
(45) Date of Patent: Sep. 22, 2015

(54) **METHOD FOR PRODUCING PROTEINS IN *PICHIA PASTORIS* THAT LACK DETECTABLE CROSS BINDING ACTIVITY TO ANTIBODIES AGAINST HOST CELL ANTIGENS**

(75) Inventors: Piotr Bobrowicz, Hanover, NH (US); Sujatha Gomathinayagam, Hanover, NH (US); Stephen Hamilton, Enfield, NH (US); Huijuan Li, Hanover, NH (US); Natarajan Sethuraman, Hanover, NH (US); Terrance A. Stadheim, Lyme, NH (US); Stefan Wildt, New York, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 137 days.

(21) Appl. No.: 13/501,350

(22) PCT Filed: Oct. 11, 2010

(86) PCT No.: PCT/US2010/052140
§ 371 (c)(1),
(2), (4) Date: May 31, 2012

(87) PCT Pub. No.: WO2011/046855
PCT Pub. Date: Apr. 21, 2011

(65) Prior Publication Data
US 2012/0232007 A1    Sep. 13, 2012

Related U.S. Application Data

(60) Provisional application No. 61/252,312, filed on Oct. 16, 2009.

(51) Int. Cl.

| | | |
|---|---|---|
| C12P 21/06 | (2006.01) | |
| C12N 1/00 | (2006.01) | |
| C12N 5/00 | (2006.01) | |
| C12P 21/04 | (2006.01) | |
| C07K 1/00 | (2006.01) | |
| C07K 14/505 | (2006.01) | |
| C07K 14/47 | (2006.01) | |
| C07K 14/485 | (2006.01) | |
| C07K 14/52 | (2006.01) | |
| C07K 14/535 | (2006.01) | |
| C07K 14/54 | (2006.01) | |
| C07K 14/555 | (2006.01) | |
| C07K 14/59 | (2006.01) | |
| C07K 14/605 | (2006.01) | |
| C07K 14/705 | (2006.01) | |
| C07K 14/715 | (2006.01) | |
| C07K 14/755 | (2006.01) | |
| C07K 14/81 | (2006.01) | |
| C07K 16/18 | (2006.01) | |
| C07K 16/22 | (2006.01) | |
| C12N 9/10 | (2006.01) | |
| C12P 21/00 | (2006.01) | |

(52) U.S. Cl.
CPC .............. *C07K 14/505* (2013.01); *C07K 14/47* (2013.01); *C07K 14/4715* (2013.01); *C07K 14/4721* (2013.01); *C07K 14/4743* (2013.01); *C07K 14/485* (2013.01); *C07K 14/52* (2013.01); *C07K 14/523* (2013.01); *C07K 14/535* (2013.01); *C07K 14/54* (2013.01); *C07K 14/555* (2013.01); *C07K 14/59* (2013.01); *C07K 14/605* (2013.01); *C07K 14/705* (2013.01); *C07K 14/70546* (2013.01); *C07K 14/70578* (2013.01); *C07K 14/7151* (2013.01); *C07K 14/755* (2013.01); *C07K 14/8114* (2013.01); *C07K 14/8125* (2013.01); *C07K 14/8128* (2013.01); *C07K 16/18* (2013.01); *C07K 16/22* (2013.01); *C12N 9/1051* (2013.01); *C12P 21/005* (2013.01); *C07K 2317/33* (2013.01)

(58) Field of Classification Search
None
See application file for complete search history.

(56) References Cited

U.S. PATENT DOCUMENTS

| | | | | |
|---|---|---|---|---|
| 7,465,577 | B2 | 12/2008 | Bobrowicz | |
| 2006/0286637 | A1 | 12/2006 | Hamilton | |
| 2007/0037248 | A1* | 2/2007 | Bobrowicz et al. | .......... 435/69.1 |
| 2007/0293420 | A1 | 12/2007 | Schumann et al. | |
| 2008/0124763 | A1 | 5/2008 | Sablon et al. | |
| 2008/0305992 | A1 | 12/2008 | DeFrees et al. | |

(Continued)

FOREIGN PATENT DOCUMENTS

WO    WO 2005/106010    11/2005

OTHER PUBLICATIONS

Hopkins et al. 2011. Glycobiology. 21:1616-1626.*

(Continued)

*Primary Examiner* — Shulamith H Shafer

(57) ABSTRACT

Methods for producing proteins and glycoproteins in *Pichia pastoris* that lack detectable cross binding activity to antibodies made against host cell antigens are described. In particular, methods are described wherein recombinant *Pichia pastoris* strains that do not display a β-mannosyltransferase 2 activity with respect to an N-glycan or O-glycan and do not display at least one activity selected from a β-mannosyltransferase 1, 3, and 4 activity to produce recombinant proteins and glycoproteins. These recombinant *Pichia pastoris* strains can produce proteins and glycoproteins that lack detectable α-mannosidase resistant β-mannose residues thereon and thus, lack cross binding activity to antibodies against host cell antigens. Further described are methods for producing bi-sialylated human erythropoietin in *Pichia pastoris* that lack detectable cross binding activity to antibodies against host cell antigens.

10 Claims, 54 Drawing Sheets

(56) References Cited

U.S. PATENT DOCUMENTS

2009/0170159 A1 7/2009 Bobrowicz et al.
2009/0181041 A1 7/2009 Holgersson et al.

OTHER PUBLICATIONS

Hermeling et al. 2004. Pharm. Res. 21:897-903.*
Schellekens et al. 2004. J. Neurol. 251 (Suppl 2):II/4-II/9.*
Hopkins D, Gomathinayagam S, Rittenhour Am, Du M, Hoyt E, Karaveg K, Mitchell T, Nett JH, Sharkey NJ, Stadheim TA, Li H, Hamilton Sr. Elimination of β-mannose glycan structures in Pichia pastoris. Glycobiology. Dec. 2011; 21(12):1616-26. Epub Aug. 12, 2011
Hermeling S, Crommelin DJ, Schellekens H, Jiskoot W. Structure-immunogenicity relationships of therapeutic proteins. Pharm Res. Jun. 2004; 21(6):897-903.
Schellekens H, Casadevall N. Immunogenicity of recombinant human proteins: causes and consequences. J Neurol. Jun. 2004; 251 Suppl 2:II4-9.
Mille C, Bobrowicz P, Trinel PA, Li H, Maes E, Guerardel Y, Fradin C, Martinez-Esparza M, Davidson RC, Janbon G, Poulain D, Wildt S. Identification of a new family of genes involved in beta-1,2-mannosylation of glycans in Pichia pastoris and Candida albicans. J Biol Chem. Apr. 11, 2008; 283(15):9724-36. Epub Jan. 30, 2008
Tanaka H, Okuno T, Moriyama S, Muguruma M, Ohta K. Acidophilic xylanase from Aureobasidium pullulans: efficient expression and secretion in Pichia pastoris and mutational analysis. J Biosci Bioeng. 2004;98(5):338-43.
Miyake T, Kung CK, Goldwasser E. Purification of human erythropoietin. J Biol Chem. Aug. 10, 1977; 252(15):5558-64.

* cited by examiner

YGLY14-3
[*ura5Δ::ScSUC2 och1Δ::lacZ bmt2Δ::lacZ/KlMNN2-2 mnn4L1Δ::lacZ/MmSLC35A3 pno1Δmnn4Δ::lacZ-URA5-lacZ*]

↓ Counterselect on 5-FOA

YGLY16-3
[*ura5Δ::ScSUC2 och1Δ::lacZ bmt2Δ::lacZ/KlMNN2-2 mnn4L1Δ::lacZ/MmSLC35A3 pno1Δmnn4Δ::lacZ*]

pGLY247 ↓

YGLY20-3
[*ura5Δ::ScSUC2 och1Δ::lacZ bmt2Δ::lacZ/KlMNN2-2 mnn4L1Δ::lacZ/MmSLC35A3 pno1Δmnn4Δ::lacZ met16Δ::lacZ-URA5-lacZ*]

pGLY248 ↓

YGLY22-3
[*ura5Δ::MET16 och1Δ::lacZ bmt2Δ::lacZ/KlMNN2-2 mnn4L1Δ::lacZ/MmSLC35A3 pno1Δmnn4Δ::lacZ met16Δ::lacZ-URA5-lacZ*]

↓ Counterselect on 5-FOA

YGLY24-3
[*ura5Δ::MET16 och1Δ::lacZ bmt2Δ::lacZ/KlMNN2-2 mnn4L1Δ::lacZ/MmSLC35A3 pno1Δmnn4Δ::lacZ met16Δ::lacZ*]

pGLY582 ↓

FIG. 1B

YGLY58
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ-URA5-lacZ/ScGAL10/XB33/DmUGT]

pGLY167b ↓

YGLY73
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ-URA5-lacZ/ScGAL10/XB33/DmUGT
arg1Δ::HIS1/KD53/TC54]

↓ Counterselect on 5-FOA

YGLY1272
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54]

pGLY1430 ↓

YGLY1305
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ-URA5-lacZ/NA10/MmSLC35A3/FB8]

↓ Counterselect on 5-FOA

FIG. 1C

YGLY1461

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8]

pGFI-165 ↓

YGLY1703

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1]

pGLY2088 ↓

YGLY2849

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1
AOX1:Sh ble/AOX1p/ScαMFpre-GFI800 ]

pGLY2456 ↓

FIG. 1D

YGLY3159
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ-URA5-lacZ/TrMDS1
AOX1:Sh ble/AOX1p/ScαMFpre-GFI800
TRP2::ARG1/MmCST/HsGNE/HsCSS/HsSPS/MmST6-33]

↓ Counterselect on 5-FOA

YGLY3225
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33]

pGLY2057 ↓

YGLY3229
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ-URA5-lacZ]

FIG. 1E pGLY2680 ↓

YGLY4209

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ-URA5-lacZ
AOX1:ADE2tr/AOX1p/CLSP-GFI800]

↓ Counterselect on 5-FOA

YGLY4244

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800]

pGLY2713 ↓

FIG. 1F

YGLY5053

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800
pep4::lacZ-URA5-lacZ/PpPNO1]

↓ Counterselect on 5-FOA

YGLY5597

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800
pep4::lacZ/PpPNO1]

pGLY3411 ↓

FIG. 1G

YGLY5618

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800
pep4::lacZ/PpPNO1
bmt4::lacZ-URA5-lacZ]

pGLY3430 ↓

YGLY7110

[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800
pep4::lacZ/PpPNO1
bmt4::lacZ-URA5-lacZ bmt1::Nat$^R$ ]

pGLY4472 ↓

FIG. 1H

YGLY7113-7122
[ura5Δ::MET16 och1Δ::lacZ bmt2Δ::lacZ/KlMNN2-2
mnn4L1Δ::lacZ/MmSLC35A3 pno1Δmnn4Δ::lacZ met16Δ::lacZ
his1Δ::lacZ/ScGAL10/XB33/DmUGT
arg1Δ::HIS1/KD53/TC54
ADE1::lacZ/NA10/MmSLC35A3/FB8
PRO1::lacZ/TrMDS1
AOX1:Sh ble/AOX1p/ScαMFpre-GFI800
TRP2::ARG1/MmCST/HsGNE/HsCSS/HsSPS/MmST6-33
ade2::lacZ
AOX1:ADE2tr/AOX1p/CLSP-GFI800
pep4::lacZ/PpPNO1
bmt4::lacZ-URA5-lacZ bmt1::Nat$^R$ bmt3::Hyg$^R$]

FIG. 1I

Glossary:

| | |
|---|---|
| Sc*SUC2* | *S. cerevisiae* Invertase |
| *OCH1* | Alpha-1,6-mannosyltransferase |
| Kl*MNN2-2*: | *K. lactis* UDP-GlcNAc transporter |
| *BMT1*: | Beta-mannose-transfer (beta-mannose elimination) |
| *BMT2*: | Beta-mannose-transfer (beta-mannose elimination) |
| *BMT3*: | Beta-mannose-transfer (beta-mannose elimination) |
| *BMT4*: | Beta-mannose-transfer (beta-mannose elimination) |
| *MNN4L1*: | MNN4-like 1 (charge elimination) |
| MmSLC35A3 | Mouse homologue of UDP-GlcNAc transporter |
| *PNO1*: | Phosphomannosylation of *N*-glycans (charge elimination) |
| *MNN4*: | Mannosyltransferase (charge elimination) |
| Sc*GAL10* | UDP-glucose 4-epimerase |
| XB33 | Truncated HsGalT1 fused to Sc*KRE2* leader |
| Dm*UGT* | UDP-Galactose transporter |
| KD53 | Truncated DmMNSII fused to Sc*MNN2* leader |
| TC54 | Truncated RnGNTII fused to Sc*MNN2* leader |
| NA10 | Truncated HsGNTI fused to Pp*SEC12* leader |
| FB8: | Truncated MmMNS1A fused to Sc*SEC12* leader |
| Tr*MDS1*: | Secreted *T. reseei MNS1* |
| Sh ble: | Zeocin resistance marker |
| ScαMFpre-GFI800 | Sc alpha mating factor presequence fusion to HsEPO |
| MmCST | Mouse CMP-sialic acid transporter |
| HsGNE | Human UDP-GlcNAc 2-epimerase/*N*-acetylmannosamine kinase |
| HsCSS | Human CMP-sialic acid synthase |
| HsSPS | Human *N*-acetylneuraminate-9-phosphate synthase |
| MmST6-33 | Truncated Mouse α-2,6-sailyl transferase fused to Sc*KRE2* leader |
| *ADE2*tr | Truncated *ADE2* marker |
| CLSP | Chicken Lysozyme signal peptide |
| PEP4 | Proteinase A |

FIG. 1J

Fermentation Process Flow

Reactivity of anti-HCP with rhIgG1 produced in *Pichia pastoris*

Lane 1: rhIgG1 produced in GS2.0 containing detectable $Man_9GlcNAc_2$ N-glycans that were α1,2-mannosidase resistant
Lane 2: Marker
Lane 3: rhIgG1 produced in WT
Lane 3: rhIgG1 produced in WT+PNGaseF
Lane 5: Marker SDS-PAGE - Commassie Blue Stained Western Blot

HCA Detection in rhEPO and Other Protein Preparations Produced in *Pichia pastoris*

SDS-PAGE - Commassie Blue Stained rhEPO —

Western Blot

FIG. 25

SDS – PAGE Gel - Coomassie Blue Stained
Quadruple *BMT* Knockout Strains Screening
F080240 – YGLY 7398 – Blue pool/HA pool 1

| SDS – PAGE Coomassie stain | Western Blot Anti-HCA Ab 1:3000 | Western Blot Anti-HCA Ab* 1:2000 |
|---|---|---|
|  |  |  |

*GiF2 polyclonal rabbit::6316

| Sample Name | % neutral | % A1 | % A2 |
|---|---|---|---|
| SA lot (YGLY3159) | 5 (3% non-human high mannose glycoforms, >$Man_9GlcNAc_2$, α-mannosidase resistant) | 17 | 78 |

SEQUENCE LISTING

<160> NUMBER OF SEQ ID NOS: 106

<210> SEQ ID NO 1
<211> LENGTH: 3029
<212> TYPE: DNA
<213> ORGANISM: Saccharomyces cerevisiae
<220> FEATURE:
<221> NAME/KEY: CDS
<222> LOCATION: (909)...(2504)
<223> OTHER INFORMATION: Encodes invertase

<400> SEQUENCE: 1
aggcctcgca acaacctata attgagttaa gtgcctttcc aagctaaaaa gtttgaggtt    60 atagggctt agcatccaca cgtcacaatc tcgggtatcg agtatagtat gtagaattac   120
ggcaggaggt ttcccaatga acaaaggaca ggggcacggt gagctgtcga aggtatccat   180
tttatcatgt ttcgtttgta caagcacgac atactaagac atttaccgta tgggagttgt   240
tgtcctagcg tagttctcgc tcccccagca aagctcaaaa aagtacgtca tttagaatag   300
tttgtgagca aattaccagt cggtatgcta cgttagaaag gcccacagta ttcttctacc   360
aaaggcgtgc ctttgttgaa ctcgatccat tatgagggct tccattattc cccgcatttt   420
tattactctg aacaggaata aaaagaaaaa acccagtta ggaaattatc cggggcgaa    480 gaaatacgcg tagcgttaat cgaccccacg tccagggttt ttccatggag gtttctgaa    540 aaactgacga ggaatgtgat tataaatccc tttatgtgat gtctaagact tttaaggtac   600

```
gcccgatgtt tgcctattac catcatagag acgtttcttt tcgaggaatg cttaaacgac     660
tttgtttgac aaaaatgttg cctaagggct ctatagtaaa ccatttggaa gaaagatttg     720 acgactttt tttttggat ttcgatccta taatccttcc tcctgaaaag aaacatataa       780 atagatgt attattcttc aaaacattct cttgttcttg tgcttttttt ttaccatata       840
tcttactttt ttttttctct cagagaaaca agcaaaacaa aaagcttttc ttttcactaa     900 cgtatatg atg ctt ttg caa gct ttc ctt ttc ctt ttg gct ggt ttt gca      950
        Met Leu Leu Gln Ala Phe Leu Phe Leu Leu Ala Gly Phe Ala
         1               5                  10 gcc aaa ata tct gca tca atg aca aac gaa act agc gat aga cct ttg       998
Ala Lys Ile Ser Ala Ser Met Thr Asn Glu Thr Ser Asp Arg Pro Leu
 15               20                  25                  30 gtc cac ttc aca ccc aac aag ggc tgg atg aat gac cca aat ggg ttg      1046
Val His Phe Thr Pro Asn Lys Gly Trp Met Asn Asp Pro Asn Gly Leu
                  35                  40                  45 tgg tac gat gaa aaa gat gcc aaa tgg cat ctg tac ttt caa tac aac      1094
Trp Tyr Asp Glu Lys Asp Ala Lys Trp His Leu Tyr Phe Gln Tyr Asn
             50                  55                  60 cca aat gac acc gta tgg ggt acg cca ttg ttt tgg ggc cat gct act      1142
Pro Asn Asp Thr Val Trp Gly Thr Pro Leu Phe Trp Gly His Ala Thr
 65                  70                  75 tcc gat gat ttg act aat tgg gaa gat caa ccc att gct atc gct ccc      1190
Ser Asp Asp Leu Thr Asn Trp Glu Asp Gln Pro Ile Ala Ile Ala Pro
 80                  85                  90 aag cgt aac gat tca ggt gct ttc tct ggc tcc atg gtg gtt gat tac      1238
Lys Arg Asn Asp Ser Gly Ala Phe Ser Gly Ser Met Val Val Asp Tyr
 95                  100                 105                 110 aac aac acg agt ggg ttt ttc aat gat act att gat cca aga caa aga      1286
Asn Asn Thr Ser Gly Phe Phe Asn Asp Thr Ile Asp Pro Arg Gln Arg
                  115                 120                 125 tgc gtt gcg att tgg act tat aac act cct gaa agt gaa gag caa tac      1334
Cys Val Ala Ile Trp Thr Tyr Asn Thr Pro Glu Ser Glu Glu Gln Tyr
             130                 135                 140 att agc tat tct ctt gat ggt ggt tac act ttt act gaa tac caa aag      1382
Ile Ser Tyr Ser Leu Asp Gly Gly Tyr Thr Phe Thr Glu Tyr Gln Lys
 145                 150                 155 aac cct gtt tta gct gcc aac tcc act caa ttc aga gat cca aag gtg      1430
Asn Pro Val Leu Ala Ala Asn Ser Thr Gln Phe Arg Asp Pro Lys Val
 160                 165                 170 ttc tgg tat gaa cct tct caa aaa tgg att atg acg gct gcc aaa tca      1478
Phe Trp Tyr Glu Pro Ser Gln Lys Trp Ile Met Thr Ala Ala Lys Ser
175                  180                 185                 190 caa gac tac aaa att gaa att tac tcc tct gat gac ttg aag tcc tgg      1526
Gln Asp Tyr Lys Ile Glu Ile Tyr Ser Ser Asp Asp Leu Lys Ser Trp
                  195                 200                 205 aag cta gaa tct gca ttt gcc aat gaa ggt ttc tta ggc tac caa tac      1574
Lys Leu Glu Ser Ala Phe Ala Asn Glu Gly Phe Leu Gly Tyr Gln Tyr
             210                 215                 220 gaa tgt cca ggt ttg att gaa gtc cca act gag caa gat cct tcc aaa      1622
Glu Cys Pro Gly Leu Ile Glu Val Pro Thr Glu Gln Asp Pro Ser Lys
 225                 230                 235 tct tat tgg gtc atg ttt att tct atc aac cca ggt gca cct gct ggc      1670
Ser Tyr Trp Val Met Phe Ile Ser Ile Asn Pro Gly Ala Pro Ala Gly
 240                 245                 250 ggt tcc ttc aac caa tat ttt gtt gga tcc ttc aat ggt act cat ttt      1718
Gly Ser Phe Asn Gln Tyr Phe Val Gly Ser Phe Asn Gly Thr His Phe
 255                 260                 265                 270
```

```
gaa gcg ttt gac aat caa tct aga gtg gta gat ttt ggt aag gac tac    1766
Glu Ala Phe Asp Asn Gln Ser Arg Val Val Asp Phe Gly Lys Asp Tyr
            275                 280                 285 tat gcc ttg caa act ttc ttc aac act gac cca acc tac ggt tca gca    1814
Tyr Ala Leu Gln Thr Phe Phe Asn Thr Asp Pro Thr Tyr Gly Ser Ala
        290                 295                 300 tta ggt att gcc tgg gct tca aac tgg gag tac agt gcc ttt gtc cca    1862
Leu Gly Ile Ala Trp Ala Ser Asn Trp Glu Tyr Ser Ala Phe Val Pro
        305                 310                 315 act aac cca tgg aga tca tcc atg tct ttg gtc cgc aag ttt tct ttg    1910
Thr Asn Pro Trp Arg Ser Ser Met Ser Leu Val Arg Lys Phe Ser Leu
    320                 325                 330 aac act gaa tat caa gct aat cca gag act gaa ttg atc aat ttg aaa    1958
Asn Thr Glu Tyr Gln Ala Asn Pro Glu Thr Glu Leu Ile Asn Leu Lys
335                 340                 345                 350 gcc gaa cca ata ttg aac att agt aat gct ggt ccc tgg tct cgt ttt    2006
Ala Glu Pro Ile Leu Asn Ile Ser Asn Ala Gly Pro Trp Ser Arg Phe
                355                 360                 365 gct act aac aca act cta act aag gcc aat tct tac aat gtc gat ttg    2054
Ala Thr Asn Thr Thr Leu Thr Lys Ala Asn Ser Tyr Asn Val Asp Leu
            370                 375                 380 agc aac tcg act ggt acc cta gag ttt gag ttg gtt tac gct gtt aac    2102
Ser Asn Ser Thr Gly Thr Leu Glu Phe Glu Leu Val Tyr Ala Val Asn
        385                 390                 395 acc aca caa acc ata tcc aaa tcc gtc ttt gcc gac tta tca ctt tgg    2150
Thr Thr Gln Thr Ile Ser Lys Ser Val Phe Ala Asp Leu Ser Leu Trp
        400                 405                 410 ttc aag ggt tta gaa gat cct gaa gaa tat ttg aga atg ggt ttt gaa    2198
Phe Lys Gly Leu Glu Asp Pro Glu Glu Tyr Leu Arg Met Gly Phe Glu
415                 420                 425                 430 gtc agt gct tct tcc ttc ttt ttg gac cgt ggt aac tct aag gtc aag    2246
Val Ser Ala Ser Ser Phe Phe Leu Asp Arg Gly Asn Ser Lys Val Lys
                435                 440                 445 ttt gtc aag gag aac cca tat ttc aca aac aga atg tct gtc aac aac    2294
Phe Val Lys Glu Asn Pro Tyr Phe Thr Asn Arg Met Ser Val Asn Asn
            450                 455                 460 caa cca ttc aag tct gag aac gac cta agt tac tat aaa gtg tac ggc    2342
Gln Pro Phe Lys Ser Glu Asn Asp Leu Ser Tyr Tyr Lys Val Tyr Gly
        465                 470                 475 cta ctg gat caa aac atc ttg gaa ttg tac ttc aac gat gga gat gtg    2390
Leu Leu Asp Gln Asn Ile Leu Glu Leu Tyr Phe Asn Asp Gly Asp Val
        480                 485                 490 gtt tct aca aat acc tac ttc atg acc acc ggt aac gct cta gga tct    2438
Val Ser Thr Asn Thr Tyr Phe Met Thr Thr Gly Asn Ala Leu Gly Ser
495                 500                 505                 510 gtg aac atg acc act ggt gtc gat aat ttg ttc tac att gac aag ttc    2486
Val Asn Met Thr Thr Gly Val Asp Asn Leu Phe Tyr Ile Asp Lys Phe
                515                 520                 525 caa gta agg gaa gta aaa tagaggttat aaaacttatt gtcttttta           2534
Gln Val Arg Glu Val Lys
            530 ttttttcaa aagccattct aaagggcttt agctaacgag tgacgaatgt aaaactttat  2594
gatttcaaag aataccctcca aaccattgaa aatgtatttt tatttttatt ttctcccgac 2654 cccagttacc tggaatttgt tctttatgta ctttatataa gtataattct cttaaaaatt  2714
tttactactt tgcaatagac atcatttttt cacgtaataa acccacaatc gtaatgtagt  2774
tgccttacac tactaggatg gacctttttg cctttatctg ttttgttact gacacaatga  2834
aaccgggtaa agtattagtt atgtgaaaat ttaaaagcat taagtagaag tataccatat  2894
```

```
tgtaaaaaaa aaaagcgttg tcttctacgt aaaagtgttc tcaaaaagaa gtagtgaggg    2954
aaatggatac caagctatct gtaacaggag ctaaaaaatc tcagggaaaa gcttctggtt    3014
tgggaaacgg tcgac                                                     3029
```

<210> SEQ ID NO 2
<211> LENGTH: 532
<212> TYPE: PRT
<213> ORGANISM: Saccharomyces cerevisiae

<400> SEQUENCE: 2

```
Met Leu Leu Gln Ala Phe Leu Phe Leu Leu Ala Gly Phe Ala Ala Lys
 1               5                  10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
```

```
                340                 345                 350
Pro Ile Leu Asn Ile Ser Asn Ala Gly Pro Trp Ser Arg Phe Ala Thr
            355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530

<210> SEQ ID NO 3
<211> LENGTH: 2159
<212> TYPE: DNA
<213> ORGANISM: K. lactis
<220> FEATURE:
<221> NAME/KEY: CDS
<222> LOCATION: (1024)...(2007)
<223> OTHER INFORMATION: Encodes UDP-GlcNAc transporter (KlMNN2-2)

<400> SEQUENCE: 3
aaacgtaacg cctggcactc tatttctca  aacttctggg acggaagagc taaatattgt      60
gttgcttgaa caaacccaaa aaacaaaaa  aatgaacaaa ctaaaactac acctaaataa     120
accgtgtgta aaacgtagta ccatattact agaaaagatc acaagtgtat cacacatgtg    180
catctcatat tacatctttt atccaatcca ttctctctat cccgtctgtt cctgtcagat    240 tcttttttcca taaaagaag  aagaccccga atctcaccgg tacaatgcaa aactgctgaa    300
aaaaaaagaa agttcactgg atacgggaac agtgccagta ggcttcacca catggacaaa   360
acaattgacg ataaaataag caggtgagct tcttttttcaa gtcacgatcc ctttatgtct    420
cagaaacaat atatacaagc taaaccctt  tgaaccagtt ctctcttcat agttatgttc    480
acataaattg cgggaacaag actccgctgg ctgtcaggta cacgttgtaa cgttttcgtc   540
cgcccaatta ttagcacaac attggcaaaa agaaaaactg ctcgtttct ctacaggtaa    600 attacaattt ttttcagtaa ttttcgctga aaaatttaaa gggcaggaaa aaagacgat    660 ctcgactttg catgatgca  agaactgtgg tcaaaacttg aaatagtaat tttgctgtgc    720
gtgaactaat aaatatatat atatatatat atatatattt gtgtattttg tatatgtaat    780
tgtgcacgtc ttggctattg gatataagat tttcgcgggt tgatgacata gagcgtgtac    840
tactgtaata gttgtatatt caaaagctgc tgcgtggaga aagactaaaa tagataaaaa    900
```

-continued

```
gcacacattt tgacttcggt accgtcaact tagtgggaca gtctttata tttggtgtaa    960 gctcatttct ggtactattc gaaacagaac agtgttttct gtattaccgt ccaatcgttt   1020 gtc atg agt ttt gta ttg att ttg tcg tta gtg ttc gga gga tgt tgt    1068
    Met Ser Phe Val Leu Ile Leu Ser Leu Val Phe Gly Gly Cys Cys
    1               5                   10                  15 tcc aat gtg att agt ttc gag cac atg gtg caa ggc agc aat ata aat    1116
Ser Asn Val Ile Ser Phe Glu His Met Val Gln Gly Ser Asn Ile Asn
                20                  25                  30 ttg gga aat att gtt aca ttc act caa ttc gtg tct gtg acg cta att    1164
Leu Gly Asn Ile Val Thr Phe Thr Gln Phe Val Ser Val Thr Leu Ile
            35                  40                  45 cag ttg ccc aat gct ttg gac ttc tct cac ttt ccg ttt agg ttg cga    1212
Gln Leu Pro Asn Ala Leu Asp Phe Ser His Phe Pro Phe Arg Leu Arg
        50                  55                  60 cct aga cac att cct ctt aag atc cat atg tta gct gtg ttt ttg ttc    1260
Pro Arg His Ile Pro Leu Lys Ile His Met Leu Ala Val Phe Leu Phe
    65                  70                  75 ttt acc agt tca gtc gcc aat aac agt gtg ttt aaa ttt gac att tcc    1308
Phe Thr Ser Ser Val Ala Asn Asn Ser Val Phe Lys Phe Asp Ile Ser
80                  85                  90                  95 gtt ccg att cat att atc att aga ttt tca ggt acc act ttg acg atg    1356
Val Pro Ile His Ile Ile Ile Arg Phe Ser Gly Thr Thr Leu Thr Met
                100                 105                 110 ata ata ggt tgg gct gtt tgt aat aag agg tac tcc aaa ctt cag gtg    1404
Ile Ile Gly Trp Ala Val Cys Asn Lys Arg Tyr Ser Lys Leu Gln Val
            115                 120                 125 caa tct gcc atc att atg acg ctt ggt gcg att gtc gca tca tta tac    1452
Gln Ser Ala Ile Ile Met Thr Leu Gly Ala Ile Val Ala Ser Leu Tyr
        130                 135                 140 cgt gac aaa gaa ttt tca atg gac agt tta aag ttg aat acg gat tca    1500
Arg Asp Lys Glu Phe Ser Met Asp Ser Leu Lys Leu Asn Thr Asp Ser
    145                 150                 155 gtg ggt atg acc caa aaa tct atg ttt ggt atc ttt gtt gtg cta gtg    1548
Val Gly Met Thr Gln Lys Ser Met Phe Gly Ile Phe Val Val Leu Val
160                 165                 170                 175 gcc act gcc ttg atg tca ttg ttg tcg ttg ctc aac gaa tgg acg tat    1596
Ala Thr Ala Leu Met Ser Leu Leu Ser Leu Leu Asn Glu Trp Thr Tyr
                180                 185                 190 aac aag tac ggg aaa cat tgg aaa gaa act ttg ttc tat tcg cat ttc    1644
Asn Lys Tyr Gly Lys His Trp Lys Glu Thr Leu Phe Tyr Ser His Phe
            195                 200                 205 ttg gct cta ccg ttg ttt atg ttg ggg tac aca agg ctc aga gac gaa    1692
Leu Ala Leu Pro Leu Phe Met Leu Gly Tyr Thr Arg Leu Arg Asp Glu
        210                 215                 220 ttc aga gac ctc tta att tcc tca gac tca atg gat att cct att gtt    1740
Phe Arg Asp Leu Leu Ile Ser Ser Asp Ser Met Asp Ile Pro Ile Val
    225                 230                 235 aaa tta cca att gct acg aaa ctt ttc atg cta ata gca aat aac gtg    1788
Lys Leu Pro Ile Ala Thr Lys Leu Phe Met Leu Ile Ala Asn Asn Val
240                 245                 250                 255 acc cag ttc att tgt atc aaa ggt gtt aac atg cta gct agt aac acg    1836
Thr Gln Phe Ile Cys Ile Lys Gly Val Asn Met Leu Ala Ser Asn Thr
                260                 265                 270 gat gct ttg aca ctt tct gtc gtg ctt cta gtg cgt aaa ttt gtt agt    1884
Asp Ala Leu Thr Leu Ser Val Val Leu Leu Val Arg Lys Phe Val Ser
            275                 280                 285 ctt tta ctc agt gtc tac atc tac aag aac gtc cta tcc gtg act gca    1932
Leu Leu Leu Ser Val Tyr Ile Tyr Lys Asn Val Leu Ser Val Thr Ala
```

```
                    290                 295                 300
tac cta ggg acc atc acc gtg ttc ctg gga gct ggt ttg tat tca tat           1980
Tyr Leu Gly Thr Ile Thr Val Phe Leu Gly Ala Gly Leu Tyr Ser Tyr
        305                 310                 315 ggt tcg gtc aaa act gca ctg cct cgc tgaaacaatc cacgtctgta                 2027
Gly Ser Val Lys Thr Ala Leu Pro Arg
320                 325 tgatactcgt ttcagaattt ttttgatttt ctgccggata tggtttctca tctttacaat         2087
cgcattctta attataccag aacgtaattc aatgatccca gtgactcgta actcttatat         2147
gtcaatttaa gc                                                             2159

<210> SEQ ID NO 4
<211> LENGTH: 328
<212> TYPE: PRT
<213> ORGANISM: K. lactis

<400> SEQUENCE: 4

Met Ser Phe Val Leu Ile Leu Ser Leu Val Phe Gly Gly Cys Cys Ser
 1               5                  10                  15

Asn Val Ile Ser Phe Glu His Met Val Gln Gly Ser Asn Ile Asn Leu
            20                  25                  30

Gly Asn Ile Val Thr Phe Thr Gln Phe Val Ser Val Thr Leu Ile Gln
        35                  40                  45

Leu Pro Asn Ala Leu Asp Phe Ser His Phe Pro Phe Arg Leu Arg Pro
    50                  55                  60

Arg His Ile Pro Leu Lys Ile His Met Leu Ala Val Phe Leu Phe Phe
65                  70                  75                  80

Thr Ser Ser Val Ala Asn Asn Ser Val Phe Lys Phe Asp Ile Ser Val
                85                  90                  95

Pro Ile His Ile Ile Arg Phe Ser Gly Thr Thr Leu Thr Met Ile
            100                 105                 110

Ile Gly Trp Ala Val Cys Asn Lys Arg Tyr Ser Lys Leu Gln Val Gln
        115                 120                 125

Ser Ala Ile Ile Met Thr Leu Gly Ala Ile Val Ala Ser Leu Tyr Arg
    130                 135                 140

Asp Lys Glu Phe Ser Met Asp Ser Leu Lys Leu Asn Thr Asp Ser Val
145                 150                 155                 160

Gly Met Thr Gln Lys Ser Met Phe Gly Ile Phe Val Val Leu Val Ala
                165                 170                 175

Thr Ala Leu Met Ser Leu Leu Ser Leu Leu Asn Glu Trp Thr Tyr Asn
            180                 185                 190

Lys Tyr Gly Lys His Trp Lys Glu Thr Leu Phe Tyr Ser His Phe Leu
        195                 200                 205

Ala Leu Pro Leu Phe Met Leu Gly Tyr Thr Arg Leu Arg Asp Glu Phe
    210                 215                 220

Arg Asp Leu Leu Ile Ser Ser Asp Ser Met Asp Ile Pro Ile Val Lys
225                 230                 235                 240

Leu Pro Ile Ala Thr Lys Leu Phe Met Leu Ile Ala Asn Asn Val Thr
                245                 250                 255

Gln Phe Ile Cys Ile Lys Gly Val Asn Met Leu Ala Ser Asn Thr Asp
            260                 265                 270

Ala Leu Thr Leu Ser Val Val Leu Leu Val Arg Lys Phe Val Ser Leu
        275                 280                 285

Leu Leu Ser Val Tyr Ile Tyr Lys Asn Val Leu Ser Val Thr Ala Tyr
```

```
            290                 295                 300
Leu Gly Thr Ile Thr Val Phe Leu Gly Ala Gly Leu Tyr Ser Tyr Gly
305                 310                 315                 320

Ser Val Lys Thr Ala Leu Pro Arg
                325
```

<210> SEQ ID NO 5
<211> LENGTH: 108
<212> TYPE: DNA
<213> ORGANISM: Artificial Sequence
<220> FEATURE:
<223> OTHER INFORMATION: Encodes Mnn2 leader (53)

<400> SEQUENCE: 5

```
atgctgctta ccaaaaggtt ttcaaagctg ttcaagctga cgttcatagt tttgatattg    60
tgcgggctgt tcgtcattac aaacaaatac atggatgaga acacgtcg                108
```

<210> SEQ ID NO 6
<211> LENGTH: 36
<212> TYPE: PRT
<213> ORGANISM: Artificial Sequence
<220> FEATURE:
<223> OTHER INFORMATION: Mnn2 leader (53)

<400> SEQUENCE: 6

```
Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
            20                  25                  30

Glu Asn Thr Ser
        35
```

<210> SEQ ID NO 7
<211> LENGTH: 300
<212> TYPE: DNA
<213> ORGANISM: Artificial Sequence
<220> FEATURE:
<223> OTHER INFORMATION: Encodes Mnn2 leader (54).  The last 9
      nucleotides are the linker containing the AscI restriction
      site)

<400> SEQUENCE: 7

```
atgctgctta ccaaaaggtt ttcaaagctg ttcaagctga cgttcatagt tttgatattg    60
tgcgggctgt tcgtcattac aaacaaatac atggatgaga acacgtcggt caaggagtac   120
aaggagtact tagacagata tgtccagagt tactccaata agtattcatc ttcctcagac   180
gccgccagcg ctgacgattc aaccccattg agggacaatg atgaggcagg caatgaaaag   240
ttgaaaagct tctacaacaa cgttttcaac tttctaatgg ttgattcgcc cgggcgcgcc   300
```

<210> SEQ ID NO 8
<211> LENGTH: 100
<212> TYPE: PRT
<213> ORGANISM: Artificial Sequence
<220> FEATURE:
<223> OTHER INFORMATION: Mnn2 leader (54).

<400> SEQUENCE: 8

```
Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
            20                  25                  30
```

```
Glu Asn Thr Ser Val Lys Glu Tyr Lys Glu Tyr Leu Asp Arg Tyr Val
            35                  40                  45

Gln Ser Tyr Ser Asn Lys Tyr Ser Ser Ser Asp Ala Ala Ser Ala
    50                  55                  60

Asp Asp Ser Thr Pro Leu Arg Asp Asn Asp Glu Ala Gly Asn Glu Lys
65                  70                  75                  80

Leu Lys Ser Phe Tyr Asn Asn Val Phe Asn Phe Leu Met Val Asp Ser
                85                  90                  95

Pro Gly Arg Ala
            100

<210> SEQ ID NO 9
<211> LENGTH: 57
<212> TYPE: DNA
<213> ORGANISM: Artificial Sequence
<220> FEATURE:
<223> OTHER INFORMATION: Encodes S. cerevisiae Mating Factor pre signal
      sequence

<400> SEQUENCE: 9
atgagattcc catccatctt cactgctgtt ttgttcgctg cttcttctgc tttggct      57

<210> SEQ ID NO 10
<211> LENGTH: 19
<212> TYPE: PRT
<213> ORGANISM: Artificial Sequence
<220> FEATURE:
<223> OTHER INFORMATION: S. cerevisiae Mating Factor pre signal sequence

<400> SEQUENCE: 10

Met Arg Phe Pro Ser Ile Phe Thr Ala Val Leu Phe Ala Ala Ser Ser
1               5                   10                  15

Ala Leu Ala

<210> SEQ ID NO 11
<211> LENGTH: 99
<212> TYPE: DNA
<213> ORGANISM: Artificial Sequence
<220> FEATURE:
<223> OTHER INFORMATION: Encodes Pp SEC12 (10)

<400> SEQUENCE: 11
atgcccagaa aaatatttaa ctacttcatt ttgactgtat tcatggcaat tcttgctatt      60
gttttacaat ggtctataga gaatggacat gggcgcgcc                           99

<210> SEQ ID NO 12
<211> LENGTH: 33
<212> TYPE: PRT
<213> ORGANISM: Artificial Sequence
<220> FEATURE:
<223> OTHER INFORMATION: Pp SEC12 (10)

<400> SEQUENCE: 12

Met Pro Arg Lys Ile Phe Asn Tyr Phe Ile Leu Thr Val Phe Met Ala
1               5                   10                  15

Ile Leu Ala Ile Val Leu Gln Trp Ser Ile Glu Asn Gly His Gly Arg
            20                  25                  30

Ala

<210> SEQ ID NO 13
<211> LENGTH: 183
<212> TYPE: DNA
```

```
<213> ORGANISM: Artificial Sequence
<220> FEATURE:
<223> OTHER INFORMATION: Encodes ScMnt1 (Kre2) (33)

<400> SEQUENCE: 13
atggccctct ttctcagtaa gagactgttg agatttaccg tcattgcagg tgcggttatt    60
gttctcctcc taacattgaa ttccaacagt agaactcagc aatatattcc gagttccatc   120
tccgctgcat tgatttttac ctcaggatct atatcccctg aacaacaagt catcgggcgc   180
gcc                                                                  183

<210> SEQ ID NO 14
<211> LENGTH: 61
<212> TYPE: PRT
<213> ORGANISM: Artificial Sequence
<220> FEATURE:
<223> OTHER INFORMATION: ScMnt1 (Kre2) (33)

<400> SEQUENCE: 14

Met Ala Leu Phe Leu Ser Lys Arg Leu Leu Arg Phe Thr Val Ile Ala
 1               5                  10                  15

Gly Ala Val Ile Val Leu Leu Leu Thr Leu Asn Ser Asn Ser Arg Thr
            20                  25                  30

Gln Gln Tyr Ile Pro Ser Ser Ile Ser Ala Ala Phe Asp Phe Thr Ser
        35                  40                  45

Gly Ser Ile Ser Pro Glu Gln Gln Val Ile Gly Arg Ala
    50                  55                  60

<210> SEQ ID NO 15
<211> LENGTH: 318
<212> TYPE: DNA
<213> ORGANISM: Artificial Sequence
<220> FEATURE:
<223> OTHER INFORMATION: Encodes ScSEC12 (8)

<400> SEQUENCE: 15
atgaacacta tccacataat aaaattaccg cttaactacg ccaactacac ctcaatgaaa    60
caaaaaatct ctaaattttt caccaacttc atccttattg tgctgctttc ttacatttta   120
cagttctcct ataagcacaa tttgcattcc atgcttttca attacgcgaa ggacaatttt   180
ctaacgaaaa gagacaccat ctcttcgccc tacgtagttg atgaagactt acatcaaaca   240
actttgtttg caaccacgg tacaaaaaca tctgtaccta gcgtagattc cataaaagtg   300
catggcgtgg ggcgcgcc                                                 318

<210> SEQ ID NO 16
<211> LENGTH: 106
<212> TYPE: PRT
<213> ORGANISM: Artificial Sequence
<220> FEATURE:
<223> OTHER INFORMATION: ScSEC12 (8)

<400> SEQUENCE: 16

Met Asn Thr Ile His Ile Ile Lys Leu Pro Leu Asn Tyr Ala Asn Tyr
 1               5                  10                  15

Thr Ser Met Lys Gln Lys Ile Ser Lys Phe Phe Thr Asn Phe Ile Leu
            20                  25                  30

Ile Val Leu Leu Ser Tyr Ile Leu Gln Phe Ser Tyr Lys His Asn Leu
        35                  40                  45

His Ser Met Leu Phe Asn Tyr Ala Lys Asp Asn Phe Leu Thr Lys Arg
    50                  55                  60
```

```
Asp Thr Ile Ser Ser Pro Tyr Val Asp Glu Asp Leu His Gln Thr
65                  70                  75                  80

Thr Leu Phe Gly Asn His Gly Thr Lys Thr Ser Val Pro Ser Val Asp
                85                  90                  95

Ser Ile Lys Val His Gly Val Gly Arg Ala
            100                 105

<210> SEQ ID NO 17
<211> LENGTH: 981
<212> TYPE: DNA
<213> ORGANISM: Mus musculus
<220> FEATURE:
<221> NAME/KEY: CDS
<222> LOCATION: (1)...(978)
<223> OTHER INFORMATION: encodes MmSLC35A3 UDP-GlcNAc transporter

<400> SEQUENCE: 17 atg tct gcc aac cta aaa tat ctt tcc ttg gga att ttg gtg ttt cag      48
Met Ser Ala Asn Leu Lys Tyr Leu Ser Leu Gly Ile Leu Val Phe Gln
1               5                   10                  15 act acc agt ctg gtt cta acg atg cgg tat tct agg act tta aaa gag     96
Thr Thr Ser Leu Val Leu Thr Met Arg Tyr Ser Arg Thr Leu Lys Glu
            20                  25                  30 gag ggg cct cgt tat ctg tct tct aca gca gtg gtt gtg gct gaa ttt    144
Glu Gly Pro Arg Tyr Leu Ser Ser Thr Ala Val Val Val Ala Glu Phe
        35                  40                  45 ttg aag ata atg gcc tgc atc ttt tta gtc tac aaa gac agt aag tgt    192
Leu Lys Ile Met Ala Cys Ile Phe Leu Val Tyr Lys Asp Ser Lys Cys
    50                  55                  60 agt gtg aga gca ctg aat aga gta ctg cat gat gaa att ctt aat aag    240
Ser Val Arg Ala Leu Asn Arg Val Leu His Asp Glu Ile Leu Asn Lys
65                  70                  75                  80 ccc atg gaa acc ctg aag ctc gct atc ccg tca ggg ata tat act ctt    288
Pro Met Glu Thr Leu Lys Leu Ala Ile Pro Ser Gly Ile Tyr Thr Leu
                85                  90                  95 cag aac aac tta ctc tat gtg gca ctg tca aac cta gat gca gcc act    336
Gln Asn Asn Leu Leu Tyr Val Ala Leu Ser Asn Leu Asp Ala Ala Thr
            100                 105                 110 tac cag gtt aca tat cag ttg aaa ata ctt aca aca gca tta ttt tct    384
Tyr Gln Val Thr Tyr Gln Leu Lys Ile Leu Thr Thr Ala Leu Phe Ser
        115                 120                 125 gtg tct atg ctt ggt aaa aaa tta ggt gtg tac cag tgg ctc tcc cta    432
Val Ser Met Leu Gly Lys Lys Leu Gly Val Tyr Gln Trp Leu Ser Leu
    130                 135                 140 gta att ctg atg gca gga gtt gct ttt gta cag tgg cct tca gat tct    480
Val Ile Leu Met Ala Gly Val Ala Phe Val Gln Trp Pro Ser Asp Ser
145                 150                 155                 160 caa gag ctg aac tct aag gac ctt tca aca ggc tca cag ttt gta ggc    528
Gln Glu Leu Asn Ser Lys Asp Leu Ser Thr Gly Ser Gln Phe Val Gly
                165                 170                 175 ctc atg gca gtt ctc aca gcc tgt ttt tca agt ggc ttt gct gga gtt    576
Leu Met Ala Val Leu Thr Ala Cys Phe Ser Ser Gly Phe Ala Gly Val
            180                 185                 190 tat ttt gag aaa atc tta aaa gaa aca aaa cag tca gta tgg ata agg    624
Tyr Phe Glu Lys Ile Leu Lys Glu Thr Lys Gln Ser Val Trp Ile Arg
        195                 200                 205 aac att caa ctt ggt ttc ttt gga agt ata ttt gga tta atg ggt gta    672
Asn Ile Gln Leu Gly Phe Phe Gly Ser Ile Phe Gly Leu Met Gly Val
    210                 215                 220 tac gtt tat gat gga gaa ttg gtc tca aag aat gga ttt ttt cag gga    720
```

```
Tyr Val Tyr Asp Gly Glu Leu Val Ser Lys Asn Gly Phe Phe Gln Gly
225                 230                 235                 240 tat aat caa ctg acg tgg ata gtt gtt gct ctg cag gca ctt gga ggc        768
Tyr Asn Gln Leu Thr Trp Ile Val Val Ala Leu Gln Ala Leu Gly Gly
                245                 250                 255 ctt gta ata gct gct gtc atc aaa tat gca gat aac att tta aaa gga        816
Leu Val Ile Ala Ala Val Ile Lys Tyr Ala Asp Asn Ile Leu Lys Gly
            260                 265                 270 ttt gcg acc tcc tta tcc ata ata ttg tca aca ata ata tct tat ttt        864
Phe Ala Thr Ser Leu Ser Ile Ile Leu Ser Thr Ile Ile Ser Tyr Phe
        275                 280                 285 tgg ttg caa gat ttt gtg cca acc agt gtc ttt ttc ctt gga gcc atc        912
Trp Leu Gln Asp Phe Val Pro Thr Ser Val Phe Phe Leu Gly Ala Ile
    290                 295                 300 ctt gta ata gca gct act ttc ttg tat ggt tac gat ccc aaa cct gca        960
Leu Val Ile Ala Ala Thr Phe Leu Tyr Gly Tyr Asp Pro Lys Pro Ala
305                 310                 315                 320 gga aat ccc act aaa gca tag                                            981
Gly Asn Pro Thr Lys Ala
                325

<210> SEQ ID NO 18
<211> LENGTH: 326
<212> TYPE: PRT
<213> ORGANISM: Mus musculus

<400> SEQUENCE: 18

Met Ser Ala Asn Leu Lys Tyr Leu Ser Leu Gly Ile Leu Val Phe Gln
1               5                   10                  15

Thr Thr Ser Leu Val Leu Thr Met Arg Tyr Ser Arg Thr Leu Lys Glu
                20                  25                  30

Glu Gly Pro Arg Tyr Leu Ser Ser Thr Ala Val Val Ala Glu Phe
            35                  40                  45

Leu Lys Ile Met Ala Cys Ile Phe Leu Val Tyr Lys Asp Ser Lys Cys
    50                  55                  60

Ser Val Arg Ala Leu Asn Arg Val Leu His Asp Glu Ile Leu Asn Lys
65                  70                  75                  80

Pro Met Glu Thr Leu Lys Leu Ala Ile Pro Ser Gly Ile Tyr Thr Leu
                85                  90                  95

Gln Asn Asn Leu Leu Tyr Val Ala Leu Ser Asn Leu Asp Ala Ala Thr
            100                 105                 110

Tyr Gln Val Thr Tyr Gln Leu Lys Ile Leu Thr Thr Ala Leu Phe Ser
        115                 120                 125

Val Ser Met Leu Gly Lys Lys Leu Gly Val Tyr Gln Trp Leu Ser Leu
    130                 135                 140

Val Ile Leu Met Ala Gly Val Ala Phe Val Gln Trp Pro Ser Asp Ser
145                 150                 155                 160

Gln Glu Leu Asn Ser Lys Asp Leu Ser Thr Gly Ser Gln Phe Val Gly
                165                 170                 175

Leu Met Ala Val Leu Thr Ala Cys Phe Ser Ser Gly Phe Ala Gly Val
            180                 185                 190

Tyr Phe Glu Lys Ile Leu Lys Glu Thr Lys Gln Ser Val Trp Ile Arg
        195                 200                 205

Asn Ile Gln Leu Gly Phe Phe Gly Ser Ile Phe Gly Leu Met Gly Val
    210                 215                 220

Tyr Val Tyr Asp Gly Glu Leu Val Ser Lys Asn Gly Phe Phe Gln Gly
225                 230                 235                 240
```

```
Tyr Asn Gln Leu Thr Trp Ile Val Val Ala Leu Gln Ala Leu Gly Gly
                245                 250                 255

Leu Val Ile Ala Ala Val Ile Lys Tyr Ala Asp Asn Ile Leu Lys Gly
            260                 265                 270

Phe Ala Thr Ser Leu Ser Ile Ile Leu Ser Thr Ile Ile Ser Tyr Phe
        275                 280                 285

Trp Leu Gln Asp Phe Val Pro Thr Ser Val Phe Phe Leu Gly Ala Ile
    290                 295                 300

Leu Val Ile Ala Ala Thr Phe Leu Tyr Gly Tyr Asp Pro Lys Pro Ala
305                 310                 315                 320

Gly Asn Pro Thr Lys Ala
                325

<210> SEQ ID NO 19
<211> LENGTH: 1074
<212> TYPE: DNA
<213> ORGANISM: Drosophila melanogaster
<220> FEATURE:
<221> NAME/KEY: CDS
<222> LOCATION: (1)...(1071)
<223> OTHER INFORMATION: Encodes DmUGT

<400> SEQUENCE: 19
```

| | | | | | | | | | | | | | | | | |
|---|---|---|---|---|---|---|---|---|---|---|---|---|---|---|---|---|
| atg | aat | agc | ata | cac | atg | aac | gcc | aat | acg | ctg | aag | tac | atc | agc | ctg | 48 |
| Met | Asn | Ser | Ile | His | Met | Asn | Ala | Asn | Thr | Leu | Lys | Tyr | Ile | Ser | Leu | |
| 1 | | | | 5 | | | | | 10 | | | | | 15 | | |
| ctg | acg | ctg | acc | ctg | cag | aat | gcc | atc | ctg | ggc | ctc | agc | atg | cgc | tac | 96 |
| Leu | Thr | Leu | Thr | Leu | Gln | Asn | Ala | Ile | Leu | Gly | Leu | Ser | Met | Arg | Tyr | |
| | | | 20 | | | | | 25 | | | | | 30 | | | |
| gcc | cgc | acc | cgg | cca | ggc | gac | atc | ttc | ctc | agc | tcc | acg | gcc | gta | ctc | 144 |
| Ala | Arg | Thr | Arg | Pro | Gly | Asp | Ile | Phe | Leu | Ser | Ser | Thr | Ala | Val | Leu | |
| | | 35 | | | | | 40 | | | | | 45 | | | | |
| atg | gca | gag | ttc | gcc | aaa | ctg | atc | acg | tgc | ctg | ttc | ctg | gtc | ttc | aac | 192 |
| Met | Ala | Glu | Phe | Ala | Lys | Leu | Ile | Thr | Cys | Leu | Phe | Leu | Val | Phe | Asn | |
| | 50 | | | | | 55 | | | | | 60 | | | | | |
| gag | gag | ggc | aag | gat | gcc | cag | aag | ttt | gta | cgc | tcg | ctg | cac | aag | acc | 240 |
| Glu | Glu | Gly | Lys | Asp | Ala | Gln | Lys | Phe | Val | Arg | Ser | Leu | His | Lys | Thr | |
| 65 | | | | | 70 | | | | | 75 | | | | | 80 | |
| atc | att | gcg | aat | ccc | atg | gac | acg | ctg | aag | gtg | tgc | gtc | ccc | tcg | ctg | 288 |
| Ile | Ile | Ala | Asn | Pro | Met | Asp | Thr | Leu | Lys | Val | Cys | Val | Pro | Ser | Leu | |
| | | | | 85 | | | | | 90 | | | | | 95 | | |
| gtc | tat | atc | gtt | caa | aac | aat | ctg | ctg | tac | gtc | tct | gcc | tcc | cat | ttg | 336 |
| Val | Tyr | Ile | Val | Gln | Asn | Asn | Leu | Leu | Tyr | Val | Ser | Ala | Ser | His | Leu | |
| | | | 100 | | | | | 105 | | | | | 110 | | | |
| gat | gcg | gcc | acc | tac | cag | gtg | acg | tac | cag | ctg | aag | att | ctc | acc | acg | 384 |
| Asp | Ala | Ala | Thr | Tyr | Gln | Val | Thr | Tyr | Gln | Leu | Lys | Ile | Leu | Thr | Thr | |
| | | 115 | | | | | 120 | | | | | 125 | | | | |
| gcc | atg | ttc | gcg | gtt | gtc | att | ctg | cgc | cgc | aag | ctg | ctg | aac | acg | cag | 432 |
| Ala | Met | Phe | Ala | Val | Val | Ile | Leu | Arg | Arg | Lys | Leu | Leu | Asn | Thr | Gln | |
| | 130 | | | | | 135 | | | | | 140 | | | | | |
| tgg | ggt | gcg | ctg | ctg | ctc | ctg | gtg | atg | ggc | atc | gtc | ctg | gtg | cag | ttg | 480 |
| Trp | Gly | Ala | Leu | Leu | Leu | Leu | Val | Met | Gly | Ile | Val | Leu | Val | Gln | Leu | |
| 145 | | | | | 150 | | | | | 155 | | | | | 160 | |
| gcc | caa | acg | gag | ggt | ccg | acg | agt | ggc | tca | gcc | ggt | ggt | gcc | gca | gct | 528 |
| Ala | Gln | Thr | Glu | Gly | Pro | Thr | Ser | Gly | Ser | Ala | Gly | Gly | Ala | Ala | Ala | |
| | | | | 165 | | | | | 170 | | | | | 175 | | |
| gca | gcc | acg | gcc | gcc | tcc | tct | ggc | ggt | gct | ccc | gag | cag | aac | agg | atg | 576 |
| Ala | Ala | Thr | Ala | Ala | Ser | Ser | Gly | Gly | Ala | Pro | Glu | Gln | Asn | Arg | Met | |
| | | | 180 | | | | | 185 | | | | | 190 | | | |

| | | |
|---|---|---|
| ctc gga ctg tgg gcc gca ctg ggc gcc tgc ttc ctc tcc gga ttc gcg<br>Leu Gly Leu Trp Ala Ala Leu Gly Ala Cys Phe Leu Ser Gly Phe Ala<br>          195                            200                              205 | | 624 |
| ggc atc tac ttt gag aag atc ctc aag ggt gcc gag atc tcc gtg tgg<br>Gly Ile Tyr Phe Glu Lys Ile Leu Lys Gly Ala Glu Ile Ser Val Trp<br>210                               215                              220 | | 672 |
| atg cgg aat gtg cag ttg agt ctg ctc agc att ccc ttc ggc ctg ctc<br>Met Arg Asn Val Gln Leu Ser Leu Leu Ser Ile Pro Phe Gly Leu Leu<br>225                               230                              235                            240 | | 720 |
| acc tgt ttc gtt aac gac ggc agt agg atc ttc gac cag gga ttc ttc<br>Thr Cys Phe Val Asn Asp Gly Ser Arg Ile Phe Asp Gln Gly Phe Phe<br>                            245                            250                              255 | | 768 |
| aag ggc tac gat ctg ttt gtc tgg tac ctg gtc ctg cag gcc ggc<br>Lys Gly Tyr Asp Leu Phe Val Trp Tyr Leu Val Leu Leu Gln Ala Gly<br>                  260                            265                            270 | | 816 |
| ggt gga ttg atc gtt gcc gtg gtg gtc aag tac gcg gat aac att ctc<br>Gly Gly Leu Ile Val Ala Val Val Val Lys Tyr Ala Asp Asn Ile Leu<br>                            275                            280                              285 | | 864 |
| aag ggc ttc gcc acc tcg ctg gcc atc atc atc tcg tgc gtg gcc tcc<br>Lys Gly Phe Ala Thr Ser Leu Ala Ile Ile Ile Ser Cys Val Ala Ser<br>290                               295                              300 | | 912 |
| ata tac atc ttc gac ttc aat ctc acg ctg cag ttc agc ttc gga gct<br>Ile Tyr Ile Phe Asp Phe Asn Leu Thr Leu Gln Phe Ser Phe Gly Ala<br>305                               310                              315                            320 | | 960 |
| ggc ctg gtc atc gcc tcc ata ttt ctc tac ggc tac gat ccg gcc agg<br>Gly Leu Val Ile Ala Ser Ile Phe Leu Tyr Gly Tyr Asp Pro Ala Arg<br>                            325                            330                              335 | | 1008 |
| tcg gcg ccg aag cca act atg cat ggt cct ggc ggc gat gag gag aag<br>Ser Ala Pro Lys Pro Thr Met His Gly Pro Gly Gly Asp Glu Glu Lys<br>                  340                            345                            350 | | 1056 |
| ctg ctg ccg cgc gtc tag<br>Leu Leu Pro Arg Val<br>                  355 | | 1074 |

```
<210> SEQ ID NO 20
<211> LENGTH: 357
<212> TYPE: PRT
<213> ORGANISM: Drosophila melanogaster

<400> SEQUENCE: 20
```

Met Asn Ser Ile His Met Asn Ala Asn Thr Leu Lys Tyr Ile Ser Leu
1               5                   10                  15

Leu Thr Leu Thr Leu Gln Asn Ala Ile Leu Gly Leu Ser Met Arg Tyr
            20                  25                  30

Ala Arg Thr Arg Pro Gly Asp Ile Phe Leu Ser Ser Thr Ala Val Leu
        35                  40                  45

Met Ala Glu Phe Ala Lys Leu Ile Thr Cys Leu Phe Leu Val Phe Asn
    50                  55                  60

Glu Glu Gly Lys Asp Ala Gln Lys Phe Val Arg Ser Leu His Lys Thr
65                  70                  75                  80

Ile Ile Ala Asn Pro Met Asp Thr Leu Lys Val Cys Val Pro Ser Leu
                85                  90                  95

Val Tyr Ile Val Gln Asn Asn Leu Leu Tyr Val Ser Ala Ser His Leu
            100                 105                 110

Asp Ala Ala Thr Tyr Gln Val Thr Tyr Gln Leu Lys Ile Leu Thr Thr
        115                 120                 125

Ala Met Phe Ala Val Val Ile Leu Arg Arg Lys Leu Leu Asn Thr Gln
    130                 135                 140

-continued

```
Trp Gly Ala Leu Leu Leu Val Met Gly Ile Val Leu Val Gln Leu
145                 150                 155                 160

Ala Gln Thr Glu Gly Pro Thr Ser Gly Ser Ala Gly Gly Ala Ala Ala
                165                 170                 175

Ala Ala Thr Ala Ala Ser Ser Gly Gly Ala Pro Glu Gln Asn Arg Met
            180                 185                 190

Leu Gly Leu Trp Ala Ala Leu Gly Ala Cys Phe Leu Ser Gly Phe Ala
        195                 200                 205

Gly Ile Tyr Phe Glu Lys Ile Leu Lys Gly Ala Glu Ile Ser Val Trp
    210                 215                 220

Met Arg Asn Val Gln Leu Ser Leu Leu Ser Ile Pro Phe Gly Leu Leu
225                 230                 235                 240

Thr Cys Phe Val Asn Asp Gly Ser Arg Ile Phe Asp Gln Gly Phe Phe
                245                 250                 255

Lys Gly Tyr Asp Leu Phe Val Trp Tyr Leu Val Leu Leu Gln Ala Gly
            260                 265                 270

Gly Gly Leu Ile Val Ala Val Val Lys Tyr Ala Asp Asn Ile Leu
        275                 280                 285

Lys Gly Phe Ala Thr Ser Leu Ala Ile Ile Ile Ser Cys Val Ala Ser
    290                 295                 300

Ile Tyr Ile Phe Asp Phe Asn Leu Thr Leu Gln Phe Ser Phe Gly Ala
305                 310                 315                 320

Gly Leu Val Ile Ala Ser Ile Phe Leu Tyr Gly Tyr Asp Pro Ala Arg
                325                 330                 335

Ser Ala Pro Lys Pro Thr Met His Gly Pro Gly Asp Glu Glu Lys
            340                 345                 350

Leu Leu Pro Arg Val
        355
```

<210> SEQ ID NO 21
<211> LENGTH: 2100
<212> TYPE: DNA
<213> ORGANISM: Saccharomyces cerevisiea
<220> FEATURE:
<221> NAME/KEY: CDS
<222> LOCATION: (1)...(2097)
<223> OTHER INFORMATION: Encodes ScGAL10

<400> SEQUENCE: 21

```
atg aca gct cag tta caa agt gaa agt act tct aaa att gtt ttg gtt      48
Met Thr Ala Gln Leu Gln Ser Glu Ser Thr Ser Lys Ile Val Leu Val
1               5                   10                  15 aca ggt ggt gct gga tac att ggt tca cac act gtg gta gag cta att      96
Thr Gly Gly Ala Gly Tyr Ile Gly Ser His Thr Val Val Glu Leu Ile
            20                  25                  30 gag aat gga tat gac tgt gtt gtt gct gat aac ctg tcg aat tca act     144
Glu Asn Gly Tyr Asp Cys Val Val Ala Asp Asn Leu Ser Asn Ser Thr
        35                  40                  45 tat gat tct gta gcc agg tta gag gtc ttg acc aag cat cac att ccc     192
Tyr Asp Ser Val Ala Arg Leu Glu Val Leu Thr Lys His His Ile Pro
    50                  55                  60 ttc tat gag gtt gat ttg tgt gac cga aaa ggt ctg gaa aag gtt ttc     240
Phe Tyr Glu Val Asp Leu Cys Asp Arg Lys Gly Leu Glu Lys Val Phe
65                  70                  75                  80 aaa gaa tat aaa att gat tcg gta att cac ttt gct ggt tta aag gct     288
Lys Glu Tyr Lys Ile Asp Ser Val Ile His Phe Ala Gly Leu Lys Ala
                85                  90                  95 gta ggt gaa tct aca caa atc ccg ctg aga tac tat cac aat aac att     336
```

```
                Val Gly Glu Ser Thr Gln Ile Pro Leu Arg Tyr Tyr His Asn Asn Ile
                                100                 105                 110 ttg gga act gtc gtt tta tta gag tta atg caa caa tac aac gtt tcc       384
Leu Gly Thr Val Val Leu Leu Glu Leu Met Gln Gln Tyr Asn Val Ser
            115                 120                 125 aaa ttt gtt ttt tca tct tct gct act gtc tat ggt gat gct acg aga       432
Lys Phe Val Phe Ser Ser Ser Ala Thr Val Tyr Gly Asp Ala Thr Arg
130                 135                 140 ttc cca aat atg att cct atc cca gaa gaa tgt ccc tta ggg cct act       480
Phe Pro Asn Met Ile Pro Ile Pro Glu Glu Cys Pro Leu Gly Pro Thr
145                 150                 155                 160 aat ccg tat ggt cat acg aaa tac gcc att gag aat atc ttg aat gat       528
Asn Pro Tyr Gly His Thr Lys Tyr Ala Ile Glu Asn Ile Leu Asn Asp
                165                 170                 175 ctt tac aat agc gac aaa aaa agt tgg aag ttt gct atc ttg cgt tat       576
Leu Tyr Asn Ser Asp Lys Lys Ser Trp Lys Phe Ala Ile Leu Arg Tyr
            180                 185                 190 ttt aac cca att ggc gca cat ccc tct gga tta atc gga gaa gat ccg       624
Phe Asn Pro Ile Gly Ala His Pro Ser Gly Leu Ile Gly Glu Asp Pro
195                 200                 205 cta ggt ata cca aac aat ttg ttg cca tat atg gct caa gta gct gtt       672
Leu Gly Ile Pro Asn Asn Leu Leu Pro Tyr Met Ala Gln Val Ala Val
210                 215                 220 ggt agg cgc gag aag ctt tac atc ttc gga gac gat tat gat tcc aga       720
Gly Arg Arg Glu Lys Leu Tyr Ile Phe Gly Asp Asp Tyr Asp Ser Arg
225                 230                 235                 240 gat ggt acc ccg atc agg gat tat atc cac gta gtt gat cta gca aaa       768
Asp Gly Thr Pro Ile Arg Asp Tyr Ile His Val Val Asp Leu Ala Lys
                245                 250                 255 ggt cat att gca gcc ctg caa tac cta gag gcc tac aat gaa aat gaa       816
Gly His Ile Ala Ala Leu Gln Tyr Leu Glu Ala Tyr Asn Glu Asn Glu
            260                 265                 270 ggt ttg tgt cgt gag tgg aac ttg ggt tcc ggt aaa ggt tct aca gtt       864
Gly Leu Cys Arg Glu Trp Asn Leu Gly Ser Gly Lys Gly Ser Thr Val
        275                 280                 285 ttt gaa gtt tat cat gca ttc tgc aaa gct tct ggt att gat ctt cca       912
Phe Glu Val Tyr His Ala Phe Cys Lys Ala Ser Gly Ile Asp Leu Pro
290                 295                 300 tac aaa gtt acg ggc aga aga gca ggt gat gtt ttg aac ttg acg gct       960
Tyr Lys Val Thr Gly Arg Arg Ala Gly Asp Val Leu Asn Leu Thr Ala
305                 310                 315                 320 aaa cca gat agg gcc aaa cgc gaa ctg aaa tgg cag acc gag ttg cag      1008
Lys Pro Asp Arg Ala Lys Arg Glu Leu Lys Trp Gln Thr Glu Leu Gln
                325                 330                 335 gtt gaa gac tcc tgc aag gat tta tgg aaa tgg act act gag aat cct      1056
Val Glu Asp Ser Cys Lys Asp Leu Trp Lys Trp Thr Thr Glu Asn Pro
            340                 345                 350 ttt ggt tac cag tta agg ggt gtc gag gcc aga ttt tcc gct gaa gat      1104
Phe Gly Tyr Gln Leu Arg Gly Val Glu Ala Arg Phe Ser Ala Glu Asp
        355                 360                 365 atg cgt tat gac gca aga ttt gtg act att ggt gcc ggc acc aga ttt      1152
Met Arg Tyr Asp Ala Arg Phe Val Thr Ile Gly Ala Gly Thr Arg Phe
370                 375                 380 caa gcc acg ttt gcc aat ttg ggc gcc agc att gtt gac ctg aaa gtg      1200
Gln Ala Thr Phe Ala Asn Leu Gly Ala Ser Ile Val Asp Leu Lys Val
385                 390                 395                 400 aac gga caa tca gtt gtt ctt ggc tat gaa aat gag gaa ggg tat ttg      1248
Asn Gly Gln Ser Val Val Leu Gly Tyr Glu Asn Glu Glu Gly Tyr Leu
                405                 410                 415
```

```
aat cct gat agt gct tat ata ggc gcc acg atc ggc agg tat gct aat    1296
Asn Pro Asp Ser Ala Tyr Ile Gly Ala Thr Ile Gly Arg Tyr Ala Asn
            420                 425                 430 cgt att tcg aag ggt aag ttt agt tta tgc aac aaa gac tat cag tta    1344
Arg Ile Ser Lys Gly Lys Phe Ser Leu Cys Asn Lys Asp Tyr Gln Leu
        435                 440                 445 acc gtt aat aac ggc gtt aat gcg aat cat agt agt atc ggt tct ttc    1392
Thr Val Asn Asn Gly Val Asn Ala Asn His Ser Ser Ile Gly Ser Phe
    450                 455                 460 cac aga aaa aga ttt ttg gga ccc atc att caa aat cct tca aag gat    1440
His Arg Lys Arg Phe Leu Gly Pro Ile Ile Gln Asn Pro Ser Lys Asp
465                 470                 475                 480 gtt ttt acc gcc gag tac atg ctg ata gat aat gag aag gac acc gaa    1488
Val Phe Thr Ala Glu Tyr Met Leu Ile Asp Asn Glu Lys Asp Thr Glu
                485                 490                 495 ttt cca ggt gat cta ttg gta acc ata cag tat act gtg aac gtt gcc    1536
Phe Pro Gly Asp Leu Leu Val Thr Ile Gln Tyr Thr Val Asn Val Ala
            500                 505                 510 caa aaa agt ttg gaa atg gta tat aaa ggt aaa ttg act gct ggt gaa    1584
Gln Lys Ser Leu Glu Met Val Tyr Lys Gly Lys Leu Thr Ala Gly Glu
        515                 520                 525 gcg acg cca ata aat tta aca aat cat agt tat ttc aat ctg aac aag    1632
Ala Thr Pro Ile Asn Leu Thr Asn His Ser Tyr Phe Asn Leu Asn Lys
    530                 535                 540 cca tat gga gac act att gag ggt acg gag att atg gtg cgt tca aaa    1680
Pro Tyr Gly Asp Thr Ile Glu Gly Thr Glu Ile Met Val Arg Ser Lys
545                 550                 555                 560 aaa tct gtt gat gtc gac aaa aac atg att cct acg ggt aat atc gtc    1728
Lys Ser Val Asp Val Asp Lys Asn Met Ile Pro Thr Gly Asn Ile Val
                565                 570                 575 gat aga gaa att gct acc ttt aac tct aca aag cca acg gtc tta ggc    1776
Asp Arg Glu Ile Ala Thr Phe Asn Ser Thr Lys Pro Thr Val Leu Gly
            580                 585                 590 ccc aaa aat ccc cag ttt gat tgt tgt ttt gtg gtg gat gaa aat gct    1824
Pro Lys Asn Pro Gln Phe Asp Cys Cys Phe Val Val Asp Glu Asn Ala
        595                 600                 605 aag cca agt caa atc aat act cta aac aat gaa ttg acg ctt att gtc    1872
Lys Pro Ser Gln Ile Asn Thr Leu Asn Asn Glu Leu Thr Leu Ile Val
    610                 615                 620 aag gct ttt cat ccc gat tcc aat att aca tta gaa gtt tta agt aca    1920
Lys Ala Phe His Pro Asp Ser Asn Ile Thr Leu Glu Val Leu Ser Thr
625                 630                 635                 640 gag cca act tat caa ttt tat acc ggt gat ttc ttg tct gct ggt tac    1968
Glu Pro Thr Tyr Gln Phe Tyr Thr Gly Asp Phe Leu Ser Ala Gly Tyr
                645                 650                 655 gaa gca aga caa ggt ttt gca att gag cct ggt aga tac att gat gct    2016
Glu Ala Arg Gln Gly Phe Ala Ile Glu Pro Gly Arg Tyr Ile Asp Ala
            660                 665                 670 atc aat caa gag aac tgg aaa gat tgt gta acc ttg aaa aac ggt gaa    2064
Ile Asn Gln Glu Asn Trp Lys Asp Cys Val Thr Leu Lys Asn Gly Glu
        675                 680                 685 act tac ggg tcc aag att gtc tac aga ttt tcc tga                    2100
Thr Tyr Gly Ser Lys Ile Val Tyr Arg Phe Ser
    690                 695

<210> SEQ ID NO 22
<211> LENGTH: 699
<212> TYPE: PRT
<213> ORGANISM: Saccharomyces cerevisiea

<400> SEQUENCE: 22
```

```
Met Thr Ala Gln Leu Gln Ser Glu Ser Thr Ser Lys Ile Val Leu Val
  1               5                  10                 15
Thr Gly Gly Ala Gly Tyr Ile Gly Ser His Thr Val Val Glu Leu Ile
             20                  25                 30
Glu Asn Gly Tyr Asp Cys Val Val Ala Asp Asn Leu Ser Asn Ser Thr
             35                  40                 45
Tyr Asp Ser Val Ala Arg Leu Glu Val Leu Thr Lys His His Ile Pro
 50                  55                  60
Phe Tyr Glu Val Asp Leu Cys Asp Arg Lys Gly Leu Glu Lys Val Phe
 65                  70                  75                 80
Lys Glu Tyr Lys Ile Asp Ser Val Ile His Phe Ala Gly Leu Lys Ala
                 85                  90                 95
Val Gly Glu Ser Thr Gln Ile Pro Leu Arg Tyr Tyr His Asn Asn Ile
                100                 105                110
Leu Gly Thr Val Val Leu Glu Leu Met Gln Gln Tyr Asn Val Ser
                115                 120             125
Lys Phe Val Phe Ser Ser Ala Thr Val Tyr Gly Asp Ala Thr Arg
    130                 135                 140
Phe Pro Asn Met Ile Pro Ile Pro Glu Glu Cys Pro Leu Gly Pro Thr
145                 150                 155                160
Asn Pro Tyr Gly His Thr Lys Tyr Ala Ile Glu Asn Ile Leu Asn Asp
                165                 170                 175
Leu Tyr Asn Ser Asp Lys Lys Ser Trp Lys Phe Ala Ile Leu Arg Tyr
                180                 185                 190
Phe Asn Pro Ile Gly Ala His Pro Ser Gly Leu Ile Gly Glu Asp Pro
                195                 200                 205
Leu Gly Ile Pro Asn Asn Leu Leu Pro Tyr Met Ala Gln Val Ala Val
    210                 215                 220
Gly Arg Arg Glu Lys Leu Tyr Ile Phe Gly Asp Asp Tyr Asp Ser Arg
225                 230                 235                240
Asp Gly Thr Pro Ile Arg Asp Tyr Ile His Val Asp Leu Ala Lys
                245                 250                 255
Gly His Ile Ala Ala Leu Gln Tyr Leu Glu Ala Tyr Asn Glu Asn Glu
                260                 265                 270
Gly Leu Cys Arg Glu Trp Asn Leu Gly Ser Gly Lys Gly Ser Thr Val
    275                 280                 285
Phe Glu Val Tyr His Ala Phe Cys Lys Ala Ser Gly Ile Asp Leu Pro
    290                 295                 300
Tyr Lys Val Thr Gly Arg Arg Ala Gly Asp Val Leu Asn Leu Thr Ala
305                 310                 315                320
Lys Pro Asp Arg Ala Lys Arg Glu Leu Lys Trp Gln Thr Glu Leu Gln
                325                 330                 335
Val Glu Asp Ser Cys Lys Asp Leu Trp Lys Trp Thr Thr Glu Asn Pro
                340                 345                 350
Phe Gly Tyr Gln Leu Arg Gly Val Glu Ala Arg Phe Ser Ala Glu Asp
                355                 360                 365
Met Arg Tyr Asp Ala Arg Phe Val Thr Ile Gly Ala Gly Thr Arg Phe
    370                 375                 380
Gln Ala Thr Phe Ala Asn Leu Gly Ala Ser Ile Val Asp Leu Lys Val
385                 390                 395                400
Asn Gly Gln Ser Val Val Leu Gly Tyr Glu Asn Glu Glu Gly Tyr Leu
                405                 410                 415
```

```
Asn Pro Asp Ser Ala Tyr Ile Gly Ala Thr Ile Gly Arg Tyr Ala Asn
                420                 425                 430

Arg Ile Ser Lys Gly Lys Phe Ser Leu Cys Asn Lys Asp Tyr Gln Leu
            435                 440                 445

Thr Val Asn Asn Gly Val Asn Ala Asn His Ser Ser Ile Gly Ser Phe
    450                 455                 460

His Arg Lys Arg Phe Leu Gly Pro Ile Ile Gln Asn Pro Ser Lys Asp
465                 470                 475                 480

Val Phe Thr Ala Glu Tyr Met Leu Ile Asp Asn Glu Lys Asp Thr Glu
                485                 490                 495

Phe Pro Gly Asp Leu Leu Val Thr Ile Gln Tyr Thr Val Asn Val Ala
                500                 505                 510

Gln Lys Ser Leu Glu Met Val Tyr Lys Gly Lys Leu Thr Ala Gly Glu
            515                 520                 525

Ala Thr Pro Ile Asn Leu Thr Asn His Ser Tyr Phe Asn Leu Asn Lys
    530                 535                 540

Pro Tyr Gly Asp Thr Ile Glu Gly Thr Glu Ile Met Val Arg Ser Lys
545                 550                 555                 560

Lys Ser Val Asp Val Asp Lys Asn Met Ile Pro Thr Gly Asn Ile Val
                565                 570                 575

Asp Arg Glu Ile Ala Thr Phe Asn Ser Thr Lys Pro Thr Val Leu Gly
            580                 585                 590

Pro Lys Asn Pro Gln Phe Asp Cys Cys Phe Val Val Asp Glu Asn Ala
    595                 600                 605

Lys Pro Ser Gln Ile Asn Thr Leu Asn Asn Glu Leu Thr Leu Ile Val
610                 615                 620

Lys Ala Phe His Pro Asp Ser Asn Ile Thr Leu Glu Val Leu Ser Thr
625                 630                 635                 640

Glu Pro Thr Tyr Gln Phe Tyr Thr Gly Asp Phe Leu Ser Ala Gly Tyr
                645                 650                 655

Glu Ala Arg Gln Gly Phe Ala Ile Glu Pro Gly Arg Tyr Ile Asp Ala
            660                 665                 670

Ile Asn Gln Glu Asn Trp Lys Asp Cys Val Thr Leu Lys Asn Gly Glu
    675                 680                 685

Thr Tyr Gly Ser Lys Ile Val Tyr Arg Phe Ser
    690                 695

<210> SEQ ID NO 23
<211> LENGTH: 1068
<212> TYPE: DNA
<213> ORGANISM: Artificial Sequence
<220> FEATURE:
<223> OTHER INFORMATION: Encodes hGalT catalytic domain codon optimized
      (XB)

<400> SEQUENCE: 23 ggt aga gat ttg tct aga ttg cca cag ttg gtt ggt gtt tcc act cca      48 ttg caa gga ggt tct aac tct gct gct gct att ggt caa tct tcc ggt      96 gag ttg aga act ggt gga gct aga cca cct cca cca ttg gga gct tcc     144 tct caa cca aga cca ggt ggt gat tct tct cca gtt gtt gac tct ggt     192 cca ggt cca gct tct aac ttg act tcc gtt cca gtt cca cac act act     240 gct ttg tcc ttg cca gct tgt cca gaa gaa tcc cca ttg ttg gtt ggt     288 cca atg ttg atc gag ttc aac atg cca gtt gac ttg gag ttg gtt gct     336
```

-continued

```
aag cag aac cca aac gtt aag atg ggt ggt aga tac gct cca aga gac    384
tgt gtt tcc cca cac aaa gtt gct atc atc atc cca ttc aga aac aga    432
cag gag cac ttg aag tac tgg ttg tac tac ttg cac cca gtt ttg caa    480
aga cag cag ttg gac tac ggt atc tac gtt atc aac cag gct ggt gac    528
act att ttc aac aga gct aag ttg ttg aat gtt ggt ttc cag gag gct    576
ttg aag gat tac gac tac act tgt ttc gtt ttc tcc gac gtt gac ttg    624
att cca atg aac gac cac aac gct tac aga tgt ttc tcc cag cca aga    672
cac att tct gtt gct atg gac aag ttc ggt ttc tcc ttg cca tac gtt    720
caa tac ttc ggt ggt gtt tcc gct ttg tcc aag cag cag ttc ttg act    768
atc aac ggt ttc cca aac aat tac tgg gga tgg ggt ggt gaa gat gac    816
gac atc ttt aac aga ttg gtt ttc aga gga atg tcc atc tct aga cca    864
aac gct gtt gtt ggt aga tgt aga atg atc aga cac tcc aga gac aag    912
aag aac gag cca aac cca caa aga ttc gac aga atc gct cac act aag    960
gaa act atg ttg tcc gac gga ttg aac tcc ttg act tac cag gtt ttg   1008
gac gtt cag aga tac cca ttg tac act cag atc act gtt gac atc ggt   1056
act cca tcc tag                                                    1068
```

<210> SEQ ID NO 24
<211> LENGTH: 355
<212> TYPE: PRT
<213> ORGANISM: Artificial Sequence
<220> FEATURE:
<223> OTHER INFORMATION: hGalT catalytic domain (XB)

<400> SEQUENCE: 24

```
Gly Arg Asp Leu Ser Arg Leu Pro Gln Leu Val Gly Val Ser Thr Pro
  1               5                  10                  15

Leu Gln Gly Gly Ser Asn Ser Ala Ala Ile Gly Gln Ser Ser Gly
             20                  25                  30

Glu Leu Arg Thr Gly Gly Ala Arg Pro Pro Pro Leu Gly Ala Ser
         35                  40                  45

Ser Gln Pro Arg Pro Gly Gly Asp Ser Ser Pro Val Val Asp Ser Gly
     50                  55                  60

Pro Gly Pro Ala Ser Asn Leu Thr Ser Val Pro Val Pro His Thr Thr
 65                  70                  75                  80

Ala Leu Ser Leu Pro Ala Cys Pro Glu Glu Ser Pro Leu Leu Val Gly
                 85                  90                  95

Pro Met Leu Ile Glu Phe Asn Met Pro Val Asp Leu Glu Leu Val Ala
            100                 105                 110

Lys Gln Asn Pro Asn Val Lys Met Gly Gly Arg Tyr Ala Pro Arg Asp
        115                 120                 125

Cys Val Ser Pro His Lys Val Ala Ile Ile Pro Phe Arg Asn Arg
    130                 135                 140

Gln Glu His Leu Lys Tyr Trp Leu Tyr Tyr Leu His Pro Val Leu Gln
145                 150                 155                 160

Arg Gln Gln Leu Asp Tyr Gly Ile Tyr Val Ile Asn Gln Ala Gly Asp
                165                 170                 175

Thr Ile Phe Asn Arg Ala Lys Leu Leu Asn Val Gly Phe Gln Glu Ala
            180                 185                 190

Leu Lys Asp Tyr Asp Tyr Thr Cys Phe Val Phe Ser Asp Val Asp Leu
```

```
                    195                 200                 205
Ile Pro Met Asn Asp His Asn Ala Tyr Arg Cys Phe Ser Gln Pro Arg
    210                 215                 220

His Ile Ser Val Ala Met Asp Lys Phe Gly Phe Ser Leu Pro Tyr Val
225                 230                 235                 240

Gln Tyr Phe Gly Gly Val Ser Ala Leu Ser Lys Gln Gln Phe Leu Thr
                245                 250                 255

Ile Asn Gly Phe Pro Asn Asn Tyr Trp Gly Trp Gly Gly Glu Asp Asp
                260                 265                 270

Asp Ile Phe Asn Arg Leu Val Phe Arg Gly Met Ser Ile Ser Arg Pro
            275                 280                 285

Asn Ala Val Val Gly Arg Cys Arg Met Ile Arg His Ser Arg Asp Lys
    290                 295                 300

Lys Asn Glu Pro Asn Pro Gln Arg Phe Asp Arg Ile Ala His Thr Lys
305                 310                 315                 320

Glu Thr Met Leu Ser Asp Gly Leu Asn Ser Leu Thr Tyr Gln Val Leu
                325                 330                 335

Asp Val Gln Arg Tyr Pro Leu Tyr Thr Gln Ile Thr Val Asp Ile Gly
            340                 345                 350

Thr Pro Ser
        355
```

<210> SEQ ID NO 25
<211> LENGTH: 1224
<212> TYPE: DNA
<213> ORGANISM: Artificial Sequence
<220> FEATURE:
<223> OTHER INFORMATION: Encodes human GnTI catalytic doman (NA)
Codon-optimized

<400> SEQUENCE: 25

```
tcagtcagtg ctcttgatgg tgacccagca agtttgacca gagaagtgat tagattggcc      60
caagacgcag aggtggagtt ggagagacaa cgtggactgc tgcagcaaat cggagatgca     120
ttgtctagtc aaagaggtag ggtgcctacc gcagctcctc cagcacagcc tagagtgcat     180
gtgacccctg caccagctgt gattcctatc ttggtcatcg cctgtgacag atctactgtt     240
agaagatgtc tggacaagct gttgcattac agaccatctg ctgagttgtt ccctatcatc     300
gttagtcaag actgtggtca cgaggagact gcccaagcca tcgcctccta cggatctgct     360
gtcactcaca tcagacagcc tgacctgtca tctattgctg tgccaccaga ccacagaaag     420
ttccaaggtt actacaagat cgctagacac tacagatggg cattgggtca agtcttcaga     480
cagtttagat ccctgctgc tgtggtggtg gaggatgact ggaggtggc tcctgacttc      540 tttgagtact ttagagcaac ctatccattg ctgaaggcag acccatccct gtggtgtgtc     600
tctgcctgga atgacaacgg taaggagcaa atggtggacg cttctaggcc tgagctgttg     660
tacagaaccg acttctttcc tggtctggga tggttgctgt ggctgagtt gtgggctgag      720 ttggagccta agtggccaaa ggcattctgg gacgactgga tgagaagacc tgagcaaaga     780
cagggtagag cctgtatcag acctgagatc tcaagaacca tgacctttgg tagaaaggga     840
gtgtctcacg tcaattctt tgaccaacac ttgaagtta tcaagctgaa ccagcaattt      900
gtgcacttca cccaactgga cctgtcttac ttgcagagag aggcctatga cagagatttc     960
ctagctagag tctacggagc tcctcaactg caagtggaga agtgaggac caatgacaga    1020 aaggagttgg gagaggtgag agtgcagtac actggtaggg actcctttaa ggctttcgct    1080
```

```
aaggctctgg gtgtcatgga tgaccttaag tctggagttc ctagagctgg ttacagaggt    1140
attgtcacct ttcaattcag aggtagaaga gtccacttgg ctcctccacc tacttgggag    1200
ggttatgatc cttcttggaa ttag                                            1224
```

<210> SEQ ID NO 26
<211> LENGTH: 407
<212> TYPE: PRT
<213> ORGANISM: Artificial Sequence
<220> FEATURE:
<223> OTHER INFORMATION: human GnTI catalytic doman (NA)

<400> SEQUENCE: 26

```
Ser Val Ser Ala Leu Asp Gly Asp Pro Ala Ser Leu Thr Arg Glu Val
 1               5                  10                  15

Ile Arg Leu Ala Gln Asp Ala Glu Val Glu Leu Glu Arg Gln Arg Gly
                20                  25                  30

Leu Leu Gln Gln Ile Gly Asp Ala Leu Ser Ser Gln Arg Gly Arg Val
            35                  40                  45

Pro Thr Ala Ala Pro Ala Gln Pro Arg Val His Val Thr Pro Ala
        50                  55                  60

Pro Ala Val Ile Pro Ile Leu Val Ile Ala Cys Asp Arg Ser Thr Val
 65                  70                  75                  80

Arg Arg Cys Leu Asp Lys Leu Leu His Tyr Arg Pro Ser Ala Glu Leu
                85                  90                  95

Phe Pro Ile Ile Val Ser Gln Asp Cys Gly His Glu Glu Thr Ala Gln
            100                 105                 110

Ala Ile Ala Ser Tyr Gly Ser Ala Val Thr His Ile Arg Gln Pro Asp
        115                 120                 125

Leu Ser Ser Ile Ala Val Pro Pro Asp His Arg Lys Phe Gln Gly Tyr
130                 135                 140

Tyr Lys Ile Ala Arg His Tyr Arg Trp Ala Leu Gly Gln Val Phe Arg
145                 150                 155                 160

Gln Phe Arg Phe Pro Ala Ala Val Val Val Glu Asp Asp Leu Glu Val
                165                 170                 175

Ala Pro Asp Phe Phe Glu Tyr Phe Arg Ala Thr Tyr Pro Leu Leu Lys
            180                 185                 190

Ala Asp Pro Ser Leu Trp Cys Val Ser Ala Trp Asn Asp Asn Gly Lys
        195                 200                 205

Glu Gln Met Val Asp Ala Ser Arg Pro Glu Leu Leu Tyr Arg Thr Asp
    210                 215                 220

Phe Phe Pro Gly Leu Gly Trp Leu Leu Leu Ala Glu Leu Trp Ala Glu
225                 230                 235                 240

Leu Glu Pro Lys Trp Pro Lys Ala Phe Trp Asp Asp Trp Met Arg Arg
                245                 250                 255

Pro Glu Gln Arg Gln Gly Arg Ala Cys Ile Arg Pro Glu Ile Ser Arg
            260                 265                 270

Thr Met Thr Phe Gly Arg Lys Gly Val Ser His Gly Gln Phe Phe Asp
        275                 280                 285

Gln His Leu Lys Phe Ile Lys Leu Asn Gln Gln Phe Val His Phe Thr
    290                 295                 300

Gln Leu Asp Leu Ser Tyr Leu Gln Arg Glu Ala Tyr Asp Arg Asp Phe
305                 310                 315                 320

Leu Ala Arg Val Tyr Gly Ala Pro Gln Leu Gln Val Glu Lys Val Arg
                325                 330                 335
```

Thr Asn Asp Arg Lys Glu Leu Gly Glu Val Arg Val Gln Tyr Thr Gly
            340                 345                 350

Arg Asp Ser Phe Lys Ala Phe Ala Lys Ala Leu Gly Val Met Asp Asp
        355                 360                 365

Leu Lys Ser Gly Val Pro Arg Ala Gly Tyr Arg Gly Ile Val Thr Phe
    370                 375                 380

Gln Phe Arg Gly Arg Val His Leu Ala Pro Pro Thr Trp Glu
385             390                 395                 400

Gly Tyr Asp Pro Ser Trp Asn
            405

<210> SEQ ID NO 27
<211> LENGTH: 1407
<212> TYPE: DNA
<213> ORGANISM: Artificial Sequence
<220> FEATURE:
<223> OTHER INFORMATION: Encodes Mm ManI catalytic doman (FB)

<400> SEQUENCE: 27

```
gagcccgctg acgccaccat ccgtgagaag agggcaaaga tcaaagagat gatgacccat      60
gcttggaata attataaacg ctatgcgtgg ggcttgaacg aactgaaacc tatatcaaaa     120
gaaggccatt caagcagttt gtttggcaac atcaaggag ctacaatagt agatgccctg     180
gataccctt tcattatggg catgaagact gaatttcaag aagctaaatc gtggattaaa     240
aaatatttag atttaatgt gaatgctgaa gtttctgttt ttgaagtcaa catacgcttc     300
gtcggtggac tgctgtcagc ctactatttg tccggagagg agatatttcg aaagaaagca     360
gtggaacttg gggtaaaatt gctacctgca tttcatactc cctctggaat accttgggca     420
ttgctgaata tgaaaagtgg gatcgggcgg aactggccct gggcctctgg aggcagcagt     480
atcctggccg aatttggaac tctgcattta gagtttatgc acttgtccca cttatcagga     540
gacccagtct tgccgaaaaa ggttatgaaa attcgaacag tgttgaacaa actggacaaa     600
ccagaaggcc tttatcctaa ctatctgaac cccagtagtg gacagtgggg tcaacatcat     660
gtgtcggttg gaggacttgg agacagcttt tatgaatatt tgcttaaggc gtggttaatg     720
tctgacaaga cagatctcga agccaagaag atgtattttg atgctgttca ggccatcgag     780
actcacttga tccgcaagtc aagtggggga ctaacgtaca tcgcagagtg aagggggc     840
ctcctggaac acaagatggg ccacctgacg tgctttgcag gaggcatgtt tgcacttggg     900
gcagatggag ctccggaagc ccgggcccaa cactaccttg aactcggagc tgaaattgcc     960
cgcacttgtc atgaatctta taatcgtaca tatgtgaagt tgggaccgga agcgtttcga    1020
tttgatggcg gtgtggaagc tattgccacg aggcaaaatg aaaagtatta catcttacgg    1080
cccgaggtca tcgagacata catgtacatg tggcgactga ctcacgaccc caagtacagg    1140
acctgggcct gggaagccgt ggaggctcta gaaagtcact gcagagtgaa cggaggctac    1200
tcaggcttac gggatgttta cattgcccgt gagagttatg acgatgtcca gcaaagtttc    1260
ttcctggcag agacactgaa gtatttgtac ttgatatttt ccgatgatga ccttcttcca    1320
ctagaacact ggatcttcaa caccgaggct catccttcc ctatactccg tgaacagaag    1380
aaggaaattg atggcaaaga gaaatga                                        1407
```

<210> SEQ ID NO 28
<211> LENGTH: 468
<212> TYPE: PRT
<213> ORGANISM: Artificial Sequence
<220> FEATURE:

<223> OTHER INFORMATION: Mm ManI catalytic doman (FB)

<400> SEQUENCE: 28

```
Glu Pro Ala Asp Ala Thr Ile Arg Glu Lys Arg Ala Lys Ile Lys Glu
1               5                   10                  15
Met Met Thr His Ala Trp Asn Asn Tyr Lys Arg Tyr Ala Trp Gly Leu
            20                  25                  30
Asn Glu Leu Lys Pro Ile Ser Lys Glu Gly His Ser Ser Ser Leu Phe
        35                  40                  45
Gly Asn Ile Lys Gly Ala Thr Ile Val Asp Ala Leu Asp Thr Leu Phe
    50                  55                  60
Ile Met Gly Met Lys Thr Glu Phe Gln Glu Ala Lys Ser Trp Ile Lys
65                  70                  75                  80
Lys Tyr Leu Asp Phe Asn Val Asn Ala Glu Val Ser Val Phe Glu Val
                85                  90                  95
Asn Ile Arg Phe Val Gly Gly Leu Leu Ser Ala Tyr Tyr Leu Ser Gly
            100                 105                 110
Glu Glu Ile Phe Arg Lys Lys Ala Val Glu Leu Gly Val Lys Leu Leu
        115                 120                 125
Pro Ala Phe His Thr Pro Ser Gly Ile Pro Trp Ala Leu Leu Asn Met
    130                 135                 140
Lys Ser Gly Ile Gly Arg Asn Trp Pro Trp Ala Ser Gly Gly Ser Ser
145                 150                 155                 160
Ile Leu Ala Glu Phe Gly Thr Leu His Leu Glu Phe Met His Leu Ser
                165                 170                 175
His Leu Ser Gly Asp Pro Val Phe Ala Glu Lys Val Met Lys Ile Arg
            180                 185                 190
Thr Val Leu Asn Lys Leu Asp Lys Pro Glu Gly Leu Tyr Pro Asn Tyr
        195                 200                 205
Leu Asn Pro Ser Ser Gly Gln Trp Gly Gln His Val Ser Val Gly
    210                 215                 220
Gly Leu Gly Asp Ser Phe Tyr Glu Tyr Leu Leu Lys Ala Trp Leu Met
225                 230                 235                 240
Ser Asp Lys Thr Asp Leu Glu Ala Lys Met Tyr Phe Asp Ala Val
                245                 250                 255
Gln Ala Ile Glu Thr His Leu Ile Arg Lys Ser Ser Gly Gly Leu Thr
            260                 265                 270
Tyr Ile Ala Glu Trp Lys Gly Gly Leu Leu Glu His Lys Met Gly His
        275                 280                 285
Leu Thr Cys Phe Ala Gly Gly Met Phe Ala Leu Gly Ala Asp Gly Ala
    290                 295                 300
Pro Glu Ala Arg Ala Gln His Tyr Leu Glu Leu Gly Ala Glu Ile Ala
305                 310                 315                 320
Arg Thr Cys His Glu Ser Tyr Asn Arg Thr Tyr Val Lys Leu Gly Pro
                325                 330                 335
Glu Ala Phe Arg Phe Asp Gly Gly Val Glu Ala Ile Ala Thr Arg Gln
            340                 345                 350
Asn Glu Lys Tyr Tyr Ile Leu Arg Pro Glu Val Ile Glu Thr Tyr Met
        355                 360                 365
Tyr Met Trp Arg Leu Thr His Asp Pro Lys Tyr Arg Thr Trp Ala Trp
    370                 375                 380
Glu Ala Val Glu Ala Leu Glu Ser His Cys Arg Val Asn Gly Gly Tyr
385                 390                 395                 400
```

Ser Gly Leu Arg Asp Val Tyr Ile Ala Arg Glu Ser Tyr Asp Asp Val
                405                 410                 415

Gln Gln Ser Phe Phe Leu Ala Glu Thr Leu Lys Tyr Leu Tyr Leu Ile
        420                 425                 430

Phe Ser Asp Asp Leu Leu Pro Leu Glu His Trp Ile Phe Asn Thr
    435                 440                 445

Glu Ala His Pro Phe Pro Ile Leu Arg Glu Gln Lys Lys Glu Ile Asp
    450                 455                 460

Gly Lys Glu Lys
465

<210> SEQ ID NO 29
<211> LENGTH: 1494
<212> TYPE: DNA
<213> ORGANISM: Artificial Sequence
<220> FEATURE:
<223> OTHER INFORMATION: Encodes Tr ManI catalytic doman

<400> SEQUENCE: 29

```
cgcgccggat ctcccaaccc tacgagggcg gcagcagtca aggccgcatt ccagacgtcg      60
tggaacgctt accaccattt tgcctttccc catgacgacc tccacccggt cagcaacagc     120
tttgatgatg agagaaacgg ctggggctcg tcggcaatcg atggcttgga cacggctatc     180
ctcatggggg atgccgacat tgtgaacacg atccttcagt atgtaccgca gatcaacttc     240
accacgactg cggttgccaa ccaaggcatc tccgtgttcg agaccaacat tcggtacctc     300
ggtggcctgc tttctgccta tgaccctgttg cgaggtcctt tcagctcctt ggcgacaaac     360
cagaccctgg taaacagcct tctgaggcag gctcaaacac tggccaacgg cctcaaggtt     420
gcgttcacca ctcccagcgg tgtcccggac cctaccgtct tcttcaaccc tactgtccgg     480
agaagtggtg catctagcaa caacgtcgct gaaattggaa gcctggtgct cgagtggaca     540
cggttgagcg acctgacggg aaacccgcag tatgcccagc ttgcgcagaa gggcgagtcg     600
tatctcctga atccaaaggg aagcccggag gcatggcctg gcctgattgg aacgtttgtc     660
agcacgagca acggtacctt tcaggatagc agcggcagct ggtccggcct catggacagc     720
ttctacgagt acctgatcaa gatgtacctg tacgacccgg ttgcgtttgc acactacaag     780
gatcgctggg tccttgctgc cgactcgacc attgcgcatc tcgcctctca cccgtcgacg     840
cgcaaggact tgacctttt tgtcttcgtac aacggacagt ctacgtcgcc aaactcagga     900
catttggcca gttttgccgg tgcaacttc atcttgggag cattctcct gaacgagcaa     960
aagtacattg actttggaat caagcttgcc agctcgtact tgccacgta caaccagacg    1020
gcttctggaa tcggccccga aggcttcgcg tgggtggaca gcgtgacggg cgccggcggc    1080
tcgccgccct cgtcccagtc cgggttctac tcgtcggcag gattctgggt gacggcaccg    1140
tattacatcc tgcggccgga gacgctggag agcttgtact acgcataccg cgtcacgggc    1200
gactccaagt ggcaggacct ggcgtgggaa gcgttcagtg ccattgagga cgcatgccgc    1260
gccggcagcg cgtactcgtc catcaacgac gtgacgcagg ccaacggcgg gggtgcctct    1320
gacgatatgg agagcttctg gtttgccgag gcgctcaagt atgcgtacct gatctttgcg    1380
gaggagtcgg atgtgcaggt gcaggccaac ggcgggaaca aatttgtctt taacacggag    1440
gcgcacccct ttagcatccg ttcatcatca cgacggggcg gccaccttgc ttaa          1494
```

<210> SEQ ID NO 30
<211> LENGTH: 497
<212> TYPE: PRT

<213> ORGANISM: Artificial Sequence
<220> FEATURE:
<223> OTHER INFORMATION: Tr ManI catalytic doman

<400> SEQUENCE: 30

```
Arg Ala Gly Ser Pro Asn Pro Thr Arg Ala Ala Val Lys Ala Ala
 1               5                  10                  15

Phe Gln Thr Ser Trp Asn Ala Tyr His His Phe Ala Phe Pro His Asp
             20                  25                  30

Asp Leu His Pro Val Ser Ser Phe Asp Asp Glu Arg Asn Gly Trp
             35                  40                  45

Gly Ser Ser Ala Ile Asp Gly Leu Asp Thr Ala Ile Leu Met Gly Asp
 50                  55                  60

Ala Asp Ile Val Asn Thr Ile Leu Gln Tyr Val Pro Gln Ile Asn Phe
65                   70                  75                  80

Thr Thr Thr Ala Val Ala Asn Gln Gly Ile Ser Val Phe Glu Thr Asn
                 85                  90                  95

Ile Arg Tyr Leu Gly Gly Leu Leu Ser Ala Tyr Asp Leu Leu Arg Gly
                100                 105                 110

Pro Phe Ser Ser Leu Ala Thr Asn Gln Thr Leu Val Asn Ser Leu Leu
            115                 120                 125

Arg Gln Ala Gln Thr Leu Ala Asn Gly Leu Lys Val Ala Phe Thr Thr
130                 135                 140

Pro Ser Gly Val Pro Asp Pro Thr Val Phe Phe Asn Pro Thr Val Arg
145                 150                 155                 160

Arg Ser Gly Ala Ser Ser Asn Asn Val Ala Glu Ile Gly Ser Leu Val
                165                 170                 175

Leu Glu Trp Thr Arg Leu Ser Asp Leu Thr Gly Asn Pro Gln Tyr Ala
            180                 185                 190

Gln Leu Ala Gln Lys Gly Glu Ser Tyr Leu Leu Asn Pro Lys Gly Ser
        195                 200                 205

Pro Glu Ala Trp Pro Gly Leu Ile Gly Thr Phe Val Ser Thr Ser Asn
    210                 215                 220

Gly Thr Phe Gln Asp Ser Ser Gly Ser Trp Ser Gly Leu Met Asp Ser
225                 230                 235                 240

Phe Tyr Glu Tyr Leu Ile Lys Met Tyr Leu Tyr Asp Pro Val Ala Phe
                245                 250                 255

Ala His Tyr Lys Asp Arg Trp Val Leu Ala Ala Asp Ser Thr Ile Ala
            260                 265                 270

His Leu Ala Ser His Pro Ser Thr Arg Lys Asp Leu Thr Phe Leu Ser
        275                 280                 285

Ser Tyr Asn Gly Gln Ser Thr Ser Pro Asn Ser Gly His Leu Ala Ser
    290                 295                 300

Phe Ala Gly Gly Asn Phe Ile Leu Gly Gly Ile Leu Leu Asn Glu Gln
305                 310                 315                 320

Lys Tyr Ile Asp Phe Gly Ile Lys Leu Ala Ser Ser Tyr Phe Ala Thr
                325                 330                 335

Tyr Asn Gln Thr Ala Ser Gly Ile Gly Pro Glu Gly Phe Ala Trp Val
            340                 345                 350

Asp Ser Val Thr Gly Ala Gly Gly Ser Pro Pro Ser Ser Gln Ser Gly
        355                 360                 365

Phe Tyr Ser Ser Ala Gly Phe Trp Val Thr Ala Pro Tyr Tyr Ile Leu
    370                 375                 380

Arg Pro Glu Thr Leu Glu Ser Leu Tyr Tyr Ala Tyr Arg Val Thr Gly
```

Asp Ser Lys Trp Gln Asp Leu Ala Trp Glu Ala Phe Ser Ala Ile Glu
            405                 410                 415

Asp Ala Cys Arg Ala Gly Ser Ala Tyr Ser Ser Ile Asn Asp Val Thr
            420                 425                 430

Gln Ala Asn Gly Gly Ala Ser Asp Asp Met Glu Ser Phe Trp Phe
            435                 440                 445

Ala Glu Ala Leu Lys Tyr Ala Tyr Leu Ile Phe Ala Glu Glu Ser Asp
        450                 455                 460

Val Gln Val Gln Ala Asn Gly Gly Asn Lys Phe Val Phe Asn Thr Glu
465                 470                 475                 480

Ala His Pro Phe Ser Ile Arg Ser Ser Ser Arg Arg Gly Gly His Leu
                485                 490                 495

Ala

<210> SEQ ID NO 31
<211> LENGTH: 1068
<212> TYPE: DNA
<213> ORGANISM: Artificial Sequence
<220> FEATURE:
<223> OTHER INFORMATION: encodes Rat GnT II (TC) Codon-optimized

<400> SEQUENCE: 31

```
tccttggttt accaattgaa cttcgaccag atgttgagaa cgttgacaa ggacggtact       60
tggtctcctg gtgagttggt tttggttgtt caggttcaca acagaccaga gtacttgaga      120
ttgttgatcg actccttgag aaaggctcaa ggtatcagag aggttttggt tatcttctcc      180
cacgatttct ggtctgctga gatcaactcc ttgatctcct ccgttgactt ctgtccagtt      240
ttgcaggttt tcttcccatt ctccatccaa ttgtacccat ctgagttccc aggttctgat      300
ccaagagact gtccaagaga cttgaagaag aacgctgctt tgaagttggg ttgtatcaac      360
gctgaatacc cagattcttt cggtcactac agagaggcta gttctcccaa actaagcat      420
cattggtggt ggaagttgca ctttgtttgg gagagagtta aggttttgca ggactacact      480
ggattgatct tgttcttgga ggaggatcat tacttggctc cagacttcta ccacgttttc      540
aagaagatgt ggaagttgaa gcaacaagag tgtccaggtt gtgacgtttt gtccttggga      600
acttacacta ctatcagatc cttctacggt atcgctgaca aggttgacgt taagacttgg      660
aagtccactg aacacaacat gggattggct ttgactagag atgcttacca gaagttgatc      720
gagtgtactg acactttctg tacttacgac gactacaact gggactggac tttgcagtac      780
ttgactttgg cttgtttgcc aaaagtttgg aaggttttgg ttccacaggc tccaagaatt      840
ttccacgctg gtgactgtgg aatgcaccac aagaaaactt gtagaccatc cactcagtcc      900
gctcaaattg agtccttgtt gaacaacaac aagcagtact tgttcccaga cttttggtt       960
atcggagaga gtttccaat ggctgctatt tccccaccaa gaaagaatgg tggatggggt     1020
gatattagag accacgagtt gtgtaaatcc tacagaagat tgcagtag              1068
```

<210> SEQ ID NO 32
<211> LENGTH: 355
<212> TYPE: PRT
<213> ORGANISM: Artificial Sequence
<220> FEATURE:
<223> OTHER INFORMATION: Rat GnT II (TC) Codon-optimized

<400> SEQUENCE: 32

Ser Leu Val Tyr Gln Leu Asn Phe Asp Gln Met Leu Arg Asn Val Asp

|   |   | 1 |   |   |   | 5 |   |   |   | 10 |   |   |   | 15 |   |
|---|---|---|---|---|---|---|---|---|---|---|---|---|---|---|---|
| Lys | Asp | Gly | Thr | Trp | Ser | Pro | Gly | Glu | Leu | Val | Leu | Val | Gln | Val |   |

Lys Asp Gly Thr Trp Ser Pro Gly Glu Leu Val Leu Val Gln Val
1               5                   10                  15

His Asn Arg Pro Glu Tyr Leu Arg Leu Ile Asp Ser Leu Arg Lys
        20                  25                  30

Ala Gln Gly Ile Arg Glu Val Leu Val Ile Phe Ser His Asp Phe Trp
    35                  40                  45

Ala Gln Gly Ile Arg Glu Val Leu Val Ile Phe Ser His Asp Phe Trp
50                  55                  60

Ser Ala Glu Ile Asn Ser Leu Ile Ser Ser Val Asp Phe Cys Pro Val
65                  70                  75                  80

Leu Gln Val Phe Phe Pro Phe Ser Ile Gln Leu Tyr Pro Ser Glu Phe
                85                  90                  95

Pro Gly Ser Asp Pro Arg Asp Cys Pro Arg Asp Leu Lys Lys Asn Ala
                100                 105                 110

Ala Leu Lys Leu Gly Cys Ile Asn Ala Glu Tyr Pro Asp Ser Phe Gly
                115                 120                 125

His Tyr Arg Glu Ala Lys Phe Ser Gln Thr Lys His His Trp Trp Trp
                130                 135                 140

Lys Leu His Phe Val Trp Glu Arg Val Lys Val Leu Gln Asp Tyr Thr
145                 150                 155                 160

Gly Leu Ile Leu Phe Leu Glu Glu Asp His Tyr Leu Ala Pro Asp Phe
                165                 170                 175

Tyr His Val Phe Lys Lys Met Trp Lys Leu Lys Gln Glu Cys Pro
                180                 185                 190

Gly Cys Asp Val Leu Ser Leu Gly Thr Tyr Thr Thr Ile Arg Ser Phe
                195                 200                 205

Tyr Gly Ile Ala Asp Lys Val Asp Val Lys Thr Trp Lys Ser Thr Glu
210                 215                 220

His Asn Met Gly Leu Ala Leu Thr Arg Asp Ala Tyr Gln Lys Leu Ile
225                 230                 235                 240

Glu Cys Thr Asp Thr Phe Cys Thr Tyr Asp Asp Tyr Asn Trp Asp Trp
                245                 250                 255

Thr Leu Gln Tyr Leu Thr Leu Ala Cys Leu Pro Lys Val Trp Lys Val
                260                 265                 270

Leu Val Pro Gln Ala Pro Arg Ile Phe His Ala Gly Asp Cys Gly Met
                275                 280                 285

His His Lys Lys Thr Cys Arg Pro Ser Thr Gln Ser Ala Gln Ile Glu
                290                 295                 300

Ser Leu Leu Asn Asn Asn Lys Gln Tyr Leu Phe Pro Glu Thr Leu Val
305                 310                 315                 320

Ile Gly Glu Lys Phe Pro Met Ala Ala Ile Ser Pro Arg Lys Asn
                325                 330                 335

Gly Gly Trp Gly Asp Ile Arg Asp His Glu Leu Cys Lys Ser Tyr Arg
                340                 345                 350

Arg Leu Gln
        355

<210> SEQ ID NO 33
<211> LENGTH: 3105
<212> TYPE: DNA
<213> ORGANISM: Artificial Sequence
<220> FEATURE:
<223> OTHER INFORMATION: Encodes Drosophila melanogaster ManII
      codon-optimized (KD)

<400> SEQUENCE: 33

```
agagacgatc caattagacc tccattgaag gttgctagat ccccaagacc aggtcaatgt    60
caagatgttg ttcaggacgt cccaaacgtt gatgtccaga tgttggagtt gtacgataga   120
atgtccttca aggacattga tggtggtgtt tggaagcagg gttggaacat taagtacgat   180
ccattgaagt acaacgctca tcacaagttg aaggtcttcg ttgtcccaca ctcccacaac   240
gatcctggtt ggattcagac cttcgaggaa tactaccagc acgacaccaa gcacatcttg   300
tccaacgctt tgagacattt gcacgacaac ccagagatga agttcatctg gctgaaaatc   360
tcctacttcg ctagattcta ccacgatttg ggtgagaaca agaagttgca gatgaagtcc   420
atcgtcaaga acggtcagtt ggaattcgtc actggtggat gggtcatgcc agacgaggct   480
aactcccact ggagaaacgt tttgttgcag ttgaccgaag gtcaaacttg gttgaagcaa   540
ttcatgaacg tcactccaac tgcttcctgg gctatcgatc cattcggaca ctctccaact   600
atgccataca ttttgcagaa gtctggtttc aagaatatgt tgatccagag aacccactac   660
tccgttaaga aggagttggc tcaacagaga cagttggagt tcttgtggag acagatctgg   720
gacaacaaag gtgacactgc tttgttcacc cacatgatgc cattctactc ttacgacatt   780
cctcatacct gtggtccaga tccaaaggtt tgttgtcagt tcgatttcaa aagaatgggt   840
tccttcggtt tgtcttgtcc atggaaggtt ccacctagaa ctatctctga tcaaaatgtt   900
gctgctagat ccgatttgtt ggttgatcag tggaagaaga aggctgagtt gtacagaacc   960
aacgtcttgt tgattccatt gggtgacgac ttcagattca agcagaacac cgagtgggat  1020
gttcagagag tcaactacga aagattgttc gaacacatca actctcaggc tcacttcaat  1080
gtccaggctc agttcggtac tttgcaggaa tacttcgatg ctgttcacca ggctgaaaga  1140
gctggacaag ctgagttccc aaccttgtct ggtgacttct tcacttacgc tgatagatct  1200
gataactact ggtctggtta ctacacttcc agaccatacc ataagagaat ggacagagtc  1260
ttgatgcact acgttagagc tgctgaaatg ttgtccgctt ggcactcctg ggacggtatg  1320
gctagaatcg aggaaagatt ggagcaggct agaagagagt tgtccttgtt ccagcaccac  1380
gacggtatta ctggtactgc taaaactcac gttgtcgtcg actacgagca aagaatgcag  1440
gaagctttga aagcttgtca aatggtcatg caacagtctg tctacagatt gttgactaag  1500
ccatccatct actctccaga cttctccttc tcctacttca ctttggacga ctccagatgg  1560
ccaggttctg tgttgaggga ctctagaact accatcatct gggtgagga tatcttgcca  1620 tccaagcatg ttgtcatgca caacaccttg ccacactgga gagagcagtt ggttgacttc  1680
tacgtctcct ctccattcgt ttctgttacc gacttggcta acaatccagt tgaggctcag  1740
gtttctccag tttggtcttg gcaccacgac actttgacta agactatcca cccacaaggt  1800
tccaccacca agtacagaat catcttcaag gctagagttc caccaatggg tttggctacc  1860
tacgttttga ccatctccga ttccaagcca gagcacacct cctacgcttc caatttgttg  1920
cttagaaaga acccaacttc cttgccattg ggtcaatacc cagaggatgt caagttcggt  1980
gatccaagag agatctcctt gagagttggt aacggtccaa ccttggcttt ctctgagcag  2040
ggtttgttga gtccattca gttgactcag gattctccac atgttccagt tcacttcaag  2100
ttcttgaagt acggtgttag atctcatggt gatagatctg gtgcttactt gttcttgcca  2160
aatggtccag cttctccagt cgagttgggt cagccagttg tcttggtcac taagggtaaa  2220
ttggagtctt ccgtttctgt tggttttgcca tctgtcgttc accagaccat catgagaggt  2280
ggtgctccag agattagaaa tttggtcgat attggttctt tggacaacac tgagatcgtc  2340
atgagattgg agactcatat cgactctggt gatatcttct acactgattt gaatggattg  2400
```

```
caattcatca agaggagaag attggacaag ttgccattgc aggctaacta ctacccaatt    2460
ccatctggta tgttcattga ggatgctaat accagattga ctttgttgac cggtcaacca    2520
ttgggtggat cttctttggc ttctggtgag ttggagatta tgcaagatag aagattggct    2580
tctgatgatg aaagaggttt gggtcagggt gttttggaca acaagccagt tttgcatatt    2640
tacagattgg tcttggagaa ggttaacaac tgtgtcagac catctaagtt gcatccagct    2700
ggttacttga cttctgctgc tcacaaagct tctcagtctt tgttggatcc attggacaag    2760
ttcatcttcg ctgaaaatga gtggatcggt gctcagggtc aattcggtgg tgatcatcca    2820
tctgctagag aggatttgga tgtctctgtc atgagaagat tgaccaagtc ttctgctaaa    2880
acccagagag ttggttacgt tttgcacaga accaatttga tgcaatgtgg tactccagag    2940
gagcatactc agaagttgga tgtctgtcac ttgttgccaa atgttgctag atgtgagaga    3000
actaccttga ctttcttgca gaatttggag cacttggatg gtatggttgc tccagaagtt    3060
tgtccaatgg aaaccgctgc ttacgtctct tctcactctt cttga                    3105
```

<210> SEQ ID NO 34
<211> LENGTH: 1034
<212> TYPE: PRT
<213> ORGANISM: Artificial Sequence
<220> FEATURE:
<223> OTHER INFORMATION: Drosophila melanogaster ManII codon-optimized (KD)

<400> SEQUENCE: 34

```
Arg Asp Asp Pro Ile Arg Pro Pro Leu Lys Val Ala Arg Ser Pro Arg
  1               5                  10                  15

Pro Gly Gln Cys Gln Asp Val Val Gln Asp Val Pro Asn Val Asp Val
             20                  25                  30

Gln Met Leu Glu Leu Tyr Asp Arg Met Ser Phe Lys Asp Ile Asp Gly
         35                  40                  45

Gly Val Trp Lys Gln Gly Trp Asn Ile Lys Tyr Asp Pro Leu Lys Tyr
     50                  55                  60

Asn Ala His His Lys Leu Lys Val Phe Val Pro His Ser His Asn
 65                  70                  75                  80

Asp Pro Gly Trp Ile Gln Thr Phe Glu Glu Tyr Tyr Gln His Asp Thr
                 85                  90                  95

Lys His Ile Leu Ser Asn Ala Leu Arg His Leu His Asp Asn Pro Glu
            100                 105                 110

Met Lys Phe Ile Trp Ala Glu Ile Ser Tyr Phe Ala Arg Phe Tyr His
        115                 120                 125

Asp Leu Gly Glu Asn Lys Lys Leu Gln Met Lys Ser Ile Val Lys Asn
    130                 135                 140

Gly Gln Leu Glu Phe Val Thr Gly Gly Trp Val Met Pro Asp Glu Ala
145                 150                 155                 160

Asn Ser His Trp Arg Asn Val Leu Leu Gln Leu Thr Glu Gly Gln Thr
                165                 170                 175

Trp Leu Lys Gln Phe Met Asn Val Thr Pro Thr Ala Ser Trp Ala Ile
            180                 185                 190

Asp Pro Phe Gly His Ser Pro Thr Met Pro Tyr Ile Leu Gln Lys Ser
        195                 200                 205

Gly Phe Lys Asn Met Leu Ile Gln Arg Thr His Tyr Ser Val Lys Lys
    210                 215                 220

Glu Leu Ala Gln Gln Arg Gln Leu Glu Phe Leu Trp Arg Gln Ile Trp
```

-continued

```
225                 230                 235                 240

Asp Asn Lys Gly Asp Thr Ala Leu Phe Thr His Met Met Pro Phe Tyr
                245                 250                 255

Ser Tyr Asp Ile Pro His Thr Cys Gly Pro Asp Pro Lys Val Cys Cys
                260                 265                 270

Gln Phe Asp Phe Lys Arg Met Gly Ser Phe Gly Leu Ser Cys Pro Trp
                275                 280                 285

Lys Val Pro Pro Arg Thr Ile Ser Asp Gln Asn Val Ala Ala Arg Ser
                290                 295                 300

Asp Leu Leu Val Asp Gln Trp Lys Lys Lys Ala Glu Leu Tyr Arg Thr
305                 310                 315                 320

Asn Val Leu Leu Ile Pro Leu Gly Asp Asp Phe Arg Phe Lys Gln Asn
                325                 330                 335

Thr Glu Trp Asp Val Gln Arg Val Asn Tyr Glu Arg Leu Phe Glu His
                340                 345                 350

Ile Asn Ser Gln Ala His Phe Asn Val Gln Ala Gln Phe Gly Thr Leu
                355                 360                 365

Gln Glu Tyr Phe Asp Ala Val His Gln Ala Glu Arg Ala Gly Gln Ala
                370                 375                 380

Glu Phe Pro Thr Leu Ser Gly Asp Phe Phe Thr Tyr Ala Asp Arg Ser
385                 390                 395                 400

Asp Asn Tyr Trp Ser Gly Tyr Tyr Thr Ser Arg Pro Tyr His Lys Arg
                405                 410                 415

Met Asp Arg Val Leu Met His Tyr Val Arg Ala Ala Glu Met Leu Ser
                420                 425                 430

Ala Trp His Ser Trp Asp Gly Met Ala Arg Ile Glu Glu Arg Leu Glu
                435                 440                 445

Gln Ala Arg Arg Glu Leu Ser Leu Phe Gln His His Asp Gly Ile Thr
                450                 455                 460

Gly Thr Ala Lys Thr His Val Val Val Asp Tyr Glu Gln Arg Met Gln
465                 470                 475                 480

Glu Ala Leu Lys Ala Cys Gln Met Val Met Gln Gln Ser Val Tyr Arg
                485                 490                 495

Leu Leu Thr Lys Pro Ser Ile Tyr Ser Pro Asp Phe Ser Phe Ser Tyr
                500                 505                 510

Phe Thr Leu Asp Asp Ser Arg Trp Pro Gly Ser Gly Val Glu Asp Ser
                515                 520                 525

Arg Thr Thr Ile Ile Leu Gly Glu Asp Ile Leu Pro Ser Lys His Val
                530                 535                 540

Val Met His Asn Thr Leu Pro His Trp Arg Glu Gln Leu Val Asp Phe
545                 550                 555                 560

Tyr Val Ser Ser Pro Phe Val Ser Val Thr Asp Leu Ala Asn Asn Pro
                565                 570                 575

Val Glu Ala Gln Val Ser Pro Val Trp Ser Trp His His Asp Thr Leu
                580                 585                 590

Thr Lys Thr Ile His Pro Gln Gly Ser Thr Thr Lys Tyr Arg Ile Ile
                595                 600                 605

Phe Lys Ala Arg Val Pro Pro Met Gly Leu Ala Thr Tyr Val Leu Thr
                610                 615                 620

Ile Ser Asp Ser Lys Pro Glu His Thr Ser Tyr Ala Ser Asn Leu Leu
625                 630                 635                 640

Leu Arg Lys Asn Pro Thr Ser Leu Pro Leu Gly Gln Tyr Pro Glu Asp
                645                 650                 655
```

Val Lys Phe Gly Asp Pro Arg Glu Ile Ser Leu Arg Val Gly Asn Gly
            660                 665                 670

Pro Thr Leu Ala Phe Ser Glu Gln Gly Leu Leu Lys Ser Ile Gln Leu
        675                 680                 685

Thr Gln Asp Ser Pro His Val Pro Val His Phe Lys Phe Leu Lys Tyr
    690                 695                 700

Gly Val Arg Ser His Gly Asp Arg Ser Gly Ala Tyr Leu Phe Leu Pro
705                 710                 715                 720

Asn Gly Pro Ala Ser Pro Val Glu Leu Gly Gln Pro Val Val Leu Val
                725                 730                 735

Thr Lys Gly Lys Leu Glu Ser Ser Val Ser Val Gly Leu Pro Ser Val
            740                 745                 750

Val His Gln Thr Ile Met Arg Gly Gly Ala Pro Glu Ile Arg Asn Leu
        755                 760                 765

Val Asp Ile Gly Ser Leu Asp Asn Thr Glu Ile Val Met Arg Leu Glu
    770                 775                 780

Thr His Ile Asp Ser Gly Asp Ile Phe Tyr Thr Asp Leu Asn Gly Leu
785                 790                 795                 800

Gln Phe Ile Lys Arg Arg Leu Asp Lys Leu Pro Leu Gln Ala Asn
                805                 810                 815

Tyr Tyr Pro Ile Pro Ser Gly Met Phe Ile Glu Asp Ala Asn Thr Arg
            820                 825                 830

Leu Thr Leu Leu Thr Gly Gln Pro Leu Gly Gly Ser Ser Leu Ala Ser
        835                 840                 845

Gly Glu Leu Glu Ile Met Gln Asp Arg Arg Leu Ala Ser Asp Asp Glu
    850                 855                 860

Arg Gly Leu Gly Gln Gly Val Leu Asp Asn Lys Pro Val Leu His Ile
865                 870                 875                 880

Tyr Arg Leu Val Leu Glu Lys Val Asn Asn Cys Val Arg Pro Ser Lys
                885                 890                 895

Leu His Pro Ala Gly Tyr Leu Thr Ser Ala Ala His Lys Ala Ser Gln
            900                 905                 910

Ser Leu Leu Asp Pro Leu Asp Lys Phe Ile Phe Ala Glu Asn Glu Trp
        915                 920                 925

Ile Gly Ala Gln Gly Gln Phe Gly Gly Asp His Pro Ser Ala Arg Glu
    930                 935                 940

Asp Leu Asp Val Ser Val Met Arg Arg Leu Thr Lys Ser Ser Ala Lys
945                 950                 955                 960

Thr Gln Arg Val Gly Tyr Val Leu His Arg Thr Asn Leu Met Gln Cys
                965                 970                 975

Gly Thr Pro Glu Glu His Thr Gln Lys Leu Asp Val Cys His Leu Leu
            980                 985                 990

Pro Asn Val Ala Arg Cys Glu Arg Thr Thr Leu Thr Phe Leu Gln Asn
        995                 1000                1005

Leu Glu His Leu Asp Gly Met Val Ala Pro Glu Val Cys Pro Met Glu
    1010                1015                1020

Thr Ala Ala Tyr Val Ser Ser His Ser Ser
1025                1030

<210> SEQ ID NO 35
<211> LENGTH: 1014
<212> TYPE: DNA
<213> ORGANISM: Artificial Sequence
<220> FEATURE:

<223> OTHER INFORMATION: Encodes Mouse CMP-sialic acid transporter
      (MmCST) Codon optimized

<400> SEQUENCE: 35

```
atggctccag ctagagaaaa cgtttccttg ttcttcaagt tgtactgttt ggctgttatg     60
actttggttg ctgctgctta cactgttgct ttgagataca ctagaactac tgctgaggag    120
ttgtacttct ccactactgc tgtttgtatc actgaggtta tcaagttgtt gatctccgtt    180
ggttgttgg ctaaggagac tggttctttg ggaagattca aggcttcctt gtccgaaaac    240
gttttgggtt ccccaaagga gttggctaag ttgtctgttc catccttggt ttacgctgtt    300
cagaacaaca tggctttctt ggctttgtct aacttggacg ctgctgttta ccaagttact    360
taccagttga agatcccatg tactgctttg tgtactgttt tgatgttgaa cagaacattg    420
tccaagttgc agtggatctc cgttttcatg ttgtgtggtg gtgttacttt ggttcagtgg    480
aagccagctc aagcttccaa agttgttgtt gctcagaacc cattgttggg tttcggtgct    540
attgctatcg ctgttttgtg ttccggtttc gctggtgttt acttcgagaa ggttttgaag    600
tcctccgaca cttctttgtg ggttagaaac atccagatgt acttgtccgg tatcgttgtt    660
actttggctg gtacttactt gtctgacggt gctgagattc aagagaaggg attcttctac    720
ggttacactt actatgtttg gttcgttatc ttcttggctt ccgttggtgg tttgtacact    780
tccgttgttg ttaagtacac tgacaacatc atgaagggat ctctgctgc tgctgctatt    840
gttttgtcca ctatcgcttc cgttttgttg ttcggattgc agatcacatt gtcctttgct    900
ttgggagctt tgttggtttg tgtttccatc tacttgtacg gattgccaag acaagacact    960
acttccattc agcaagaggc tacttccaag gagagaatca tcggtgttta gtag         1014
```

<210> SEQ ID NO 36
<211> LENGTH: 336
<212> TYPE: PRT
<213> ORGANISM: Artificial Sequence
<220> FEATURE:
<223> OTHER INFORMATION: Mouse CMP-sialic acid transporter (MmCST)
      Codon optimized

<400> SEQUENCE: 36

```
Met Ala Pro Ala Arg Glu Asn Val Ser Leu Phe Phe Lys Leu Tyr Cys
  1               5                  10                  15

Leu Ala Val Met Thr Leu Val Ala Ala Ala Tyr Thr Val Ala Leu Arg
             20                  25                  30

Tyr Thr Arg Thr Thr Ala Glu Glu Leu Tyr Phe Ser Thr Thr Ala Val
         35                  40                  45

Cys Ile Thr Glu Val Ile Lys Leu Leu Ile Ser Val Gly Leu Leu Ala
     50                  55                  60

Lys Glu Thr Gly Ser Leu Gly Arg Phe Lys Ala Ser Leu Ser Glu Asn
 65                  70                  75                  80

Val Leu Gly Ser Pro Lys Glu Leu Ala Lys Leu Ser Val Pro Ser Leu
                 85                  90                  95

Val Tyr Ala Val Gln Asn Asn Met Ala Phe Leu Ala Leu Ser Asn Leu
            100                 105                 110

Asp Ala Ala Val Tyr Gln Val Thr Tyr Gln Leu Lys Ile Pro Cys Thr
        115                 120                 125

Ala Leu Cys Thr Val Leu Met Leu Asn Arg Thr Leu Ser Lys Leu Gln
    130                 135                 140

Trp Ile Ser Val Phe Met Leu Cys Gly Gly Val Thr Leu Val Gln Trp
145                 150                 155                 160
```

```
Lys Pro Ala Gln Ala Ser Lys Val Val Ala Gln Asn Pro Leu Leu
                165                 170                 175
Gly Phe Gly Ala Ile Ala Ile Ala Val Leu Cys Ser Gly Phe Ala Gly
            180                 185                 190
Val Tyr Phe Glu Lys Val Leu Lys Ser Ser Asp Thr Ser Leu Trp Val
        195                 200                 205
Arg Asn Ile Gln Met Tyr Leu Ser Gly Ile Val Thr Leu Ala Gly
    210                 215                 220
Thr Tyr Leu Ser Asp Gly Ala Glu Ile Gln Glu Lys Gly Phe Phe Tyr
225                 230                 235                 240
Gly Tyr Thr Tyr Tyr Val Trp Phe Val Ile Phe Leu Ala Ser Val Gly
            245                 250                 255
Gly Leu Tyr Thr Ser Val Val Lys Tyr Thr Asp Asn Ile Met Lys
        260                 265                 270
Gly Phe Ser Ala Ala Ala Ile Val Leu Ser Thr Ile Ala Ser Val
    275                 280                 285
Leu Leu Phe Gly Leu Gln Ile Thr Leu Ser Phe Ala Leu Gly Ala Leu
            290                 295                 300
Leu Val Cys Val Ser Ile Tyr Leu Tyr Gly Leu Pro Arg Gln Asp Thr
305                 310                 315                 320
Thr Ser Ile Gln Gln Glu Ala Thr Ser Lys Glu Arg Ile Ile Gly Val
                325                 330                 335

<210> SEQ ID NO 37
<211> LENGTH: 2172
<212> TYPE: DNA
<213> ORGANISM: Artificial Sequence
<220> FEATURE:
<223> OTHER INFORMATION: Encodes Human UDP-GlcNAc
      2-epimerase/N-acetylmannosamine kinase (HsGNE)
      codon opitimized

<400> SEQUENCE: 37
atggaaaaga acggtaacaa cagaaagttg agagtttgtg ttgctacttg taacagagct      60
gactactcca gttggctcc aatcatgttc ggtatcaaga ctgagccaga gttcttcgag     120
ttggacgttg ttgttttggg ttcccacttg attgatgact acggtaacac ttacagaatg     180
atcgagcagg acgacttcga catcaacact agattgcaca ctattgttag aggagaggac     240
gaagctgcta tggttgaatc tgttggattg gctttggtta agttgccaga cgttttgaac     300
agattgaagc cagacatcat gattgttcac ggtgacagat cgatgctttt ggcttttggct     360
acttccgctg cttttgatgaa cattagaatc ttgcacatcg agggtggtga agtttctggt     420
actatcgacg actccatcag acacgctatc actaagttgg ctcactacca tgtttgttgt     480
actagatccg ctgagcaaca cttgattttcc atgtgtgagg accacgacag aattttgttg     540
gctggttgtc catcttacga caagttgttg tccgctaaga acaaggacta catgtccatc     600
atcagaatgt ggttgggtga cgacgttaag tctaaggact acatcgttgc tttgcagcac     660
ccagttacta ctgacatcaa gcactccatc aagatgttcg agttgacttt ggacgctttg     720
atctccttca caagagaaac tttggttttg ttcccaaaca ttgacgctgg ttccaaagag     780
atggttagag ttatgagaaa aaagggtatc gaacaccacc caaacttcag agctgttaag     840
cacgttccat cgaccaaatt catccagttg gttgctcatg ctggttgtat gatcggtaac     900
tcctcctgtg tgttagaga agttggtgct tccggtactc cagttatcaa cttgggtact     960
agacagatcg gtagagagac tggagaaaac gttttgcatg ttagagatgc tgacactcag    1020
```

-continued

```
gacaagattt tgcaggcttt gcacttgcaa ttcggaaagc agtacccatg ttccaaaatc    1080
tacggtgacg gtaacgctgt tccaagaatc ttgaagtttt tgaagtccat cgacttgcaa    1140
gagccattgc agaagaagtt ctgtttccca ccagttaagg agaacatctc ccaggacatt    1200
gaccacatct tggagacatt gtccgctttg gctgttgatt tgggtggaac taacttgaga    1260
gttgctatcg tttccatgaa gggagagatc gttaagaagt acactcagtt caacccaaag    1320
acttacgagg agagaatcaa cttgatcttg cagatgtgtg ttgaagctgc tgctgaggct    1380
gttaagttga actgtagaat cttgggtgtt ggtatctcta ctggtggtag agttaatcca    1440
agagagggta tcgttttgca ctccactaag ttgattcagg agtggaactc cgttgatttg    1500
agaactccat tgtccgacac attgcacttg ccagtttggg ttgacaacga cggtaattgt    1560
gctgctttgg ctgagagaaa gttcggtcaa ggaaagggat tggagaactt cgttactttg    1620
atcactggta ctggtattgg tggtggtatc attcaccagc acgagttgat tcacggttct    1680
tccttctgtg ctgctgaatt gggacacttg gttgtttctt tggacggtcc agactgttct    1740
tgtggttccc acggttgtat tgaagcttac gcatcaggaa tggcattgca gagagaggct    1800
aagaagttgc acgacgagga cttgttgttg gttgagggaa tgtctgttcc aaaggacgag    1860
gctgttggtg ctttgcattt gatccaggct gctaagttgg gtaatgctaa ggctcagtcc    1920
atcttgagaa ctgctggtac tgctttggga ttgggtgttg ttaatatctt gcacactatg    1980
aacccatcct tggttatctt gtccggtgtt ttggcttctc actacatcca catcgttaag    2040
gacgttatca gacagcaagc tttgtcctcc gttcaagacg ttgatgttgt tgtttccgac    2100
ttggttgacc cagctttgtt gggtgctgct tccatggttt tggactacac tactagaaga    2160
atctactaat ag                                                       2172
```

<210> SEQ ID NO 38
<211> LENGTH: 722
<212> TYPE: PRT
<213> ORGANISM: Artificial Sequence
<220> FEATURE:
<223> OTHER INFORMATION: Human UDP-GlcNAc 2-epimerase/N-
      acetylmannosamine kinase (HsGNE) codon opitimized

<400> SEQUENCE: 38

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140
```

```
Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
            245                 250                 255

Gly Ser Lys Glu Met Val Arg Val Met Arg Lys Lys Gly Ile Glu His
        260                 265                 270

His Pro Asn Phe Arg Ala Val Lys His Val Pro Phe Asp Gln Phe Ile
    275                 280                 285

Gln Leu Val Ala His Ala Gly Cys Met Ile Gly Asn Ser Ser Cys Gly
290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
            325                 330                 335

Ala Asp Thr Gln Asp Lys Ile Leu Gln Ala Leu His Leu Gln Phe Gly
        340                 345                 350

Lys Gln Tyr Pro Cys Ser Lys Ile Tyr Gly Asp Gly Asn Ala Val Pro
    355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
            405                 410                 415

Thr Asn Leu Arg Val Ala Ile Val Ser Met Lys Gly Glu Ile Val Lys
        420                 425                 430

Lys Tyr Thr Gln Phe Asn Pro Lys Thr Tyr Glu Glu Arg Ile Asn Leu
    435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
            485                 490                 495

Ser Val Asp Leu Arg Thr Pro Leu Ser Asp Thr Leu His Leu Pro Val
        500                 505                 510

Trp Val Asp Asn Asp Gly Asn Cys Ala Ala Leu Ala Glu Arg Lys Phe
    515                 520                 525

Gly Gln Gly Lys Gly Leu Glu Asn Phe Val Thr Leu Ile Thr Gly Thr
530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
```

```
                      565                 570                 575
Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile Tyr

<210> SEQ ID NO 39
<211> LENGTH: 1308
<212> TYPE: DNA
<213> ORGANISM: Artificial Sequence
<220> FEATURE:
<223> OTHER INFORMATION: Encodes Human CMP-sialic acid synthase (HsCSS)
      codon optimized

<400> SEQUENCE: 39
atggactctg ttgaaaaggg tgctgctact tctgtttcca acccaagagg tagaccatcc      60
agaggtagac tcctaagtt gcagagaaac tccagaggtg gtcaaggtag aggtgttgaa     120
aagccaccac acttggctgc tttgatcttg gctagaggag gttctaaggg tatcccattg     180
aagaacatca gcacttggc tggtgttcca ttgattggat gggttttgag agctgctttg     240
gactctggtg ctttccaatc tgtttgggtt ccactgacc acgacgagat tgagaacgtt     300
gctaagcaat tcggtgctca ggttcacaga gatcctctg aggtttccaa ggactcttct     360
acttccttgg acgctatcat cgagttcttg aactaccaca cgaggttga catcgttggt     420 aacatccaag ctacttcccc atgtttgcac ccaactgact gcaaaaagt tgctgagatg     480 atcagagaag agggttacga ctccgttttc tccgttgtta aaggcacca gttcagatgg     540 tccgagattc agaagggtgt tagagaggtt acagagccat tgaacttgaa cccagctaaa     600
agaccaagaa ggcaggattg ggacggtgaa ttgtacgaaa acgttcctt ctacttcgct     660 aagagacact tgatcgagat gggatacttg caaggtggaa agatggctta ctacgagatg     720
agagctgaac actccgttga catcgacgtt gatatcgact ggccaattgc tgagcagaga     780
gttttgagat acggttactt cggaaaggag aagttgaagg agatcaagtt gttggttgt     840 aacatcgacg ttgttgac taacggtcac atctacgttt ctggtgacca gaaggagatt     900
atctcctacg acgttaagga cgctattggt atctccttgt gaagaagtc cggtatcgaa     960 gttagattga tctccgagag agcttgttcc aagcaaacat tgtcctcttt gaagttggac    1020
tgtaagatga aggtttccgt ttctgacaag ttggctgttg ttgacgaatg agaaaaggag    1080
atgggtttgt gttggaagga agttgcttac ttgggtaacg aagtttctga cgaggagtgt    1140
```

-continued

```
ttgaagagag ttggtttgtc tggtgctcca gctgatgctt gttccactgc tcaaaaggct   1200
gttggttaca tctgtaagtg taacggtggt agaggtgcta ttagagagtt cgctgagcac   1260
atctgtttgt tgatggagaa agttaataac tcctgtcaga agtagtag                1308
```

<210> SEQ ID NO 40
<211> LENGTH: 434
<212> TYPE: PRT
<213> ORGANISM: Artificial Sequence
<220> FEATURE:
<223> OTHER INFORMATION: Human CMP-sialic acid synthase (HsCSS) codon optimized

<400> SEQUENCE: 40

```
Met Asp Ser Val Glu Lys Gly Ala Ala Thr Ser Val Ser Asn Pro Arg
1               5                   10                  15

Gly Arg Pro Ser Arg Gly Arg Pro Lys Leu Gln Arg Asn Ser Arg
            20                  25                  30

Gly Gly Gln Gly Arg Gly Val Glu Lys Pro Pro His Leu Ala Ala Leu
        35                  40                  45

Ile Leu Ala Arg Gly Gly Ser Lys Gly Ile Pro Leu Lys Asn Ile Lys
50                  55                  60

His Leu Ala Gly Val Pro Leu Ile Gly Trp Val Leu Arg Ala Ala Leu
65              70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
            100                 105                 110

Ser Glu Val Ser Lys Asp Ser Ser Thr Ser Leu Asp Ala Ile Ile Glu
        115                 120                 125

Phe Leu Asn Tyr His Asn Glu Val Asp Ile Val Gly Asn Ile Gln Ala
130                 135                 140

Thr Ser Pro Cys Leu His Pro Thr Asp Leu Gln Lys Val Ala Glu Met
145                 150                 155                 160

Ile Arg Glu Glu Gly Tyr Asp Ser Val Phe Ser Val Val Arg Arg His
                165                 170                 175

Gln Phe Arg Trp Ser Glu Ile Gln Lys Gly Val Arg Glu Val Thr Glu
            180                 185                 190

Pro Leu Asn Leu Asn Pro Ala Lys Arg Pro Arg Arg Gln Asp Trp Asp
        195                 200                 205

Gly Glu Leu Tyr Glu Asn Gly Ser Phe Tyr Ala Lys Arg His Leu
    210                 215                 220

Ile Glu Met Gly Tyr Leu Gln Gly Gly Lys Met Ala Tyr Tyr Glu Met
225                 230                 235                 240

Arg Ala Glu His Ser Val Asp Ile Asp Val Asp Ile Asp Trp Pro Ile
                245                 250                 255

Ala Glu Gln Arg Val Leu Arg Tyr Gly Tyr Phe Gly Lys Glu Lys Leu
            260                 265                 270

Lys Glu Ile Lys Leu Leu Val Cys Asn Ile Asp Gly Cys Leu Thr Asn
        275                 280                 285

Gly His Ile Tyr Val Ser Gly Asp Gln Lys Glu Ile Ile Ser Tyr Asp
    290                 295                 300

Val Lys Asp Ala Ile Gly Ile Ser Leu Leu Lys Lys Ser Gly Ile Glu
305                 310                 315                 320

Val Arg Leu Ile Ser Glu Arg Ala Cys Ser Lys Gln Thr Leu Ser Ser
```

```
                325                 330                 335
Leu Lys Leu Asp Cys Lys Met Glu Val Ser Val Ser Asp Lys Leu Ala
            340                 345                 350

Val Val Asp Glu Trp Arg Lys Glu Met Gly Leu Cys Trp Lys Glu Val
            355                 360                 365

Ala Tyr Leu Gly Asn Glu Val Ser Asp Glu Glu Cys Leu Lys Arg Val
        370                 375                 380

Gly Leu Ser Gly Ala Pro Ala Asp Ala Cys Ser Thr Ala Gln Lys Ala
385                 390                 395                 400

Val Gly Tyr Ile Cys Lys Cys Asn Gly Gly Arg Gly Ala Ile Arg Glu
                405                 410                 415

Phe Ala Glu His Ile Cys Leu Leu Met Glu Lys Val Asn Asn Ser Cys
                420                 425                 430

Gln Lys
```

<210> SEQ ID NO 41
<211> LENGTH: 1080
<212> TYPE: DNA
<213> ORGANISM: Artificial Sequence
<220> FEATURE:
<223> OTHER INFORMATION: Encodes Human N-acetylneuraminate-9-phosphate
      synthase (HsSPS) codon optimized

<400> SEQUENCE: 41

```
atgccattgg aattggagtt gtgtcctggt agatgggttg gtggtcaaca cccatgtttc      60
atcatcgctg agatcggtca aaaccaccaa ggagacttgg acgttgctaa gagaatgatc     120
agaatggcta aggaatgtgg tgctgactgt gctaagttcc agaagtccga gttggagttc     180
aagttcaaca gaaaggcttt ggaaagacca tacacttcca agcactcttg ggaaagact      240 tacggagaac acaagagaca cttggagttc tctcacgacc aatacagaga gttgcagaga     300
tacgctgagg aagttggtat cttcttcact gcttctggaa tggacgaaat ggctgttgag     360
ttcttgcacg agttgaacgt tccattcttc aaagttggtt ccggtgacac taacaacttc     420
ccatacttgg aaaagactgc taagaaaggt agaccaatgg ttatctcctc tggaatgcag     480
tctatggaca ctatgaagca ggtttaccag atcgttaagc cattgaaccc aaacttttgt     540
ttcttgcagt gtacttccgc ttacccattg caaccagagg acgttaattt gagagttatc     600
tccgagtacc agaagttgtt cccagacatc ccaattggtt actctggtca cgagactggt     660
attgctattt ccgttgctgc tgttgctttg ggtgctaagg ttttggagag acacatcact     720
ttggacaaga cttggaaggg ttctgatcac tctgcttctt ggaacctggt gagttggct     780 gaacttgtta gatcagttag attggttgag agagctttgg gttccccaac taagcaattg     840
ttgccatgtg agatggcttg taacgagaag ttgggaaagt ccgttgttgc taaggttaag     900
atcccagagg gtactatctt gactatggac atgttgactg ttaaagttgg agagccaaag     960
ggttacccac cagaggacat ctttaacttg gttggtaaaa aggttttggt tactgttgag    1020
gaggacgaca ctattatgga ggagttggtt gacaaccacg gaaagaagat caagtcctag   1080
```

<210> SEQ ID NO 42
<211> LENGTH: 359
<212> TYPE: PRT
<213> ORGANISM: Artificial Sequence
<220> FEATURE:
<223> OTHER INFORMATION: Human N-acetylneuraminate-9-phosphate synthase
      (HsSPS) codon optimized

<400> SEQUENCE: 42

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
            35                  40                  45

Asp Cys Ala Lys Phe Gln Lys Ser Glu Leu Glu Phe Lys Phe Asn Arg
50                  55                  60

Lys Ala Leu Glu Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
            100                 105                 110

Gly Met Asp Glu Met Ala Val Glu Phe Leu His Glu Leu Asn Val Pro
            115                 120                 125

Phe Phe Lys Val Gly Ser Gly Asp Thr Asn Asn Phe Pro Tyr Leu Glu
130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
            165                 170                 175

Pro Asn Phe Cys Phe Leu Gln Cys Thr Ser Ala Tyr Pro Leu Gln Pro
            180                 185                 190

Glu Asp Val Asn Leu Arg Val Ile Ser Glu Tyr Gln Lys Leu Phe Pro
            195                 200                 205

Asp Ile Pro Ile Gly Tyr Ser Gly His Glu Thr Gly Ile Ala Ile Ser
210                 215                 220

Val Ala Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
            245                 250                 255

Gly Glu Leu Ala Glu Leu Val Arg Ser Val Arg Leu Val Glu Arg Ala
            260                 265                 270

Leu Gly Ser Pro Thr Lys Gln Leu Leu Pro Cys Glu Met Ala Cys Asn
            275                 280                 285

Glu Lys Leu Gly Lys Ser Val Val Ala Lys Val Lys Ile Pro Glu Gly
            290                 295                 300

Thr Ile Leu Thr Met Asp Met Leu Thr Val Lys Val Gly Glu Pro Lys
305                 310                 315                 320

Gly Tyr Pro Pro Glu Asp Ile Phe Asn Leu Val Gly Lys Val Leu
            325                 330                 335

Val Thr Val Glu Glu Asp Asp Thr Ile Met Glu Glu Leu Val Asp Asn
            340                 345                 350

His Gly Lys Lys Ile Lys Ser
            355

<210> SEQ ID NO 43
<211> LENGTH: 1092
<212> TYPE: DNA
<213> ORGANISM: Artificial Sequence
<220> FEATURE:
<223> OTHER INFORMATION: Encodes Mouse alpha-2,6-sialyl transferase
      catalytic domain (MmmST6) codon optimized

<400> SEQUENCE: 43

```
gtttttcaaa tgccaaagtc ccaggagaaa gttgctgttg gtccagctcc acaagctgtt      60
ttctccaact ccaagcaaga tccaaaggag ggtgttcaaa tcttgtccta cccaagagtt     120
actgctaagg ttaagccaca accatccttg caagtttggg acaaggactc cacttactcc     180
aagttgaacc caagattgtt gaagatttgg agaaactact tgaacatgaa caagtacaag     240
gtttcctaca agggtccagg tccaggtgtt aagttctccg ttgaggcttt tgagatgtcac    300
ttgagagacc acgttaacgt ttccatgatc gaggctactg acttcccatt caacactact     360
gaatgggagg atacttgcc aaaggagaac ttcagaacta aggctggtcc atggcataag      420
tgtgctgttg tttcttctgc tggttccttg aagaactccc agttgggtag agaaattgac     480
aaccacgacg ctgttttgag attcaacggt gctccaactg acaacttcca gcaggatgtt     540
ggtactaaga ctactatcag attggttaac tcccaattgg ttactactga aagagattc     600
ttgaaggact ccttgtacac tgagggaatc ttgattttgt gggacccatc tgtttaccac    660
gctgacattc cacaatggta tcagaagcca gactacaact tcttcgagac ttacaagtcc    720
tacagaagat tgcacccatc ccagccattc tacatcttga agccacaaat gccatgggaa    780
ttgtgggaca tcatccagga aatttccca gacttgatcc aaccaaaccc accatcttct     840
ggaatgttgg gtatcatcat catgatgact ttgtgtgacc aggttgacat ctacgagttc    900
ttgccatcca agaaaagac tgatgttgt tactaccacc agaagttctt cgactccgct      960
tgtactatgg gagcttacca cccattgttg ttcgagaaga acatggttaa gcacttgaac   1020
gaaggtactg acgaggacat ctacttgttc ggaaaggcta ctttgtccgg tttcagaaac  1080
aacagatgtt ag                                                         1092
```

<210> SEQ ID NO 44
<211> LENGTH: 363
<212> TYPE: PRT
<213> ORGANISM: Artificial Sequence
<220> FEATURE:
<223> OTHER INFORMATION: Mouse alpha-2,6-sialyl transferase catalytic
domain (MmmST6) codon optimized

<400> SEQUENCE: 44

```
Val Phe Gln Met Pro Lys Ser Gln Glu Lys Val Ala Val Gly Pro Ala
  1               5                  10                  15

Pro Gln Ala Val Phe Ser Asn Ser Lys Gln Asp Pro Lys Glu Gly Val
                 20                  25                  30

Gln Ile Leu Ser Tyr Pro Arg Val Thr Ala Lys Val Lys Pro Gln Pro
             35                  40                  45

Ser Leu Gln Val Trp Asp Lys Asp Ser Thr Tyr Ser Lys Leu Asn Pro
         50                  55                  60

Arg Leu Leu Lys Ile Trp Arg Asn Tyr Leu Asn Met Asn Lys Tyr Lys
 65                  70                  75                  80

Val Ser Tyr Lys Gly Pro Gly Pro Gly Val Lys Phe Ser Val Glu Ala
                 85                  90                  95

Leu Arg Cys His Leu Arg Asp His Val Asn Val Ser Met Ile Glu Ala
            100                 105                 110

Thr Asp Phe Pro Phe Asn Thr Thr Glu Trp Glu Gly Tyr Leu Pro Lys
        115                 120                 125

Glu Asn Phe Arg Thr Lys Ala Gly Pro Trp His Lys Cys Ala Val Val
    130                 135                 140

Ser Ser Ala Gly Ser Leu Lys Asn Ser Gln Leu Gly Arg Glu Ile Asp
```

-continued

```
                145                 150                 155                 160
Asn His Asp Ala Val Leu Arg Phe Asn Gly Ala Pro Thr Asp Asn Phe
                    165                 170                 175
Gln Gln Asp Val Gly Thr Lys Thr Thr Ile Arg Leu Val Asn Ser Gln
                    180                 185                 190
Leu Val Thr Thr Glu Lys Arg Phe Leu Lys Asp Ser Leu Tyr Thr Glu
                    195                 200                 205
Gly Ile Leu Ile Leu Trp Asp Pro Ser Val Tyr His Ala Asp Ile Pro
        210                 215                 220
Gln Trp Tyr Gln Lys Pro Asp Tyr Asn Phe Phe Glu Thr Tyr Lys Ser
225                 230                 235                 240
Tyr Arg Arg Leu His Pro Ser Gln Pro Phe Tyr Ile Leu Lys Pro Gln
                    245                 250                 255
Met Pro Trp Glu Leu Trp Asp Ile Ile Gln Glu Ile Ser Pro Asp Leu
                    260                 265                 270
Ile Gln Pro Asn Pro Pro Ser Ser Gly Met Leu Gly Ile Ile Ile Met
                    275                 280                 285
Met Thr Leu Cys Asp Gln Val Asp Ile Tyr Glu Phe Leu Pro Ser Lys
                    290                 295                 300
Arg Lys Thr Asp Val Cys Tyr Tyr His Gln Lys Phe Phe Asp Ser Ala
305                 310                 315                 320
Cys Thr Met Gly Ala Tyr His Pro Leu Leu Phe Glu Lys Asn Met Val
                    325                 330                 335
Lys His Leu Asn Glu Gly Thr Asp Glu Asp Ile Tyr Leu Phe Gly Lys
                    340                 345                 350
Ala Thr Leu Ser Gly Phe Arg Asn Asn Arg Cys
                    355                 360
```

<210> SEQ ID NO 45
<211> LENGTH: 1037
<212> TYPE: DNA
<213> ORGANISM: Artificial Sequence
<220> FEATURE:
<223> OTHER INFORMATION: PpPMA1 promoter

<400> SEQUENCE: 45

```
aaatgcgtac ctcttctacg agattcaagc gaatgagaat aatgtaatat gcaagatcag     60
aaagaatgaa aggagttgaa aaaaaaaacc gttgcgtttt gaccttgaat ggggtggagg    120
tttccattca agtaaagcc tgtgtcttgg tattttcggc ggcacaagaa atcgtaattt    180
tcatcttcta aacgatgaag atcgcagccc aacctgtatg tagttaaccg gtcggaatta    240
taagaaagat tttcgatcaa caaaccctag caaatagaaa gcagggttac aactttaaac    300
cgaagtcaca aacgataaac cactcagctc ccacccaaat tcattcccac tagcagaaag    360
gaattattta atccctcagg aaacctcgat gattctcccg ttcttccatg ggcgggtatc    420
gcaaaatgag gaattttca aatttctcta ttgtcaagac tgtttattat ctaagaaata    480
gcccaatccg aagctcagtt ttgaaaaaat cacttccgcg tttctttttt acagcccgat    540
gaatatccaa atttggaata tggattactc tatcgggact gcagataata tgacaacaac    600
gcagattaca ttttaggtaa ggcataaaca ccagccagaa atgaaacgcc cactagccat    660
ggtcgaatag tccaatgaat tcagatagct atggtctaaa agctgatgtt ttttattggg    720
taatggcgaa gagtccagta cgacttccag cagagctgag atggccattt ttgggggtat    780
tagtaacttt tgagctctt ttcacttcga tgaagtgtcc cattcgggat ataatcggat    840
```

```
cgcgtcgttt tctcgaaaat acagcttagc gtcgtccgct tgttgtaaaa gcagcaccac    900
attcctaatc tcttatataa acaaaacaac ccaaattatc agtgctgttt tcccaccaga    960
tataagtttc ttttctcttc cgcttttga tttttatct ctttcctta aaaacttctt     1020 taccttaaag ggcggcc                                                   1037
```

<210> SEQ ID NO 46
<211> LENGTH: 512
<212> TYPE: DNA
<213> ORGANISM: Artificial Sequence
<220> FEATURE:
<223> OTHER INFORMATION: PpPMA1 terminator

<400> SEQUENCE: 46

```
taagcttcac gatttgtgtt ccagtttatc ccccctttat ataccgttaa cccttcccct     60
gttgagctga ctgttgttgt attaccgcaa ttttccaag tttgccatgc ttttcgtgtt    120
atttgaccga tgtcttttt cccaaatcaa actatatttg ttaccattta aaccaagtta    180 tctttgtat taagagtcta agttgtgttcc caggcttcat gtgagagtga taaccatcca    240
gactatgatt cttgttttt attgggtttg tttgtgtgat acatctgagt tgtgattcgt    300
aaagtatgtc agtctatcta gatttttaat agttaattgg taatcaatga cttgtttgtt    360 ttaacttta aattgtgggt cgtatccacg cgtttagtat agctgttcat ggctgttaga    420
ggagggcgat gtttatatac agaggacaag aatgaggagg cggcgtgtat ttttaaaatg    480
gagacgcgac tcctgtacac cttatcggtt gg                                 512
```

<210> SEQ ID NO 47
<211> LENGTH: 798
<212> TYPE: DNA
<213> ORGANISM: Artificial Sequence
<220> FEATURE:
<223> OTHER INFORMATION: PpOCH1 promoter

<400> SEQUENCE: 47

```
tggacacagg agactcagaa acagacacag agcgttctga gtcctggtgc tcctgacgta     60
ggcctagaac aggaattatt ggctttattt gtttgtccat ttcataggct tggggtaata    120
gatagatgac agagaaatag agaagaccta atatttttg ttcatggcaa atcgcgggtt    180
cgcggtcggg tcacacacgg agaagtaatg agaagagctg gtaatctggg gtaaaagggt    240
tcaaaagaag gtcgcctggt agggatgcaa tacaaggttg tcttggagtt tacattgacc    300
agatgatttg gcttttctc tgttcaattc acatttttca gcgagaatcg gattgacgga    360
gaaatggcgg ggtgtggggt ggatagatgg cagaaatgct cgcaatcacc gcgaaagaaa    420
gactttatgg aatagaacta ctgggtggtg taaggattac atagctagtc caatggagtc    480
cgttggaaag gtaagaagaa gctaaaaccg gctaagtaac tagggaagaa tgatcagact    540
ttgatttgat gaggtctgaa aatactctgc tgctttttca gttgctttt ccctgcaacc    600 tatcatttc cttttcataa gcctgccttt tctgttttca cttatatgag ttccgccgag    660
acttccccaa attctctcct ggaacattct ctatcgctct ccttccaagt tgcgccccct    720
ggcactgcct agtaatatta ccacgcgact tatattcagt tccacaattt ccagtgttcg    780
tagcaaatat catcagcc                                                  798
```

<210> SEQ ID NO 48
<211> LENGTH: 302
<212> TYPE: DNA
<213> ORGANISM: Artificial Sequence
<220> FEATURE:
<223> OTHER INFORMATION: PpALG12 terminator

<400> SEQUENCE: 48

```
aatatatacc tcatttgttc aatttggtgt aaagagtgtg gcggatagac ttcttgtaaa     60
tcaggaaagc tacaattcca attgctgcaa aaaataccaa tgcccataaa ccagtatgag    120
cggtgccttc gacggattgc ttactttccg acccttgtc gtttgattct tctgcctttg    180
gtgagtcagt ttgtttcgac tttatatctg actcatcaac ttcctttacg gttgcgtttt    240
taatcataat tttagccgtt ggcttattat cccttgagtt ggtaggagtt ttgatgatgc    300
tg                                                                  302
```

<210> SEQ ID NO 49
<211> LENGTH: 435
<212> TYPE: DNA
<213> ORGANISM: Artificial Sequence
<220> FEATURE:
<223> OTHER INFORMATION: PpSEC4 promoter

<400> SEQUENCE: 49

```
gaagtaaagt tggcgaaact ttgggaacct ttggttaaaa ctttgtaatt tttgtcgcta     60
cccattaggc agaatctgca tcttgggagg gggatgtggt ggcgttctga gatgtacgcg    120
aagaatgaag agccagtggt aacaacaggc ctagagagat acgggcataa tgggtataac    180
ctacaagtta agaatgtagc agccctggaa accagattga aacgaaaaac gaaatcattt    240
aaactgtagg atgttttggc tcattgtctg gaaggctggc tgtttattgc cctgttcttt    300
gcatgggaat aagctattat atccctcaca taatcccaga aaatagattg aagcaacgcg    360
aaatccttac gtatcgaagt agccttctta cacattcacg ttgtacggat aagaaaacta    420
ctcaaacgaa caatc                                                    435
```

<210> SEQ ID NO 50
<211> LENGTH: 404
<212> TYPE: DNA
<213> ORGANISM: Artificial Sequence
<220> FEATURE:
<223> OTHER INFORMATION: PpOCH1 terminator

<400> SEQUENCE: 50

```
aatagatata gcgagattag agaatgaata ccttcttcta agcgatcgtc cgtcatcata     60
gaatatcatg gactgtatag ttttttttt gtacatataa tgattaaacg gtcatccaac    120
atctcgttga cagatctctc agtacgcgaa atccctgact atcaaagcaa gaaccgatga    180
agaaaaaaac aacagtaacc caaacaccac aacaaacact ttatcttctc ccccccaaca    240
ccaatcatca aagagatgtc ggaacacaaa caccaagaag caaaaactaa ccccatataa    300
aaacatcctg gtagataatg ctggtaaccc gctctccttc catattctgg gctacttcac    360
gaagtctgac cggtctcagt tgatcaacat gatcctcgaa atgg                    404
```

<210> SEQ ID NO 51
<211> LENGTH: 600
<212> TYPE: DNA
<213> ORGANISM: Artificial Sequence
<220> FEATURE:
<223> OTHER INFORMATION: PpTEF1 promoter

<400> SEQUENCE: 51

```
ttaaggtttg gaacaacact aaactacctt gcggtactac cattgacact acacatcctt     60
```

```
aattccaatc ctgtctggcc tccttcacct tttaaccatc ttgcccattc caactcgtgt    120
cagattgcgt atcaagtgaa aaaaaaaaaa ttttaaatct ttaacccaat caggtaataa    180
ctgtcgcctc ttttatctgc cgcactgcat gaggtgtccc cttagtggga aagagtactg    240
agccaaccct ggaggacagc aagggaaaaa tacctacaac ttgcttcata atggtcgtaa    300
aaacaatcct tgtcggatat aagtgttgta gactgtccct tatcctctgc gatgttcttc    360
ctctcaaagt ttgcgatttc tctctatcag aattgccatc aagagactca ggactaattt    420
cgcagtccca cacgcactcg tacatgattg gctgaaattt ccctaaagaa tttcttttc     480 acgaaaattt ttttttaca caagattttc agcagatata aaatggagag caggacctcc     540
gctgtgactc ttctttttttt tcttttattc tcactacata catttttagtt attcgccaac    600
```

<210> SEQ ID NO 52
<211> LENGTH: 301
<212> TYPE: DNA
<213> ORGANISM: Artificial Sequence
<220> FEATURE:
<223> OTHER INFORMATION: PpTEF1 terminator

<400> SEQUENCE: 52

```
attgcttgaa gctttaattt attttattaa cataataata atacaagcat gatatatttg     60
tattttgttc gttaacattg atgttttctt catttactgt tattgtttgt aactttgatc    120
gatttatctt ttctacttta ctgtaatatg gctggcgggt gagccttgaa ctccctgtat    180
tactttacct tgctattact taatctattg actagcagcg acctcttcaa ccgaagggca    240
agtacacagc aagttcatgt ctccgtaagt gtcatcaacc ctggaaacag tgggccatgt    300
c                                                                    301
```

<210> SEQ ID NO 53
<211> LENGTH: 486
<212> TYPE: DNA
<213> ORGANISM: Artificial Sequence
<220> FEATURE:
<223> OTHER INFORMATION: PpGAPDH promoter

<400> SEQUENCE: 53

```
tttttgtaga aatgtcttgg tgtcctcgtc caatcaggta gccatctctg aaatatctgg     60
ctccgttgca actccgaacg acctgctggc aacgtaaaat tctccggggt aaaacttaaa    120
tgtggagtaa tggaaccaga aacgtctctt cccttctctc tccttccacc gcccgttacc    180
gtccctagga aattttactc tgctggagag cttcttctac ggccccttg cagcaatgct     240 cttcccagca ttacgttgcg ggtaaaacgg aggtcgtgta cccgacctag cagcccaggg    300
atggaaaagt cccggccgtc gctggcaata atagcgggcg gacgcatgtc atgagattat    360
tggaaaccac cagaatcgaa tataaaaggc gaacaccttt cccaattttg gtttctcctg    420
acccaaagac tttaaattta atttatttgt ccctatttca atcaattgaa caactatcaa    480
aacaca                                                               486
```

<210> SEQ ID NO 54
<211> LENGTH: 376
<212> TYPE: DNA
<213> ORGANISM: Artificial Sequence
<220> FEATURE:
<223> OTHER INFORMATION: PpALG3 terminator

<400> SEQUENCE: 54

```
atttacaatt agtaatatta aggtggtaaa aacattcgta gaattgaaat gaattaatat     60
```

```
agtatgacaa tggttcatgt ctataaatct ccggcttcgg taccttctcc ccaattgaat        120
acattgtcaa aatgaatggt tgaactatta ggttcgccag tttcgttatt aagaaaactg        180
ttaaaatcaa attccatatc atcggttcca gtgggaggac cagttccatc gccaaaatcc        240
tgtaagaatc cattgtcaga acctgtaaag tcagtttgag atgaaatttt tccggtcttt        300
gttgacttgg aagcttcgtt aaggttaggt gaaacagttt gatcaaccag cggctcccgt        360
tttcgtcgct tagtag                                                       376

<210> SEQ ID NO 55
<211> LENGTH: 934
<212> TYPE: DNA
<213> ORGANISM: Artificial Sequence
<220> FEATURE:
<223> OTHER INFORMATION: PpAOX1 promoter and integration locus

<400> SEQUENCE: 55
aacatccaaa gacgaaaggt tgaatgaaac cttttttgcca tccgacatcc acaggtccat        60
tctcacacat aagtgccaaa cgcaacagga ggggatacac tagcagcaga ccgttgcaaa        120
cgcaggacct ccactcctct tctcctcaac acccactttt gccatcgaaa aaccagccca        180
gttattgggc ttgattggag ctcgctcatt ccaattcctt ctattaggct actaacacca        240
tgactttatt agcctgtcta tcctggcccc cctggcgagg ttcatgtttg tttatttccg        300
aatgcaacaa gctccgcatt acacccgaac atcactccag atgagggctt tctgagtgtg        360
gggtcaaata gtttcatgtt ccccaaatgg cccaaaactg acagtttaaa cgctgtcttg        420
gaacctaata tgacaaaagc gtgatctcat ccaagatgaa ctaagtttgg ttcgttgaaa        480
tgctaacggc cagttggtca aaaagaaact tccaaaagtc ggcataccgt ttgtcttgtt        540
tggtattgat tgacgaatgc tcaaaaataa tctcattaat gcttagcgca gtctctctat        600
cgcttctgaa ccccggtgca cctgtgccga aacgcaaatg gggaaacacc cgcttttttgg       660 atgattatgc attgtctcca cattgtatgc ttccaagatt ctggtgggaa tactgctgat        720
agcctaacgt tcatgatcaa aatttaactg ttctaacccc tacttgacag caatatataa        780
acagaaggaa gctgccctgt cttaaaacctt ttttttatc atcattatta gcttactttc        840
ataattgcga ctggttccaa ttgacaagct tttgatttta acgacttttta acgacaactt        900 gagaagatca aaaacaact aattattcga aacg                                    934

<210> SEQ ID NO 56
<211> LENGTH: 293
<212> TYPE: DNA
<213> ORGANISM: Artificial Sequence
<220> FEATURE:
<223> OTHER INFORMATION: ScCYC1 terminator

<400> SEQUENCE: 56
acaggcccct ttcctttgt cgatatcatg taattagtta tgtcacgctt acattcacgc         60
cctcctccca catccgctct aaccgaaaag gaaggagtta gacaacctga agtctaggtc        120
cctatttatt tttttaata gttatgttag tattaagaac gttatttata ttcaaatttt        180 ttctttttttt tctgtacaaa cgcgtgtacg catgtaacat tatactgaaa accttgcttg      240
agaaggtttt gggacgctcg aaggctttaa tttgcaagct gccggctctt aag              293

<210> SEQ ID NO 57
<211> LENGTH: 427
<212> TYPE: DNA
```

<213> ORGANISM: Artificial Sequence
<220> FEATURE:
<223> OTHER INFORMATION: ScTEF1 promoter

<400> SEQUENCE: 57

```
gatcccccac acaccatagc ttcaaaatgt ttctactcct tttttactct tccagattt      60
ctcggactcc gcgcatcgcc gtaccacttc aaaacaccca agcacagcat actaaatttc   120
ccctctttct tcctctaggg tgtcgttaat tacccgtact aaaggtttgg aaaagaaaaa   180
agagaccgcc tcgtttcttt ttcttcgtcg aaaaaggcaa taaaaatttt tatcacgttt   240
cttttcttg aaaatttttt tttttgattt ttttctcttt cgatgacctc ccattgatat    300
ttaagttaat aaacggtctt caatttctca gtttcagtt tcattttcct tgttctatta    360
caacttttt tacttcttgc tcattagaaa gaaagcatag caatctaatc taagttttaa   420
ttacaaa                                                                427
```

<210> SEQ ID NO 58
<211> LENGTH: 375
<212> TYPE: DNA
<213> ORGANISM: Artificial Sequence
<220> FEATURE:
<223> OTHER INFORMATION: Encodes Sh ble ORF (Zeocin resistance marker):

<400> SEQUENCE: 58

```
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt   120
gtggtccggg acgacgtgac cctgttcatc agcgcggtcc aggaccaggt ggtgccggac   180
aacaccctgg cctgggtgtg ggtgcgcggc ctggacgagc tgtacgccga gtggtcggag   240
gtcgtgtcca cgaacttccg ggacgcctcc gggccggcca tgaccgagat cggcgagcag   300
ccgtgggggc gggagttcgc cctgcgcgac ccggccggca actgcgtgca cttcgtggcc   360
gaggagcagg actga                                                       375
```

<210> SEQ ID NO 59
<211> LENGTH: 898
<212> TYPE: DNA
<213> ORGANISM: Artificial Sequence
<220> FEATURE:
<223> OTHER INFORMATION: 5'-Region of PpURA5

<400> SEQUENCE: 59

```
atcggccttt gttgatgcaa gttttacgtg gatcatggac taaggagttt tatttggacc      60
aagttcatcg tcctagacat tacggaaagg gttctgctcc tcttttttgga aacttttttgg  120
aacctctgag tatgacagct tggtggattg tacccatggt atggcttcct gtgaatttct    180
atttttcta cattggattc accaatcaaa acaaattagt cgccatggct ttttggcttt     240
tgggtctatt tgtttggacc ttcttggaat atgctttgca tagattttg ttccacttgg    300
actactatct tccagagaat caaattgcat ttaccattca tttcttattg catgggatac   360
accactattt accaatggat aaatacagat tggtgatgcc acctacactt tcattgtac    420
tttgctaccc aatcaagacg ctcgtctttt ctgttctacc atattacatg gcttgttctg   480
gatttgcagg tggattcctg ggctatatca tgtatgatgt cactcattac gttctgcatc   540
actccaagct gcctcgttat ttccaagagt tgaagaaata tcatttggaa catcactaca   600
agaattacga gttaggcttt ggtgtcactt ccaaattctg ggacaaagtc tttgggactt   660
atctgggtcc agacgatgtg tatcaaaaga caaattagag tatttataaa gttatgtaag   720
```

```
caaatagggg ctaataggga agaaaaatt ttggttcttt atcagagctg gctcgcgcgc      780 agtgttttc gtgctccttt gtaatagtca tttttgacta ctgttcagat tgaaatcaca      840
ttgaagatgt cactcgaggg gtaccaaaaa aggttttgg atgctgcagt ggcttcgc        898
```

<210> SEQ ID NO 60
<211> LENGTH: 1060
<212> TYPE: DNA
<213> ORGANISM: Artificial Sequence
<220> FEATURE:
<223> OTHER INFORMATION: 3'-Region of PpURA5

<400> SEQUENCE: 60

```
ggtcttttca acaaagctcc attagtgagt cagctggctg aatcttatgc acaggccatc      60
attaacagca acctggagat agacgttgta tttggaccag cttataaagg tattcctttg     120
gctgctatta ccgtgttgaa gttgtacgag ctcggcggca aaaatacga aaatgtcgga     180 tatgcgttca atagaaaaga aaagaaagac cacgagaag gtggaagcat cgttggagaa     240
agtctaaaga ataaaagagt actgattatc gatgatgtga tgactgcagg tactgctatc     300
aacgaagcat ttgctataat tggagctgaa ggtgggagag ttgaaggtag tattattgcc     360
ctagatagaa tggagactac aggagatgac tcaaatacca gtgctaccca ggctgttagt     420
cagagatatg gtaccctgt cttgagtata gtgacattgg accatattgt ggcccatttg     480
ggcgaaactt tcacagcaga cgagaaatct caaatggaaa cgtatagaaa aaagtatttg     540
cccaaataag tatgaatctg cttcgaatga atgaattaat ccaattatct tctcaccatt     600
attttcttct gtttcggagc tttgggcacg gcggcgggtg gtgcgggctc aggttccctt     660
tcataaacag atttagtact tggatgctta atagtgaatg gcgaatgcaa aggaacaatt     720
tcgttcatct ttaacccttt cactcggggt acacgttctg gaatgtaccc gccctgttgc     780
aactcaggtg gaccgggcaa ttcttgaact ttctgtaacg ttgttggatg ttcaaccaga     840
aattgtccta ccaactgtat tagtttcctt ttggtcttat attgttcatc gagatacttc     900
ccactctcct tgatagccac tctcactctt cctggattac caaaatcttg aggatgagtc     960
ttttcaggct ccaggatgca aggtatatcc aagtacctgc aagcatctaa tattgtcttt    1020 gccaggggt tctccacacc atactccttt tggcgcatgc                           1060
```

<210> SEQ ID NO 61
<211> LENGTH: 957
<212> TYPE: DNA
<213> ORGANISM: Artificial Sequence
<220> FEATURE:
<223> OTHER INFORMATION: Encodes PpURA5 auxotrophic marker

<400> SEQUENCE: 61

```
tctagaggga cttatctggg tccagacgat gtgtatcaaa agacaaatta gagtatttat      60
aaagttatgt aagcaaatag gggctaatag ggaaagaaaa attttggttc tttatcagag     120
ctggctcgcg cgcagtgttt ttcgtgctcc tttgtaatag tcattttga ctactgttca     180 gattgaaatc acattgaaga tgtcactgga ggggtaccaa aaaggtttt tggatgctgc     240 agtggcttcg caggccttga agtttggaac tttcaccttg aaaagtggaa gacagtctcc     300
atacttcttt aacatgggtc ttttcaacaa agctccatta gtgagtcagc tggctgaatc     360
ttatgctcag gccatcatta acagcaacct ggagatagac gttgtatttg gaccagctta     420
taaaggtatt cctttggctg ctattaccgt gttgaagttg tacgagctgg gcggcaaaaa     480
```

| | |
|---|---|
| atacgaaaat gtcggatatg cgttcaatag aaaagaaaag aaagaccacg gagaaggtgg | 540 |
| aagcatcgtt ggagaaagtc taaagaataa aagagtactg attatcgatg atgtgatgac | 600 |
| tgcaggtact gctatcaacg aagcatttgc tataattgga gctgaaggtg ggagagttga | 660 |
| aggttgtatt attgccctag atagaatgga gactacagga gatgactcaa ataccagtgc | 720 |
| tacccaggct gttagtcaga gatatggtac ccctgtcttg agtatagtga cattggacca | 780 |
| tattgtggcc catttgggcg aaactttcac agcagacgag aaatctcaaa tggaaacgta | 840 |
| tagaaaaaag tatttgccca ataagtatg aatctgcttc gaatgaatga attaatccaa | 900 |
| ttatcttctc accattattt tcttctgttt cggagctttg ggcacggcgg cggatcc | 957 |

<210> SEQ ID NO 62
<211> LENGTH: 709
<212> TYPE: DNA
<213> ORGANISM: Artificial Sequence
<220> FEATURE:
<223> OTHER INFORMATION: Part of the Ec lacZ gene

<400> SEQUENCE: 62

| | |
|---|---|
| cctgcactgg atggtggcgc tggatggtaa gccgctggca agcggtgaag tgcctctgga | 60 |
| tgtcgctcca caaggtaaac agttgattga actgcctgaa ctaccgcagc cggagagcgc | 120 |
| cgggcaactc tggctcacag tacgcgtagt gcaaccgaac gcgaccgcat ggtcagaagc | 180 |
| cgggcacatc agcgcctggc agcagtggcg tctggcggaa aacctcagtg tgacgctccc | 240 |
| cgccgcgtcc cacgccatcc gcatctgac caccagcgaa atggattttt gcatcgagct | 300 |
| gggtaataag cgttggcaat ttaaccgcca gtcaggcttt ctttcacaga tgtggattgg | 360 |
| cgataaaaaa caactgctga cgccgctgcg cgatcagttc acccgtgcac cgctggataa | 420 |
| cgacattggc gtaagtgaag cgacccgcat tgaccctaac gcctgggtcg aacgctggaa | 480 |
| ggcggcgggc cattaccagg ccgaagcagc gttgttgcag tgcacggcag atacacttgc | 540 |
| tgatgcggtg ctgattacga ccgctcacgc gtggcagcat caggggaaaa ccttatttat | 600 |
| cagccggaaa acctaccgga ttgatggtag tggtcaaatg gcgattaccg ttgatgttga | 660 |
| agtggcgagc gatacaccgc atccggcgcg gattggcctg aactgccag | 709 |

<210> SEQ ID NO 63
<211> LENGTH: 222
<212> TYPE: PRT
<213> ORGANISM: Pichia pastoris

<400> SEQUENCE: 63

Met Ser Leu Glu Gly Tyr Gln Lys Arg Phe Leu Asp Ala Ala Val Ala
1               5                   10                  15

Ser Gln Ala Leu Lys Phe Gly Thr Phe Thr Leu Lys Ser Gly Arg Gln
            20                  25                  30

Ser Pro Tyr Phe Phe Asn Met Gly Leu Phe Asn Lys Ala Pro Leu Val
        35                  40                  45

Ser Gln Leu Ala Glu Ser Tyr Ala Gln Ala Ile Ile Asn Ser Asn Leu
    50                  55                  60

Glu Ile Asp Val Val Phe Gly Pro Ala Tyr Lys Gly Ile Pro Leu Ala
65                  70                  75                  80

Ala Ile Thr Val Leu Lys Leu Tyr Glu Leu Gly Gly Lys Lys Tyr Glu
                85                  90                  95

Asn Val Gly Tyr Ala Phe Asn Arg Lys Glu Lys Lys Asp His Gly Glu
            100                 105                 110

```
Gly Gly Ser Ile Val Gly Glu Ser Leu Lys Asn Lys Arg Val Leu Ile
            115                 120                 125

Ile Asp Asp Val Met Thr Ala Gly Thr Ala Ile Asn Glu Ala Phe Ala
    130                 135                 140

Ile Ile Gly Ala Glu Gly Gly Arg Val Glu Gly Cys Ile Ile Ala Leu
145                 150                 155                 160

Asp Arg Met Glu Thr Thr Gly Asp Asp Ser Asn Thr Ser Ala Thr Gln
                165                 170                 175

Ala Val Ser Gln Arg Tyr Gly Thr Pro Val Leu Ser Ile Val Thr Leu
            180                 185                 190

Asp His Ile Val Ala His Leu Gly Glu Thr Phe Thr Ala Asp Glu Lys
        195                 200                 205

Ser Gln Met Glu Thr Tyr Arg Lys Lys Tyr Leu Pro Lys Glx
    210                 215                 220
```

<210> SEQ ID NO 64
<211> LENGTH: 2875
<212> TYPE: DNA
<213> ORGANISM: Artificial Sequence
<220> FEATURE:
<223> OTHER INFORMATION: 5'-Region of PpOCH1

<400> SEQUENCE: 64

```
aaaacctttt ttcctattca aacacaaggc attgcttcaa cacgtgtgcg tatccttaac      60
acagatactc catacttcta ataatgtgat agacgaatac aaagatgttc actctgtgtt     120
gtgtctacaa gcatttctta ttctgattgg ggatattcta gttacagcac taaacaactg     180
gcgatacaaa cttaaattaa ataatccgaa tctagaaaat gaacttttgg atggtccgcc     240
tgttggttgg ataaatcaat accgattaaa tggattctat tccaatgaga gagtaatcca     300
agacactctg atgtcaataa tcatttgctt gcaacaacaa acccgtcatc taatcaaagg     360
gtttgatgag gcttaccttc aattgcagat aaactcattg ctgtccactg ctgtattatg     420
tgagaatatg ggtgatgaat ctggtcttct ccactcagct aacatggctg tttgggcaaa     480
ggtggtacaa ttatacggag atcaggcaat agtgaaattg ttgaatatgg ctactggacg     540
atgcttcaag gatgtacgtc tagtaggagc cgtgggaaga ttgctggcag aaccagttgg     600
cacgtcgcaa caatccccaa gaaatgaaat aagtgaaaac gtaacgtcaa agacagcaat     660
ggagtcaata ttgataacac cactggcaga gcggttcgta cgtcgttttg gagccgatat     720
gaggctcagc gtgctaacag cacgattgac aagaagactc tcgagtgaca gtaggttgag     780
taaagtattc gcttagattc ccaaccttcg ttttattctt tcgtagacaa agaagctgca     840
tgcgaacata gggacaactt ttataaatcc aattgtcaaa ccaacgtaaa accctctggc     900
accatttca acatatattt gtgaagcagt acgcaatatc gataaatact caccgttgtt     960
tgtaacagcc ccaacttgca tacgccttct aatgacctca aatggataag ccgcagcttg    1020
tgctaacata ccagcagcac cgcccgcggt cagctgcgcc cacacatata aaggcaatct    1080
acgatcatgg gaggaattag ttttgaccgt caggtcttca agagttttga actcttcttc    1140
ttgaactgtg taacctttta aatgacggga tctaaatacg tcatggatga gatcatgtgt    1200
gtaaaaactg actccagcat atggaatcat tccaaagatt gtaggagcga acccacgata    1260
aaagtttccc aaccttgcca aagtgtctaa tgctgtgact tgaaatctgg gttcctcgtt    1320
gaagaccctg cgtactatgc ccaaaaactt tcctccacga gccctattaa cttctctatg    1380
agtttcaaat gccaaacgga cacggattag gtccaatggg taagtgaaaa acacagagca    1440
```

```
aacccccagct aatgagccgg ccagtaaccg tcttggagct gtttcataag agtcattagg    1500
gatcaataac gttctaatct gttcataaca tacaaatttt atggctgcat agggaaaaat    1560
tctcaacagg gtagccgaat gaccctgata tagacctgcg acaccatcat acccatagat    1620
ctgcctgaca gccttaaaga gcccgctaaa agacccggaa aaccgagaga actctggatt    1680
agcagtctga aaaagaatct tcactctgtc tagtggagca attaatgtct tagcggcact    1740
tcctgctact ccgccagcta ctcctgaata gatcacatac tgcaaagact gcttgtcgat    1800
gaccttgggg ttatttagct tcaagggcaa ttttttggac attttggaca caggagactc    1860
agaaacagac acagagcgtt ctgagtcctg gtgctcctga cgtaggccta gaacaggaat    1920
tattggcttt atttgtttgt ccatttcata ggcttggggt aatagataga tgacagagaa    1980
atagagaaga cctaatattt tttgttcatg gcaaatcgcg ggttcgcggt cgggtcacac    2040
acggagaagt aatgagaaga gctggtaatc tggggtaaaa gggttcaaaa gaaggtcgcc    2100
tggtagggat gcaatacaag gttgtcttgg agtttacatt gaccagatga tttggctttt    2160
tctctgttca attcacattt ttcagcgaga atcggattga cggagaaatg gcggggtgtg    2220
gggtggatag atggcagaaa tgctcgcaat caccgcgaaa gaaagacttt atggaataga    2280
actactgggt ggtgtaagga ttacatagct agtccaatgg agtccgttgg aaaggtaaga    2340
agaagctaaa accggctaag taactaggga agaatgatca actttgatt tgatgaggtc    2400
tgaaaatact ctgctgcttt ttcagttgct ttttccctgc aacctatcat tttccttttc    2460
ataagcctgc ctttttctgtt tcacttata tgagttccgc cgagacttcc ccaaattctc    2520
tcctggaaca ttctctatcg ctctccttcc aagttgcgcc ccctggcact gcctagtaat    2580
attaccacgc gacttatatt cagttccaca atttccagtg ttcgtagcaa atatcatcag    2640
ccatggcgaa ggcagatggc agtttgctct actataatcc tcacaatcca cccagaaggt    2700
attacttcta catggctata ttcgccgttt ctgtcatttg cgttttgtac ggaccctcac    2760
aacaattatc atctccaaaa atagactatg atccattgac gctccgatca cttgatttga    2820
agactttgga agctccttca cagttgagtc caggcaccgt agaagataat cttcg         2875
```

<210> SEQ ID NO 65
<211> LENGTH: 997
<212> TYPE: DNA
<213> ORGANISM: Artificial Sequence
<220> FEATURE:
<223> OTHER INFORMATION: 3'-Region of PpOCH1

<400> SEQUENCE: 65

```
aaagctagag taaaatagat atagcgagat tagagaatga atacccttctt ctaagcgatc     60
gtccgtcatc atagaatatc atggactgta tagttttttt tttgtacata taatgattaa    120
acggtcatcc aacatctcgt tgacagatct ctcagtacgc gaaatccctg actatcaaag    180
caagaaccga tgaagaaaaa aacaacagta acccaaacac cacaacaaac actttatctt    240
ctccccccca acaccaatca tcaaagagat gtcggaacca acaccaaga agcaaaaact    300
aaccccatat aaaaacatcc tggtagataa tgctggtaac ccgctctcct tccatattct    360
gggctacttc acgaagtctg accggtctca gttgatcaac atgatcctcg aaatgggtgg    420
caagatcgtt ccagacctgc ctcctctggt agatggagtg ttgttttga cagggggatta    480
caagtctatt gatgaagata ccctaaagca actggggggac gttccaatat acagagactc    540
cttcatctac cagtgttttg tgcacaagac atctcttccc attgacactt tccgaattga    600
caagaacgtc gacttggctc aagatttgat caataggggcc cttcaagagt ctgtggatca    660
```

```
tgtcacttct gccagcacag ctgcagctgc tgctgttgtt gtcgctacca acggcctgtc    720
ttctaaacca gacgctcgta ctagcaaaat acagttcact cccgaagaag atcgttttat    780
tcttgacttt gttaggagaa atcctaaacg aagaaacaca catcaactgt acactgagct    840
cgctcagcac atgaaaaacc atacgaatca ttctatccgc cacagatttc gtcgtaatct    900
ttccgctcaa cttgattggg tttatgatat cgatccattg accaaccaac ctcgaaaaga    960
tgaaaacggg aactacatca aggtacaagg ccttcca                             997
```

```
<210> SEQ ID NO 66
<211> LENGTH: 870
<212> TYPE: DNA
<213> ORGANISM: Artificial Sequence
<220> FEATURE:
<223> OTHER INFORMATION: 5'-Region of PpBMT2

<400> SEQUENCE: 66
ggccgagcgg gcctagattt tcactacaaa tttcaaaact acgcggattt attgtctcag     60
agagcaattt ggcatttctg agcgtagcag gaggcttcat aagattgtat aggaccgtac    120
caacaaattg ccgaggcaca acacggtatg ctgtgcactt atgtggctac ttccctacaa    180
cggaatgaaa ccttcctctt tccgcttaaa cgagaaagtg tgtcgcaatt gaatgcaggt    240
gcctgtgcgc cttggtgtat tgttttttgag ggcccaattt atcaggcgcc ttttttcttg    300
gttgttttcc cttagcctca agcaaggttg gtctatttca tctccgcttc tataccgtgc    360
ctgatactgt tggatgagaa cacgactcaa cttcctgctg ctctgtattg ccagtgtttt    420
gtctgtgatt tggatcggag tcctccttac ttggaatgat aataatcttg gcggaatctc    480
cctaaacgga ggcaaggatt ctgcctatga tgatctgcta tcattgggaa gcttcaacga    540
catggaggtc gactcctatg tcaccaacat ctacgacaat gctccagtgc taggatgtac    600
ggatttgtct tatcatggat tgttgaaagt caccccaaag catgacttag cttgcgattt    660
ggagttcata agagctcaga ttttggacat tgacgtttac tccgccataa aagacttaga    720
agataaagcc ttgactgtaa aacaaaaggt tgaaaacac tggtttacgt tttatggtag     780
ttcagtcttt ctgcccgaac acgatgtgca ttacctggtt agacgagtca tcttttcggc    840
tgaaggaaag gcgaactctc cagtaacatc                                     870
```

```
<210> SEQ ID NO 67
<211> LENGTH: 1733
<212> TYPE: DNA
<213> ORGANISM: Artificial Sequence
<220> FEATURE:
<223> OTHER INFORMATION: 3'-Region of PpBMT2

<400> SEQUENCE: 67
ccatatgatg ggtgtttgct cactcgtatg gatcaaaatt ccatggtttc ttctgtacaa     60
cttgtacact tatttggact tttctaacgg ttttctggt gatttgagaa gtccttattt    120
tggtgttcgc agcttatccg tgattgaacc atcagaaata ctgcagctcg ttatctagtt    180
tcagaatgtg ttgtagaata caatcaattc tgagtctagt ttgggtgggt cttggcgacg    240
ggaccgttat atgcatctat gcagtgttaa ggtacataga atgaaaatgt aggggttaat    300
cgaaagcatc gttaatttca gtagaacgta gttctattcc ctacccaaat aatttgccaa    360
gaatgcttcg tatccacata cgcagtggac gtagcaaatt tcactttgga ctgtgacctc    420
aagtcgttat cttctacttg gacattgatg gtcattacgt aatccacaaa gaattggata    480
```

```
gcctctcgtt ttatctagtg cacagcctaa tagcacttaa gtaagagcaa tggacaaatt    540
tgcatagaca ttgagctaga tacgtaactc agatcttgtt cactcatggt gtactcgaag    600
tactgctgga accgttacct cttatcattt cgctactggc tcgtgaaact actggatgaa    660
aaaaaaaaaa gagctgaaag cgagatcatc ccattttgtc atcatacaaa ttcacgcttg    720
cagttttgct tcgttaacaa dacaagatgt ctttatcaaa gacccgtttt ttcttcttga    780
agaatacttc cctgttgagc acatgcaaac catatttatc tcagatttca ctcaacttgg    840
gtgcttccaa gagaagtaaa attcttccca ctgcatcaac ttccaagaaa cccgtagacc    900
agtttctctt cagccaaaag aagttgctcg ccgatcaccg cggtaacaga ggagtcagaa    960
ggtttcacac ccttccatcc cgatttcaaa gtcaaagtgc tgcgttgaac caaggttttc   1020
aggttgccaa agcccagtct gcaaaaacta gttccaaatg gcctattaat tcccataaaa   1080
gtgttggcta cgtatgtatc ggtacctcca ttctggtatt tgctattgtt gtcgttggtg   1140
ggttgactag actgaccgaa tccggtcttt ccataacgga gtggaaacct atcactggtt   1200
cggttccccc actgactgag gaagactgga agttggaatt tgaaaaatac aaacaaagcc   1260
ctgagtttca ggaactaaat tctcacataa cattggaaga gttcaagttt atattttcca   1320
tggaatgggg acatagattg ttgggaaggg tcatcggcct gtcgtttgtt cttcccacgt   1380
tttacttcat tgcccgtcga aagtgttcca agatgttgc attgaaactg cttgcaatat   1440
gctctatgat aggattccaa ggtttcatcg gctggtggat ggtgtattcc ggattggaca   1500
aacagcaatt ggctgaacgt aactccaaac caactgtgtc tccatatcgc ttaactaccc   1560
atcttggaac tgcatttgtt atttactgtt acatgattta cacagggctt caagttttga   1620
agaactataa gatcatgaaa cagcctgaag cgtatgttca aattttcaag caaattgcgt   1680
ctccaaaatt gaaaactttc aagagactct cttcagttct attaggcctg gtg           1733

<210> SEQ ID NO 68
<211> LENGTH: 411
<212> TYPE: DNA
<213> ORGANISM: Artificial Sequence
<220> FEATURE:
<223> OTHER INFORMATION: 5'-Region of PpBMT1

<400> SEQUENCE: 68
catatggtga gagccgttct gcacaactag atgttttcga gcttcgcatt gtttcctgca     60
gctcgactat tgaattaaga tttccggata tctccaatct cacaaaaact tatgttgacc    120
acgtgctttc ctgaggcgag gtgttttata tgcaagctgc caaaaatgga aaacgaatgg    180
ccatttttcg cccaggcaaa ttattcgatt actgctgtca taagacagt gttgcaaggc     240
tcacattttt ttttaggatc cgagataaag tgaatacagg acagcttatc tctatatctt    300
gtaccattcg tgaatcttaa gagttcggtt aggggactc tagttgaggg ttggcactca    360
cgtatggctg ggcgcagaaa taaaattcag gcgcagcagc acttatcgat g              411

<210> SEQ ID NO 69
<211> LENGTH: 692
<212> TYPE: DNA
<213> ORGANISM: Artificial Sequence
<220> FEATURE:
<223> OTHER INFORMATION: 3'-Region of PpBMT1

<400> SEQUENCE: 69
gaattcacag ttataaataa aaacaaaaac tcaaaaagtt tgggctccac aaaataactt     60
aatttaaatt tttgtctaat aaatgaatgt aattccaaga ttatgtgatg caagcacagt    120
```

```
atgcttcagc cctatgcagc tactaatgtc aatctcgcct gcgagcgggc ctagattttc      180
actacaaatt tcaaaactac gcggatttat tgtctcagag agcaatttgg catttctgag      240
cgtagcagga ggcttcataa gattgtatag gaccgtacca acaaattgcc gaggcacaac      300
acggtatgct gtgcacttat gtggctactt ccctacaacg gaatgaaacc ttcctctttc      360
cgcttaaacg agaaagtgtg tcgcaattga atgcaggtgc ctgtgcgcct tggtgtattg      420 ttttgaggg cccaatttat caggcgcctt ttttcttggt tgttttccct tagcctcaag       480
caaggttggt ctatttcatc tccgcttcta taccgtgcct gatactgttg gatgagaaca      540
cgactcaact tcctgctgct ctgtattgcc agtgttttgt ctgtgatttg gatcggagtc      600
ctccttactt ggaatgataa taatcttggc ggaatctccc taaacggagg caaggattct      660
gcctatgatg atctgctatc attgggaagc tt                                    692

<210> SEQ ID NO 70
<211> LENGTH: 546
<212> TYPE: DNA
<213> ORGANISM: Artificial Sequence
<220> FEATURE:
<223> OTHER INFORMATION: 5'-Region of PpBMT3

<400> SEQUENCE: 70
gatatctccc tggggacaat atgtgttgca actgttcgtt gttggtgccc cagtccccca       60
accggtacta atcggtctat gttcccgtaa ctcatattcg gttagaacta gaacaataag      120
tgcatcattg ttcaacattg tggttcaatt gtcgaacatt gctggtgctt atatctacag      180
ggaagacgat aagcctttgt acaagagagg taacagacag ttaattggta tttctttggg      240
agtcgttgcc ctctacgttg tctccaagac atactacatt ctgagaaaca gatggaagac      300
tcaaaaatgg gagaagctta gtgaagaaga gaaagttgcc tacttggaca gagctgagaa      360
ggagaacctg ggttctaaga ggctggactt tttgttcgag agttaaactg cataattttt      420
tctaagtaaa tttcatagtt atgaaatttc tgcagcttag tgtttactgc atcgtttact      480
gcatcaccct gtaaataatg tgagcttttt tccttccatt gcttggtatc ttccttgctg      540
ctgttt                                                                 546

<210> SEQ ID NO 71
<211> LENGTH: 378
<212> TYPE: DNA
<213> ORGANISM: Artificial Sequence
<220> FEATURE:
<223> OTHER INFORMATION: 3'-Region of PpBMT3

<400> SEQUENCE: 71
acaaaacagt catgtacaga actaacgcct ttaagatgca gaccactgaa aagaattggg       60
tcccattttt cttgaaagac gaccaggaat ctgtccattt tgtttactcg ttcaatcctc      120
tgagagtact caactgcagt cttgataacg gtgcatgtga tgttctattt gagttaccac      180
atgattttgg catgtcttcc gagctacgtg gtgccactcc tatgctcaat cttcctcagg      240
caatcccgat ggcagacgac aaagaaattt gggtttcatt cccaagaacg agaatatcag      300
attgcgggtg ttctgaaaca atgtacaggc caatgttaat gcttttgtt agagaaggaa       360 caaactttt tgctgagc                                                     378

<210> SEQ ID NO 72
<211> LENGTH: 1043
<212> TYPE: DNA
```

<213> ORGANISM: Artificial Sequence
<220> FEATURE:
<223> OTHER INFORMATION: 5'-Region of PpBMT4

<400> SEQUENCE: 72

```
aagcttgttc accgttggga cttttccgtg gacaatgttg actactccag gagggattcc      60
agctttctct actagctcag caataatcaa tgcagcccca ggcgcccgtt ctgatggctt     120
gatgaccgtt gtattgcctg tcactatagc caggggtagg gtccataaag gaatcatagc     180
agggaaatta aaagggcata ttgatgcaat cactcccaat ggctctcttg ccattgaagt     240
ctccatatca gcactaactt ccaagaagga cccctttcaag tctgacgtga tagagcacgc    300
ttgctctgcc acctgtagtc ctctcaaaac gtcaccttgt gcatcagcaa agactttacc     360
ttgctccaat actatgacgg aggcaattct gtcaaaattc tctctcagca attcaaccaa     420
cttgaaagca aattgctgtc tcttgatgat ggagactttt ttccaagatt gaaatgcaat     480
gtgggacgac tcaattgctt cttccagctc ctcttcggtt gattgaggaa cttttgaaac     540
cacaaaattg gtcgttgggt catgtacatc aaaccattct gtagatttag attcgacgaa     600
agcgttgttg atgaaggaaa aggttggata cggtttgtcg gtctctttgg tatggccggt     660
ggggtatgca attgcagtag aagataattg gacagccatt gttgaaggta gagaaaaggt    720
cagggaactt gggggttatt tataccattt taccccacaa ataacaactg aaaagtaccc     780
attccatagt gagaggtaac cgacggaaaa agacgggccc atgttctggg accaatagaa     840
ctgtgtaatc cattgggact aatcaacaga cgattggcaa tataatgaaa tagttcgttg     900
aaaagccacg tcagctgtct tttcattaac tttggtcgga cacaacattt tctactgttg     960
tatctgtcct actttgctta tcatctgcca cagggcaagt ggatttcctt ctcgcgcggc    1020
tgggtgaaaa cggttaacgt gaa                                           1043
```

<210> SEQ ID NO 73
<211> LENGTH: 695
<212> TYPE: DNA
<213> ORGANISM: Artificial Sequence
<220> FEATURE:
<223> OTHER INFORMATION: 3'-Region of PpBMT4

<400> SEQUENCE: 73

```
gccttggggg acttcaagtc tttgctagaa actagatgag gtcaggccct cttatggttg      60
tgtcccaatt gggcaatttc actcacctaa aaagcatgac aattatttag cgaaataggt     120
agtatatttt ccctcatctc ccaagcagtt tcgtttttgc atccatatct ctcaaatgag     180
cagctacgac tcattagaac cagagtcaag tagggggtgag ctcagtcatc agccttcgtt    240
tctaaaacga ttgagttctt tgttgctac aggaagcgcc ctagggaact ttcgcacttt      300
ggaaatagat tttgatgacc aagagcggga gttgatatta gagaggctgt ccaaagtaca     360
tgggatcagg ccggccaaat tgattggtgt gactaaacca ttgtgtactt ggacactcta     420
ttacaaaagc gaagatgatt tgaagtatta caagtcccga agtgttagag gattctatcg     480
agcccagaat gaaatcatca accgttatca gcagattgat aaactcttgg aaagcggtat     540
cccattttca ttattgaaga actacgataa tgaagatgtg agagacggcg accctctgaa     600
cgtagacgaa gaaacaaatc tacttttggg gtacaataga gaaagtgaat caagggaggt     660
atttgtggcc ataatactca actctatcat taatg                                695
```

<210> SEQ ID NO 74
<211> LENGTH: 937

<212> TYPE: DNA
<213> ORGANISM: Artificial Sequence
<220> FEATURE:
<223> OTHER INFORMATION: 5'-Region of PpPNO1 and PpMNN4

<400> SEQUENCE: 74

```
tcattctata tgttcaagaa aagggtagtg aaaggaaaga aaaggcatat aggcgaggga      60
gagttagcta gcatacaaga taatgaagga tcaatagcgg tagttaaagt gcacaagaaa     120
agagcacctg ttgaggctga tgataaagct ccaattacat tgccacagag aaacacagta    180
acagaaatag gagggatgc accacgagaa gagcattcag tgaacaactt tgccaaattc     240
ataaccccaa gcgctaataa gccaatgtca agtcggcta ctaacattaa tagtacaaca     300
actatcgatt ttcaaccaga tgtttgcaag gactacaaac agacaggtta ctgcggatat    360
ggtgacactt gtaagttttt gcacctgagg atgatttca acagggatg gaaattagat      420
agggagtggg aaaatgtcca aaagaagaag cataatactc tcaaaggggt taaggagatc    480
caaatgttta tgaagatga gctcaaagat atcccgttta atgcattat atgcaaagga     540
gattacaaat cacccgtgaa aacttcttgc aatcattatt tttgcgaaca atgtttcctg    600
caacggtcaa gaagaaaacc aaattgtatt atatgtggca gagacacttt aggagttgct    660
ttaccagcaa agaagttgtc ccaatttctg gctaagatac ataataatga agtaataaa    720
gtttagtaat tgcattgcgt tgactattga ttgcattgat gtcgtgtgat actttcaccg    780
aaaaaaaaca cgaagcgcaa taggagcggt tgcatattag tccccaaagc tatttaattg    840
tgcctgaaac tgtttttta gctcatcaag cataattgta tgcattgcga cgtaaccaac    900
gtttaggcgc agtttaatca tagcccactg ctaagcc                             937
```

<210> SEQ ID NO 75
<211> LENGTH: 1906
<212> TYPE: DNA
<213> ORGANISM: Artificial Sequence
<220> FEATURE:
<223> OTHER INFORMATION: 3'-Region of PpPNO1 and PpMNN4

<400> SEQUENCE: 75

```
cggaggaatg caaataataa tctccttaat tacccactga taagctcaag agacgcggtt     60
tgaaaacgat ataatgaatc atttggattt tataataaac cctgacagtt tttccactgt    120
attgtttaa cactcattgg aagctgtatt gattctaaga agctagaaat caatacggcc     180
atacaaaaga tgacattgaa taagcaccgg cttttttgat tagcatatac cttaaagcat    240
gcattcatgg ctacatagtt gttaaagggc ttcttccatt atcagtataa tgaattacat    300
aatcatgcac ttatatttgc ccatctctgt tctctcactc ttgcctgggt atattctatg    360
aaattgcgta tagcgtgtct ccagttgaac cccaagcttg gcgagtttga agagaatgct    420
aaccttgcgt attccttgct tcaggaaaca ttcaggaga aacaggtcaa gaagccaaac    480
attttgatcc ttcccgagtt agcattgact ggctacaatt tcaaagcca gcagcggata    540
gagcctttt tggaggaaac aaccaaggga gctagtaccc aatgggctca aaaagtatcc   600
aagacgtggg attgctttac tttaatagga tacccagaaa aagtttaga gagccctccc   660
cgtatttaca acagtgcggt acttgtatcg cctcaggaa aagtaatgaa caactacaga   720
aagtccttct tgtatgaagc tgatgaacat tggggatgtt cggaatcttc tgatgggttt   780
caaacagtag atttattaat tgaaggaaag actgtaaaga catcatttgg aatttgcatg   840
gatttgaatc cttataaatt tgaagctcca ttcacagact tcgagttcag tggccattgc   900
```

```
ttgaaaaccg gtacaagact cattttgtgc ccaatggcct ggttgtcccc tctatcgcct      960
tccattaaaa aggatcttag tgatatagag aaaagcagac ttcaaaagtt ctaccttgaa     1020
aaaatagata ccccggaatt tgacgttaat tacgaattga aaaagatga agtattgccc      1080
acccgtatga atgaaacgtt ggaaacaatt gactttgagc cttcaaaacc ggactactct    1140
aatataaatt attggatact aaggtttttt ccctttctga ctcatgtcta taaacgagat    1200
gtgctcaaag agaatgcagt tgcagtctta tgcaaccgag ttggcattga gagtgatgtc    1260
ttgtacggag atcaaccac gattctaaac ttcaatggta agttagcatc gacacaagag     1320
gagctggagt tgtacgggca gactaatagt ctcaaccca gtgtggaagt attggggggcc    1380
cttggcatgg gtcaacaggg aattctagta cgagacattg aattaacata atatacaata   1440
tacaataaac acaataaag aatacaagcc tgacaaaaat tcacaaatta ttgcctagac     1500
ttgtcgttat cagcagcgac ctttttccaa tgctcaattt cacgatatgc cttttctagc   1560
tctgctttaa gcttctcatt ggaattggct aactcgttga ctgcttggtc agtgatgagt    1620
ttctccaagg tccatttctc gatgttgttg ttttcgtttt cctttaatct cttgatataa    1680
tcaacagcct tctttaatat ctgagccttg ttcgagtccc ctgttggcaa cagagcggcc    1740
agttccttta ttccgtggtt tatattttct cttctacgcc tttctacttc tttgtgattc    1800
tctttacgca tcttatgcca ttcttcagaa ccagtggctg gcttaaccga atagccagag    1860
cctgaagaag ccgcactaga agaagcagtg gcattgttga ctatgg                   1906
```

<210> SEQ ID NO 76
<211> LENGTH: 1128
<212> TYPE: DNA
<213> ORGANISM: Artificial Sequence
<220> FEATURE:
<223> OTHER INFORMATION: 5'-Region of PpMNN4L1

<400> SEQUENCE: 76

```
gatctggcca ttgtgaaact tgacactaaa gacaaaactc ttagagtttc caatcactta      60
ggagacgatg tttcctacaa cgagtacgat ccctcattga tcatgagcaa tttgtatgtg     120
aaaaaagtca tcgaccttga caccttggat aaaagggctg gaggaggtgg aaccacctgt    180
gcaggcggtc tgaaagtgtt caagtacgga tctactacca aatatacatc tggtaacctg    240
aacgcgtca ggttagtata ctggaacgaa ggaaagttgc aaagctccaa atttgtggtt     300
cgatcctcta attactctca aaagcttgga ggaaacagca acgccgaatc aattgacaac    360
aatggtgtgg ttttgcctc agctggagac tcaggcgcat ggattctttc caagctacaa    420
gatgttaggg agtaccagtc attcactgaa aagctaggtg aagctacgat gagcattttc   480
gatttccacg gtcttaaaca ggagacttct actacagggc ttggggtagt tggtatgatt    540
cattcttacg acggtgagtt caaacagttt ggtttgttca ctccaatgac atctattcta    600
caaagacttc aacgagtgac caatgtgaaa tggtgtgtag cgggttgcga agatggggat    660
gtggacactg aaggagaaca cgaattgagt gatttggaac aactgcatat gcatagtgat    720
tccgactagt caggcaagag agagccctca aatttacctc tctgccctc ctcactcctt     780
ttggtacgca taattgcagt ataaagaact tgctgccagc cagtaatctt atttcatacg    840
cagttctata tagcacataa tcttgcttgt atgtatgaaa tttaccgcgt tttagttgaa    900
attgtttatg ttgtgtgcct tgcatgaaat ctctcgttag ccctatcctt acatttaact    960
ggtctcaaaa cctctaccaa ttccattgct gtacaacaat atgaggcggc attactgtag   1020
ggttggaaaa aaattgtcat tccagctaga gatcacacga cttcatcacg cttattgctc    1080
```

```
ctcattgcta aatcatttac tcttgacttc gacccagaaa agttcgcc        1128
```

<210> SEQ ID NO 77
<211> LENGTH: 1231
<212> TYPE: DNA
<213> ORGANISM: Artificial Sequence
<220> FEATURE:
<223> OTHER INFORMATION: 3'-Region of PpMNN4L1

<400> SEQUENCE: 77

```
gcatgtcaaa cttgaacaca acgactagat agttgttttt tctatataaa acgaaacgtt    60
atcatcttta ataatcattg aggtttaccc ttatagttcc gtattttcgt ttccaaactt   120
agtaatcttt tggaaatatc atcaaagctg gtgccaatct tcttgtttga agtttcaaac   180
tgctccacca agctacttag agactgttct aggtctgaag caacttcgaa cacagagaca   240
gctgccgccg attgttcttt tttgtgtttt tcttctggaa gaggggcatc atcttgtatg   300
tccaatgccc gtatcctttc tgagttgtcc gacacattgt ccttcgaaga gtttcctgac   360
attgggcttc ttctatccgt gtattaattt tgggttaagt tcctcgtttg catagcagtg   420
gatacctcga tttttttggc tcctatttac ctgacataat attctactat aatccaactt   480
ggacgcgtca tctatgataa ctaggctctc ctttgttcaa aggggacgtc ttcataatcc   540
actggcacga agtaagtctg caacgaggcg gcttttgcaa cagaacgata gtgtcgtttc   600
gtacttggac tatgctaaac aaaaggatct gtcaaacatt tcaaccgtgt ttcaaggcac   660
tctttacgaa ttatcgacca agaccttcct agacgaacat ttcaacatat ccaggctact   720
gcttcaaggt ggtgcaaatg ataaaggtat agatattaga tgtgtttggg acctaaaaca   780
gttcttgcct gaagattccc ttgagcaaca ggcttcaata gccaagttag agaagcagta   840
ccaaatcggt aacaaaaggg ggaagcatat aaaaccttta ctattgcgac aaaatccatc   900
cttgaaagta aagctgtttg ttcaatgtaa agcatacgaa acgaaggagg tagatcctaa   960
gatggttaga gaacttaacg ggacatactc cagctgcatc ccatattacg atcgctggaa  1020
gacttttttc atgtacgtat cgcccaccaa cctttcaaag caagctaggt atgattttga  1080
cagttctcac aatccattgg ttttcatgca acttgaaaaa acccaactca aacttcatgg  1140
ggatccatac aatgtaaatc attacgagag ggcgaggttg aaaagtttcc attgcaatca  1200
cgtcgcatca tggctactga aaggccttaa c                                 1231
```

<210> SEQ ID NO 78
<211> LENGTH: 1815
<212> TYPE: DNA
<213> ORGANISM: Artificial Sequence
<220> FEATURE:
<223> OTHER INFORMATION: PpTRP2 gene integration locus

<400> SEQUENCE: 78

```
taatggccaa acggtttctc aattactata tactactaac catttacctg tagcgtattt    60
cttttccctc ttcgcgaaag ctcaagggca tcttcttgac tcatgaaaaa tatctggatt   120
tcttctgaca gatcatcacc cttgagccca actctctagc ctatgagtgt aagtgatagt   180
catcttgcaa cagattattt tggaacgcaa ctaacaaagc agatacaccc ttcagcagaa   240
tcctttctgg atattgtgaa gaatgatcgc caaagtcaca gtcctgagac agttcctaat   300
ctttacccca tttacaagtt catccaatca gacttcttaa cgcctcatct ggcttatatc   360
aagcttacca acagttcaga aactcccagt ccaagtttct tgcttgaaag tgcgaagaat   420
```

```
ggtgacaccg ttgacaggta cacctttatg ggacattccc ccagaaaaat aatcaagact    480
gggcctttag agggtgctga agttgacccc ttggtgcttc tggaaaaaga actgaagggc    540
accagacaag cgcaacttcc tggtattcct cgtctaagtg gtggtgccat aggatacatc    600
tcgtacgatt gtattaagta ctttgaacca aaaactgaaa gaaaactgaa agatgttttg    660
caacttccgg aagcagcttt gatgttgttc gacacgatcg tggcttttga caatgtttat    720
caaagattcc agtaattgg aaacgtttct ctatccgttg atgactcgga cgaagctatt    780
cttgagaaat attataagac aagagaagaa gtggaaaaga tcagtaaagt ggtatttgac    840
aataaaactg ttccctacta tgaacagaaa gatattattc aaggccaaac gttcacctct    900
aatattggtc aggaagggta tgaaaaccat gttcgcaagc tgaaagaaca tattctgaaa    960
ggagacatct tccaagctgt tccctctcaa agggtagcca ggccgacctc attgcaccct   1020
ttcaacatct atcgtcattt gagaactgtc aatccttctc catacatgtt ctatattgac   1080
tatctagact tccaagttgt tggtgcttca cctgaattac tagttaaatc cgacaacaac   1140
aacaaaatca tcacacatcc tattgctgga actcttccca gaggtaaaac tatcgaagag   1200
gacgacaatt atgctaagca attgaagtcg tctttgaaag acagggccga gcacgtcatg   1260
ctggtagatt tggccagaaa tgatattaac cgtgtgtgtg agcccaccag taccacggtt   1320
gatcgtttat tgactgtgga gatttttct catgtgatgc atcttgtgtc agaagtcagt   1380
ggaacattga gaccaaacaa gactcgcttc gatgctttca gatccatttt cccagcagga   1440
accgtctccg gtgctccgaa ggtaagagca atgcaactca taggagaatt ggaaggagaa   1500
aagagaggtg tttatgcggg ggccgtagga cactggtcgt acgatggaaa atcgatggac   1560
acatgtattg ccttaagaac aatggtcgtc aaggacggtg tcgcttacct tcaagccgga   1620
ggtgaattg tctacgattc tgaccccct acgagtaca tcgaaaccat gaacaaaatg   1680
agatccaaca ataacaccat cttggaggct gagaaaatct ggaccgatag gttggccaga   1740
gacgagaatc aaagtgaatc cgaagaaaac gatcaatgaa cggaggacgt aagtaggaat   1800
ttatggtttg gccat                                                    1815
```

<210> SEQ ID NO 79
<211> LENGTH: 1373
<212> TYPE: DNA
<213> ORGANISM: Artificial Sequence
<220> FEATURE:
<223> OTHER INFORMATION: 5'-Region of PpARG1

<400> SEQUENCE: 79

```
gatctggcct tccctgaatt tttacgtcca gctatacgat ccgttgtgac tgtatttcct     60
gaaatgaagt ttcaacctaa agttttggtt gtacttgctc cacctaccac ggaaactaat    120
atcgaaacca atgaaaaagt agaactggaa tcgtcaatcg aaattcgcaa ccaagtggaa    180
cccaaagact tgaatctttc taaagtctat tctagtgaca ctaatggcaa cagaagattt    240
gagctgactt tcaaatgaa tctcaataat gcaatatcaa catcagacaa tcaatgggct    300
ttgtctagtg acacaggatc aattatagta gtgtcttctg caggaagaat aacttccccg    360
atcctagaag tcggggcatc cgtctgtgtc ttaagatcgt acaacgaaca cctttttggca   420
ataacttgtg aaggaacatg cttttcatgg aatttaaaga agcaagaatg tgttctaaac    480
agcatttcat tagcacctat agtcaattca cacatgctag ttaagaaagt tggagatgca    540
aggaactatt ctattgtatc tgccgaagga gacaacaatc cgttacccca gattctagac    600
tgcgaacttt ccaaaaatgg cgctccaatt gtggctctta gcacgaaaga catctactct    660
```

```
tattcaaaga aaatgaaatg ctggatccat ttgattgatt cgaaatactt tgaattgttg    720
ggtgctgaca atgcactgtt tgagtgtgtg aagcgctag aaggtccaat tggaatgcta    780
attcatagat tggtagatga gttcttccat gaaaacactg ccggtaaaaa actcaaactt    840
tacaacaagc gagtactgga ggacctttca aattcacttg aagaactagg tgaaaatgcg    900
tctcaattaa gagagaaact tgacaaactc tatggtgatg aggttgaggc ttcttgacct    960
cttctctcta tctgcgtttc tttttttttt tttttttttt tttttttcag ttgagccaga   1020
ccgcgctaaa cgcataccaa ttgccaaatc aggcaattgt gagacagtgg taaaaaagat   1080
gcctgcaaag ttagattcac acagtaagag agatcctact cataaatgag gcgcttattt   1140
agtagctagt gatagccact gcggttctgc tttatgctat ttgttgtatg ccttactatc   1200
tttgtttggc tccttttctt tgacgttttc cgttggaggg actccctatt ctgagtcatg   1260
agccgcacag attatcgccc aaaattgaca aaatcttctg gcgaaaaaag tataaaagga   1320 gaaaaagct cacccttttc cagcgtagaa agtatatatc agtcattgaa gac           1373
```

<210> SEQ ID NO 80
<211> LENGTH: 1470
<212> TYPE: DNA
<213> ORGANISM: Artificial Sequence
<220> FEATURE:
<223> OTHER INFORMATION: 3'-Region of PpARG1

<400> SEQUENCE: 80

```
gggactttaa ctcaagtaaa aggatagttg tacaattata tatacgaaga ataaatcatt     60
acaaaaagta ttcgtttctt tgattcttaa caggattcat tttctgggtg tcatcaggta    120
cagcgctgaa tatcttgaag ttaacatcga gctcatcatc gacgttcatc acactagcca    180
cgtttccgca acggtagcaa taattaggag cggaccacac agtgacgaca tctttctctt    240
tgaaatggta tctgaagcct tccatgacca attgatgggc tctagcgatg agttgcaagt    300
tattaatgtg gttgaactca cgtgctactc gagcaccgaa taaccagcca gctccacgag    360
gagaaacagc ccaactgtcg acttcatctg ggtcagacca aaccaagtca caaaatcctc    420
cttcatgagg gacctcttgc gctcggctga gaactctgat ttgatctaac atgcgaatat    480
cgggagagag accaccatgg atacataata ttttaccatc aatgatggca ctaagggtta    540
aaaagtcgaa cacctggcaa cagtacttcc agacagtggt ggaaccatat ttattgagac    600
attcctcata aaatccataa acctgagtga tctgtctgga ttcatgattt ccccttacca    660
atgtgatatg ttgaggaaac ttaattttta aaatcatgag taacgtgaac gtctccaacg    720
agaaatagcc tctatccaca tagtctccta ggaagatata gttctgtttt attccattag    780
aggaggatcc gggaaaccca ccactaatct tgaaagttc cagtagatcg tgaaattggc    840
cgtgaatatc tccgcatact gtcactggac tctgcactgg ctgtatattg gattcctcca    900
tcagcaaatc cttcacccgt tcgcaaagat gcttcatatc attttcactt aaagccttgc    960
agcttttgac ttcttcaaac cactgatctg gtcctctttc tggcatgatt aaggtctata   1020
atatttctga gctgagatgt aaaaaaaaat aataaaaatg gggagtgaaa agtgtgtag   1080 cttttaggag tttgggattg atacccaaa atgatcttta tgagaattaa aaggtagata   1140
cgcttttaat aagaacacct atctatagta ctttgtggtc ttgagtaatt gagatgttca   1200
gcttctgagg tttgccgtta ttctgggata gtagtgcgcg accaaacaac ccgccaggca   1260
aagtgtgttg tgctcgaaga cgattgccag aagagtaagt ccgtcctgcc tcagatgtta   1320
```

```
cacactttct tccctagaca gtcgatgcat catcggattt aaacctgaaa ctttgatgcc    1380
atgatacgcc tagtcacgtc gactgagatt ttagataagc cccgatccct ttagtacatt    1440
cctgttatcc atggatggaa tggcctgata                                     1470

<210> SEQ ID NO 81
<211> LENGTH: 1854
<212> TYPE: DNA
<213> ORGANISM: Artificial Sequence
<220> FEATURE:
<223> OTHER INFORMATION: PpARG1 auxotrophic marker

<400> SEQUENCE: 81
cagttgagcc agaccgcgct aaacgcatac caattgccaa atcaggcaat tgtgagacag      60
tggtaaaaaa gatgcctgca aagttagatt cacacagtaa gagagatcct actcataaat     120
gaggcgctta tttagtagct agtgatagcc actgcggttc tgctttatgc tatttgttgt     180
atgccttact atctttgttt ggctcctttt tcttgacgtt ttccgttgga gggactccct     240
attctgagtc atgagccgca cagattatcg cccaaaattg acaaaatctt ctggcgaaaa     300
aagtataaaa ggagaaaaaa gctcacccct ttccagcgta gaaagtatat atcagtcatt     360
gaagactatt atttaaataa cacaatgtct aaaggaaaag tttgtttggc ctactccggt     420
ggtttggata cctccatcat cctagcttgg ttgttggagc agggatacga agtcgttgcc     480
tttttagcca acattggtca agaggaagac tttgaggctg ctagagagaa agctctgaag     540
atcggtgcta ccaagtttat cgtcagtgac gttaggaagg aatttgttga ggaagttttg     600
ttcccagcag tccaagttaa cgctatctac gagaacgtct acttactggg tacctctttg     660
gccagaccag tcattgccaa ggcccaaata gaggttgctg aacaagaagg ttgttttgct     720
gttgcccacg gttgtaccgg aaagggtaac gatcaggtta gatttgagct ttcctttat      780 gctctgaagc ctgacgttgt ctgtatcgcc ccatggagag acccagaatt cttcgaaaga     840
ttcgctggta gaaatgactt gctgaattac gctgctgaga aggatattcc agttgctcag     900
actaaagcca agccatggtc tactgatgag aacatggctc acatctcctt cgaggctggt     960
attctagaag atccaaacac tactcctcca aaggacatgt ggaagctcac tgttgaccca    1020
gaagatgcac cagacaagcc agagttcttt gacgtccact ttgagaaggg taagccagtt    1080
aaattagttc tcgagaacaa aactgaggtc accgatccgg ttgagatctt tttgactgct    1140
aacgccattg ctagaagaaa cggtgttggt agaattgaca ttgtcgagaa cagattcatc    1200
ggaatcaagt ccagaggttg ttatgaaact ccaggtttga ctctactgag aaccactcac    1260
atcgacttgg aaggtcttac cgttgaccgt gaagttagat cgatcagaga cacttttgtt    1320
accccaacct actctaagtt gttatacaac gggttgtact ttaccccaga aggtgagtac    1380
gtcagaacta tgattcagcc ttctcaaaac accgtcaacg tgttgttag agccaaggcc    1440 tacaaaggta atgtgtataa cctaggaaga tactctgaaa ccgagaaatt gtacgatgct    1500
accgaatctt ccatggatga gttgaccgga ttccaccctc aagaagctgg aggatttatc    1560
acaacacaag ccatcagaat caagaagtac ggagaaagtg tcagagagaa gggaaagttt    1620
ttgggacttt aactcaagta aaaggatagt tgtacaatta tatatacgaa gaataaatca    1680
ttacaaaaag tattcgtttc tttgattctt aacaggattc attttctggg tgtcatcagg    1740
tacagcgctg aatatcttga agttaacatc gagctcatca tcgacgttca tcacactagc    1800
cacgtttccg caacggtagc aataattagg agcggaccac acagtgacga catc           1854
```

<210> SEQ ID NO 82
<211> LENGTH: 1250
<212> TYPE: DNA
<213> ORGANISM: Artificial Sequence
<220> FEATURE:
<223> OTHER INFORMATION: 5'-region of PpADE1

<400> SEQUENCE: 82

```
gagtcggcca agagatgata actgttacta agcttctccg taattagtgg tattttgtaa      60
cttttaccaa taatcgttta tgaatacgga tattttttcga ccttatccag tgccaaatca    120
cgtaacttaa tcatggttta aatactccac ttgaacgatt cattattcag aaaaaagtca    180
ggttggcaga aacacttggg cgctttgaag agtataagag tattaagcat taaacatctg    240
aactttcacc gccccaatat actactctag gaaactcgaa aaattccttt ccatgtgtca    300
tcgcttccaa cacactttgc tgtatccttc caagtatgtc cattgtgaac actgatctgg    360
acggaatcct acctttaatc gccaaaggaa aggttagaga catttatgca gtcgatgaga    420
acaacttgct gttcgtcgca actgaccgta tctccgctta cgatgtgatt atgacaaacg    480
gtattcctga taagggaaag attttgactc agctctcagt tttctggttt gattttttgg    540
caccctacat aaagaatcat ttggttgctt ctaatgacaa ggaagtcttt gctttactac    600
catcaaaact gtctgaagaa aaatacaaat ctcaattaga gggacgatcc ttgatagtaa    660
aaaagcacag actgatacct ttggaagcca ttgtcagagg ttacatcact ggaagtgcat    720
ggaaagagta caagaactca aaaactgtcc atggagtcaa ggttgaaaac gagaaccttc    780
aagagagcga cgccttttcca actccgattt tcacaccttc aacgaaagct gaacagggtg    840
aacacgatga aaacatctct attgaacaag ctgctgagat tgtaggtaaa gacatttgtg    900
agaaggtcgc tgtcaaggcg gtcgagttgt attctgctgc aaaaaacctc gccctttga    960
aggggatcat tattgctgat acgaaaattcg aatttggact ggacgaaaac aatgaattgg   1020
tactagtaga tgaagttttta actccagatt cttctagatt ttggaatcaa aagacttacc   1080
aagtgggtaa atcgcaagag agttacgata agcagtttct cagagattgg ttgacggcca   1140
acggattgaa tggcaaagag ggcgtagcca tggatgcaga aattgctatc aagagtaaag   1200
aaaagtatat tgaagcttat gaagcaatta ctggcaagaa atgggcttga              1250
```

<210> SEQ ID NO 83
<211> LENGTH: 882
<212> TYPE: DNA
<213> ORGANISM: Artificial Sequence
<220> FEATURE:
<223> OTHER INFORMATION: 3'-region of PpADE1

<400> SEQUENCE: 83

```
atgattagta ccctcctcgc cttttttcaga catctgaaat ttcccttatt cttccaattc      60
catataaaat cctatttagg taattagtaa acaatgatca taaagtgaaa tcattcaagt    120
aaccattccg tttatcgttg atttaaaatc aataacgaat gaatgtcggt ctgagtagtc    180
aatttgttgc cttggagctc attggcaggg ggtcttttgg ctcagtatgg aaggttgaaa    240
ggaaaacaga tggaaagtgg ttcgtcagaa aagaggtatc ctacatgaag atgaatgcca    300
aagagatatc tcaagtgata gctgagttca gaattcttag tgagttaagc catcccaaca    360
ttgtgaagta ccttcatcac gaacatattt ctgagaataa aactgtcaat ttatacatgg    420
aatactgtga tggtggagat ctctccaagc tgattcgaac acatagaagg aacaaagagt    480
acatttcaga agaaaaaata tggagtattt ttacgcaggt tttattagca ttgtatcgtt    540
```

| | |
|---|---:|
| gtcattatgg aactgatttc acggcttcaa aggagtttga atcgctcaat aaaggtaata | 600 |
| gacgaaccca gaatccttcg tgggtagact cgacaagagt tattattcac agggatataa | 660 |
| aacccgacaa catctttctg atgaacaatt caaaccttgt caaactggga gattttggat | 720 |
| tagcaaaaat tctggaccaa gaaaacgatt ttgccaaaac atacgtcggt acgccgtatt | 780 |
| acatgtctcc tgaagtgctg ttggaccaac cctactcacc attatgtgat atatggtctc | 840 |
| ttgggtgcgt catgtatgag ctatgtgcat tgaggcctcc tt | 882 |

<210> SEQ ID NO 84
<211> LENGTH: 909
<212> TYPE: DNA
<213> ORGANISM: Artificial Sequence
<220> FEATURE:
<223> OTHER INFORMATION: 5'-region of MET16

<400> SEQUENCE: 84

| | |
|---|---:|
| gggtgggcct ggtaatgttc actcctagga actactagaa aaactgtgct aaacggatta | 60 |
| cgtaattatt atacaaattc tctatggtct atggtacata tgggctggtt caataatgaa | 120 |
| tctatgaaga atttgtgccc atggggaccg tttctataaa cgttctcttc tttatgtttt | 180 |
| ccacctgctc tttgagttcc ggaaattcgt tgacaatctt ttgtcccaat gtcgattggg | 240 |
| cgtatttaaa gcccagctgt tttcctctga gaaattgatt caacttcctc accacctcca | 300 |
| caaactcacg cgtgtatata tcagggtttc taccgtcttc gatataattg actacgtcca | 360 |
| cggggatggg aatgttcaaa tctgtgttgt ggagcttttg caagtgctct acaaccttgt | 420 |
| taatgttgtt ggaaagaccc aattgacttt ccgctgtacc ggcgtaatcg tgcacctgaa | 480 |
| cacccaaatg gatgagggtt tcgatgagtt gacttagttc attttcaact tgatctaatg | 540 |
| ttgtcgcagg tgcactcata cttgtcatgg agaatgaaag taagttgata gagagcagac | 600 |
| ttcgaggatg ggatgaactt gattaggtaa tctttgacaa tgtcttagag gtaggcagag | 660 |
| gatgctggaa aaaaaaatt gaaaacgccc aagcttccag ctttgcaagg aaagaagaaa | 720 |
| agggagttgc cagcacgaaa tcggcttcct ccgaaaggtt cacaattgca gaattgtcac | 780 |
| cattcaaatg cctttaccct tcatctgtgg tacctcaggc taagaacggg tcacgtgata | 840 |
| tttcgacact catcgccaca atatgtacta gcaagaactt ttcagattta gtaatccgtt | 900 |
| cgaaacggg | 909 |

<210> SEQ ID NO 85
<211> LENGTH: 825
<212> TYPE: DNA
<213> ORGANISM: Artificial Sequence
<220> FEATURE:
<223> OTHER INFORMATION: 3'-region of MET16

<400> SEQUENCE: 85

| | |
|---|---:|
| ctagatttgc acaatatttg aaagctcagc aaaacatatg aatataattt ttttttttctc | 60 |
| tacactattt atcctgtaag tttctgtttc cccatgtagg atcttttttct ccttctctgt | 120 |
| ctcccatttt ttttgttccc tgtagtcttg ccttgcctga gatgcgagct cgtccgccca | 180 |
| tccagtcgtg tgaagggcct agcttttcaa aaagaaaata cctcccgcta aggaggcgt | 240 |
| tgcccccttct atcagtagtg tcgtaaccaa ttttcacaaa caataaaaaa aggacaccaa | 300 |
| caacgaaatc aactatttac acacatccag atccgtcccc ctccccatcc aagagttaaa | 360 |
| gacaaatatg gctgttaata atccgtctga atttagaaag aagttggtcg tagtaggaga | 420 |
| tggtgcttgc ggtaaaactt gtctattgat ggtgtttgcc gagggcgagt tccctccatc | 480 |

```
ttatgttcca actgtttttg agaactatgc caccccagta gaggttgaca acagaatagt    540
acaactcact ctatgggata ctgccggaca ggaagattat gatagactga gacctctttc    600
ctatcccgat gccaatgtgg tcttgatttg ttttgctatt gacattcctg acaccttaga    660
taacgttcaa gagaagtgga ttagtgaggt gttgcatttc tgtcctggag tccctatcat    720
tttagttggt tgtaaacttg acttgagaaa cgatccagag gttatccgtg aattacaagc    780
tgttggaaag caaccagtct ccaccagtga gggtcaggcc gttgc                    825
```

<210> SEQ ID NO 86  
<211> LENGTH: 1796  
<212> TYPE: DNA  
<213> ORGANISM: Artificial Sequence  
<220> FEATURE:  
<223> OTHER INFORMATION: PpMET16 auxotrophic marker

<400> SEQUENCE: 86

```
caacttcctc accacctcca caaactcacg cgtgtatata tcagggtttc taccgtcttc     60
gatataattg actacgtcca cggggatggg aatgttcaaa tctgtgttgt ggagcttttg    120
caagtgctct acaaccttgt taatgttgtt ggaaagaccc aattgacttt ccgctgtacc    180
ggcgtaatcg tgcacctgaa cacccaaatg gatgagggtt tcgatgagtt gacttagttc    240
attttcaact tgatctaatg ttgtcgcagg tgcactcata cttgtcatgg agaatgaaag    300
taagttgata gagagcagac ttcgaggatg ggatgaactt gattaggtaa tctttgacaa    360
tgtcttagag gtaggcagag gatgctggaa aaaaaaatt gaaaacgccc aagcttccag    420 cttttgcaagg aaagaagaaa agggagttgc cagcacgaaa tcggcttcct ccgaaaggtt    480
cacaattgca gaattgtcac cattcaaatg cctttaccct tcatctgtgg tacctcaggc    540
taagaacggg tcacgtgata tttcgacact catcgccaca atatgtacta gcaagaactt    600
ttcagattta gtaatccgtt cgaaacggga aaaatgtttt tacccttct atcaactgct    660 aatctttcta ggtttatact gccagcagcc cgttccagat accaacatgc cattcactat    720
aggccagtca aaaaccagtt tgaacctctc caaggtccaa gtggaccacc ttaacctttc    780
tcttcagaat ctcagtccag aagaaatcat acaatggtct atcattaccct tcccacacct    840 gtatcaaact acggcattcg gattgactgg gttgtgtata actgacatgg ttcacaaaat    900
aacagccaaa gagggcaaaa agcatgctat tgacttgatt ttcatagaca ccttacatca    960 tttttccacag actttagatc tcgttgaacg agtcaaagat aaataccact gcaatgttca   1020
tgtcttcaaa ccacagaatg ccactactga gctcgagttt ggggcgcaat atggcgaaaa   1080
cttatgggaa acagatgata acaagtatga ctacctcgta aaagttgaac cctcacaacg   1140
tgcctaccat gcattagacg tctgcgccgt cttcacagga agaagacggt ctcaaggtgg   1200
taaaagggga gaattgcccg tgattgaaat tgatgaaatt tctcaggtgg tcaagattaa   1260
tccgttagca tcctgggggt ttgaacaagt tcaaaactat atccaagcta atagcgttcc   1320
atacaacgaa ttgctggatt tgggatacaa gtcagttgga gattaccatt ccacacaacc   1380
cactaaaaat ggtgaagatg aaagagcagg caggtggaga ggtaaacaaa agagtgagtg   1440
tggtatccac gaagcttcta gatttgcaca atatttgaaa gctcagcaaa acatatgaat   1500
ataatttttt ttttctctac actatttatc ctgtaagttt ctgtttcccc atgtaggatc   1560
tttttctcct tctctgtctc ccatttttt tgttccctgt agtcttgcct tgcctgagat   1620
gcgagctcgt ccgcccatcc agtcgtgtga agggcctagc ttttcaaaaa gaaaatacct   1680
```

```
cccgctaaag gaggcgttgc cccttctatc agtagtgtcg taaccaattt tcacaaacaa    1740
taaaaaaagg acaccaacaa cgaaatcaac tatttacaca catccagatc cgtccc        1796

<210> SEQ ID NO 87
<211> LENGTH: 461
<212> TYPE: DNA
<213> ORGANISM: Artificial Sequence
<220> FEATURE:
<223> OTHER INFORMATION: 5'-Region of PpHIS1

<400> SEQUENCE: 87
taactggccc tttgacgttt ctgacaatag ttctagagga gtcgtccaaa aactcaactc      60
tgacttgggt gacaccacca cgggatccgg ttcttccgag gaccttgatg accttggcta    120
atgtaactgg agttttagta tccatttaa gatgtgtgtt tctgtaggtt ctgggttgga    180
aaaaaatttt agacaccaga agagaggagt gaactggttt gcgtgggttt agactgtgta    240
aggcactact ctgtcgaagt tttagatagg ggttacccgc tccgatgcat gggaagcgat    300
tagcccggct gttgccgtt tggttttga agggtaattt tcaatatctc tgtttgagtc    360
atcaatttca tattcaaaga ttcaaaaaca aatctggtc caaggagcgc atttaggatt    420
atggagttgg cgaatcactt gaacgataga ctattatttg c                        461

<210> SEQ ID NO 88
<211> LENGTH: 1841
<212> TYPE: DNA
<213> ORGANISM: Artificial Sequence
<220> FEATURE:
<223> OTHER INFORMATION: 3'-Region of PpHIS1

<400> SEQUENCE: 88
gtgacattct tgtctttgag atcagtaatt gtagagcata gatagaataa tattcaagac      60
caacggcttc tcttcggaag ctccaagtag cttatagtga tgagtaccgg catatattta    120
taggcttaaa atttcgaggg ttcactatat tcgtttagtg ggaagagttc ctttcactct    180
tgttatctat attgtcagcg tggactgttt ataactgtac caacttagtt tctttcaact    240
ccaggttaag agacataaat gtcctttgat gctgacaata atcagtggaa ttcaaggaag    300
gacaatcccg acctcaatct gttcattaat gaagagttcg aatcgtcctt aaatcaagcg    360
ctagactcaa ttgtcaatga gaaccctttc tttgaccaag aaactataaa tagatcgaat    420
gacaaagttg gaaatgagtc cattagctta catgatattg agcaggcaga ccaaaataaa    480
ccgtcctttg agagcgatat tgatggttcg gcgccgttga taagagacga caaattgcca    540
aagaaacaaa gctgggggct gagcaatttt ttttcaagaa gaaatagcat atgtttacca    600
ctacatgaaa atgattcaag tgttgttaag accgaaagat ctattgcagt gggaacaccc    660
catcttcaat actgcttcaa tggaatctcc aatgccaagt acaatgcatt tacctttttc    720
ccagtcatcc tatacgagca attcaaattt tttttcaatt tatactttac tttagtggct    780
ctctctcaag cgataccgca acttcgcatt ggatatcttt cttcgtatgt cgtcccactt    840
ttgtttgtac tcatagtgac catgtcaaaa gaggcgatgg atgatattca acgccgaaga    900
agggatagag aacagaacaa tgaaccatat gaggttctgt ccagcccatc accagttttg    960
tccaaaaact taaatgtgg tcacttggtt cgattgcata agggaatgag agtgcccgca    1020
gatatggttc ttgtccagtc aagcgaatcc accggagagt catttatcaa gacagatcag    1080
ctggatggtg agactgattg gaagcttcgg attgttctc cagttacaca atcgttacca    1140
atgactgaac ttcaaaatgt cgccatcact gcaagcgcac cctcaaaatc aattcactcc    1200
```

```
tttcttggaa gattgaccta caatgggcaa tcatatggtc ttacgataga caacacaatg    1260
tggtgtaata ctgtattagc ttctggttca gcaattggtt gtataattta cacaggtaaa    1320
gatactcgac aatcgatgaa cacaactcag cccaaactga aaacgggctt gttagaactg    1380
gaaatcaata gtttgtccaa gatcttatgt gtttgtgtgt ttgcattatc tgtcatctta    1440
gtgctattcc aaggaatagc tgatgattgg tacgtcgata tcatgcggtt tctcattcta    1500
ttctccacta ttatcccagt gtctctgaga gttaaccttg atcttggaaa gtcagtccat    1560
gctcatcaaa tagaaactga tagctcaata cctgaaaccg ttgttagaac tagtacaata    1620
ccggaagacc tgggaagaat tgaataccta ttaagtgaca aaactggaac tcttactcaa    1680
aatgatatgg aaatgaaaaa actacaccta ggaacagtct cttatgctgg tgataccatg    1740
gatattattt ctgatcatgt taaaggtctt aataacgcta aacatcgag gaaagatctt     1800 ggtatgagaa taagagattt ggttacaact ctggccatct g                        1841
```

<210> SEQ ID NO 89
<211> LENGTH: 1729
<212> TYPE: DNA
<213> ORGANISM: Artificial Sequence
<220> FEATURE:
<223> OTHER INFORMATION: PpHIS1 auxotrophic marker

<400> SEQUENCE: 89

```
caagttgcgt ccggtatacg taacgtctca cgatgatcaa agataatact taatcttcat    60
ggtctactga ataactcatt taaacaattg actaattgta cattatattg aacttatgca    120
tcctattaac gtaatcttct ggcttctctc tcagactcca tcagacacag aatatcgttc    180
tctctaactg gtcctttgac gtttctgaca atagttctag aggagtcgtc caaaaactca    240
actctgactt gggtgacacc accacgggat ccggttcttc cgaggacctt gatgaccttg    300
gctaatgtaa ctggagtttt agtatccatt ttaagatgtg tgtttctgta ggttctgggt    360
tggaaaaaaa ttttagacac cagaagagag gagtgaactg gtttgcgtgg gtttagactg    420
tgtaaggcac tactctgtcg aagttttaga taggggttac ccgctccgat gcatgggaag    480
cgattagccc ggctgttgcc cgtttggttt ttgaagggta atttcaata tctctgtttg     540 agtcatcaat ttcatattca aagattcaaa aacaaaatct ggtccaagga gcgcatttag    600
gattatggag ttggcgaatc acttgaacga tagactatta tttgctgttc ctaaagaggg    660
cagattgtat gagaaatgcg ttgaattact taggggatca gatattcagt ttcgaagatc    720
cagtagattg gatatagctt tgtgcactaa cctgccoctg gcattggttt tccttccagc    780
tgctgacatt cccacgtttg taggagaggg taaatgtgat ttgggtataa ctggtattga    840
ccaggttcag gaaagtgacg tagatgtcat acctttatta gacttgaatt tcggtaagtg    900
caagttgcag attcaagttc ccgagaatgg tgacttgaaa gaacctaaac agctaattgg    960
taaagaaatt gttcctcct ttactagctt aaccaccagg tactttgaac aactggaagg    1020
agttaagcct ggtgagccac taaagacaaa aatcaaatat gttggagggt ctgttgaggc    1080
ctcttgtgcc ctaggagttg ccgatgctat tgtggatctt gttgagagtg agaaaccat    1140 gaaagcggca gggctgatcg atattgaaac tgttctttct acttccgctt acctgatctc    1200
ttcgaagcat cctcaacacc cagaactgat ggatactatc aaggagagaa ttgaaggtgt    1260
actgactgct cagaagtatg tcttgtgtaa ttacaacgca cctagaggta accttcctca    1320
gctgctaaaa ctgactccag gcaagagagc tgctaccgtt tctccattag atgaagaaga    1380
```

```
ttgggtggga gtgtcctcga tggtagagaa gaaagatgtt ggaagaatca tggacgaatt   1440
aaagaaacaa ggtgccagtg acattcttgt ctttgagatc agtaattgta gagcatagat   1500
agaataatat tcaagaccaa cggcttctct tcggaagctc caagtagctt atagtgatga   1560
gtaccggcat atatttatag gcttaaaatt tcgagggttc actatattcg tttagtggga   1620
agagttcctt tcactcttgt tatctatatt gtcagcgtgg actgtttata actgtaccaa   1680
cttagtttct ttcaactcca ggttaagaga cataaatgtc ctttgatgc               1729
```

<210> SEQ ID NO 90
<211> LENGTH: 1231
<212> TYPE: DNA
<213> ORGANISM: Artificial Sequence
<220> FEATURE:
<223> OTHER INFORMATION: 5'-region of PpPRO1

<400> SEQUENCE: 90

```
gaagggccat cgaattgtca tcgtctcctc aggtgccatc gctgtgggca tgaagagagt     60
caacatgaag cggaaaccaa aaaagttaca gcaagtgcag gcattggctg ctataggaca    120
aggccgtttg ataggacttt gggacgacct tttccgtcag ttgaatcagc ctattgcgca    180
gattttactg actagaacgg atttggtcga ttacacccag tttaagaacg ctgaaaatac    240
attggaacag cttattaaaa tgggtattat tcctattgtc aatgagaatg cacccctatc    300
cattcaagaa atcaaatttg gtgacaatga caccttatcc gccataacag ctggtatgtg    360
tcatgcagac tacctgtttt tggtgactga tgtggactgt ctttacacgg ataaccctcg    420
tacgaatccg gacgctgagc caatcgtgtt agttagaaat atgaggaatc taaacgtcaa    480
taccgaaagt ggaggttccg ccgtaggaac aggaggaatg caactaaat tgatcgcagc    540 tgatttgggt gtatctgcag gtgttacaac gattatttgc aaaagtgaac atcccgagca    600 gatttggac attgtagagt acagtatccg tgctgataga gtcgaaaatg aggctaaata    660
tctggtcatc aacgaagagg aaactgtgga acaatttcaa gagatcaatc ggtcagaact    720
gagggagttg aacaagctgg acattccttt gcatacacgt ttcgttggcc acagttttaa    780
tgctgttaat aacaaagagt tttggttact ccatggacta aaggccaacg gagccattat    840
cattgatcca ggttgttata aggctatcac tagaaaaaac aaagctggta ttcttccagc    900
tggaattatt tccgtagagg gtaatttcca tgaatacgag tgtgttgatg ttaaggtagg    960
actaagagat ccagatgacc cacattcact agaccccaat gaagaacttt acgtcgttgg   1020
ccgtgcccgt tgtaattacc ccagcaatca aatcaacaaa attaagggtc tacaaagctc   1080
gcagatcgag caggttctag ttacgctgac cggtgagtat gttgttcaca gggacaactt   1140
ggctttccca gtatttgccg atccagaact gttggatgtt gttgagagta ccctgtctga   1200
acaggagaga gaatccaaac caaataaata g                                  1231
```

<210> SEQ ID NO 91
<211> LENGTH: 1425
<212> TYPE: DNA
<213> ORGANISM: Artificial Sequence
<220> FEATURE:
<223> OTHER INFORMATION: 3'-region of PpPRO1

<400> SEQUENCE: 91

```
aatttcacat atgctgcttg attatgtaat tataccttgc gttcgatggc atcgatttcc     60
tcttctgtca atcgcgcatc gcattaaaag tatacttttt ttttttttcct atagtactat   120 tcgccttatt ataaactttg ctagtatgag ttctaccccc aagaaagagc ctgatttgac   180
```

```
tcctaagaag agtcagcctc caaagaatag tctcggtggg ggtaaaggct ttagtgagga     240
gggtttctcc caaggggact tcagcgctaa gcatatacta aatcgtcgcc ctaacaccga     300
aggctcttct gtggcttcga acgtcatcag ttcgtcatca ttgcaaaggt taccatcctc     360
tggatctgga agcgttgctg tgggaagtgt gttgggatct tcgccattaa ctctttctgg     420
agggttccac gggcttgatc caaccaagaa taaaatagac gttccaaagt cgaaacagtc     480
aaggagacaa agtgttcttt ctgacatgat ttccacttct catgcagcta gaaatgatca     540
ctcagagcag cagttacaaa ctggacaaca atcagaacaa aaagaagaag atggtagtcg     600
atcttctttt tctgtttctt cccccgcaag agatatccgg cacccagatg tactgaaaac     660
tgtcgagaaa catcttgcca atgacagcga gatcgactca tctttacaac ttcaaggtgg     720
agatgtcact agaggcattt atcaatgggt aactggagaa agtagtcaaa aagataaccc     780
gcctttgaaa cgagcaaata gttttaatga ttttcttct gtgcatggtg acgaggtagg     840
caaggcagat gctgaccacg atcgtgaaag cgtattcgac gaggatgata tctccattga     900
tgatatcaaa gttccgggag ggatgcgtcg aagttttta ttacaaaagc atagagacca     960
acaactttct ggactgaata aaacggctca ccaaccaaaa caacttacta aacctaattt    1020
cttcacgaac aactttatag agtttttggc attgtatggg cattttgcag gtgaagattt    1080
ggaggaagac gaagatgaag atttagacag tggttccgaa tcagtcgcag tcagtgatag    1140
tgagggagaa ttcagtgagg ctgacaacaa tttgttgtat gatgaagagt ctctcctatt    1200
agcacctagt acctccaact atgcgagatc aagaatagga agtattcgta ctcctactta    1260
tggatctttc agttcaaatg ttggttcttc gtctattcat cagcagttaa tgaaaagtca    1320
aatcccgaag ctgaagaaac gtggacagca caagcataaa acacaatcaa aaatacgctc    1380
gaagaagcaa actaccaccg taaaagcagt gttgctgcta ttaaa                     1425

<210> SEQ ID NO 92
<211> LENGTH: 501
<212> TYPE: DNA
<213> ORGANISM: Artificial Sequence
<220> FEATURE:
<223> OTHER INFORMATION: Encodes Truncated hEPO DNA (codon optimized)

<400> SEQUENCE: 92
gctccaccaa gattgatttg tgactccaga gttttggaga gatacttgtt ggaggctaaa      60
gaggctgaga acatcactac tggttgtgct gaacactgtt ccttgaacga gaacatcaca     120
gttccagaca ctaaggttaa cttctacgct tggaagagaa tggaagttgg acaacaggct     180
gttgaagttt ggcaaggatt ggctttgttg tccgaggctg ttttgagagg tcaagctttg     240
ttggttaact cctcccaacc atgggaacca ttgcaattgc acgttgacaa ggctgttttct     300 ggattgagat ccttgactac tttgttgaga gctttgggtg ctcagaaaga ggctatttct     360
ccaccagatg ctgcttcagc tgctccattg agaactatca ctgctgacac tttcagaaag     420
ttgttcagag tttactccaa cttcttgaga ggaaagttga agttgtacac tggtgaagct     480
tgtagaactg gtgactagta a                                                501

<210> SEQ ID NO 93
<211> LENGTH: 165
<212> TYPE: PRT
<213> ORGANISM: Artificial Sequence
<220> FEATURE:
<223> OTHER INFORMATION: Truncated hEPO
```

<400> SEQUENCE: 93

```
Ala Pro Pro Arg Leu Ile Cys Asp Ser Arg Val Leu Glu Arg Tyr Leu
  1               5                  10                  15
Leu Glu Ala Lys Glu Ala Glu Asn Ile Thr Thr Gly Cys Ala Glu His
             20                  25                  30
Cys Ser Leu Asn Glu Asn Ile Thr Val Pro Asp Thr Lys Val Asn Phe
         35                  40                  45
Tyr Ala Trp Lys Arg Met Glu Val Gly Gln Gln Ala Val Glu Val Trp
     50                  55                  60
Gln Gly Leu Ala Leu Leu Ser Glu Ala Val Leu Arg Gly Gln Ala Leu
 65                  70                  75                  80
Leu Val Asn Ser Ser Gln Pro Trp Glu Pro Leu Gln Leu His Val Asp
                 85                  90                  95
Lys Ala Val Ser Gly Leu Arg Ser Leu Thr Thr Leu Leu Arg Ala Leu
             100                 105                 110
Gly Ala Gln Lys Glu Ala Ile Ser Pro Pro Asp Ala Ala Ser Ala Ala
         115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp
                165
```

<210> SEQ ID NO 94
<211> LENGTH: 78
<212> TYPE: DNA
<213> ORGANISM: Artificial Sequence
<220> FEATURE:
<223> OTHER INFORMATION: encodes chicken lysozyme signal peptide (CLSP)

<400> SEQUENCE: 94

```
atgctgggta agaacgaccc aatgtgtctt gttttggtct tgttgggatt gactgctttg    60
ttgggtatct gtcaaggt                                                 78
```

<210> SEQ ID NO 95
<211> LENGTH: 26
<212> TYPE: PRT
<213> ORGANISM: Artificial Sequence
<220> FEATURE:
<223> OTHER INFORMATION: chicken lysozyme signal peptide (CLSP)

<400> SEQUENCE: 95

```
Met Leu Gly Lys Asn Asp Pro Met Cys Leu Val Leu Val Leu Leu Gly
  1               5                  10                  15
Leu Thr Ala Leu Leu Gly Ile Cys Gln Gly
             20                  25
```

<210> SEQ ID NO 96
<211> LENGTH: 1892
<212> TYPE: DNA
<213> ORGANISM: Artificial Sequence
<220> FEATURE:
<223> OTHER INFORMATION: Encodes PpAde2

<400> SEQUENCE: 96

```
atggattctc aggtaatagg tattctagga ggaggccagc taggccgaat gattgttgag    60
gccgctagca ggctcaatat caagaccgtg attcttgatg atggttttc acctgctaag   120
```

```
cacattaatg ctgcgcaaga ccacatcgac ggatcattca aagatgagga ggctatcgcc    180
aagttagctg ccaaatgtga tgttctcact gtagagattg agcatgtcaa cacagatgct    240
ctaaagagag ttcaagacag aactggaatc aagatatatc ctttaccaga gacaatcgaa    300
ctaatcaagg ataagtactt gcaaaaggaa catttgatca agcacaacat ttcggtgaca    360
aagtctcagg gtatagaatc taatgaaaag gcgctgcttt tgtttggaga gagaatgga    420 tttccatatc tgttgaagtc ccggactatg gcttatgatg aagaggcaa ttttgtagtg    480 gagtctaaag aggacatcag taaggcatta gaattcttga agatcgtcc attgtatgcc    540 gagaagtttg ctcctttgt taagaatta gcggtaatgg ttgtgagatc actggaaggc    600
gaagtattct cctacccaac cgtagaaact gtgcacaagg acaatatctg tcatattgtg    660
tatgctccgg ccagagttaa tgacaccatc aaaagaaag ctcaaatatt agctgaaaac    720
actgtgaaga ctttcccagg cgctggaatc ttcggagttg agatgttcct attgtctgat    780
ggagaacttc ttgtaaatga gattgctcca aggccccaca attctggtca ctatacaatc    840
gatgcatgtg taacatctca gttcgaagca catgtaagag ccataactgg tctgccaatg    900
ccactagatt tcaccaaaact atctacttcc aacaccaacg ctattatgct caatgttttg    960
ggtgctgaaa atctcacgg ggaattagag ttttgtagaa gagccttaga aacacccggt   1020
gcttctgtat atctgtacgg aaagaccacc cgattggctc gtaagatggg tcatatcaac   1080
ataataggat cttccatgtt ggaagcagaa caaaagttag agtacattct agaagaatca   1140
acccacttac catccagtac tgtatcagct gacactaaac cgttggttgg agttatcatg   1200
ggttcagact ctgatctacc tgtgatttcg aaaggttgcg atattttaaa acagtttggt   1260
gttccattcg aagttactat tgtctctgct catagaacac cacagagaat gaccagatat   1320 gccttttgaag ccgctagtag aggtatcaag gctatcattg caggtgctgg tggtgctgct   1380
catcttccag gaatggttgc tgccatgact ccgttgccag tcattggtgt tcctgtcaag   1440
ggctctacgt tggatggtgt agactcgcta cactcgattg tccaaatgcc tagaggtgtt   1500
cctgtggcta cggttgctat caacaacgcc accaatgccg ctctgttggc catcaggatt   1560
ttaggtacaa ttgaccacaa atggcaaaag gaaatgtcca agtatatgaa tgcaatggag   1620
accgaagtgt tggggaaggc atccaacttg gaatctgaag gtatgaatc ctatttgaag   1680 aatcgtcttt gaatttagta ttgtttttta atagatgtat atataatagt acacgtaact   1740
tatctattcc attcataatt ttattttaaa ggttcggtag aaatttgtcc tccaaaaagt   1800
tggttagagc ctggcagttt tgataggcat tattatagat tgggtaatat ttaccctgca   1860
cctggaggaa ctttgcaaag agcctcatgt gc                                1892
```

<210> SEQ ID NO 97  
<211> LENGTH: 563  
<212> TYPE: PRT  
<213> ORGANISM: Pichia pastoris

<400> SEQUENCE: 97

```
Met Asp Ser Gln Val Ile Gly Ile Gly Gly Gly Gln Leu Gly Arg
 1               5                  10                  15

Met Ile Val Glu Ala Ala Ser Arg Leu Asn Ile Lys Thr Val Ile Leu
                20                  25                  30

Asp Asp Gly Phe Ser Pro Ala Lys His Ile Asn Ala Ala Gln Asp His
            35                  40                  45

Ile Asp Gly Ser Phe Lys Asp Glu Glu Ala Ile Ala Lys Leu Ala Ala
        50                  55                  60
```

-continued

```
Lys Cys Asp Val Leu Thr Val Glu Ile Glu His Val Asn Thr Asp Ala
 65                  70                  75                  80

Leu Lys Arg Val Gln Asp Arg Thr Gly Ile Lys Ile Tyr Pro Leu Pro
                 85                  90                  95

Glu Thr Ile Glu Leu Ile Lys Asp Lys Tyr Leu Gln Lys Glu His Leu
            100                 105                 110

Ile Lys His Asn Ile Ser Val Thr Lys Ser Gln Gly Ile Glu Ser Asn
            115                 120                 125

Glu Lys Ala Leu Leu Leu Phe Gly Glu Glu Asn Gly Phe Pro Tyr Leu
130                 135                 140

Leu Lys Ser Arg Thr Met Ala Tyr Asp Gly Arg Gly Asn Phe Val Val
145                 150                 155                 160

Glu Ser Lys Glu Asp Ile Ser Lys Ala Leu Glu Phe Leu Lys Asp Arg
                165                 170                 175

Pro Leu Tyr Ala Glu Lys Phe Ala Pro Phe Val Lys Glu Leu Ala Val
            180                 185                 190

Met Val Val Arg Ser Leu Glu Gly Glu Val Phe Ser Tyr Pro Thr Val
            195                 200                 205

Glu Thr Val His Lys Asp Asn Ile Cys His Ile Val Tyr Ala Pro Ala
210                 215                 220

Arg Val Asn Asp Thr Ile Gln Lys Lys Ala Gln Ile Leu Ala Glu Asn
225                 230                 235                 240

Thr Val Lys Thr Phe Pro Gly Ala Gly Ile Phe Gly Val Glu Met Phe
                245                 250                 255

Leu Leu Ser Asp Gly Glu Leu Leu Val Asn Glu Ile Ala Pro Arg Pro
            260                 265                 270

His Asn Ser Gly His Tyr Thr Ile Asp Ala Cys Val Thr Ser Gln Phe
            275                 280                 285

Glu Ala His Val Arg Ala Ile Thr Gly Leu Pro Met Pro Leu Asp Phe
290                 295                 300

Thr Lys Leu Ser Thr Ser Asn Thr Asn Ala Ile Met Leu Asn Val Leu
305                 310                 315                 320

Gly Ala Glu Lys Ser His Gly Glu Leu Glu Phe Cys Arg Arg Ala Leu
                325                 330                 335

Glu Thr Pro Gly Ala Ser Val Tyr Leu Tyr Gly Lys Thr Thr Arg Leu
            340                 345                 350

Ala Arg Lys Met Gly His Ile Asn Ile Ile Gly Ser Ser Met Leu Glu
            355                 360                 365

Ala Glu Gln Lys Leu Glu Tyr Ile Leu Glu Glu Ser Thr His Leu Pro
370                 375                 380

Ser Ser Thr Val Ser Ala Asp Thr Lys Pro Leu Val Gly Val Ile Met
385                 390                 395                 400

Gly Ser Asp Ser Asp Leu Pro Val Ile Ser Lys Gly Cys Asp Ile Leu
                405                 410                 415

Lys Gln Phe Gly Val Pro Phe Glu Val Thr Ile Val Ser Ala His Arg
            420                 425                 430

Thr Pro Gln Arg Met Thr Arg Tyr Ala Phe Glu Ala Ala Ser Arg Gly
            435                 440                 445

Ile Lys Ala Ile Ile Ala Gly Ala Gly Gly Ala Ala His Leu Pro Gly
            450                 455                 460

Met Val Ala Ala Met Thr Pro Leu Pro Val Ile Gly Val Pro Val Lys
465                 470                 475                 480
```

```
Gly Ser Thr Leu Asp Gly Val Asp Ser Leu His Ser Ile Val Gln Met
                485                 490                 495

Pro Arg Gly Val Pro Val Ala Thr Val Ala Ile Asn Asn Ala Thr Asn
                500                 505                 510

Ala Ala Leu Leu Ala Ile Arg Ile Leu Gly Thr Ile Asp His Lys Trp
            515                 520                 525

Gln Lys Glu Met Ser Lys Tyr Met Asn Ala Met Glu Thr Glu Val Leu
        530                 535                 540

Gly Lys Ala Ser Asn Leu Glu Ser Glu Gly Tyr Glu Ser Tyr Leu Lys
545                 550                 555                 560

Asn Arg Leu

<210> SEQ ID NO 98
<211> LENGTH: 1302
<212> TYPE: DNA
<213> ORGANISM: Artificial Sequence
<220> FEATURE:
<223> OTHER INFORMATION: Pp TRP2: 5' and ORF

<400> SEQUENCE: 98
actgggcctt tagagggtgc tgaagttgac cccttggtgc ttctggaaaa agaactgaag      60
ggcaccagac aagcgcaact tcctggtatt cctcgtctaa gtggtggtgc cataggatac     120
atctcgtacg attgtattaa gtactttgaa ccaaaaactg aaagaaaact gaaagatgtt     180
ttgcaacttc cggaagcagc tttgatgttg ttcgacacga tcgtggcttt tgacaatgtt     240
tatcaaagat tccaggtaat tggaaacgtt tctctatccg ttgatgactc ggacgaagct     300
attcttgaga atattataa gacaagagaa gaagtggaaa agatcagtaa agtggtattt      360
gacaataaaa ctgttcccta ctatgaacag aaagatatta ttcaaggcca aacgttcacc     420
tctaatattg gtcaggaagg tatgaaaac catgttcgca agctgaaaga acatattctg      480
aaaggagaca tcttccaagc tgttccctct caaagggtag ccaggccgac ctcattgcac     540
cctttcaaca tctatcgtca tttgagaact gtcaatcctt ctccatacat gttctatatt     600
gactatctag acttccaagt tgttggtgct tcacctgaat tactagttaa atccgacaac     660
aacaacaaaa tcatcacaca tcctattgct ggaactcttc ccagaggtaa aactatcgaa     720
gaggacgaca attatgctaa gcaattgaag tcgtctttga agacagggc cgagcacgtc      780 atgctggtag atttggccag aaatgatatt aaccgtgtgt gtgagcccac cagtaccacg     840
gttgatcgtt tattgactgt ggagagattt tctcatgtga tgcatcttgt gtcagaagtc     900
agtggaacat tgagaccaaa caagactcgc ttcgatgctt tcagatccat tttcccagca     960
ggtaccgtct ccggtgctcc gaaggtaaga gcaatgcaac tcataggaga attggaagga    1020
gaaaagagag tgtttatgc gggggccgta ggacactggt cgtacgatgg aaaatcgatg     1080
gacacatgta ttgccttaag aacaatggtc gtcaaggacg tgtcgctta ccttcaagcc    1140 ggaggtggaa ttgtctacga ttctgacccc tatgacgagt acatcgaaac catgaacaaa    1200
atgagatcca acaataacac catcttggag gctgagaaaa tctggaccga taggttggcc    1260
agagacgaga atcaaagtga atccgaagaa aacgatcaat ga                       1302

<210> SEQ ID NO 99
<211> LENGTH: 1085
<212> TYPE: DNA
<213> ORGANISM: Artificial Sequence
<220> FEATURE:
<223> OTHER INFORMATION: Pp TRP2: 3'
```

<400> SEQUENCE: 99

```
acggaggacg taagtaggaa tttatgtaat catgccaata catctttaga tttcttcctc    60
ttcttttttaa cgaaagacct ccagttttgc actctcgact ctctagtatc ttcccatttc   120
tgttgctgca acctcttgcc ttctgtttcc tcaattgtt cttctttctt ctgttgcact    180
tggccttctt cctccatctt tcgttttttt tcaagccttt tcagcagttc ttcttccaag   240
agcagttctt tgattttctc tctccaatcc accaaaaaac tggatgaatt caaccgggca   300
tcatcaatgt tccactttct ttctcttatc aataatctac gtgcttcggc atacgaggaa   360
tccagttgct ccctaatcga gtcatccaca aggttagcat gggccttttt cagggtgtca   420
aaagcatctg gagctcgttt attcggagtc ttgtctggat ggatcagcaa agacttttg    480
cggaaagtct ttcttatatc ttccggagaa caacctggtt tcaaatccaa gatggcatag   540
ctgtccaatt tgaaagtgga aagaatcctg ccaatttcct tctctcgtgt cagctcgttc   600
tcctcctttt gcaacaggtc cacttcatct ggcattttc tttatgttaa ctttaattat    660
tattaattat aaagttgatt atcgttatca aaataatcat attcgagaaa taatccgtcc   720
atgcaatata taaataagaa ttcataataa tgtaatgata acagtacctc tgatgacctt   780
tgatgaaccg caattttctt tccaatgaca agacatccct ataatacaat tatacagttt   840
atatatcaca aataatcacc tttttataag aaaaccgtcc tctccgtaac agaacttatt   900
atccgcacgt tatggttaac acactactaa taccgtatata gtgtatgaag tcgctacgag   960
atagccatcc aggaaactta ccaattcatc agcactttca tgatccgatt gttggcttta  1020
ttctttgcga gacagatact tgccaatgaa ataactgatc ccacagatga gaatccggtg  1080
ctcgt                                                              1085
```

<210> SEQ ID NO 100
<211> LENGTH: 1007
<212> TYPE: DNA
<213> ORGANISM: Artificial Sequence
<220> FEATURE:
<223> OTHER INFORMATION: Pp ADE2 5' region

<400> SEQUENCE: 100

```
cttaaaatca tctgcctcac cccaccgacc aatgggaatt ctagaaacaa tttcattgct    60
cttcttctcg ttaccataag aatcggctgt catgtttgac ttaacgaacc ctggaacaag   120
ggaattcacg gtaataccctt ttggagcaag ttcaaccgat agagccttca ttaatgagtt   180
gattgcacct ttggtggtcg catataccga ttgattcggg taggtcactt cgaaactgta   240
cagggaggca gtaaagatga tcctaccctt aatctggttc ttaataaagt gtttagtgac   300
tagctgtgtc aatctaaatg gaaaatcgac atttacctttt tggatagccg cgtaatcttt   360
ctccgtaaaa cttgtaaact cagatttaat ggcaatggca gcgttgttga ttaaaatgtc   420
aatctttcca gtggaactct ctccaccgc aggactcgtt acggtctctt ccagctttgc    480
aagatcggca tccactagat ccaactcaat tgtatgtatg gaggcaccat cggcatttga   540
cattctcacc tcttcaatga agccgttgg gtctgtagaa ggtctatgga taagaataag   600
ttctgcacct gcttcataaa gtcctcgaac tattccttgg cctaatccgc tggtaccacc   660
ggtgatcaag gcgaccttac cattcaaaga aaacaaatca gcggacatta gcgacttgaa   720
tagggaatgg gttagacaaa tgaaagccga cgagccagca ctttatagta agtgcaggtg   780
agtcaataag aataaatgta tggcttgctg tccctatcgc gtaagaagct tactaagatc   840
gcctaaattg aaaagttgaa caaatcagtt ctagctggcc tccatcagca tttcgttctc   900
```

```
ctctgatcat ctttgccaat cgctagcatg ccctcagcgt gcaaggaaaa gcacgcttct    960
ttcttatcga cgtatttttca actatggcag agccaggtta gcaagtc               1007
```

<210> SEQ ID NO 101
<211> LENGTH: 1676
<212> TYPE: DNA
<213> ORGANISM: Artificial Sequence
<220> FEATURE:
<223> OTHER INFORMATION: Pp ADE2 3' region

<400> SEQUENCE: 101

```
atttagtatt gttttttaat agatgtatat ataatagtac acgtaactta tctattccat     60
tcataatttt attttaaagg ttcggtagaa atttgtcctc caaaaagttg gttagagcct    120
ggcagttttg ataggcatta ttatagattg ggtaatattt accctgcacc tggaggaact    180
ttgcaaagag cctcatgtgc tctaaaagga tgtcagaatt ccaacatttc aaaattatat    240
ctgcatgcgt ctgtaatact ggaactgtta tttttctggt caggatttca ccgctcttgt    300
cgtcatgttt ctcgtcgtct gaaagtaaac tgactttcct cttttccataa acacaaaaat    360 cgattgcaac ttggttattc ttgagattga aatttgctgt gtcttcagtg cttagctgaa    420
tatcaacaaa cttacttagt actaataacg aagcactatg gtaagtggca taacatagtg    480
gtattgaagc gaacagtgga tattgaaccc aagcattggc aacatctggc tctgttgata    540
ctgatccgga tcgtttggca ccaattcctg aaacggcgta gtgccaccaa ggtttcgatt    600
tgagaacagg ttcatcatca gagtcaacca ccccaatgtc aatggcaggc tccaacgaag    660
taggtccaac aacaacagga agtatttgac cttgaagatc tgttcctttta tgatccacca    720 caccttgccc caattccaat aactttacca gtcccgatgc agacatgata actggtacta    780
atgatctcca ttgattttcg tcggcactac gtaaagcctc caaaaatgaa ttcagaatat    840
cttctgaaac tagattctgc ttctgtgatt caagcattgc tttatgtaga catctcttga    900
ataaaagcaa ttctccacat attggtgtgt gtaagataga tctggaaaga tgtatctgga    960
atagtccagt caacgttgtg caattgatta gcattacctt actgtgaaca tctctatcta   1020
caacaacaga ctcaattcga tagacgttcc gggaaagttt ttcaagcgca ttcagtttgc   1080
tgttgaacaa agtgactttg cttttccaatg tgcaaatacc cctgtatatc aagtccatca   1140
catcactcaa gaccttggtg gaaaagaatg aaacagctgg agcataattt tcgaatgaat   1200
taggtaaggt cacttcatcc ttatctgttg taatgctata atcaatagcg gaactaacat   1260
cttcccatgt aacaggtttc ttgatctctg aatctgaatc tttatttgaa aaagaattga   1320
aaaaagactc atcactcatt gggaattcaa ggtcattagg gtattccatt gttagttctg   1380
gtctaggttt aaagggatca ccttcgttaa gacgatggaa aatagctaat ctgtacaata   1440
accagatact tctaacgaag ctctctctat ccatcagttg acgtgttgag gatatctgaa   1500 ctagctctttt ccactgcgaa tcaggcatgc tcgtatagct ggcaagcatg ttattcagct   1560
ttaccaagtt agaagccctt tggaaaccat ctatagattc ccgaaaaaac ttatacccac   1620
tgagggtttc actgagcata gtcagtgaca tcaaagagca tttcaaatcc atctca       1676
```

<210> SEQ ID NO 102
<211> LENGTH: 582
<212> TYPE: DNA
<213> ORGANISM: Artificial Sequence
<220> FEATURE:
<223> OTHER INFORMATION: NATR ORF

<400> SEQUENCE: 102

```
atgggtacca ctcttgacga cacggcttac cggtaccgca ccagtgtccc gggggacgcc    60
gaggccatcg aggcactgga tgggtccttc accaccgaca ccgtcttccg cgtcaccgcc   120
accggggacg gcttcaccct gcgggaggtg ccggtggacc cgcccctgac caaggtgttc   180
cccgacgacg aatcggacga cgaatcggac gacggggagg acggcgaccc ggactcccgg   240
acgttcgtcg cgtacgggga cgacggcgac ctggcgggct tcgtggtcgt ctcgtactcc   300
ggctggaacc gccggctgac cgtcgaggac atcgaggtcg ccccggagca ccgggggcac   360
ggggtcgggc gcgcgttgat ggggctcgcg acggagttcg cccgcgagcg gggcgccggg   420
cacctctggc tggaggtcac caacgtcaac gcaccggcga tccacgcgta ccggcggatg   480
gggttcaccc tctgcggcct ggacaccgcc ctgtacgacg gcaccgcctc ggacggcgag   540
caggcgctct acatgagcat gccctgcccc taatcagtac tg                      582
```

<210> SEQ ID NO 103
<211> LENGTH: 1029
<212> TYPE: DNA
<213> ORGANISM: Artificial Sequence
<220> FEATURE:
<223> OTHER INFORMATION: HygR ORF

<400> SEQUENCE: 103

```
atgggtaaaa agcctgaact caccgcgacg tctgtcgaga agtttctgat cgaaaagttc    60
gacagcgtct ccgacctgat gcagctctcg gagggcgaag aatctcgtgc tttcagcttc   120
gatgtaggag ggcgtggata tgtcctgcgg gtaaatagct gcgccgatgg tttctacaaa   180
gatcgttatg tttatcggca ctttgcatcg gccgcgctcc cgattccgga agtgcttgac   240
attgggggaat tcagcgagag cctgacctat tgcatctccc gccgtgcaca gggtgtcacg   300
ttgcaagacc tgcctgaaac cgaactgccc gctgttctgc agccggtcgc ggaggccatg   360
gatgcgatcg ctgcggccga tcttagccag acgagcgggt tcggcccatt cggaccgcaa   420
ggaatcggtc aatacactac atggcgtgat ttcatatgcg cgattgctga tccccatgtg   480
tatcactggc aaactgtgat ggacgacacc gtcagtgcgt ccgtcgcgca ggctctcgat   540
gagctgatgc tttgggccga ggactgcccc gaagtccggc acctcgtgca cgcggatttc   600
ggctccaaca atgtcctgac ggacaatggc cgcataacag cggtcattga ctggagcgag   660
gcgatgttcg ggattccca atacgaggtc gccaacatct tcttctggag gccgtggttg   720
gcttgtatgg agcagcagac gcgctacttc gagcggaggc atccggagct tgcaggatcg   780
ccgcggctcc gggcgtatat gctccgcatt ggtcttgacc aactctatca gagcttggtt   840
gacggcaatt tcgatgatgc agcttgggcg cagggtcgat gcgacgcaat cgtccgatcc   900
ggagccggga ctgtcgggcg tacacaaatc gcccgcagaa gcgcggccgt ctggaccgat   960
ggctgtgtag aagtactcgc cgatagtgga aaccgacgcc ccagcactcg tccgagggca  1020
aaggaatag                                                         1029
```

<210> SEQ ID NO 104
<211> LENGTH: 2957
<212> TYPE: DNA
<213> ORGANISM: Artificial Sequence
<220> FEATURE:
<223> OTHER INFORMATION: PpPEP4 region

```
<400> SEQUENCE: 104
atttgagtca cctgctttag ggctggaaga tatttggtta ctagatttta gtacaaactc      60
ttgctttgtc aatgacatta aaataggcaa gaatcgcaaa actcaaatat ttcatggaga     120
tgagatatgc ttgttcaaag atgcccagaa aaaagagcaa ctcgtttata gggttcatat     180
tgatgatgga acaggccttt tccagggagg tgaaagaacc caagccaatt ctgatgacat     240
tctggatatt gatgaggttg atgaaaagtt aagagaacta ttgacaagag cctcaaggaa     300
acggcatatc acccctgcat tggaaactcc tgataaacgt gtaaaaagag cttatttgaa     360
cagtattact gataactctt gatggaccct aaagatgtat aatagtagac agaattcata     420
atggtgagat taggtaatcg tccggaatag gaatagtggt ttggggcgat taatcgcacc     480
tgccttatat ggtaagtacc ttgaccgata aggtggcaac tatttagaac aaagcaagcc     540
acctttcttt atctgtaact ctgtcgaagc aagcatcttt actagagaac atctaaacca     600
ttttacattc tagagttcca tttctcaatt actgataatc aatttaaaga tgatatttga     660
cggtactacg atgtcaattg ccattggttt gctctctact ctaggtattg gtgctgaagc     720
caaagttcat tctgctaaga tacacaagca tccagtctca gaaactttaa agaggccaa     780 ttttgggcag tatgtctctg ctctggaaca taaatatgtt tctctgttca acgaacaaaa     840
tgctttgtcc aagtcgaatt ttatgtctca gcaagatggt tttgccgttg aagcttcgca     900
tgatgctcca cttacaaact atcttaacgc tcagtatttt actgaggtat cattaggtac     960
ccctccacaa tcgttcaagg tgattcttga cacaggatcc tccaatttat gggttcctag    1020
caaagattgt ggatcattag cttgcttctt gcatgctaag tatgaccatg atgagtcttc    1080
tacttataag aagaatggta gtagctttga aattaggtat ggatccggtt ccatggaagg    1140
gtatgtttct caggatgtgt tgcaaattgg ggatttgacc attcccaaag ttgattttgc    1200
tgaggccaca tcggagccgg ggttggcctt cgcttttggc aaatttgacg aattttggg    1260 gcttgcttat gattcaatat cagtaaataa gattgttcct ccaatttaca aggctttgga    1320
attagatctc cttgacgaac caaaatttgc cttctacttg ggggatacgg acaaagatga    1380
atccgatggc ggtttggcca catttggtgg tgtggacaaa tctaagtatg aaggaaagat    1440
cacctggttg cctgtcagaa gaaaggctta ctgggaggtc tcttttgatg gtgtaggttt    1500
gggatccgaa tatgctgaat tgcaaaaaac tggtgcagcc atcgacactg gaacctcatt    1560
gattgctttg cccagtggcc tagctgaaat tctcaatgca gaaattggtg ctaccaaggg    1620
ttggtctggt caatacgctg tggactgtga cactagagac tctttgccag acttaacttt    1680
aaccttcgcc ggttacaact ttaccattac tccatatgac tatactttgg aggtttctgg    1740
gtcatgtatt agtgctttca cccccatgga ctttcctgaa ccaataggtc ctttggcaat    1800
cattggtgac tcgttcttga gaaaatatta ctcagtttat gacctaggca agatgcagt     1860 aggtttagcc aagtctattt aggcaagaat aaaagttgct cagctgaact tatttggtta    1920
cttatcaggt agtgaagatg tagagaatat atgtttaggt attttttttt agttttctc     1980 ctataactca tcttcagtac gtgattgctt gtcagctacc ttgacagggg cgcataagtg    2040
atatcgtgta ctgctcaatc aagatttgcc tgctccattg ataagggtat aagagaccca    2100
cctgctcctc tttaaaattc tctcttaact gttgtgaaaa tcatcttcga agcaaattcg    2160
agtttaaatc tatgcggttg gtaactaaag gtatgtcatg gtggtatata gttttcatt     2220 ttaccttta ctaatcagtt ttacagaaga ggaacgtctt tctcaagatc gaaataggac     2280
taaatactgg agacgatggg gtccttattt gggtgaaagg cagtgggcta cagtaaggga    2340
```

-continued

```
agactattcc gatgatggag atgcttggtc tgcttttcct tttgagcaat ctcatttgag    2400
aacttatcgc tggggagagg atggactagc tggagtctca gacaatcatc aactaatttg    2460
tttctcaatg gcactgtgga atgagaatga tgatattttg aaggagcgat tatttggggt    2520
cactggagag gctgcaaatc atggagagga tgttaaggag ctttattatt atcttgataa    2580
tacaccttct cactcttata tgaaatacct ttacaaatat ccacaatcga aatttcctta    2640
cgaagaattg atttcagaga accgtaaacg ttccagatta gaaagagagt acgagattac    2700
tgactctgaa gtactgaagg ataacagata ttttgatgtg atctttgaaa tggcaaagga    2760
cgatgaagat gagaatgaac tttactttag aattaccgct tacaaccgag gtcccacccc    2820
tgccccttta catgtcgctc cacaggtaac ctttagaaat acctggtcct ggggtataga    2880
tgaggaaaag gatcacgaca aacctatagc ttgcaaggaa taccaagaca acaactattc    2940
tattcggtta gatagtt                                                   2957

<210> SEQ ID NO 105
<211> LENGTH: 388
<212> TYPE: DNA
<213> ORGANISM: Artificial Sequence
<220> FEATURE:
<223> OTHER INFORMATION: Ashbya gossypii TEF1 promoter

<400> SEQUENCE: 105
gatctgttta gcttgcctcg tccccgccgg gtcacccggc cagcgacatg gaggcccaga     60
ataccctcct tgacagtctt gacgtgcgca gctcaggggc atgatgtgac tgtcgcccgt    120
acatttagcc catacatccc catgtataat catttgcatc catacatttt gatggccgca    180
cggcgcgaag caaaaattac ggctcctcgc tgcagacctg cgagcaggga aacgctcccc    240
tcacagacgc gttgaattgt ccccacgccg cgccctgta gagaaatata aaaggttagg    300
atttgccact gaggttcttc tttcatatac ttccttttaa aatcttgcta ggatacagtt    360
ctcacatcac atccgaacat aaacaacc                                       388

<210> SEQ ID NO 106
<211> LENGTH: 247
<212> TYPE: DNA
<213> ORGANISM: Artificial Sequence
<220> FEATURE:
<223> OTHER INFORMATION: Ashbya gossypii TEF1 termination sequence

<400> SEQUENCE: 106
taatcagtac tgacaataaa aagattcttg ttttcaagaa cttgtcattt gtatagtttt     60
tttatattgt agttgttcta ttttaatcaa atgttagcgt gatttatatt ttttttcgcc    120
tcgacatcat ctgcccagat gcgaagttaa gtgcgcagaa agtaatatca tgcgtcaatc    180
gtatgtgaat gctggtcgct atactgctgt cgattcgata ctaacgccgc catccagtgt    240
cgaaaac                                                              247
```

US 9,139,632 B2

METHOD FOR PRODUCING PROTEINS IN *PICHIA PASTORIS* THAT LACK DETECTABLE CROSS BINDING ACTIVITY TO ANTIBODIES AGAINST HOST CELL ANTIGENS

CROSS REFERENCE TO RELATED APPLICATIONS

This application is the U.S. National stage filing under 35 U.S.C. §371 of International Patent Application No. PCT/US2010/052140 filed Oct. 11, 2010, which claims benefit of U.S. Provisional Application No. 61/252,312 filed Oct. 16, 2009, the disclosures of which are hereby incorporated by reference in their entireties.

BACKGROUND OF THE INVENTION (1) Field of the Invention

The present invention relates to methods for producing protein and glycoproteins in *Pichia pastoris* that lack detectable cross binding activity to antibodies made against host cell antigens. In particular, the present invention relates to using recombinant *Pichia pastoris* strains that do not display a β-mannosyltransferase 2 activity with respect to an N-glycan or O-glycan and do not display at least one activity selected from the group consisting of β-mannosyltransferase 1, 3, and 4 activity with respect to an N-glycan or O-glycan. These recombinant *Pichia pastoris* strains can produce proteins and glycoproteins that lack detectable α-mannosidase resistant β-mannose residues thereon. The present invention further relates to methods for producing bi-sialylated human erythropoietin in *Pichia pastoris* that lack detectable cross binding activity to antibodies against host cell antigens.

(2) Description of Related Art

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human scrum. For therapeutic use in humans, glycoproteins require human-like N-glycosylation. Mammalian cell lines (e.g., CHO cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as the methylotrophic yeast *Pichia pastoris* have distinct advantages for therapeutic protein expression, for example, they do not secrete high amounts of endogenous proteins, strong inducible promoters for producing heterologous proteins are available, they can be grown in defined chemical media and without the use of animal sera, and they can produce high titers of recombinant proteins (Cregg et al., FEMS Microbiol. Rev. 24: 45-66 (2000)). However, glycosylated proteins expressed in *P. pastoris* generally contain additional mannose sugars resulting in "high mannose" glycans, as well as mannosylphosphate groups which impart a negative charge onto glycoproteins. Glycoproteins with either high mannose glycans or charged mannans present the risk of eliciting an unwanted immune response in humans (Takeuchi, Trends in Glycosci. Glycotechnol. 9:S29-S35 (1997); Rosenfeld and Ballou, J. Biol. Chem. 249: 2319-2321 (1974)). Accordingly, it is desirable to produce therapeutic glycoproteins in fungal host cells wherein the pattern of glycosylation on the glycoprotein is identical to or similar to that which occurs on glycoproteins produced in humans and which do not have detectable β-mannosylation.

As evidenced by the presence of protective antibodies in uninfected individuals, β-linked mannans are likely to be immunogenic or adversely affect the individual administered a therapeutic protein or glycoprotein comprising β-linked mannans. Additionally, exposed mannose groups on therapeutic proteins are rapidly cleared by mannose receptors on macrophage cells, resulting in low drug efficacy. Thus, the presence of β-linked mannose residues on N- or O-linked glycans of heterologous therapeutic proteins expressed in a fungal host, for example, *P. pastoris*, is not desirable given their immunogenic potential and their ability to bind to clearance factors.

Glycoproteins made in *P. pastoris* have been reported to contain β-linked mannose residues. In 2003, Trimble et al. (Glycobiol. 14: 265-274, Epub December 23) reported the presence of β-1,2-linked mannose residues in the recombinant human bile salt-stimulated lipase (hBSSL) expressed in *P. pastoris*. The genes encoding several β-mannosyltransferases have been identified in *Pichia pastoris* and *Candida albicans* (See U.S. Pat. No. 7,465,577 and Mille et al., J. Biol. Chem. 283: 9724-9736 (2008)).

In light of the above, there is a need to provide methods for making recombinant therapeutic proteins or glycoproteins in methylotrophic yeast such as *Pichia pastoris* that lack epitopes that might elicit an adverse reaction in an individual administered the recombinant therapeutic protein or glycoprotein. A method for determining whether a recombinant therapeutic protein or glycoprotein provides a risk of eliciting an adverse reaction when administered to an individual is to contact the recombinant therapeutic protein or glycoprotein to an antibody prepared against total host cell antigens. This is of particular concern for proteins or glycoproteins intended for chronic administration. The lack of cross binding to the antibody indicates that the recombinant therapeutic protein or glycoprotein lacks detectable cross binding activity to the antibody and is unlikely to elicit an adverse reaction when administered to an individual. Thus, there is a need for methods for producing a recombinant therapeutic protein or glycoprotein that lacks detectable cross binding activity to the antibody and is unlikely to elicit an adverse reaction when administered to an individual.

BRIEF SUMMARY OF THE INVENTION

The present invention provides methods for producing protein and glycoproteins in methylotrophic yeast such as *Pichia pastoris* that lack detectable cross binding activity to antibodies made against host cell antigens. In particular, the present invention provides methods using recombinant methylotrophic yeast such as *Pichia pastoris* strains, which do not display β-mannosyltransferase 2 activity with respect to an N-glycan or O-glycan and do not display at least one activity with respect to an N-glycan or O-glycan selected from β-mannosyltransferase 1, β-mannosyltransferase 3, and β-mannosyltransferase 4 to produce recombinant proteins and glycoproteins. In one aspect, the host cell is a *Pichia pastoris* strain in which the BMT2 gene encoding β-mannosyltransferase 2 and at least one gene encoding a β-mannosyltransferase selected from β-mannosyltransferase 1, 3, and 4 (genes BMT1, BMT3, BMT4, respectively) have been deleted or disrupted or mutated to produce an inactive β-mannosyltransferase to produce recombinant proteins and glycoproteins. In other aspects, the activity of one or more of the β-mannosyltransferase 1, β-mannosyltransferase 3, and β-mannosyltransferase 4 is abrogated using β-mannosyltransferase inhibitors which includes but is not limited to chemical compounds, antisense DNA to one or more mRNA encoding a β-mannosyltransferase, siRNA to one or more mRNA encoding a β-mannosyltransferase.

These recombinant *Pichia pastoris* strains can produce proteins and glycoproteins that lack detectable α-mannosidase resistant β-mannose residues thereon. The present invention further provides methods for producing bi-sialylated human erythropoietin in *Pichia pastoris* that lack detectable cross binding activity to antibodies against host cell antigens. The methods and host cells enable recombinant therapeutic proteins and glycoproteins to be produced that have a reduced risk of eliciting an adverse reaction in an individual administered the recombinant therapeutic proteins and glycoproteins compared to the same being produced in strains not modified as disclosed herein. The methods and host cells are also useful for producing recombinant proteins or glycoproteins that have a lower potential for binding clearance factors.

In one aspect, the present invention provides a recombinant methylotrophic yeast such as *Pichia pastoris* host cell that does not display β-mannosyltransferase 2 activity with respect to an N-glycan or O-glycan and does not display at least one activity with respect to an N-glycan or O-glycan selected from β-mannosyltransferase 1 activity and β-mannosyltransferase 3 activity and which includes a nucleic acid molecule encoding the recombinant glycoprotein. In further embodiments, the host cell does not display β-mannosyltransferase 2 activity, β-mannosyltransferase 1 activity, and β-mannosyltransferase 3 activity with respect to an N-glycan or O-glycan. In further embodiments, the host cell further does not display β-mannosyltransferase 4 activity with respect to an N-glycan or O-glycan.

In another aspect, the present invention provides a recombinant methylotrophic yeast such as *Pichia pastoris* host cell that has a deletion or disruption of the gene encoding β-mannosyltransferase 2 activity and a deletion or disruption of at least one gene selected a gene encoding a β-mannosyltransferase 1 activity and a β-mannosyltransferase 3 activity and which includes a nucleic acid molecule encoding the recombinant glycoprotein. In further embodiments, the host cell has a deletion or disruption of the genes encoding a β-mannosyltransferase 2 activity, a β-mannosyltransferase 1 activity, and a β-mannosyltransferase 3 activity. In further embodiments, the host cell has a deletion or disruption of the gene encoding a β-mannosyltransferase 4 activity.

In another aspect, the present invention provides a recombinant *Pichia pastoris* host cell in which the β-mannosyltransferase 2 (BMT2) gene and at least one gene selected from β-mannosyltransferase 1 (BMT1) and β-mannosyltransferase 3 (BMT3) has been deleted or disrupted and which includes a nucleic acid molecule encoding the recombinant protein or glycoprotein. In further embodiments, the β-mannosyltransferase 2 (BMT2), β-mannosyltransferase 1 (BMT1), and β-mannosyltransferase 3 (BMT3) genes are deleted. In further embodiments, the host cell further includes a deletion or disruption of the β-mannosyltransferase 4 (BMT4) gene.

In another aspect, the present invention provides a method for producing a recombinant glycoprotein in methylotrophic yeast such as *Pichia pastoris* that lacks detectable cross binding activity with antibodies made against host cell antigens, comprising providing a recombinant host cell that does not display a β-mannosyltransferase 2 activity with respect to an N-glycan or O-glycan and does not display at least one activity with respect to an N-glycan or O-glycan selected from β-mannosyltransferase 1 and β-mannosyltransferase 3 and which includes a nucleic acid molecule encoding the recombinant protein or glycoprotein; growing the host cell in a medium under conditions effective for expressing the recombinant glycoprotein; and recovering the recombinant glycoprotein from the medium to produce the recombinant glycoprotein that lacks detectable cross binding activity with antibodies made against host cell antigens. In further embodiments, the host cell does not display β-mannosyltransferase 2 activity, β-mannosyltransferase 1 activity, and β-mannosyltransferase 3 activity with respect to an N-glycan or O-glycan. In further embodiments, the host cell further does not display β-mannosyltransferase 4 activity with respect to an N-glycan or O-glycan.

In another aspect, the present invention provides a method for producing a recombinant glycoprotein in methylotrophic yeast such as *Pichia pastoris* that lacks detectable cross binding activity with antibodies made against host cell antigens, comprising providing a recombinant host cell that has a deletion or disruption of the gene encoding a β-mannosyltransferase 2 activity and a deletion or disruption of at least one gene encoding an activity selected from β-mannosyltransferase 1 activity and β-mannosyltransferase 3 activity and which includes a nucleic acid molecule encoding the recombinant protein or glycoprotein; growing the host cell in a medium under conditions effective for expressing the recombinant glycoprotein; and recovering the recombinant glycoprotein from the medium to produce the recombinant glycoprotein that lacks detectable cross binding activity with antibodies made against host cell antigens. In further embodiments, the host cell has a deletion or disruption of the genes encoding a β-mannosyltransferase 2 activity, a β-mannosyltransferase 1 activity, and a β-mannosyltransferase 3 activity. In further embodiments, the host cell has a deletion or disruption of the gene encoding a β-mannosyltransferase 4 activity.

In another aspect, the present invention provides a method for producing a recombinant glycoprotein in *Pichia pastoris* that lacks detectable cross binding activity with antibodies made against host cell antigens, comprising providing a recombinant *Pichia pastoris* host cell in which the β-mannosyltransferase 2 (BMT2) gene and at least one gene selected from β-mannosyltransferase 1 (BMT1) and β-mannosyltransferase 3 (BMT3) has been deleted or disrupted and which includes a nucleic acid molecule encoding the recombinant protein or glycoprotein; growing the host cell in a medium under conditions effective for expressing the recombinant glycoprotein; and recovering the recombinant glycoprotein from the medium to produce the recombinant glycoprotein that lacks detectable cross binding activity with antibodies made against host cell antigens. In further embodiments, the β-mannosyltransferase 2 (BMT2), β-mannosyltransferase 1 (BMT1), and β-mannosyltransferase 3 (BMT3) genes have been deleted or disrupted. In further embodiments, the host cell further includes a deletion or disruption of the β-mannosyltransferase (BMT4) gene.

In general, the detectable cross binding activity with antibodies made against host cell antigens is determined in an assay such as sandwich ELISA or a Western blot. The method is particularly useful for producing therapeutic proteins or glycoproteins. Examples of therapeutic proteins or glycoproteins include but are not limited to erythropoietin (EPO); cytokines such as interferon α, interferon β, interferon γ, and interferon ω; and granulocyte-colony stimulating factor (GCSF); GM-CSF; coagulation factors such as factor VIII, factor IX, and human protein C; antithrombin III; thrombin;

soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; and urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4—Ig; transmembrane activator and calcium modulator and cyclophilin ligand; glucagon like protein 1; and IL-2 receptor agonist.

In particular embodiments of the host cell or method, the codons of the nucleic acid sequence of the nucleic acid molecule encoding the recombinant protein or glycoprotein is optimized for expression in *Pichia pastoris*.

In a further still embodiment of the host cell or method, the host cell is genetically engineered to produce glycoproteins that have human-like N-glycans.

In a further embodiment of the host cell or method, the host cell further does not display α1,6-mannosyltransferase activity with respect to the N-glycan on a glycoprotein and includes an α1,2-mannosidase catalytic domain fused to a cellular targeting signal peptide not normally associated with the catalytic domain and selected to target α1,2-mannosidase activity to the ER or Golgi apparatus of the host cell.

In a further still embodiment of the host cell or method, the host cell further includes a GlcNAc transferase I catalytic domain fused to a cellular targeting signal peptide not normally associated with the catalytic domain of and selected to target GlcNAc transferase I activity to the ER or Golgi apparatus of the host cell.

In a further still embodiment of the host cell or method, the host cell further includes a mannosidase II catalytic domain fused to a cellular targeting signal peptide not normally associated with the catalytic domain and selected to target mannosidase II activity to the ER or Golgi apparatus of the host cell.

In a further still embodiment of the host cell or method, the host cell further includes a GlcNAc transferase II catalytic domain fused to a cellular targeting signal peptide not normally associated with the catalytic domain and selected to target GlcNAc transferase II activity to the ER or Golgi apparatus of the host cell.

In a further still embodiment of the host cell or method the host cell further includes a galactosyltransferase catalytic domain fused to a cellular targeting signal peptide not normally associated with the catalytic domain and selected to target galactosyltransferase activity to the ER or Golgi apparatus of the host cell.

In a further still embodiment of the host cell or method, the host cell further includes a sialyltransferase catalytic domain fused to a cellular targeting signal peptide not normally associated with the catalytic domain and selected to target sialyltransferase activity to the ER or Golgi apparatus of the host cell.

In a further still embodiment of the host cell or method, the host cell further includes a fucosyltransferase catalytic domain fused to a cellular targeting signal peptide not normally associated with the catalytic domain and selected to target fucosyltransferase activity to the ER or Golgi apparatus of the host cell.

In a further still embodiment of the host cell or method, the host cell further includes one or more GlcNAc transferases selected from the group consisting of GnTIII, GnTIV, GnTV, GnTVI, and GnTIX.

In a further still embodiment of the host cell or method, the host cell is genetically engineered to produce glycoproteins that have predominantly an N-glycan selected from $Man_5GlcNAc_2$, $GlcNAcMan_5GlcNAc_2$, $GalGlcNAcMan_5GlcNAc_2$, $NANAGalGlcNAcMan_5GlcNAc_2$, $GlcNAcMan_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}GlcNAc_{(1-4)}Man_3GlcNAc_2$, wherein the subscript indicates the number of the particular sugar residues on the N-glycan structure. Examples of N-glycan structures include but are not limited to $Man_5GlcNAc_2$, $GlcNAcMan_5GlcNAc_2$, $GlcNAcMan_3GlcNAc_2$, $GlcNAc_2Man_3GlcNAc_2$, $GlcNAc_3Man_3GlcNAc_2$, $GlcNAc_4Man_3GlcNAc_2$, $GalGlcNAc_2Man_3GlcNAc_2$, $Gal_2GlcNAc_2Man_3GlcNAc_2$, $Gal_2GlcNAc_3Man_3GlcNAc_2$, $Gal_2GlcNAc_4Man_3GlcNAc_2$, $Gal_3GlcNAc_3Man_3GlcNAc_2$, $Gal_3GlcNAc_4Man_3GlcNAc_2$, $Gal_4GlcNAc_4Man_3GlcNAc_2$, $NANAGal_2GlcNAc_2Man_3GlcNAc_2$, $NANA_2Gal_2GlcNAc_2Man_3GlcNAc_2$, $NANA_3Gal_3GlcNAc_3Man_3GlcNAc_2$, and $NANA_4Gal_4GlcNAc_4Man_3GlcNAc_2$.

Further provided are compositions, which comprise one or more recombinant glycoproteins obtained by the above method using any one of the above host cells.

In a further aspect, the present invention provides a recombinant methylotrophic yeast such as *Pichia pastoris* host cell that does not display β-mannosyltransferase 2 activity and at least one activity selected from β-mannosyltransferase 1 activity and β-mannosyltransferase 3 activity and which includes two or more nucleic acid molecules, each encoding a fusion protein comprising a mature human erythropoietin fused to a signal peptide that targets the ER and which is removed when the fusion protein is in the ER. In particular embodiments, the host cell further does not display β-mannosyltransferase 4 activity.

In a further aspect, the present invention provides a recombinant methylotrophic yeast such as *Pichia pastoris* host cell that has a deletion or disruption of the genes encoding β-mannosyltransferase 2 activity, β-mannosyltransferase 1 activity, and β-mannosyltransferase 3 activity and which includes two or more nucleic acid molecules, each encoding a fusion protein comprising a mature human erythropoietin fused to a signal peptide that targets the ER and which is removed when the fusion protein is in the ER. In particular embodiments, the host cell further includes a deletion or disruption of the gene encoding β-mannosyltransferase 4 activity.

In a further aspect, the present invention provides a recombinant *Pichia pastoris* host cell that has a deletion or disruption of the β-mannosyltransferase 2 (BMT2) gene and at least one gene selected from a β-mannosyltransferase 1 (BMT1) and β-mannosyltransferase 3 (BMT3) gene and which includes two or more nucleic acid molecules, each encoding a fusion protein comprising a mature human erythropoietin fused to a signal peptide that targets the ER and which is removed when the fusion protein is in the ER. In particular embodiments, the host cell further includes a deletion or disruption of the gene encoding β-mannosyltransferase 4 (BMT4) gene.

In a further still aspect, the present invention provides a method for producing a mature human erythropoietin in methylotrophic yeast such as *Pichia pastoris* comprising predominantly sialic acid-terminated biantennary N-glycans and having no detectable cross binding activity with antibodies made against host cell antigens, comprising: providing a recombinant host cell that does not display β-mannosyltransferase 2 activity with respect to an N-glycan or O-glycan and does not display at least one activity with respect to an N-glycan or O-glycan selected from β-mannosyltransferase 1 activity and β-mannosyltransferase 3 activity and is genetically engineered to produce sialic acid-terminated biantennary N-glycans and which includes two or more nucleic acid molecules, each encoding a fusion protein comprising a mature human erythropoietin fused to a signal peptide that targets the ER and which is removed when the fusion protein is in the ER; growing the host cell in a medium under conditions effective for expressing and processing the first and second fusion proteins; and recovering the mature human erythropoietin from the medium to produce the mature human erythropoietin comprising predominantly sialic acid-terminated biantennary N-glycans and having no detectable cross binding activity with antibodies made against host cell antigens. In further embodiments, the host cell does not display β-mannosyltransferase 2 activity, β-mannosyltransferase 1 activity, and β-mannosyltransferase 3 activity with respect to an N-glycan or O-glycan. In further embodiments, the host cell further does not display β-mannosyltransferase 4 activity.

In a further still aspect, the present invention provides a method for producing a mature human erythropoietin in methylotrophic yeast such as *Pichia pastoris* comprising predominantly sialic acid-terminated biantennary N-glycans and having no detectable cross binding activity with antibodies made against host cell antigens, comprising: providing a recombinant host cell genetically engineered to produce sialic acid-terminated biantennary N-glycans and in which the gene encoding a β-mannosyltransferase 2 activity and at least one gene encoding an activity selected from a β-mannosyltransferase 1 activity and a β-mannosyltransferase 3 activity has been deleted or disrupted and which includes two or more nucleic acid molecules, each encoding a fusion protein comprising a mature human erythropoietin fused to a signal peptide that targets the ER and which is removed when the fusion protein is in the ER; growing the host cell in a medium under conditions effective for expressing and processing the first and second fusion proteins; and recovering the mature human erythropoietin from the medium to produce the mature human erythropoietin comprising predominantly sialic acid-terminated biantennary N-glycans and having no detectable cross binding activity with antibodies made against host cell antigens. In further embodiments, the host comprises a deletion or disruption of the genes encoding a β-mannosyltransferase 2 activity, a β-mannosyltransferase 1 activity, and a β-mannosyltransferase 3 activity have been deleted or disrupted. In further embodiments, the host cell further includes a deletion or disruption of a gene encoding a β-mannosyltransferase 3 activity.

In a further still aspect, the present invention provides a method for producing a mature human erythropoietin in *Pichia pastoris* comprising predominantly sialic acid-terminated biantennary N-glycans and having no detectable cross binding activity with antibodies made against host cell antigens, comprising: providing a recombinant *Pichia pastoris* host cell genetically engineered to produce sialic acid-terminated biantennary N-glycans and in which the β-mannosyltransferase 2 (BMT2) gene and at least one gene selected from a β-mannosyltransferase 1 (BMT1) and β-mannosyltransferase 3 (BMT3) gene has been deleted or disrupted and which includes two or more nucleic acid molecules, each encoding a fusion protein comprising a mature human erythropoietin fused to a signal peptide that targets the ER and which is removed when the fusion protein is in the ER; growing the host cell in a medium under conditions effective for expressing and processing the first and second fusion proteins; and recovering the mature human erythropoietin from the medium to produce the mature human erythropoietin comprising predominantly sialic acid-terminated biantennary N-glycans and having no detectable cross binding activity with antibodies made against host cell antigens. In further embodiments, the host comprises a deletion or disruption of the β-mannosyltransferase 2 (BMT2) gene, β-mannosyltransferase 1 (BMT1) gene, and β-mannosyltransferase 3 (BMT3) gene have been deleted or disrupted. In further embodiments, the host cell further includes a deletion or disruption of a β-mannosyltransferase 3 gene (BMT4).

In particular embodiments of the host cell or method, the signal peptide fused to the N-terminus of the erythropoietin is a *S. cerevisiae* αMATpre signal peptide or a chicken lysozyme signal peptide.

In further embodiments of the host cell or method, at least one nucleic acid molecule encodes a fusion protein wherein the erythropoietin is fused to the *S. cerevisiae* αMATpre signal peptide and at least one nucleic acid molecule encodes a fusion protein wherein the erythropoietin is fused to the *S. cerevisiae* αMATpre signal peptide a chicken lysozyme signal peptide.

In further embodiments of the host cell or method, the codons of the nucleic acid sequence of the nucleic acid molecule encoding the erythropoietin is optimized for expression in *Pichia pastoris*.

In further embodiments of the method, recovering the mature human erythropoietin comprising predominantly sialic acid-terminated biantennary N-glycans and having no detectable cross binding activity with antibodies made against host cell antigens from the medium includes a cation exchange chromatography step.

In further embodiments of the method, recovering the mature human erythropoietin comprising predominantly sialic acid-terminated biantennary N-glycans and having no detectable cross binding activity with antibodies made against host cell antigens from the medium includes a hydroxyapatite chromatography step.

In further embodiments of the method, recovering the mature human erythropoietin comprising predominantly sialic acid-terminated biantennary N-glycans and having no detectable cross binding activity with antibodies made against host cell antigens from the medium includes an anion exchange chromatography step.

In further embodiments of the method, recovering the mature human erythropoietin comprising predominantly sialic acid-terminated biantennary N-glycans and having no detectable cross binding activity with antibodies made against host cell antigens from the medium includes a cation exchange chromatography step followed by a hydroxyapatite chromatography step, which is optionally followed by an anion exchange chromatography step.

The present invention further provides a composition comprising a mature human erythropoietin comprising predominantly sialic acid-terminated biantennary N-glycans and having no detectable cross binding activity with antibodies made against host cell antigens obtained from the above method using the above host cells and a pharmaceutically acceptable salt. In particular embodiments, about 50 to 60% of the N-glycans comprise sialic acid residues on both antennae; in further embodiments, greater than 70% of the N-glycans comprise sialic acid residues on both antennae; in further embodiments, greater than 80% of the N-glycans comprise sialic acid residues on both antennae. In further aspects, less than 30% of the N-glycans are neutral N-glycans (i.e., are not sialylated on at least one terminus at the non-reducing end of the N-glycan). In further still aspects, less than 20% of the N-glycans are neutral N-glycans. In particular aspects, about 99% of the N-glycans contain one or more sialic acid residues and less than 1% of the N-glycans are neutral N-glycans. In further aspects, compositions are provided wherein there is 4.5 moles or more of sialic acid per mole of rhEPO. In further aspects, compositions are provided wherein there is at least 5.0 moles of sialic acid per mole of rhEPO.

In further embodiments of the composition, the mature human erythropoietin comprising predominantly sialic acid-terminated biantennary N-glycans and having no detectable cross binding activity with antibodies made against host cell antigens is conjugated to a hydrophilic polymer, which in particular aspects is a polyethylene glycol polymer. In particular embodiments, the polyethylene glycol polymer is conjugated to the N-terminus of the mature human erythropoietin comprising predominantly sialic acid-terminated bi-antennary N-glycans and having no detectable cross binding activity with antibodies made against host cell antigens.

DEFINITIONS

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

A host cell that "does not display" an enzyme activity refers to a host cell in which the enzyme activity has been abrogated or disrupted. For example, the enzyme activity can be abrogated or disrupted by deleting or disrupting the gene encoding the enzyme activity (included deleting or disrupting the upstream or downstream regulatory sequences controlling expression of the gene; the enzyme activity can be abrogated or disrupted by mutating the gene encoding the enzyme activity to render the enzyme activity encoded gene non-functional; the enzyme activity can be abrogated or disrupted by use of a chemical, peptide, or protein inhibitor of the enzyme activity; the enzyme activity can be abrogated or disrupted by use of nucleic acid-based expression inhibitors such as antisense DNA and siRNA; and, the enzyme activity can be abrogated or disrupted by use of transcription inhibitors or inhibitors of the expression or activity of regulatory factors that control or regulate expression of the gene encoding the enzyme activity.

When referring to "mole percent" of a glycan present in a preparation of a glycoprotein, the term means the molar percent of a particular glycan present in the pool of N-linked oligosaccharides released when the protein preparation is treated with PNG'ase and then quantified by a method that is not affected by glycoform composition, (for instance, labeling a PNG'ase released glycan pool with a fluorescent tag such as 2-aminobenzamide and then separating by high performance liquid chromatography or capillary electrophoresis and then quantifying glycans by fluorescence intensity). For example, 50 mole percent $NANA_2Gal_2GlcNAc_2Man_3GlcNAc_2$ means that 50 percent of the released glycans are $NANA_2Gal_2GlcNAc_2Man_3GlcNAc_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

As used herein, the term "predominantly" or variations such as "the predominant" or "which is predominant" will be understood to mean the glycan species that has the highest mole percent (%) of total N-glycans after the glycoprotein has been treated with PNGase and released glycans analyzed by mass spectroscopy, for example, MALDI-TOF MS. In other words, the phrase "predominantly" is defined as an individual entity, such as a specific glycoform, is present in greater mole percent than any other individual entity. For example, if a composition consists of species A in 40 mole percent, species B in 35 mole percent and species C in 25 mole percent, the composition comprises predominantly species A.

The term "therapeutically effective amount" refers to an amount of the recombinant erythropoietin of the invention which gives an increase in hematocrit that provides benefit to a patient. The amount will vary from one individual to another and will depend upon a number of factors, including the overall physical condition of the patient and the underlying cause of anemia. For example, a therapeutically effective amount of erythropoietin of the present invention for a patient suffering from chronic renal failure can be in the range of 20 to 300 units/kg or 0.5 ug/kg to 500 ug/kg based on therapeutic indication. The term "unit" refers to units commonly known in the art for assessing the activity of erythropoietin compositions. A milligram of pure erythropoietin is approximately equivalent to 150,000 units. A dosing schedule can be from about three times per week to about once every four or six weeks. The actual schedule will depend on a number of factors including the type of erythropoietin administered to a patient (EPO or PEGylated-EPO) and the response of the individual patient. The higher dose ranges are not typically used in anemia applications but can be useful on other therapeutic applications. The means of achieving and establishing an appropriate dose of erythropoietin for a patient is well known and commonly practiced in the art.

Variations in the amount given and dosing schedule from patient to patient are including by reference to the term "about" in conjunction with an amount or schedule. The amount of erythropoietin used for therapy gives an acceptable rate of hematocrit increase and maintains the hematocrit at a beneficial level (for example, usually at least about 30% and typically in a range of 30% to 36%). A therapeutically effective amount of the present compositions may be readily ascertained by one skilled in the art using publicly available materials and procedures. Additionally, iron may be given to the patient to maintain increased erythropoiesis during therapy. The amount to be given may be readily determined by methods commonly used by those skilled in the art.

All flanked by the 5' region of the HIS1 gene (PpHIS1-5') and the 3' region of the HIS1 gene (PpHIS1-3'). PMA1 is the *P. pastoris* PMA1 promoter; PpPMA1 TT is the *P. pastoris* PMA1 termination sequence; GAPDH is the *P. pastoris* GADPH promoter and ScCYC TT is the *S. cerevisiae* CYC termination sequence; PpOCH1 Prom is the *P. pastoris* OCH1 promoter and PpALG12 TT is the *P. pastoris* ALG12 termination sequence.

Figure 10:
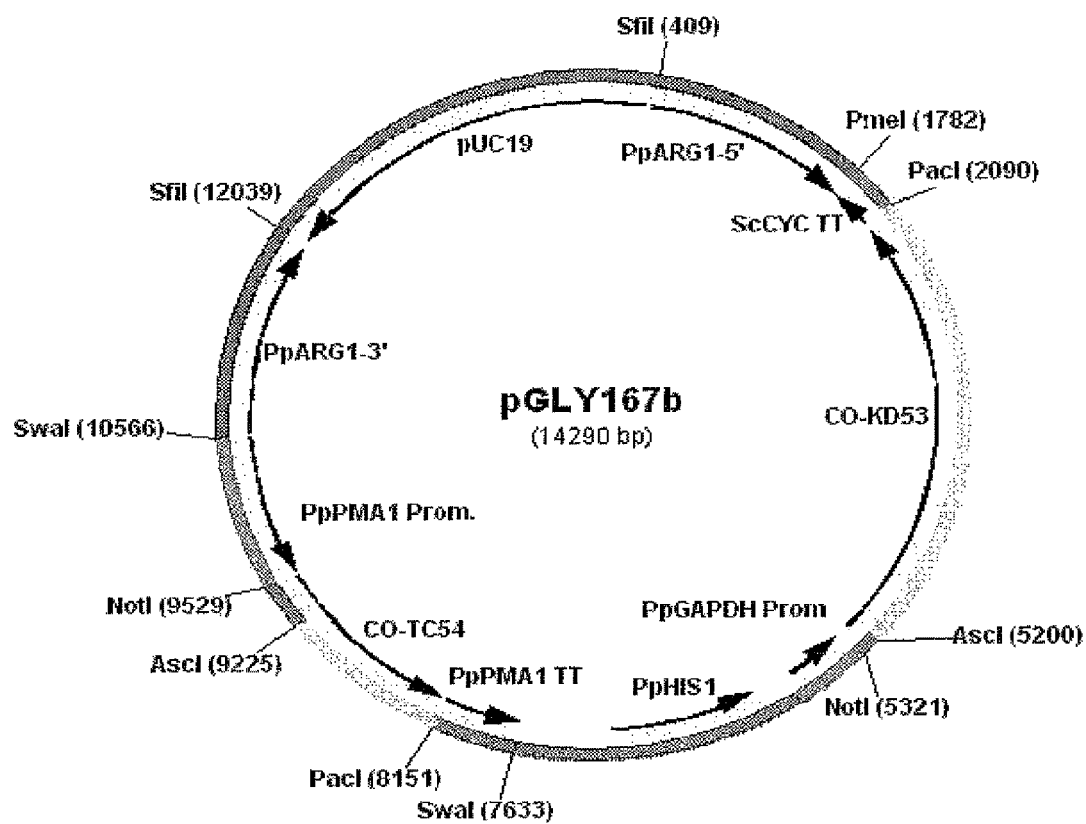

FIG. 10 shows a map of plasmid pGLY167b. Plasmid pGLY167b is an integration vector that targets the ARG1 locus and contains in tandem three expression cassettes encoding (1) the *D. melanogaster* mannosidase II catalytic domain (codon optimized) fused at the N-terminus to *S. cerevisiae* MNN2 leader peptide (CO-KD53), (2) the *P. pastoris* HIS1 gene or transcription unit, and (3) the rat N-acetylglucosamine (GlcNAc) transferase II catalytic domain (codon optimized) fused at the N-terminus to *S. cerevisiae* MNN2 leader peptide (CO-TC54). All flanked by the 5' region of the ARG1 gene (PpARG1-5') and the 3' region of the ARG1 gene (PpARG1-3'). PpPMA1 prom is the *P. pastoris* PMA1 promoter; PpPMA1 TT is the *P. pastoris* PMA1 termination sequence; PpGAPDH is the *P. pastoris* GADPH promoter; ScCYC TT is the *S. cerevisiae* CYC termination sequence; PpOCH1 Prom is the *P. pastoris* OCH1 promoter; and PpALG12 TT is the *P. pastoris* ALG12 termination sequence.

Figure 11:
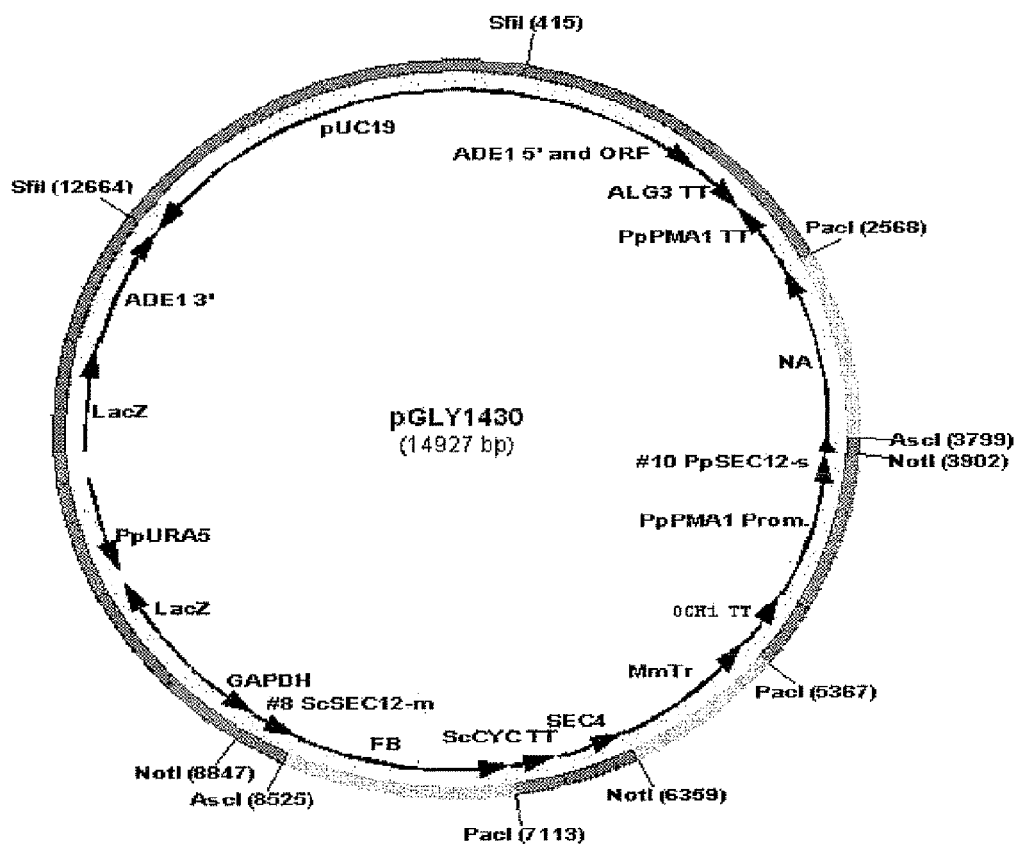

FIG. 11 shows a map of plasmid pGLY1430. Plasmid pGLY1430 is a KINKO integration vector that targets the ADE1 locus without disrupting expression of the locus and contains in tandem four expression cassettes encoding (1) the human GlcNAc transferase I catalytic domain (codon optimized) fused at the N-terminus to *P. pastoris* SEC12 leader peptide (CO-NA10), (2) mouse homologue of the UDP-GlcNAc transporter (MmTr), (3) the mouse mannosidase IA catalytic domain (FB) fused at the N-terminus to *S. cerevisiae* SEC12 leader peptide (FB8), and (4) the *P. pastoris* URA5 gene or transcription unit (PpURA5) flanked by lacZ repeats (lacZ). All flanked by the 5' region of the ADE1 gene and ORF (ADE1 5' and ORF) and the 3' region of the ADE1 gene (PpADE1-3'). PpPMA1 prom is the *P. pastoris* PMA1 promoter; PpPMA1 TT is the *P. pastoris* PMA1 termination sequence; SEC4 is the *P. pastoris* SEC4 promoter; OCH1 TT is the *P. pastoris* OCH1 termination sequence; ScCYC TT is the *S. cerevisiae* CYC termination sequence; PpOCH1 Prom is the *P. pastoris* OCH1 promoter; PpALG3 TT is the *P. pastoris* ALG3 termination sequence; and PpGAPDH is the *P. pastoris* GADPH promoter.

Figure 12:
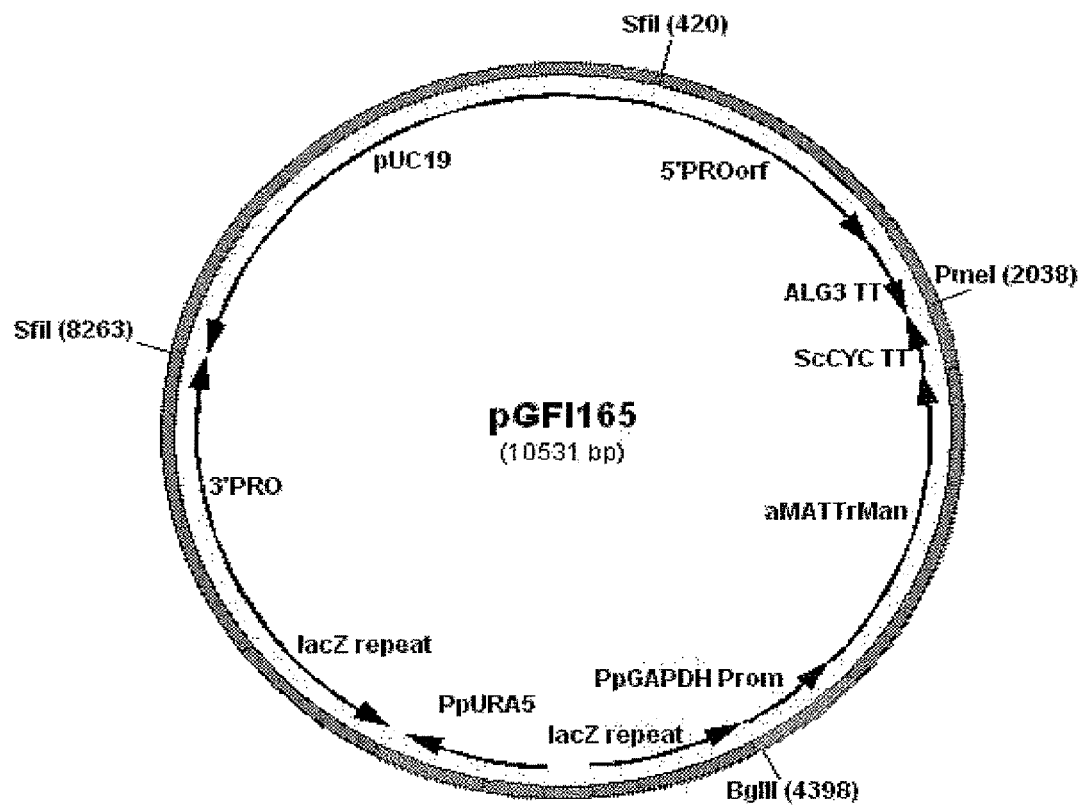

FIG. 12 shows a map of plasmid pGF1165. Plasmid pGF1165 is a KINKO integration vector that targets the PRO1 locus without disrupting expression of the locus and contains expression cassettes encoding (1) the *T. reesei* α-1,2-mannosidase catalytic domain fused at the N-terminus to *S. cerevisiae* αMATpre signal peptide (aMATTrMan) to target the chimeric protein to the secretory pathway and secretion from the cell and (2) the *P. pastoris* URA5 gene or transcription unit flanked by lacZ repeats (lacZ repeat). All flanked by the 5' region of the PRO1 gene and ORF (5'PRO1orf) and the 3' region of the PRO1 gene (3'PRO). ScCYC TT is the *S. cerevisiae* CYC termination sequence; PpALG3 TT is the *P. pastoris* ALG3 termination sequence; and PpGAPDH is the *P. pastoris* GADPH promoter.

Figure 13:
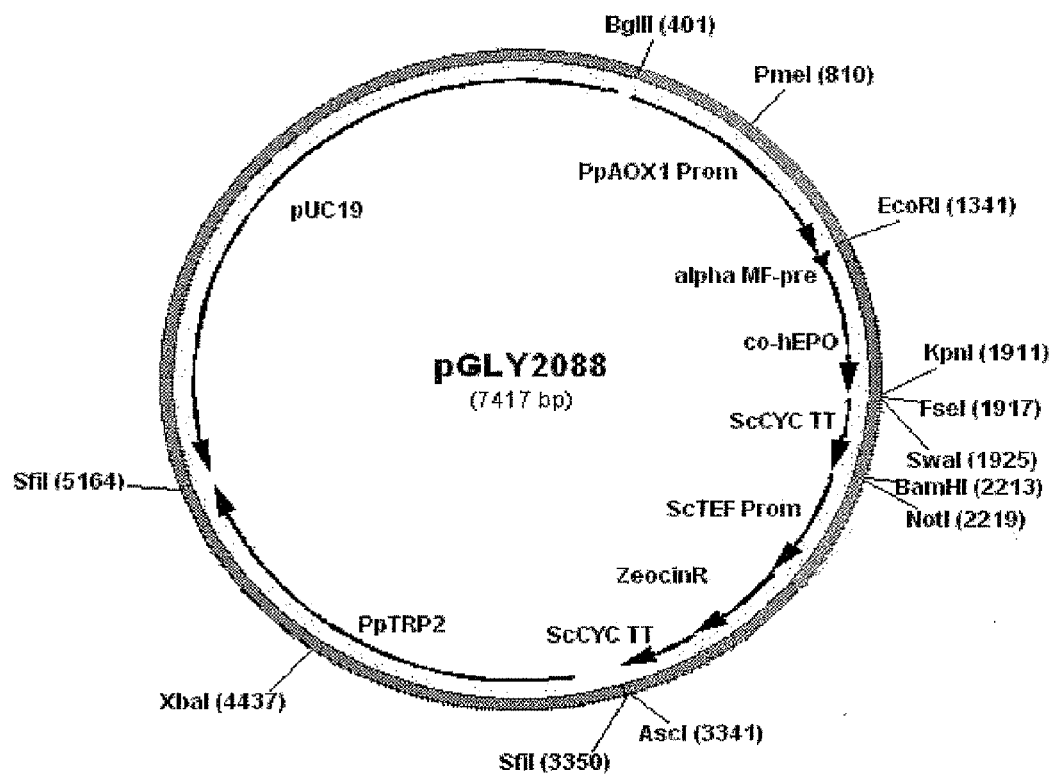

FIG. 13 shows a map of plasmid pGLY2088. Plasmid pGLY2088 is an integration vector that targets the TRP2 or AOX1 locus and contains expression cassettes encoding (1) mature human erythropoetin (co-hEPO) codon optimized fused at the N-terminus to a *S. cerevisiae* αMATpre signal peptide (alpha MF-pre) to target the chimeric protein to the secretory pathway and secretion from the cell and (2) the zeocin resistance protein (ZeocinR). The cassettes are flanked on one end with the *P. pastoris* AOX1 promoter (PpAOX1 Prom) and on the other end with the *P. pastoris* TRP2 gene or transcription unit (PpTRP2). ScCYC TT is the *S. cerevisiae* CYC termination sequence and ScTEF Prom is the *S. cerevisiae* TEF1 promoter.

Figure 14:
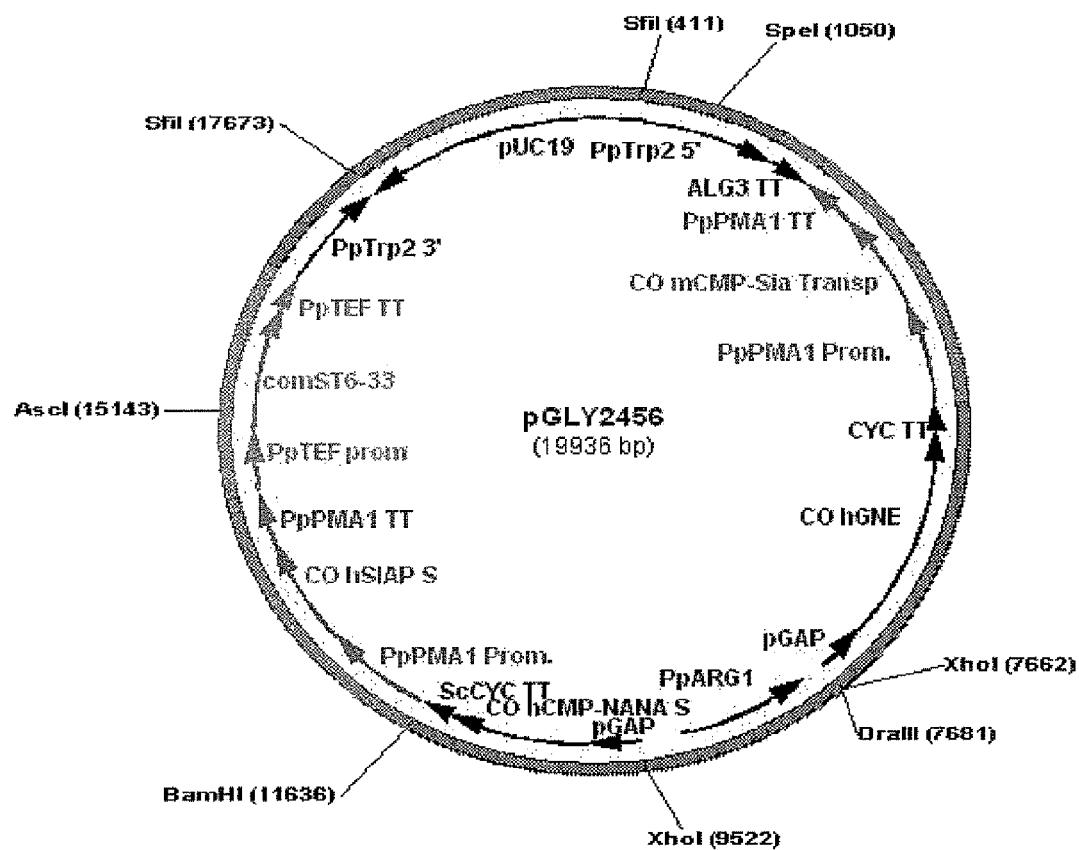

FIG. 14 shows a map of plasmid pGLY2456. Plasmid pGLY2456 is a KINKO integration vector that targets the TRP2 locus without disrupting expression of the locus and contains six expression cassettes encoding (1) the mouse CMP-sialic acid transporter codon optimized (CO mCMP-Sia Transp), (2) the human UDP-GlcNAc 2-epimerase/N-acetylmannosamine kinase codon optimized (CO hGNE), (3) the *Pichia pastoris* ARG1 gene or transcription unit, (4) the human CMP-sialic acid synthase codon optimized (CO hCMP-NANA S), (5) the human N-acetylneuraminate-9-phosphate synthase codon optimized (CO hSIAP S), and, (6) the mouse α-2,6-sialyltransferase catalytic domain codon optimized fused at the N-terminus to *S. cerevisiae* KRE2 leader peptide (comST6-33). All flanked by the 5' region of the TRP2 gene and ORF (PpTRP2 5') and the 3' region of the TRP2 gene (PpTRP2-3'). PpPMA1 prom is the *P. pastoris* PMA1 promoter; PpPMA1 TT is the *P. pastoris* PMA1 termination sequence; CYC TT is the *S. cerevisiae* CYC termination sequence; PpTEF Prom is the *P. pastoris* TEF1 promoter; PpTEF TT is the *P. pastoris* TEF1 termination sequence; PpALG3 TT is the *P. pastoris* ALG3 termination sequence; and pGAP is the *P. pastoris* GAPDH promoter.

Figure 15:
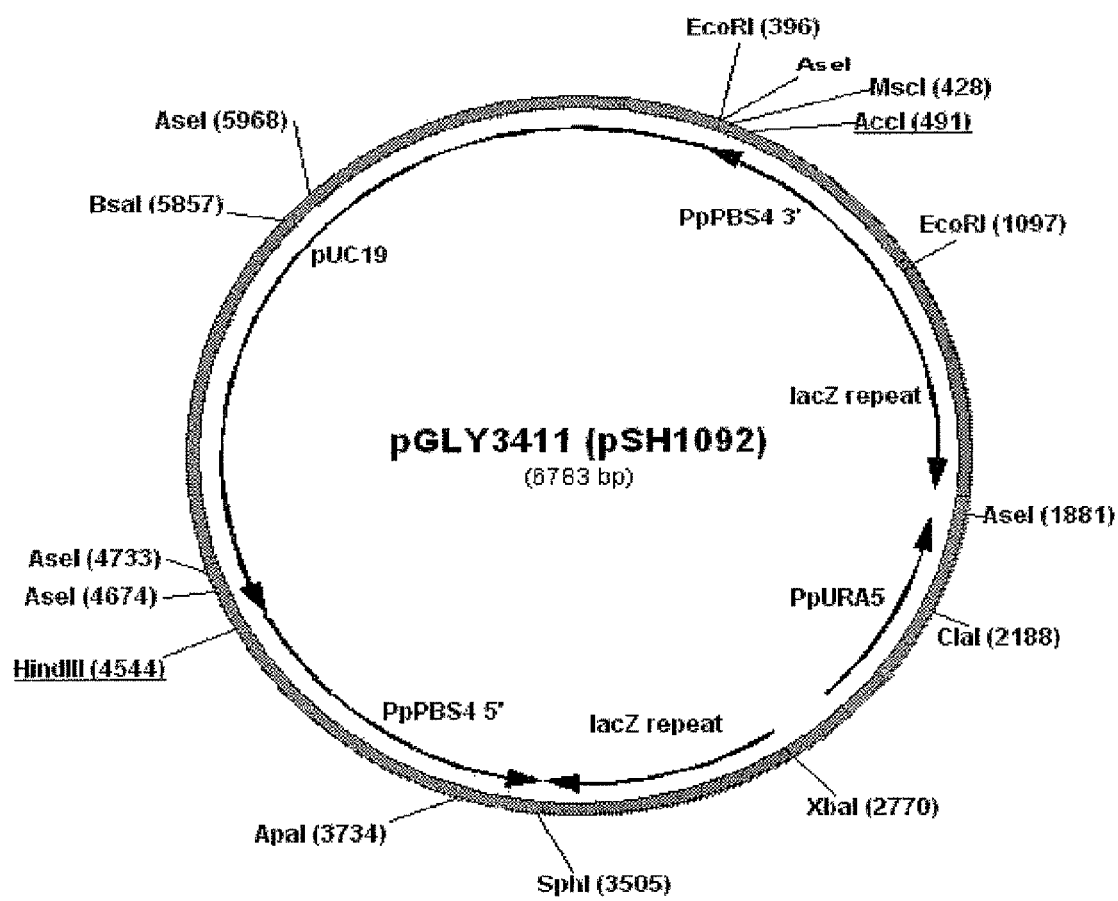

FIG. 15 shows a map of plasmid pGLY3411 (pSH1092). Plasmid pGLY3411 (pSH1092) is an integration vector that contains the expression cassette comprising the *P. pastoris* URA5 gene or transcription unit (PpURA5) flanked by lacZ repeats (lacZ repeat) flanked on one side with the 5' nucleotide sequence of the *P. pastoris* BMT4 gene (PpPBS4 5') and on the other side with the 3' nucleotide sequence of the *P. pastoris* BMT4 gene (PpPBS4 3').

Figure 16:
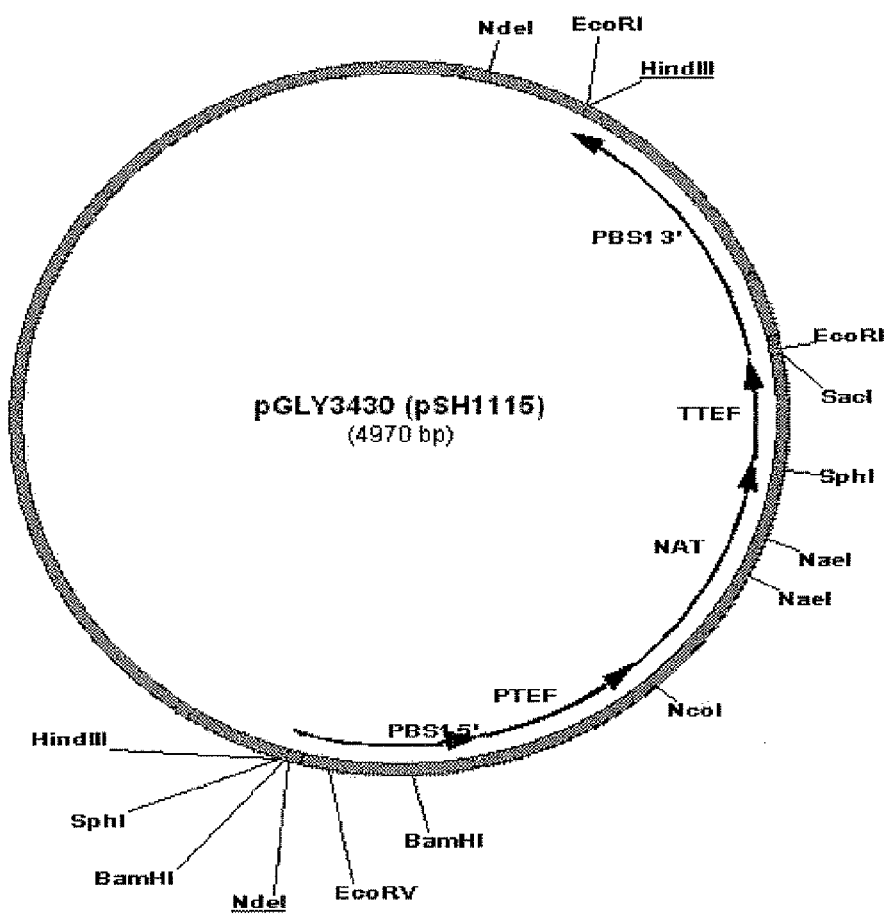

FIG. 16 shows a map of plasmid pGLY3430 (pSH1115). Plasmid pGLY3430 (pSH1115) is an integration vector that contains an expression cassette comprising a nucleic acid molecule encoding the Nourseothricin resistance ORF (NAT) operably linked to the *Ashbya gossypii* TEF1 promoter (PTEF) and *Ashbya gossypii* TEF1 termination sequence (TTEF) flanked one side with the 5' nucleotide sequence of the *P. pastoris* BMT1 gene (PBS1 5') and on the other side with the 3' nucleotide sequence of the *P. pastoris* BMT1 gene (PBS1 3').

Figure 17:
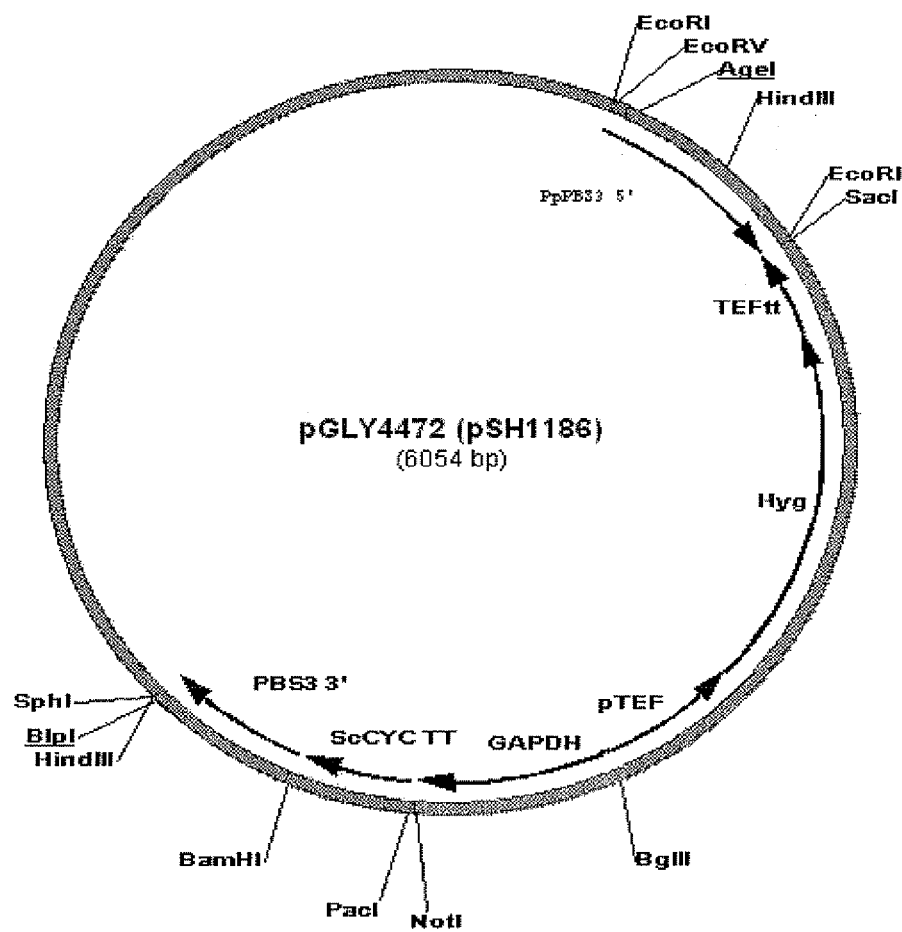

FIG. 17 shows a map of plasmid pGLY4472 (pSH1186). Plasmid pGLY4472 (pSH1186) contains an expression cassette comprising a nucleic acid molecule encoding the *E. coli* hygromycin B phosphotransferase gene ORF (Hyg) operably linked to the *Ashbya gossypii* TEF1 promoter (pTEF) and *Ashbya gossypii* TEF1 termination sequence (TRFtt) flanked one side with the 5' nucleotide sequence of the *P. pastoris* BMT3 gene (PpPBS3 5') and on the other side with the 3' nucleotide sequence of the *P. pastoris* BMT3 gene (PpPBS3 3').

Figure 18:
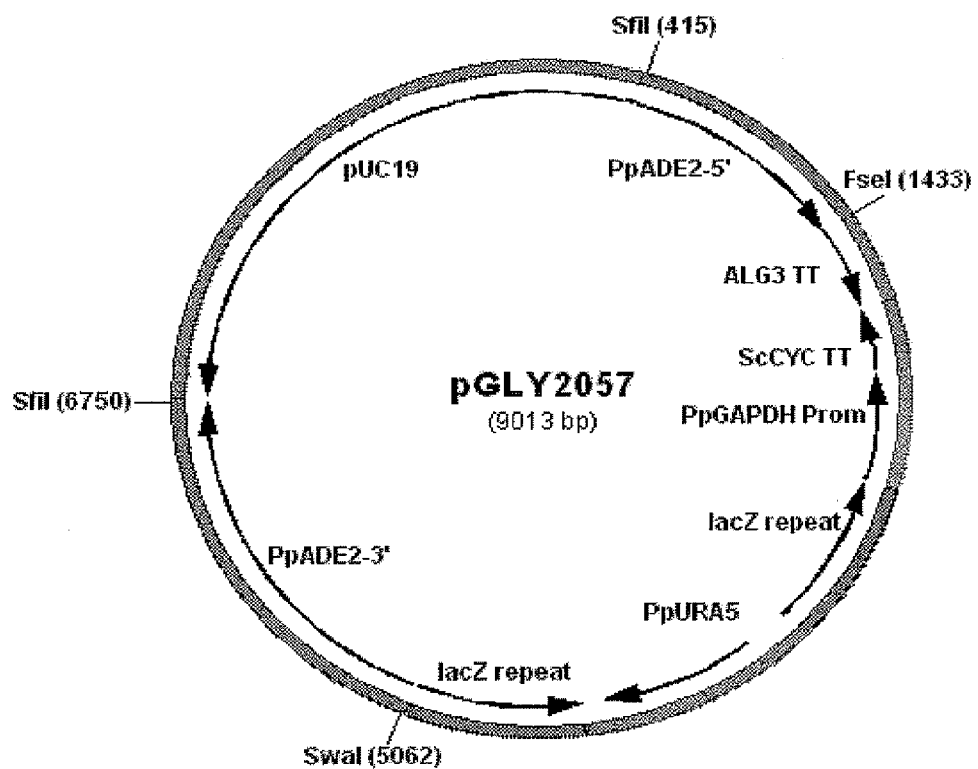

FIG. 18 shows a map of plasmid pGLY2057. Plasmid pGLY2057 is an integration plasmid that targets the ADE2 locus and contains an expression cassette encoding the *P. pastoris* URA5 gene or transcription unit (PpURA5) flanked by lacZ repeats (lacZ repeat). The expression cassette is flanked on one side by a nucleic acid molecule comprising a nucleotide sequence from the 5' region of the ADE2 gene (PpADE2-5') and on the other side by a nucleic acid molecule comprising a nucleotide sequence from the 3' region of the ADE2 gene (PpADE2-3').

Figure 19:
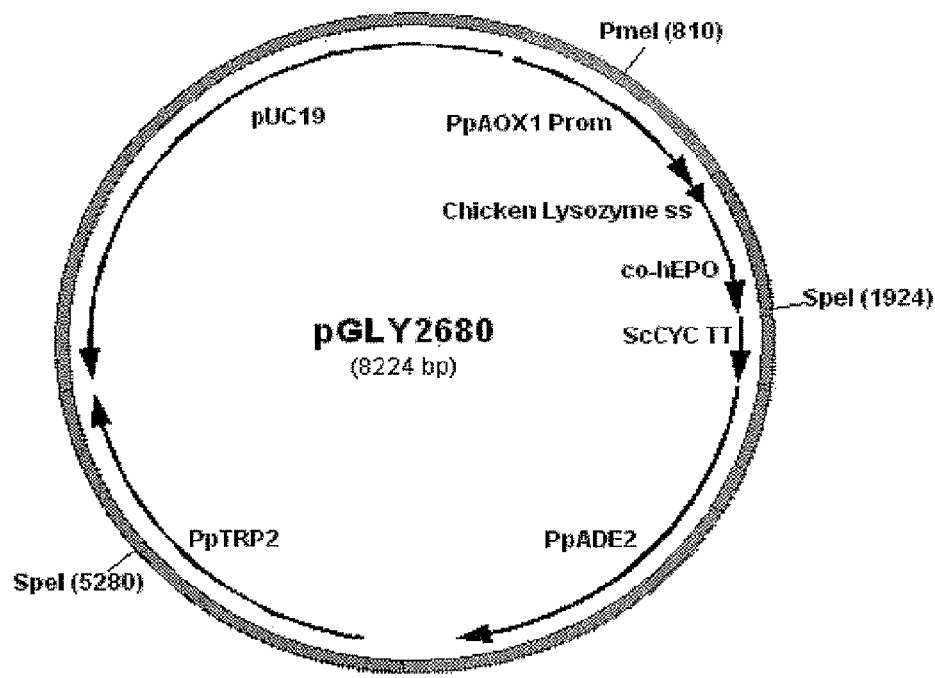

FIG. 19 shows a map of plasmid pGLY2680. Plasmid pGLY2680 is an integration vector that can target the TRP2 or AOX1 locus and contains expression cassettes encoding (1) the human mature erythropoetin codon optimized (co-hEPO) fused at the N-terminus to chicken lysozyme signal peptide (chicken Lysozyme ss) and (2) the *P. pastoris ADE*2 gene without a promoter (PpADE2). The cassettes are flanked on one end with the *P. pastoris* AOX1 promoter (PpAOX1 Prom) and on the other end with the *P. pastoris* TRP2 gene or transcription unit (PpTRP2). ScCYC TT is the *S. cerevisiae* CYC termination sequence.

Figure 20:
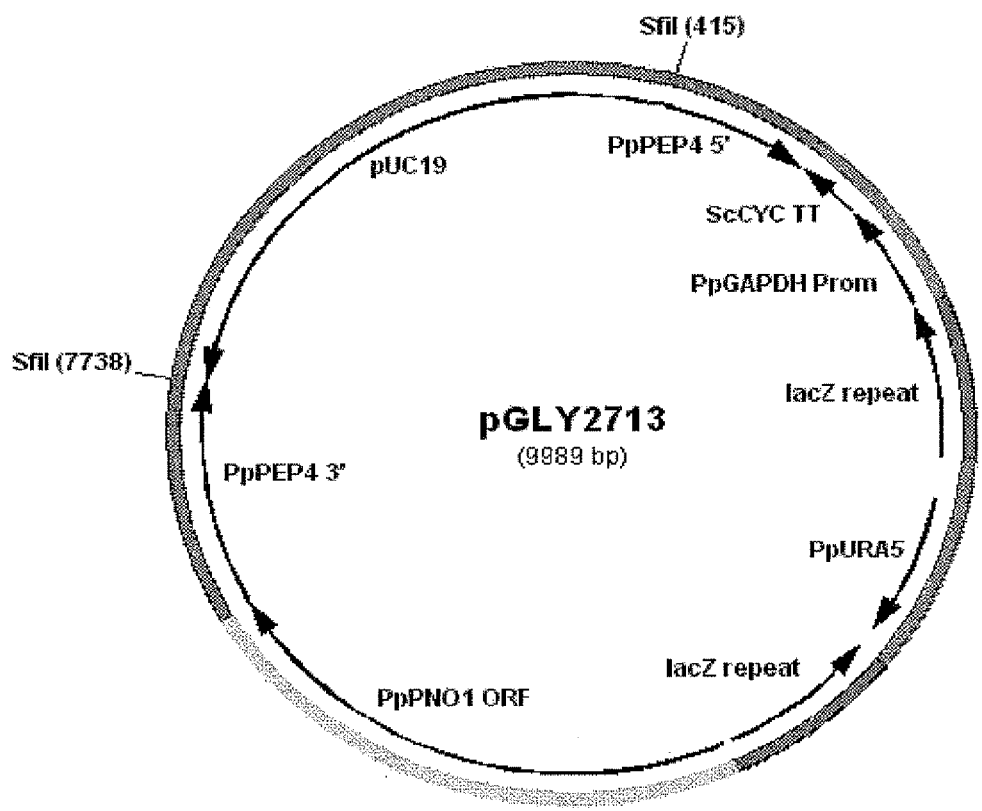

FIG. 20 shows a map of plasmid pGLY2713. Plasmid pGLY2713 is an integration vector containing the *P. pastoris* PNO1 ORF (PpPNO1 ORF) adjacent to the expression cassette comprising the *P. pastoris* URA5 gene or transcription unit (PpURA5) flanked by lacZ repeats (lacZ repeat) and flanked on one side with the 5' nucleotide sequence of the *P. pastoris* PEP4 gene (PpPEP4 5') and on the other side with the 3' nucleotide sequence of the *P. pastoris* PEP4 gene (PpPEP4 3').

Figure 21:
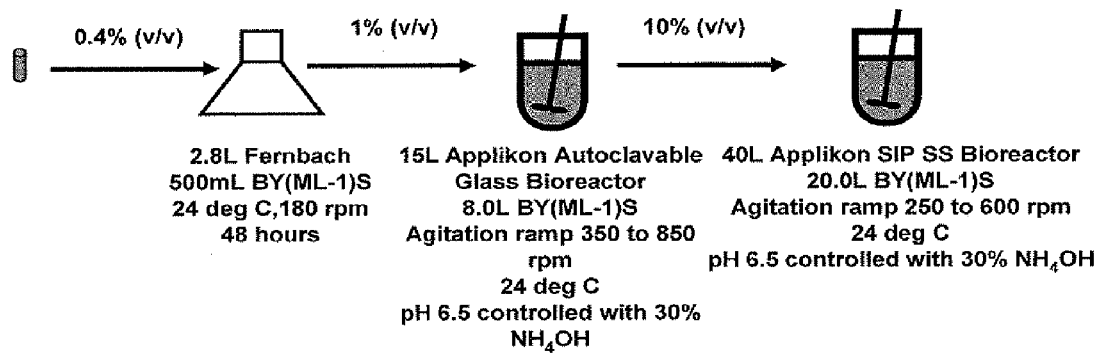

FIG. 21 shows a schematic diagram illustrating fermentation process flow.

Figure 22:
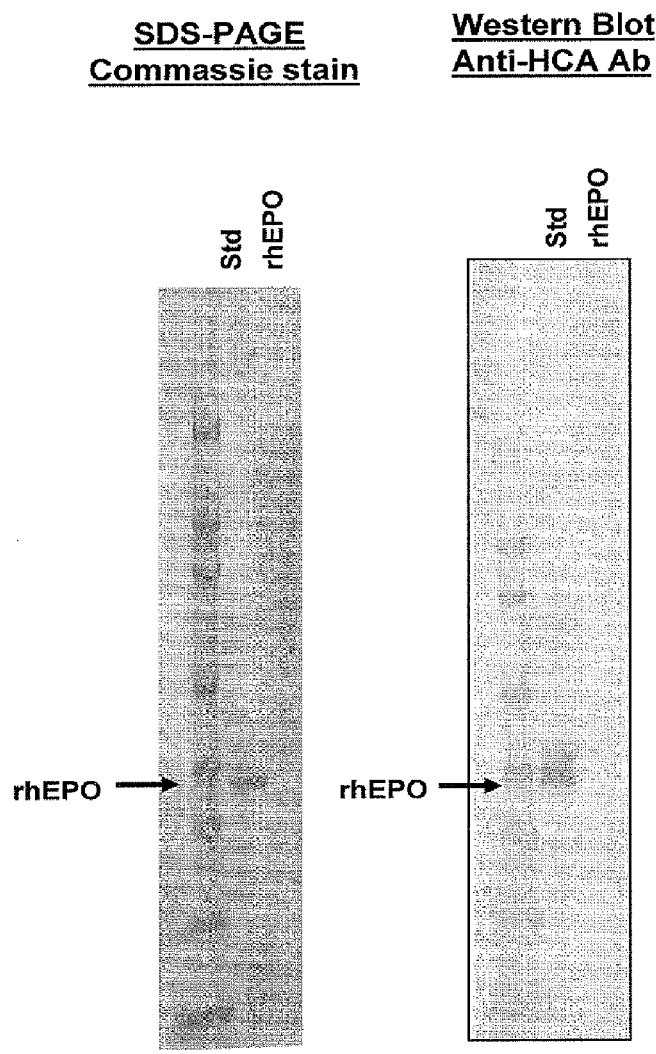

FIG. 22 shows that rhEPO produced in strain YGLY3159 has cross binding activity to anti-HCA antibodies. Left panel shows a Commassie Blue stained 4-20% SDS-PAGE gel showing the position of the rhEPO and right panel shows a Western blot of a similar gel probed with rabbit anti-HCA antibodies (SL rProA purified rabbit: 9161) at 1:3,000 dilution. Bound anti-HCA antibody was detected using goat anti-rabbit antibody conjugated to horseradish peroxidase (HRP) at a 1:5,000 dilution in PBS. Detection of bound secondary antibody used the substrate 3'3 diaminobenzidine (DAB).

Figure 23:
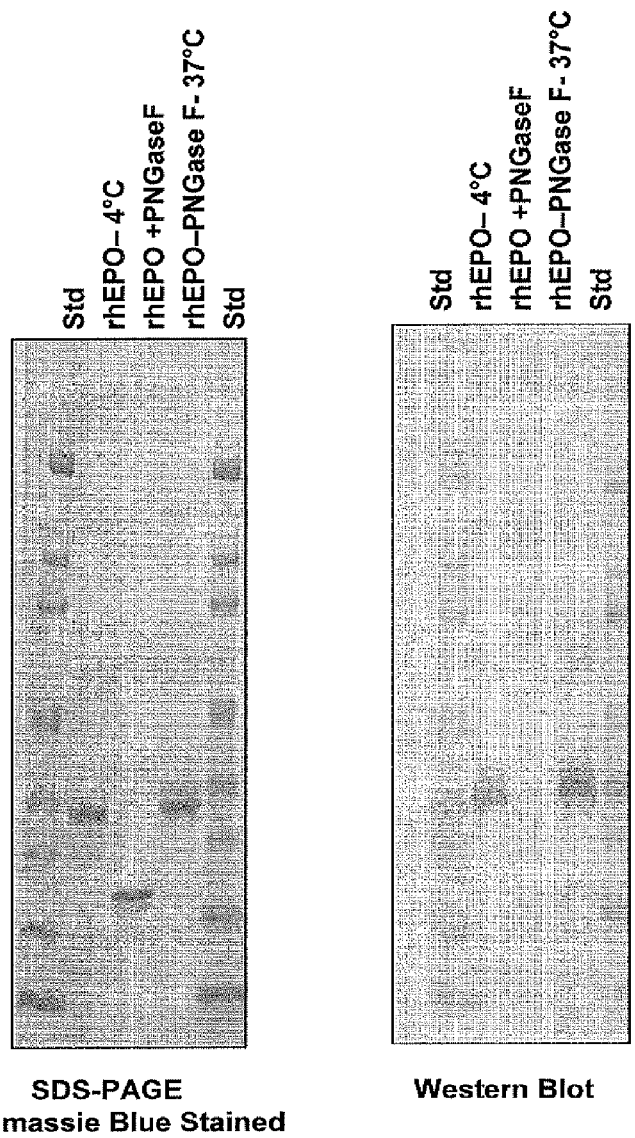

FIG. 23 shows that the cross-bind activity of the rhEPO produced in strain YGLY3159 to anti-HCA antibodies is not detected when the rhEPO is deglycosylated using PNAGase F. Left panel shows a Commassie Blue stained 4-20% SDS-PAGE gel showing the position of the glycosylated and deglycosylated forms of rhEPO and right panel shows a Western blot of a similar gel probed with anti-HCA antibodies as in FIG. 22.

Figure 24:
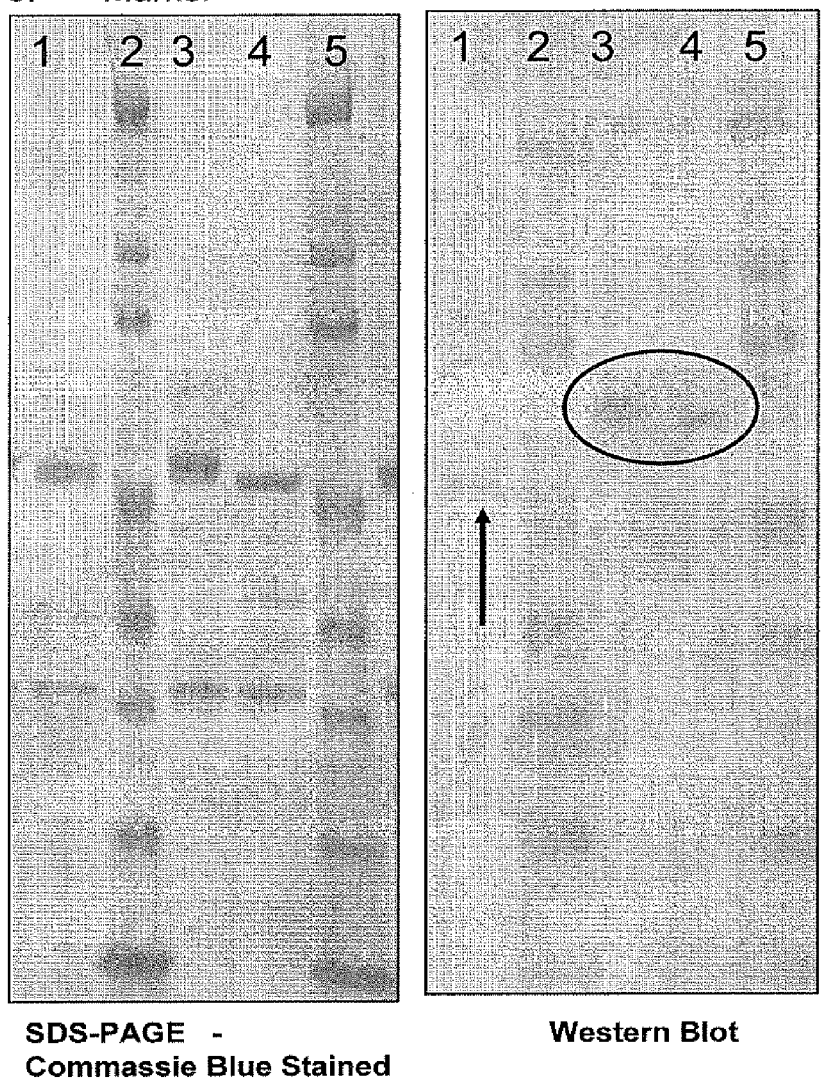

FIG. 24 shows that a recombinant antibody (rhIgG) produced in wild-type *P. pastoris* and a glycoengineered *P. pastoris* GS2.0 strain in which the BMT2 gene has been disrupted or deleted showed cross binding activity to anti-HCA antibodies. Left panel shows a Commassic Blue stained 4-20% SDS-PAGE gel and the right panel shows a Western blot of a similar gel probed with anti-HCA antibodies as in FIG. 22. GS 2.0 is a *P. pastoris* strain that produces glycoproteins that have predominantly $Man_5GlcNAc_2$ N-glycans. The shown GS 2.0 strain produced rhIgG with about 5% $Man_9GlcNAc_2$ N-glycans. WT is wild type *P. pastoris*.

FIG. 25 compares cross binding activity of rhEPO produced in strain YGLY3159 to other glycosylated proteins containing complex glycosylation patterns but not produced in *P. pastoris* to anti-HCA antibody. Upper panel shows a Commassie Blue stained 4-20% SDS-PAGE gel showing the position of the glycosylated and deglycosylated forms of rhEPO produced in *P. pastoris* and of recombinant human fetuin, asialofetuin (human fetuin with terminal sialic acid residues removed), human serum albumin (HSA), and recombinant LEUKINE produced in *S. cerevisiae* and the lower panel shows a Western blot of a similar gel probed with anti-HCA antibodies as in FIG. 22. S30S pools are rhEPO purified by cation exchange chromatography.

Figure 26:
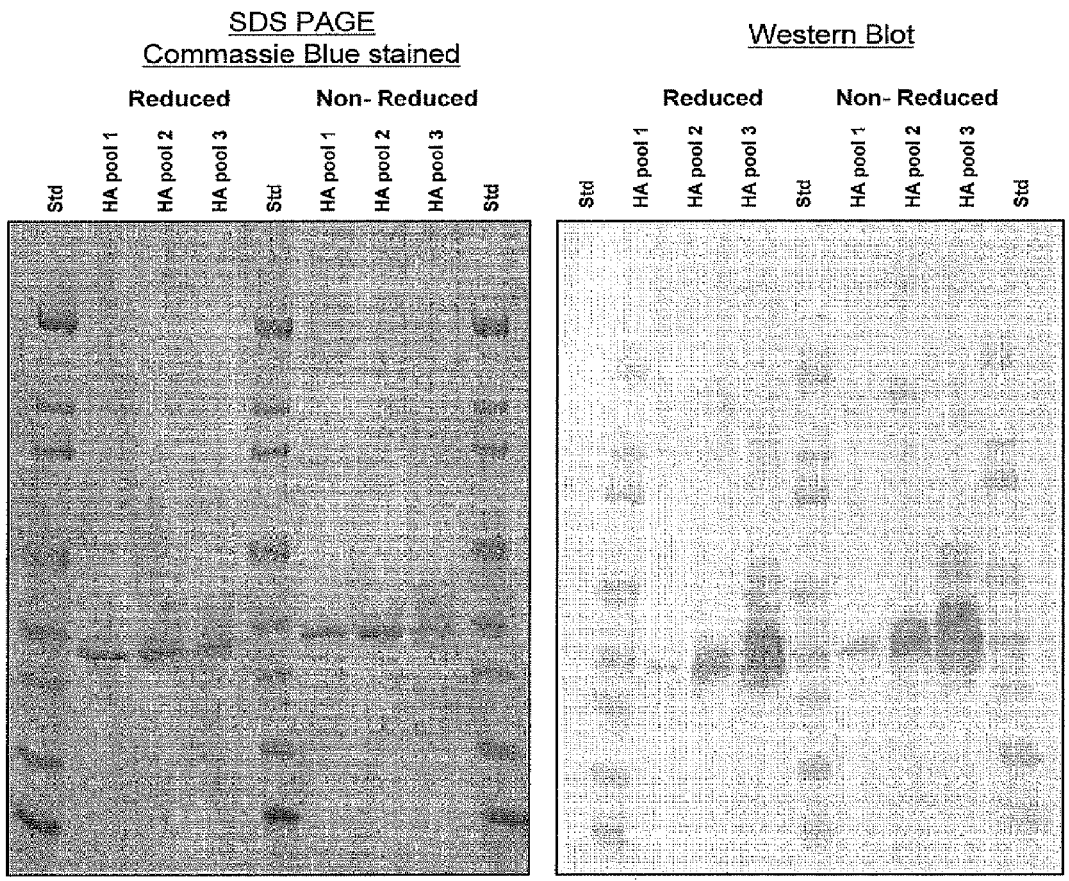

FIG. 26 shows that rhEPO produced in strain YGLY3159 and purified by hydroxyapatite chromatography still has cross binding activity to anti-HCA antibodies. Left panel shows a Commassie Blue stained 4-20% SDS-PAGE gel of chromatography elution pools 1, 2, and 3 showing the position of the rhEPO (reduced or non-reduced) and right panel shows a Western blot of a similar gel probed with anti-HCA antibodies as in FIG. 22. Below the panels is shown the results of an HPLC analysis of N-glycans in pools 1, 2, and 3.

Figure 27A:
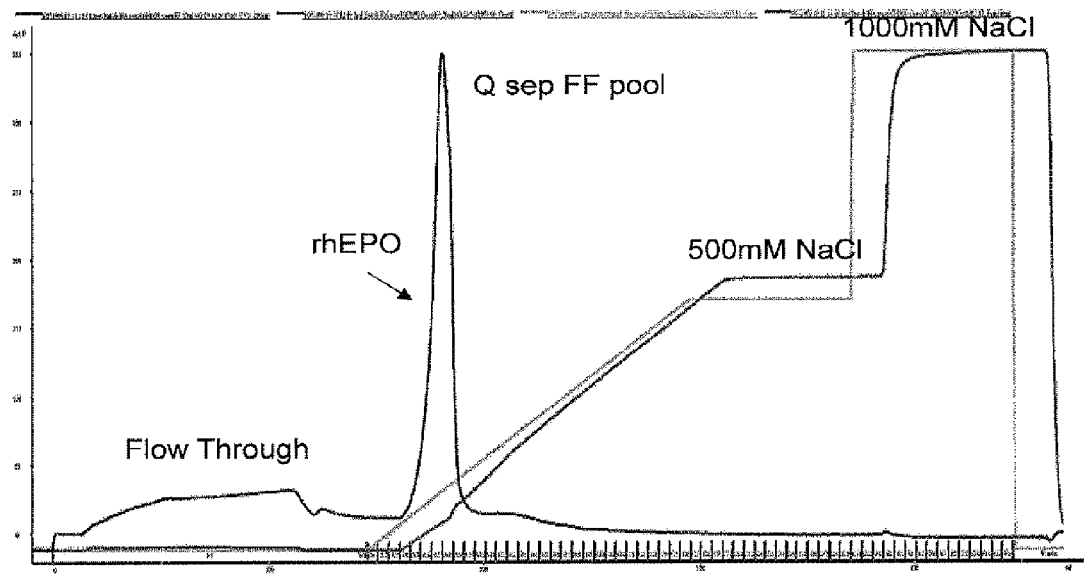

FIG. 27A shows a chromatogram of Q SEPHAROSE FF anion chromatography purification of rhEPO produced in strain YGLY3159 from hydroxyapatite pool 1.

Figure 27B:
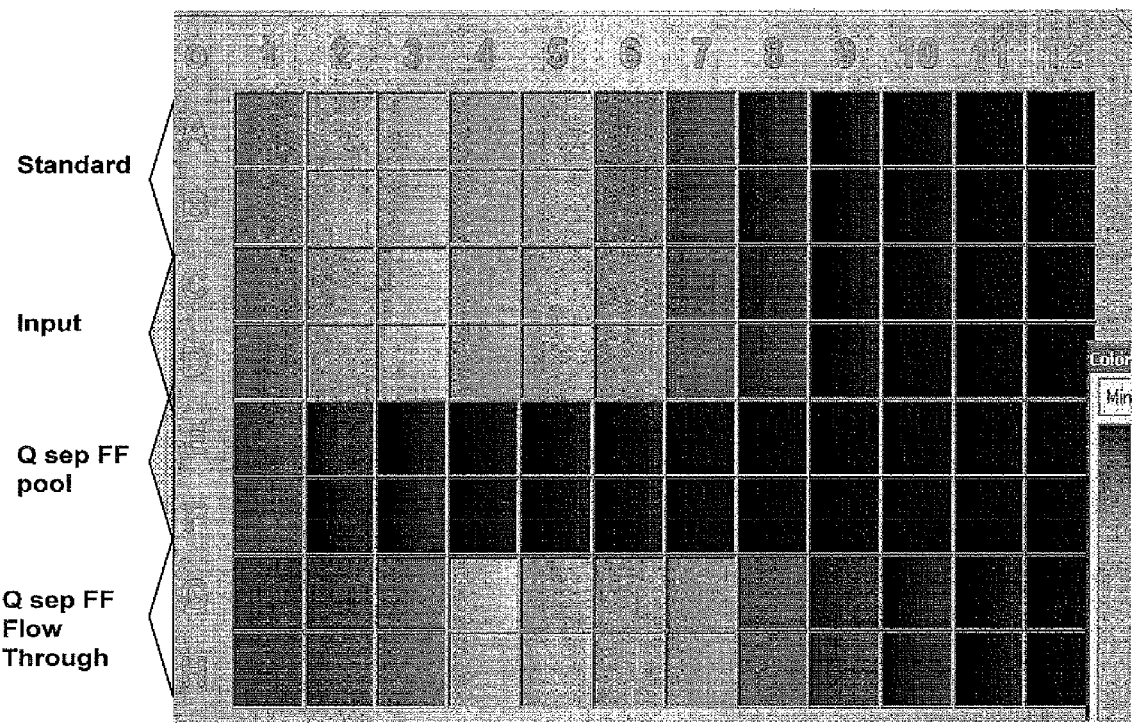

FIG. 27B shows a sandwich ELISA showing that the Q SEPHAROSE FF pool containing rhEPO from the Q SEPHAROSE FF anion chromatography has no detectable cross binding activity to anti-HCA antibodies whereas the flow through contained cross binding activity to anti-HCA antibodies. The capture antibody was anti-hEPO antibody and cross binding activity was detected with rabbit anti-HCA antibody at a 1:800 starting dilution in PBS which was then serially diluted 1:1 in PBS across a row ending with the $11^{th}$ well at a 1:819, 200 dilution (well 12: negative control). Bound anti-HCA antibody was detected using goat anti-rabbit antibody conjugated to alkaline phosphatase (AP) at a 1:10,000 dilution in PBS. Detection of bound secondary antibody used the substrate 4-Methylumbelliferyl phosphate (4-MUPS).

Figure 28:
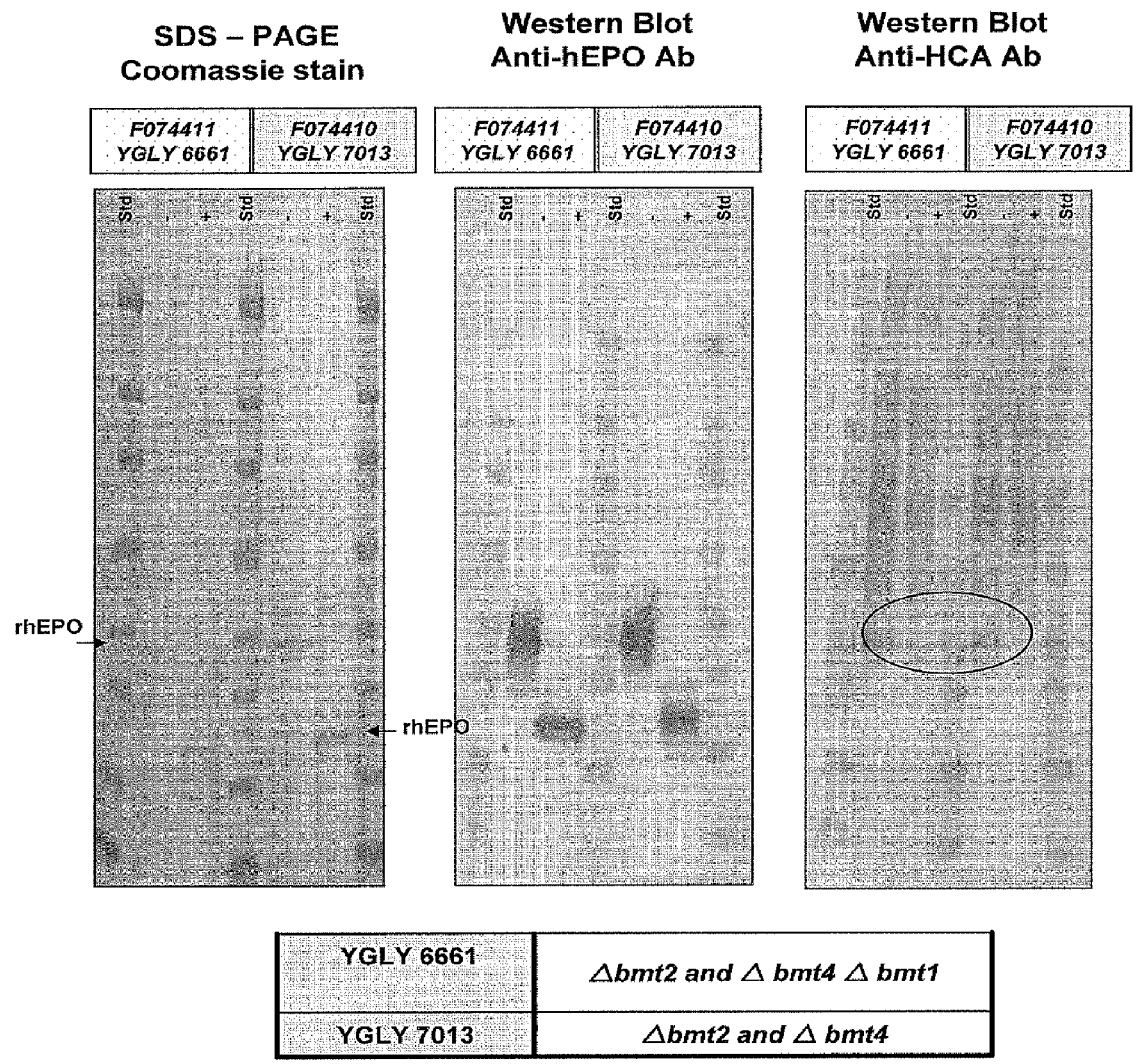

FIG. 28 shows that rhEPO produced in strains YGLY6661 (Δbmt2, Δbmt4, and Δbmt1) and YGLY7013 (Δbmt2 and Δbmt4) and captured by Blue SEPHAROSE 6 FF chromatography (Blue pools) still has cross binding activity to anti-HCA antibodies. Left panel shows a Commassie Blue stained 4-20% SDS-PAGE gel of the Blue pools with (+) and without (−) PNGase F treatment. The center panel shows a Western blot of a similar gel probed with anti-hEPO antibodies conjugated to HRP at a 1:1,000 dilution and DAB as the substrate. The right panel shows a Western blot of a similar gel probed with anti-HCA antibodies as in FIG. 22.

Figure 29:
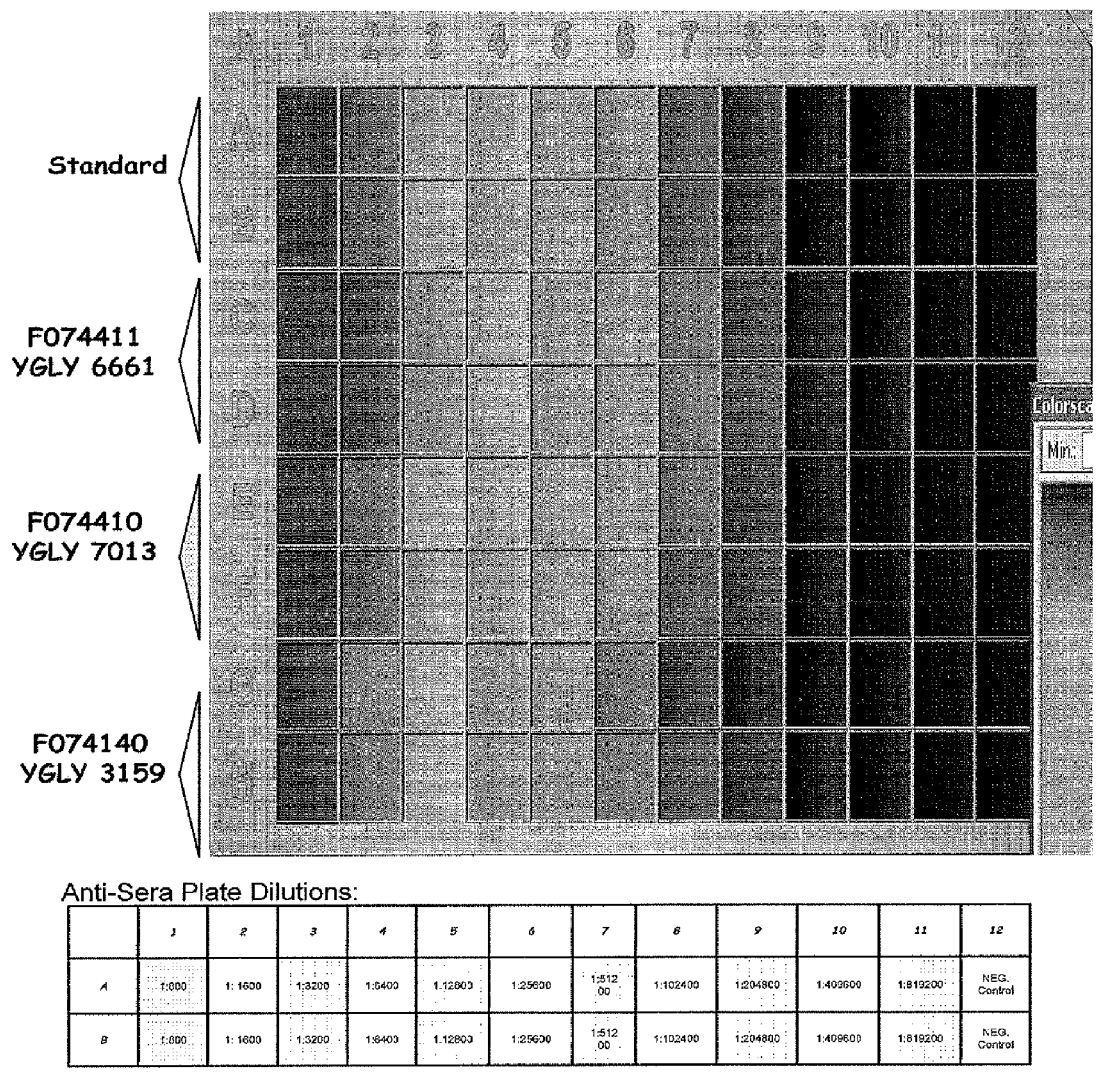

FIG. 29 shows in a sandwich ELISA to detect cross binding activity to anti-HCA antibodies that rhEPO produced in strains YGLY6661 (Δbmt2, Δbmt4, and Δbmt1) and YGLY7013 (Δbmt2 and Δbmt4) and captured by Blue SEPHAROSE 6 FF chromatography (Blue pools) still has cross binding activity to anti-HCA antibodies. The ELISA was performed as in FIG. 27B.

Figure 30:
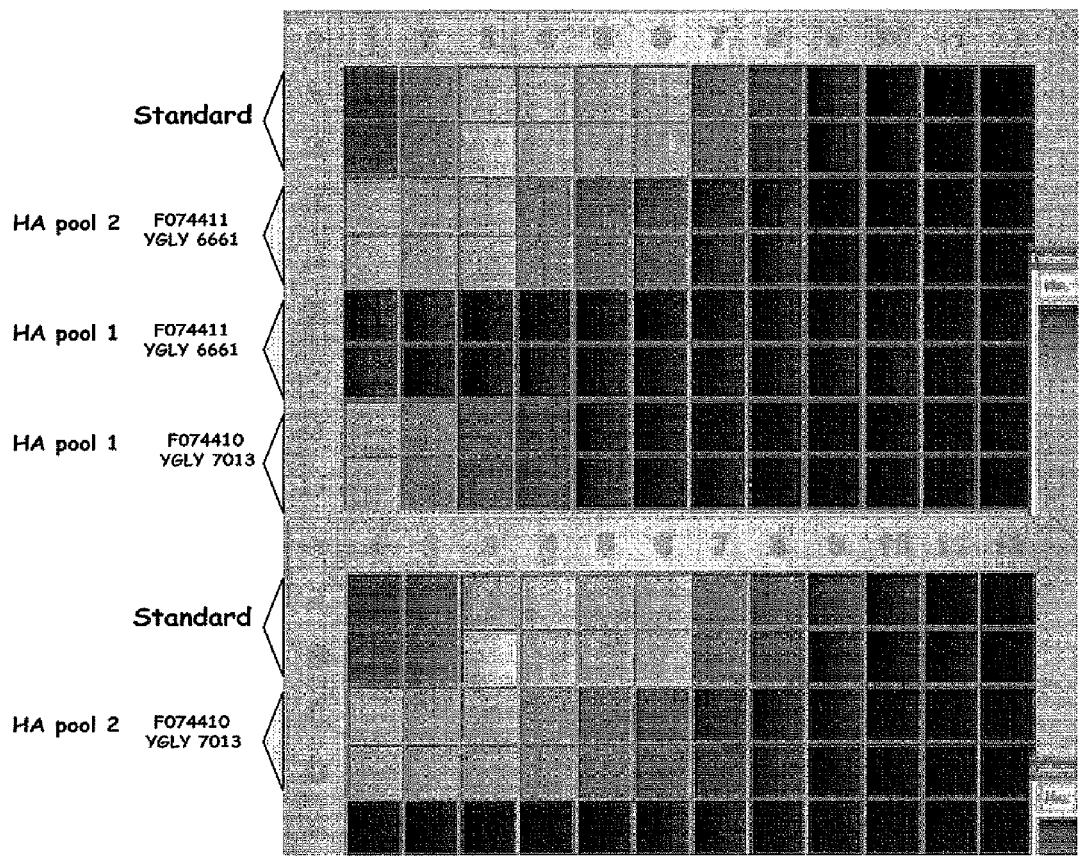

FIG. 30 shows sandwich ELISAs used to detect cross binding activity to anti-HCA antibodies of rhEPO produced in strains YGLY6661 (Δbmt2, Δbmt4, and Δbmt1) and YGLY7013 (Δbmt2 and Δbmt4), captured by Blue SEPHAROSE 6 FF chromatography, and purified by hydroxyapatite chromatography (HA pool 1). rhEPO in HA pool 1 from strain YGLY6661 had no detectable cross binding activity to anti-HCA antibodies. The ELISAs were performed as in FIG. 27B.

Figure 31:
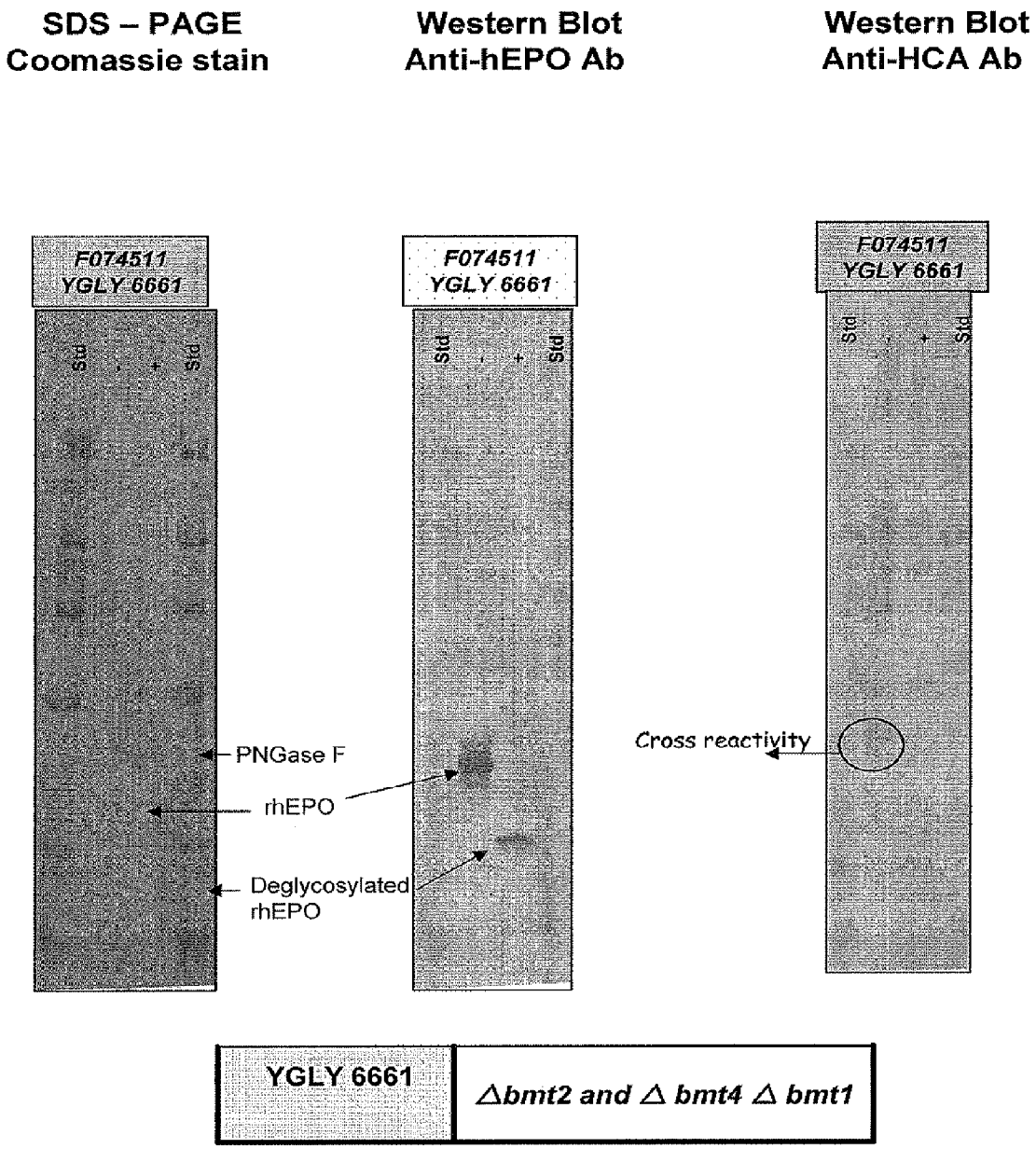

FIG. 31 shows that rhEPO produced in strain YGLY6661 (Δbmt2, Δbmt4, and Δbmt1) and captured by Blue SEPHAROSE 6 FF chromatography (Blue pools) still has cross binding activity to anti-HCA antibodies. Left panel shows a Commassie Blue stained 4-20% SDS-PAGE gel of the Blue pools with (+) and without (−) PNGase F treatment. The center panel shows a Western blot of a similar gel probed with anti-hEPO antibodies conjugated to HRP at a 1:1,000 dilution and DAB as the substrate. The right panel shows a Western blot of a similar gel probed with anti-HCA antibodies as in FIG. 22.

Figure 32A:
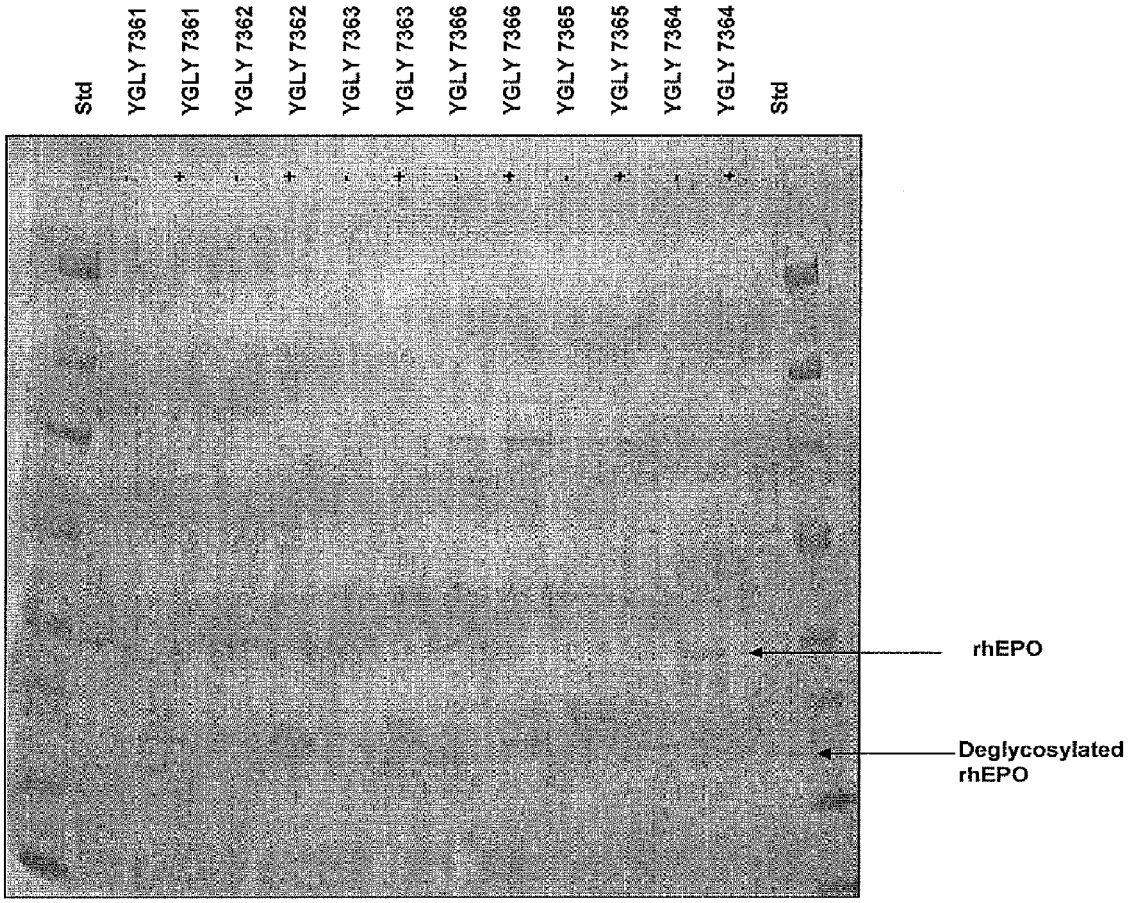

FIG. 32A shows a Commassie Blue stained 4-20% SDS-PAGE gel of the Blue Sepahrose 6 FF capture pools (Blue pools) prepared from strains YGLY7361-7366 (all Δbmt2, Δbmt4, Δbmt1, and Δbmt3) with (+) and without (−) PNGase F treatment. The strains were grown in 500 mL SixFors fermentors.

Figure 32B:
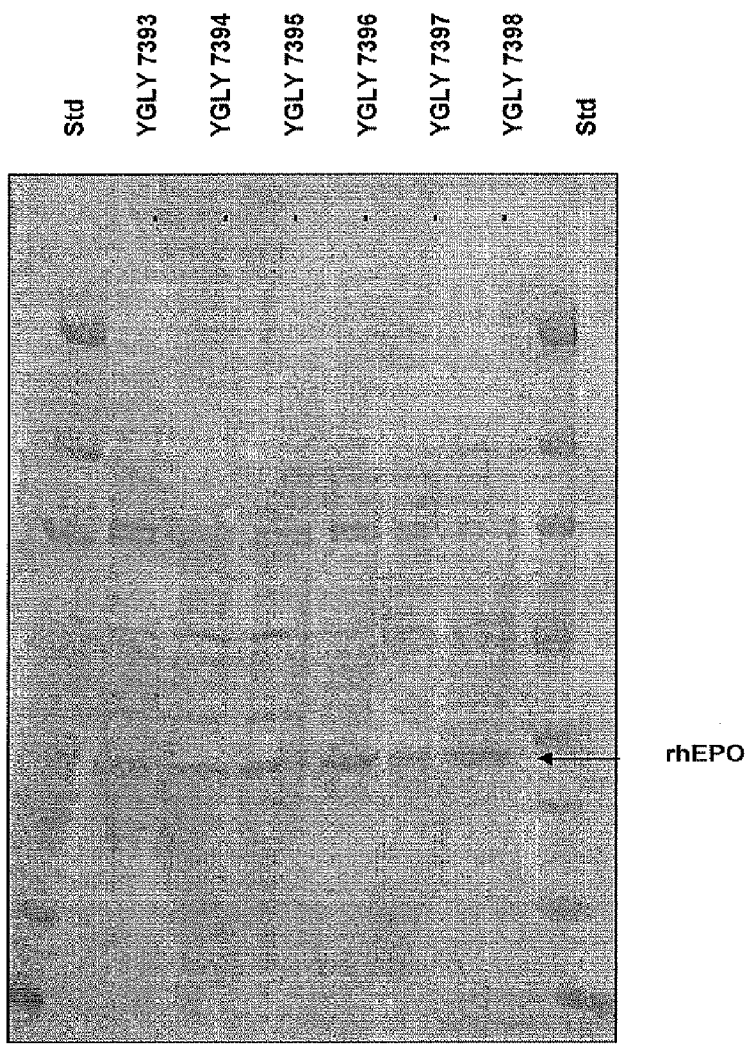

FIG. 32B shows a Commassie Blue stained 4-20% SDS-PAGE gel of the Blue Sepaharose 6 FF capture pools (Blue pools) prepared from strains YGLY7393-7398 (all Δbmt2, Δbmt4, Δbmt1, and Δbmt3) with (+) and without (−) PNGase F treatment. The strains were grown in 500 mL SixFors fermentors.

Figure 33:
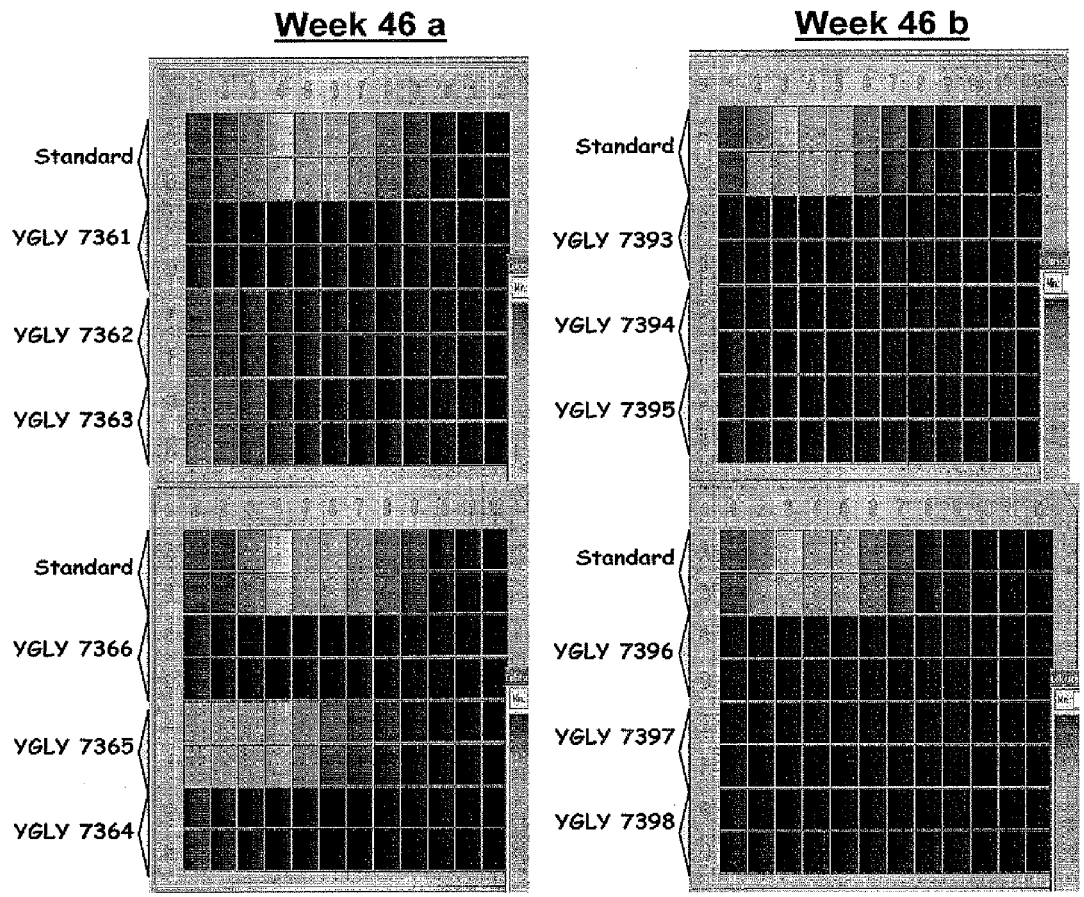

FIG. 33 shows the results of sandwich ELISAs used to detect cross binding activity to anti-HCA antibodies of rhEPO produced in strains YGLY7361-7366 (all Δbmt2, Δbmt4, Δbmt1, and Δbmt3) and YGLY7393-7398 (all Δbmt2, Δbmt4, Δbmt1, and Δbmt3) and captured by Blue SEPHAROSE 6 FF chromatography (Blue pools). Only rhEPO in the Blue pools from strain YGLY7363 and YGLY7365 had detectable cross binding activity to anti-HCA antibodies. The ELISAs were performed as in FIG. 27B.

Figure 34:
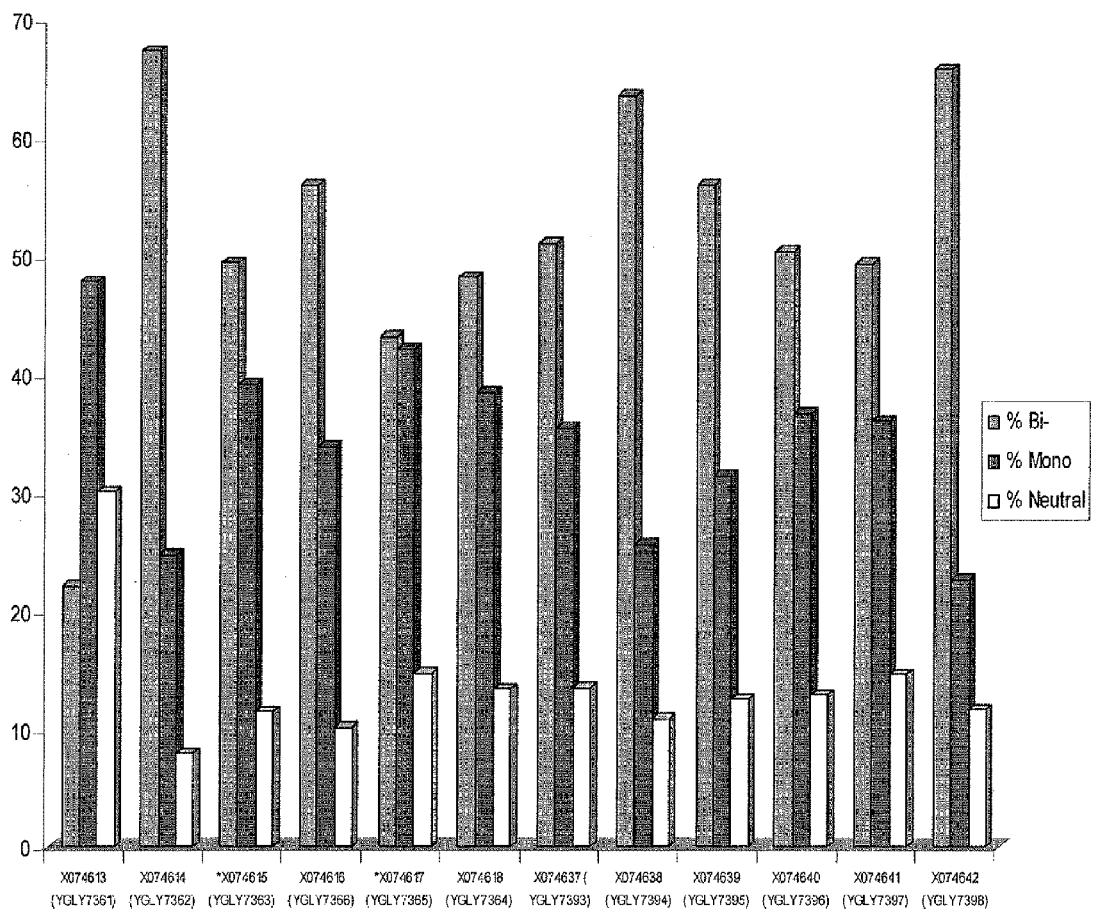

FIG. 34 shows in chart form the results from HPLC analysis of the N-glycans on the rhEPO in the Blue pools prepared from strains YGLY7361-7366 and YGLY7393-7398 (all Δbmt2, Δbmt4, Δbmt1, and Δbmt3). "Bi" refers to N-glycans in which both arms of the biantennary N-glycan are sialylated. "Mono" refers to N-glycans in which only one arm of the biantennary N-glycan is sialylated. "Neutral" refers to N-glycans that are not sialylated.

Figure 35A:
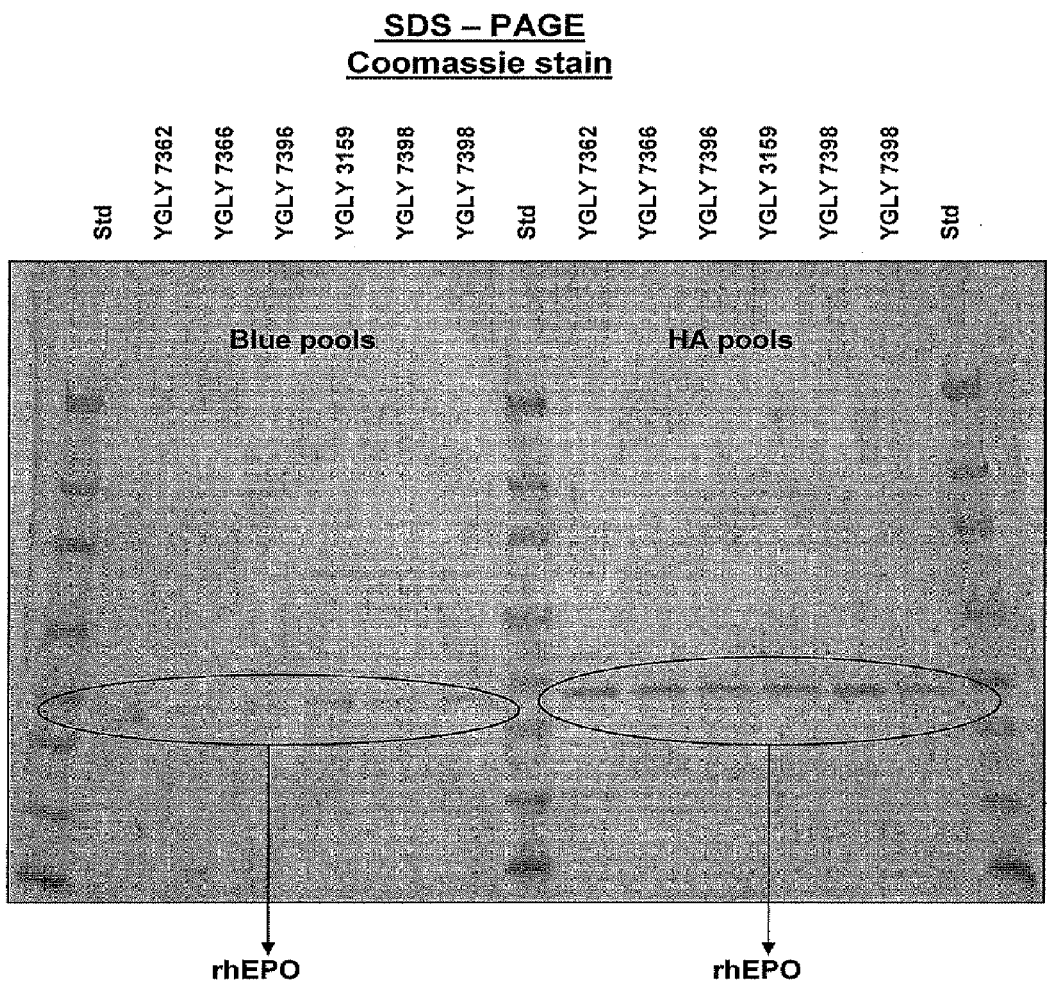

FIG. 35A shows a Commassie Blue stained 4-20% SDS-PAGE gel of the Blue SEPHAROSE 6 FF chromatography (Blue pools) and hydroxyapatite purification pools (HA pool 1s) prepared from strains YGLY7362, YGLY7366, YGLY7396, and YGLY7398 (all Δbmt2, Δbmt4, Δbmt1, and Δbmt3), and YGLY3159 (Δbmt2).

Figure 35B:
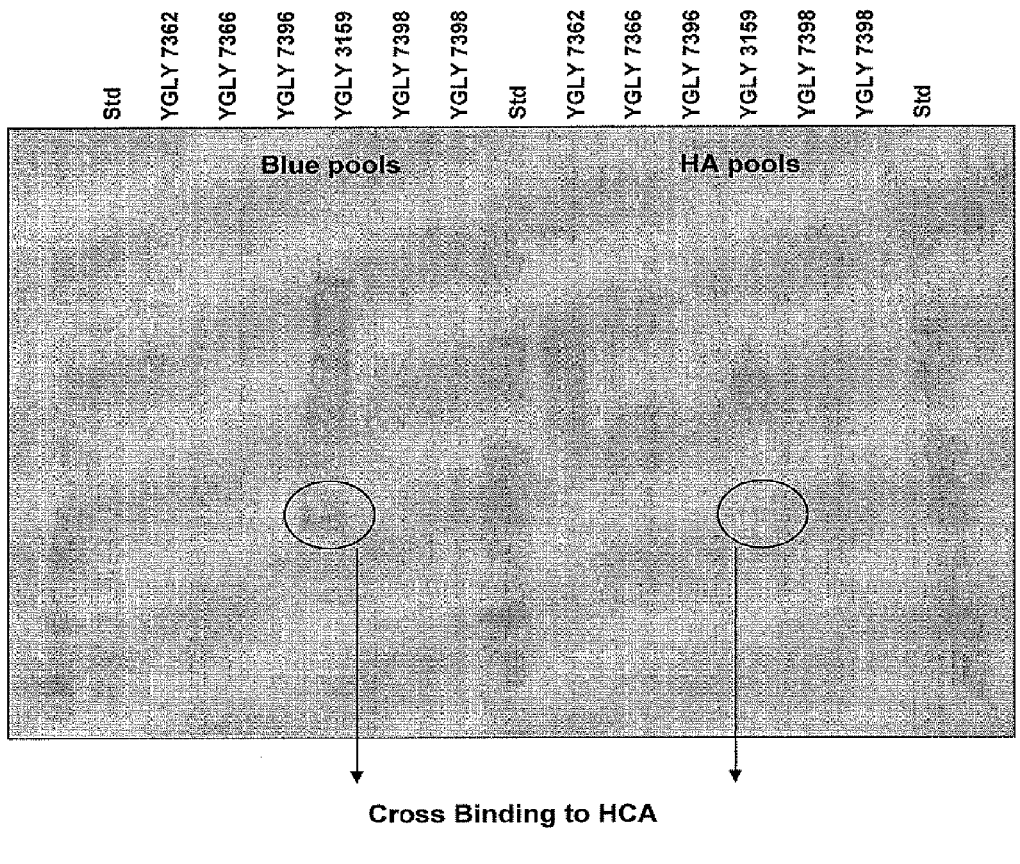

FIG. 35B shows a Western blot of a 4-20% SDS-PAGE gel of the Blue SEPHAROSE 6 FF chromatography (Blue pools) and hydroxyapatite purification pools (HA pool 1s) prepared from strains YGLY7362, YGLY7366, YGLY7396, and YGLY7398 (all Δbmt2, Δbmt4, Δbmt1, and Δbmt3), and YGLY3159 (Δbmt2) and probed with anti-HCA antibodies as in FIG. 22.

Figure 36:
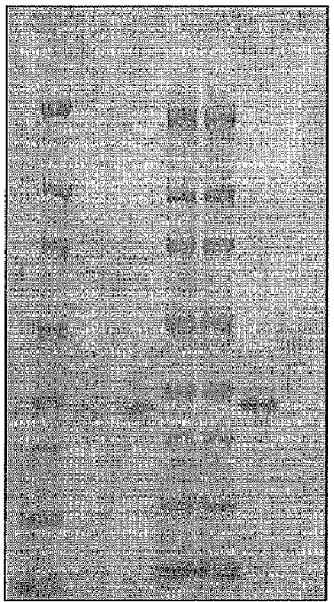
Figure 36:
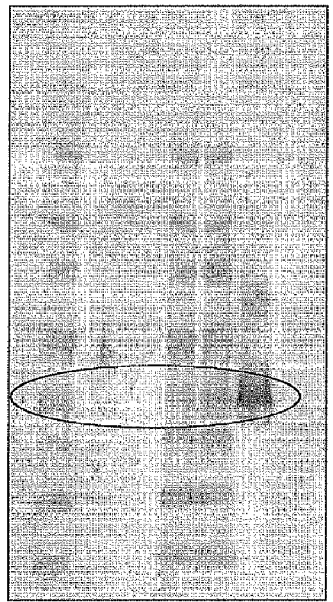
Figure 36:
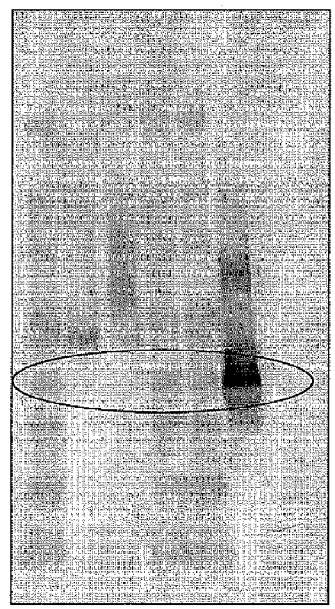

FIG. 36 shows that rhEPO produced in strain YGLY7398 (Δbmt2, Δbmt4, Δbmt1, and Δbmt3) and captured by Blue SEPHAROSE 6 FF chromatography (Blue pools) and purified by hydroxyapatite chromatography (HA pool 1s) had no detectable cross binding activity to anti-HCA antibodies. Left panel shows a Commassie Blue stained 4-20% SDS-PAGE gel of the Blue pool and HA pool 1 prepared from strain YGLY7398 compared to rhEPO prepared from strain YGLY3159. The center panel shows a Western blot of a similar gel probed with anti-HCA antibodies as in FIG. 22. The center panel shows a Western blot of a similar gel probed with anti-HCA antibodies as in FIG. 22 except anti-HCA antibodies were from another antibody preparation (GiF polyclonal rabbit::6316 at 1:2,000).

Figure 37:
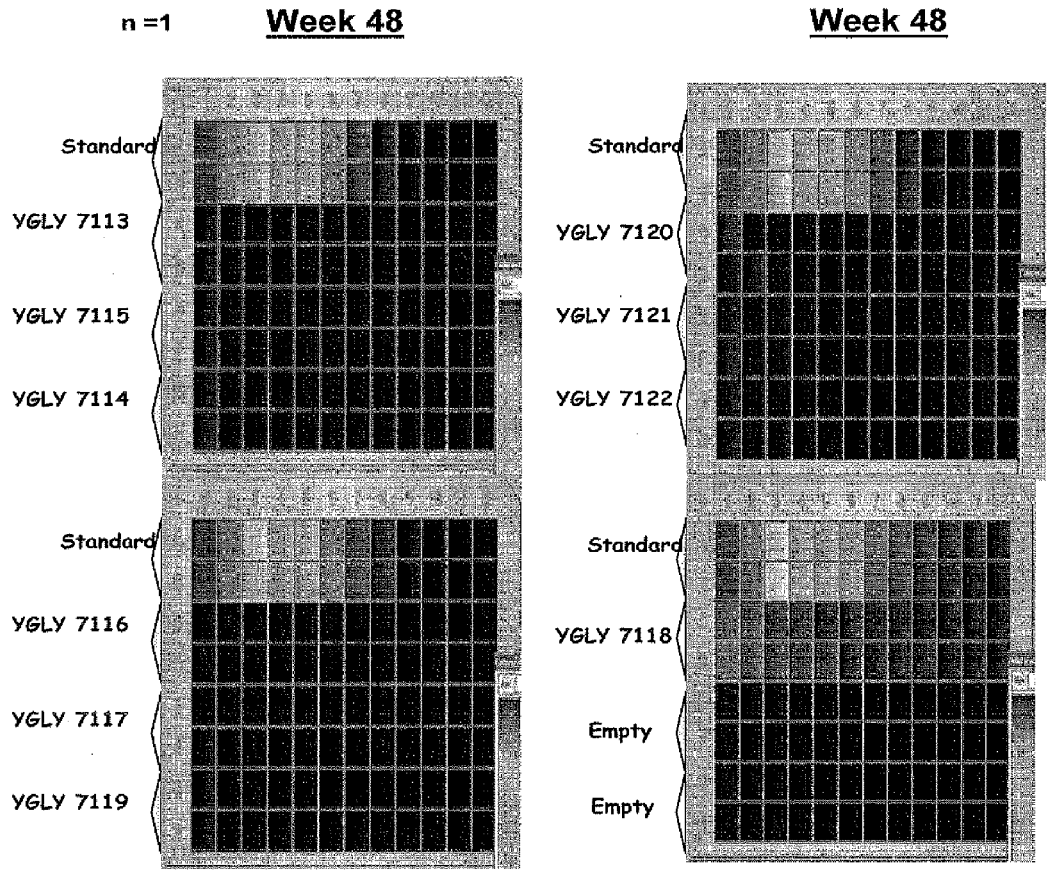

FIG. 37 shows the results of sandwich ELISAs used to detect cross binding activity to anti-HCA antibodies of rhEPO produced in strains YGLY7113-7122 (Δbmt2, Δbmt4, Δbmt1, and Δbmt3) and captured by Blue SEPHAROSE 6 FF chromatography (Blue pools). Strain YGLY7118 showed very low detectable cross binding activity to anti-HCA antibodies. None of the other strains showed any detectable cross binding activity to anti-HCA antibodies. The ELISAs were performed as in FIG. 27B.

Figure 38:
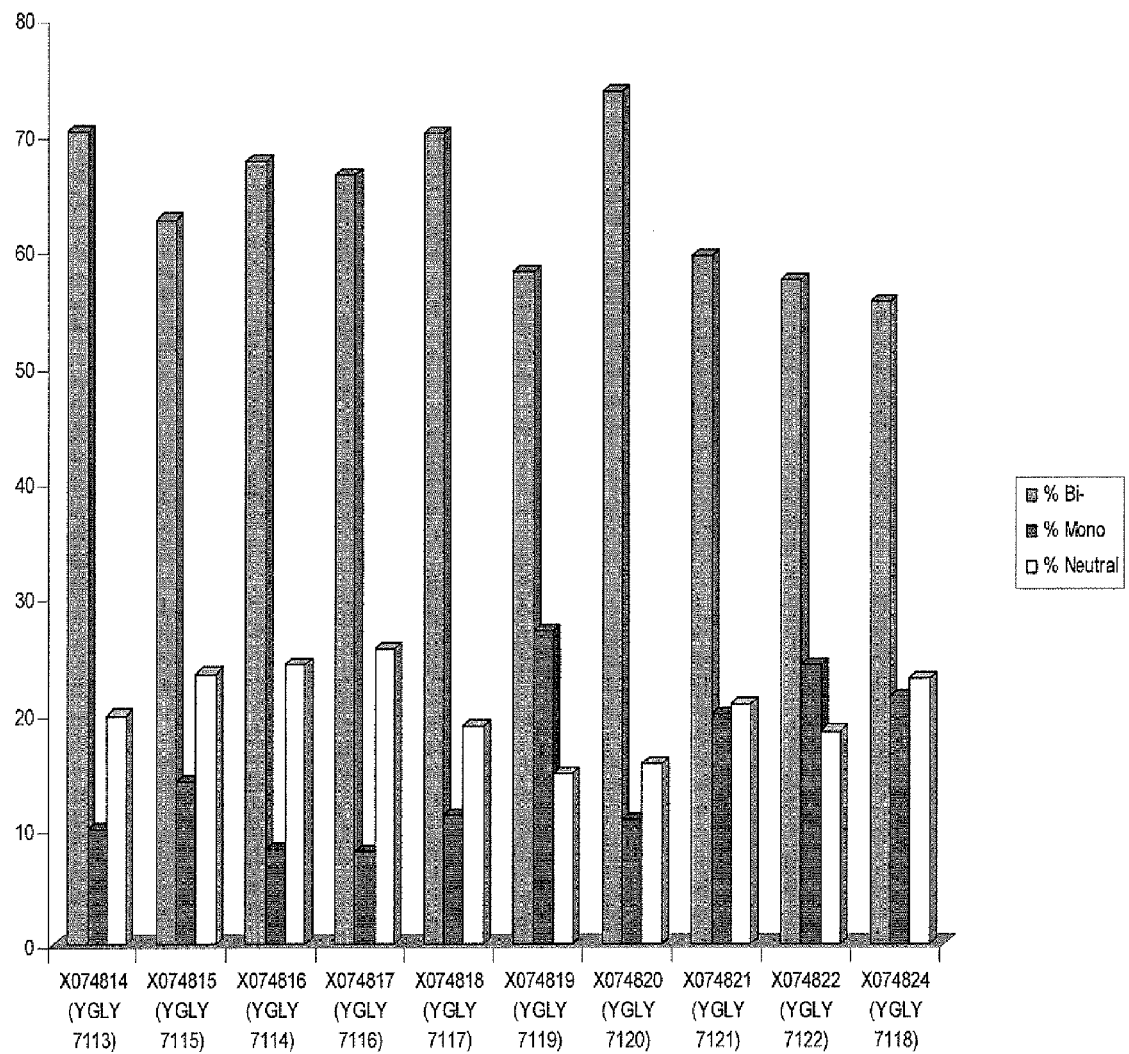

FIG. 38 shows in chart form the results from HPLC analysis of the N-glycans on the rhEPO in the Blue pools prepared from strains YGLY7113-7122 (all Δbmt2, Δbmt4, Δbmt1, and Δbmt3). "Bi" refers to N-glycans in which both arms of the biantennary N-glycan are sialylated. "Mono" refers to N-glycans in which only one arm of the biantennary N-glycan is sialylated. "Neutral" refers to N-glycans that are not sialylated.

Figure 39A:
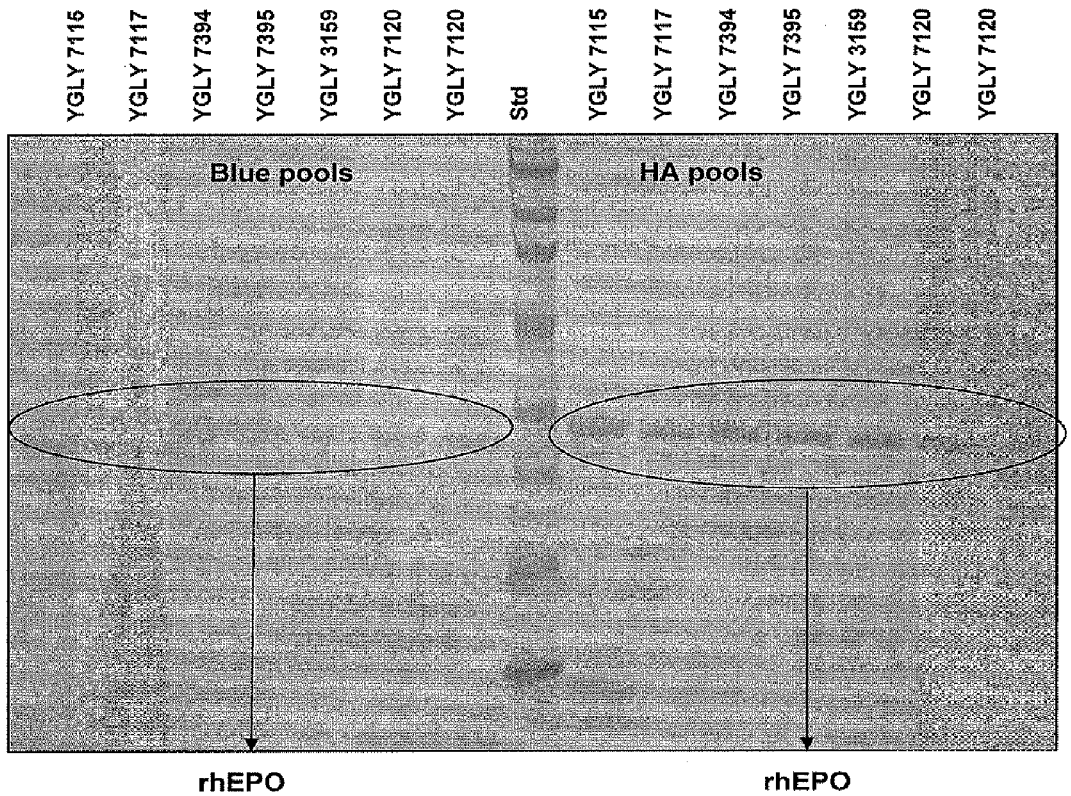

FIG. 39A shows a Commassie Blue stained 4-20% SDS-PAGE gel of the Blue SEPHAROSE 6 FF chromatography (Blue pools) and hydroxyapatite purification pools (HA pool 1s) prepared from strains YGLY7115, YGLY7117, YGLY7394, YGLY7395, and YGLY7120 (all Δbmt2, Δbmt4, Δbmt1, and Δbmt3), and YGLY3159 (Δbmt2).

Figure 39B:
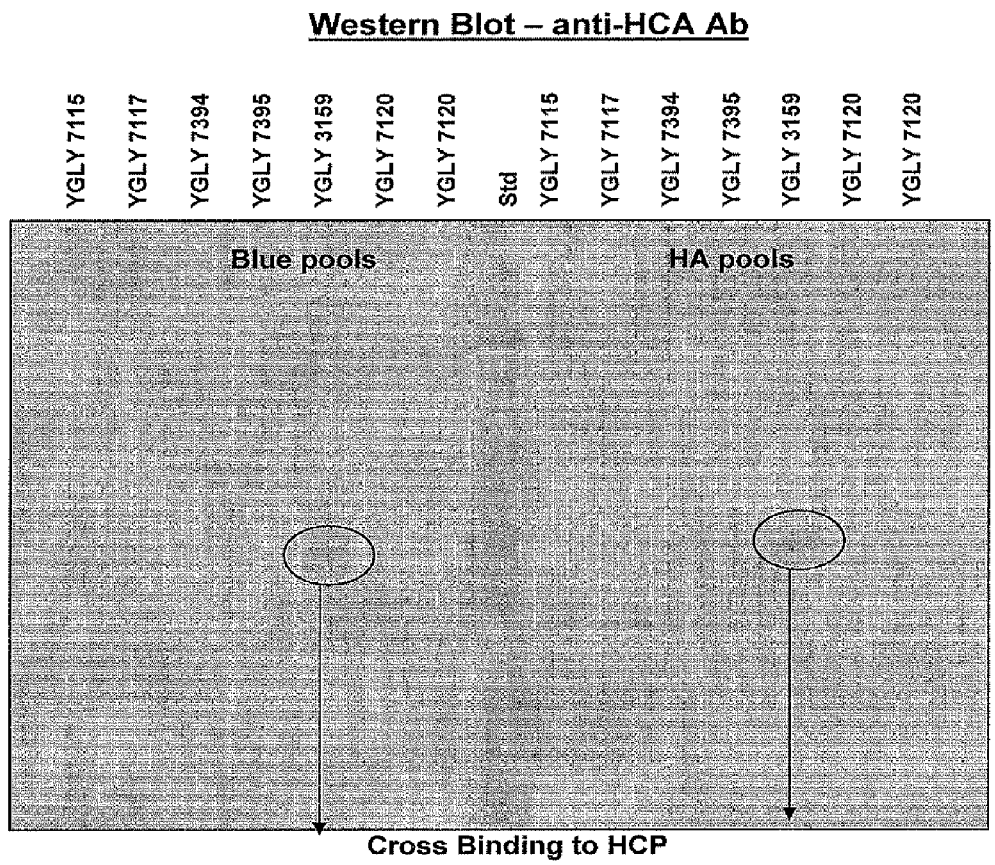

FIG. 39B shows a Western blot of a 4-20% SDS-PAGE gel of the Blue SEPHAROSE 6 FF chromatography (Blue pools) and hydroxyapatite purification pools (HA pool 1s) prepared from strains YGLY7115, YGLY7117, YGLY7394, YGLY7395, and YGLY7120 (all Δbmt2, Δbmt4, Δbmt1, and Δbmt3), and YGLY3159 (Δbmt2) and probed with anti-HCA antibodies as in FIG. 22.

Figure 40A:
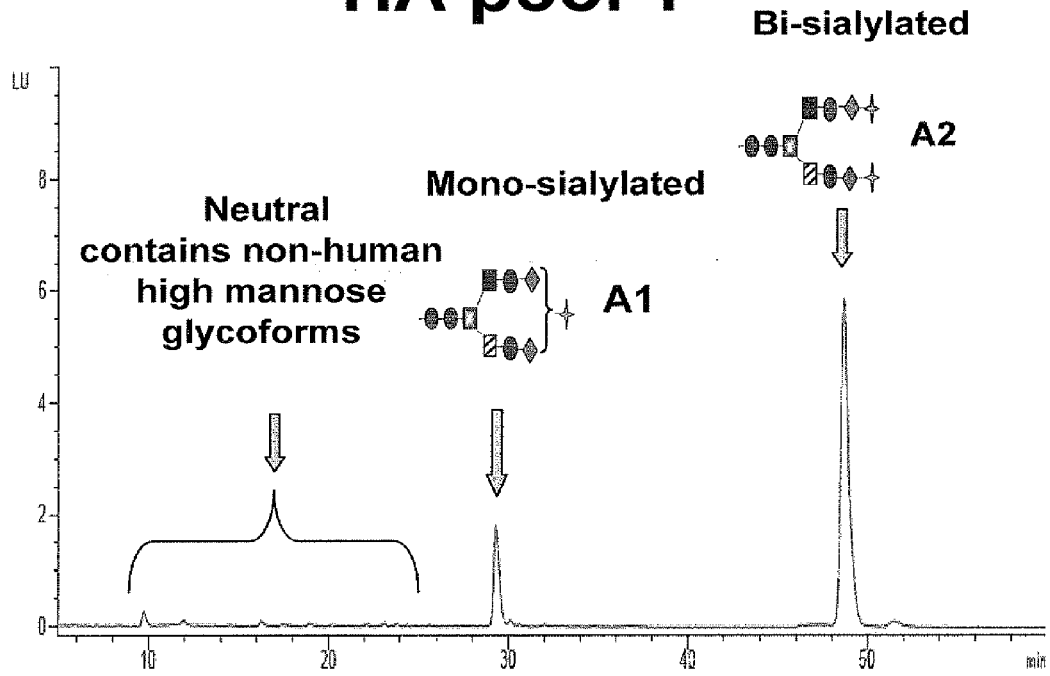

FIG. 40A shows an HPLC trace of the N-glycans from rhEPO produced in YGLY3159 (Δbmt2) and purified by hydroxyapatite column chromatography (i.e., analysis of HA pool 1).

Figure 40B:
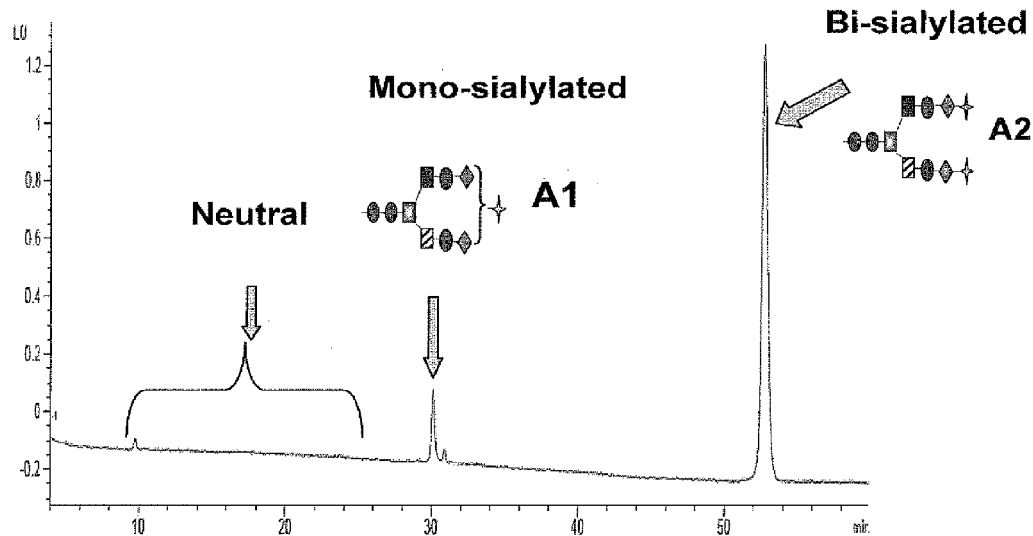

FIG. 40B shows an HPLC trace of the N-glycans from rhEPO produced in YGLY7117 (Δbmt2, Δbmt4, Δbmt1, and Δbmt3) and purified by hydroxyapatite column chromatography (i.e., analysis of HA pool 1).

DETAILED DESCRIPTION OF THE INVENTION

The present invention provides methods for producing proteins and glycoproteins in methylotrophic yeast such as *Pichia pastoris* that lack detectable cross binding to antibodies made against host cell antigens. Host cell antigens can also include residual host cell protein and cell wall contaminants that may carry over to recombinant protein compositions that can be immunogenic and which can alter therapeutic efficacy or safety of a therapeutic protein. A composition that has cross-reactivity with antibodies made against host cell antigens means that the composition contains some contaminating host cell material, usually N-glycans with phosphomannose residues or β-mannose residues or the like. Wild-type strains of *Pichia pastoris* will produce glycoproteins that have these N-glycan structures. Antibody preparations made against total host cell proteins would be expected to include antibodies against these structures. Proteins that do not contain N-glycans, however, might also include contaminating material (proteins or the like) that will cross-react with antibodies made against the host cell.

The methods and host cells enable recombinant therapeutic proteins and glycoproteins to be produced that have a reduced risk of eliciting an adverse reaction in an individual administered the recombinant therapeutic proteins and glycoproteins compared to the same being produced in strains not modified as disclosed herein. An adverse reaction includes eliciting an unwanted immune response in the individual or an unwanted or inappropriate binding to, congregating in, or interaction with a site in the individual that in general adversely affects the health of the individual. The risk of eliciting an adverse reaction in an individual being administered the therapeutic protein or glycoprotein is of particular concern for proteins or glycoproteins intended to be administered to the individual chronically (e.g., therapies intended to be conducted over an extended time period). The recombinant therapeutic proteins or glycoproteins produced according to the methods herein have no detectable cross binding activity to antibodies against host cell antigens and thus, present a reduced risk of eliciting an adverse reaction in an individual administered the recombinant proteins or glycoproteins. The methods and host cells are also useful for producing recombinant proteins or glycoproteins that have a lower potential for binding clearance factors.

The inventors have found that particular glycoproteins that are produced in some strains of *Pichia pastoris* can have N- or O-glycans thereon in which one or more of the mannose residues thereon are in a β1,2-linkage. Glycoproteins intended for therapeutic uses and which have one or more β1,2-linked mannose residues thereon provide a risk of being capable of eliciting an undesirable immune response in the individual being administered the glycoprotein. These β-linked mannose residues can be detected using antibodies made against total host cell antigens. Because it cannot be predicted which therapeutic glycoproteins will have N- or O-glycans comprising one or more β1,2-linked mannose residues and whether a therapeutic glycoprotein that does have N- or O-glycans comprising β1,2-linked mannose residues thereon will produce an unwanted immunogenic response in the individual receiving the glycoprotein, it is desirable to produce therapeutic glycoproteins in *Pichia pastoris* strains that have been genetically engineered to that lack detectable cross binding to antibodies made against host cell antigens. Such strains can be produced by deleting or disrupting the activities of at least three of the four known β-mannosyltransferases (Bmtp) in the *Pichia pastoris* β-mannosyltransferase (BMT) gene family. As shown herein, *Pichia pastoris* strains that include a deletion or disruption of at least three of the these BMT genes provides a *Pichia pastoris* strain that can produce proteins or glycoproteins that lack detectable cross binding to antibodies made against host cell antigens. These strains are useful producing therapeutic proteins and glycoproteins. The presence of β-mannose structures on N- and/or O-glycans have been demonstrated to elicit an immune response.

Identification of the β-mannosyltransferase genes in *Pichia pastoris* and *Candida albicans* was reported in U.S. Pat. No. 7,465,577 and Mille et al., J. Biol. Chem. 283: 9724-9736 (2008), which disclosed that β-mannosylation was effected by a β-mannosyltransferase that was designated AMR2 or BMT2 and that disruption or deletion of the gene in *Pichia pastoris* resulted a recombinant host that was capable of producing glycoproteins with reduced β-mannosylation. The patent also disclosed three homologues of the gene, BMT1, BMT3, and BMT4. However, when investigating the source of cross binding activity of some glycoprotein preparations to antibodies made against host cell antigens, the inventors discovered that the cross binding activity was a consequence of residual β-mannosylation persisting in some strains of recombinant *P. pastoris* host cells in which the BMT2 gene had been disrupted or deleted. Thus, heterologous glycoproteins produced in these recombinant host cells have N-glycans that still contained β-mannose residues. These β-mannose residues were detectable in ELISAs and Western blots of the heterologous glycoproteins obtained from cultures of these recombinant host cells probed with antibodies made against host cell antigens (HCA). Anti-HCA antibodies are polyclonal antibodies raised against a wild-type *Pichia pastoris* strain or a NORF strain: a recombinant host cell that is constructed in the same manner as the recombinant host cell that produces the heterologous glycoprotein except that the open reading frame (ORF) encoding the heterologous protein has been omitted. For therapeutic glycoproteins produced in *Pichia pastoris*, these residual β-mannose residues present the risk of eliciting an immune response in some individuals that receive the therapeutic protein in a treatment for a disease or disorder. The present invention provides a method for producing glycoproteins in *Pichia pastoris* that do not contain any detectable β-mannosylation and as such do not cross bind to antibodies made against host cell antigens.

BMT1, BMT2, and BMT3 demonstrate a high degree of sequence homology while BMT4 is homologous to a lower extent and is thought to be a capping alpha-mannosyltransferase. However, all four members of the BMT family appear to be involved in synthesis of N- and/or O-glycans having β-linked mannose structures. Although a MALDI-TOF of N-glycans from a test protein produced in a *Pichia pastoris* strain in which the BMT2 gene has been deleted might fail to detect β-mannosylation, the sensitive antibody-based assays herein were able to detect β-mannosylation in Δbmt2 strains. Thus, the anti-HCA antibody-based detection methods taught herein showed that deletion or disruption of also the BMT1 and BMT3 genes and optionally the BMT4 gene was needed to remove all detectable β-mannose structures. Deleting or disrupting the genes encoding the three β-mannosyltransferases can be achieved by (1) complete or partial knock-out of the gene (including the promoter sequences, open reading frame (ORF) and/or the transcription terminator sequences); (2) introduction of a frame-shift in the ORF; (3) inactivation or regulation of the promoter; (4) knock-down of message by siRNA or antisense RNA; (5) or the use of chemical inhibitors. The result is the production of a host cell that is capable of producing a glycoprotein that lacks detectable cross binding activity to anti-HCA antibodies.

To exemplify the methods for producing a glycoprotein that lacks detectable cross binding activity to anti-HCA antibodies, a strain of *Pichia pastoris*, which had been genetically engineered to lack BMT2 expression or activity and to be capable of producing recombinant mature human erythropoietin (EPO) with sialic acid-terminated bi-antennary N-glycans, was further genetically engineered to lack expression of the BMT1 and/or BMT3 and/or BMT4 genes. The strain in which only expression of the BMT2 gene had been disrupted produced recombinant mature human EPO having some detectable cross binding activity to anti-HCA antibodies. The detectable cross binding activity was found to be due to the presence of β-linked mannose residues on the EPO molecule (See FIGS. 22-27B, Example 6). When the genes encoding BMT1 and BMT4 were disrupted or deleted in the strain, the EPO produced still had detectable cross binding activity to anti-HCA antibodies (See FIGS. 28-31). However, when the BMT1, BMT2, BMT3, and BMT4 genes were disrupted or deleted, most of the strains produced glycosylated recombinant human EPO that lacked detectable cross binding activity to anti-HCA antibodies and thus lacked detectable β-mannose residues (See FIGS. 33 and 35B for example).

Thus, the present invention further provides a method for producing a recombinant protein or glycoprotein that lacks detectable cross binding activity to antibodies made against host cell antigens that involves constructing host cells intended to be used to produce the recombinant protein to further not display various combinations β-mannosyltransferase activities. By way of example, a host cell is constructed that does not display β-mannosylttransferase 2 activity with respect to an N-glycan or O-glycan. The host cell lacking display β-mannosyltransferase 2 activity is used to produce the recombinant protein or glycoprotein, which is then evaluated by Western blot or ELISA using an antibody that has been made against a NORF version of the strain. A NORF strain is a strain the same as the host strain except it lacks the open reading frame encoding the recombinant glycoprotein. If the recombinant protein or glycoprotein produced by the host cell lacks detectable binding to the antibody made against host cell antigens, then the host cell is useful for producing the recombinant protein or glycoprotein that lacks cross binding activity to the antibodies against host cell antigens.

However, if detectable cross binding activity is detected, then the host cell is further manipulated to not display β-mannosyltransferase 1, β-mannosyltransferase 3, or β-mannosyltransferase 4 activity with respect to an N-glycan or O-glycan. For example, the host cell that lacks β-mannosyltransferase 2 activity is further manipulated to lack β-mannosyltransferase 1 activity. The host cell is used to produce the recombinant protein or glycoprotein, which is then evaluated by Western blot or ELISA using an antibody that has been made against a NORF version of the strain. If the recombinant protein or glycoprotein produced by the host cell lacks detectable binding to the antibody made against host cell antigens, then the host cell is useful for producing the recombinant protein or glycoprotein that lacks cross binding activity to the antibodies against host cell antigens.

However, if detectable cross binding activity is detected, then the host cell is further manipulated to not display β-mannosyltransferase 3 activity or β-mannosyltransferase 4 activity. For example, the host cell that lacks β-mannosyltransferase 2 activity and β-mannosyltransferase 1 activity is further manipulated to lack β-mannosyltransferase 3 activity with respect to an N-glycan or O-glycan. The host cell is used to produce the protein or recombinant glycoprotein, which is then evaluated by Western blot or ELISA using an antibody that has been made against a NORF version of the strain. If the recombinant protein or glycoprotein produced by the host cell lacks detectable binding to the antibody made against host cell antigens, then the host cell is useful for producing the recombinant protein or glycoprotein that lacks cross binding activity to the antibodies against host cell antigens.

However, if detectable cross binding activity is detected, then the strain is further manipulated to not display β-mannosyltransferase 4 activity with respect to an N-glycan or O-glycan. The host cell is used to produce the recombinant protein or glycoprotein, which is then evaluated by Western blot or ELISA using an antibody that has been made against a NORF version of the strain to confirm that the recombinant protein or glycoprotein lacks detectable binding to the antibody made against host cell antigens.

By way of a further example, a *Pichia pastoris* host cell is constructed in which various combinations of BMT genes are deleted or disrupted in. By way of example, a *Pichia pastoris* host cell is constructed that has a disruption or deletion of the BMT2 gene. The Δbmt2 host cell is used to produce the recombinant protein or glycoprotein, which is then evaluated by Western blot or ELISA using an antibody that has been made against a NORF version of the strain. A NORF strain is a strain the same as the host strain except it lacks the open reading frame encoding the recombinant glycoprotein. If the recombinant protein or glycoprotein produced by the Δbmt2 host cell lacks detectable binding to the antibody made against host cell antigens, then the BMT2 deletion or disruption is sufficient to enable the host cell to produce the recombinant protein or glycoprotein that lacks cross binding activity to the antibodies against host cell antigens.

However, if detectable cross binding activity is detected, then the host cell is further manipulated to have a deletion of the BMT1, BMT3, or BMT4 genes. For example, the host cell that has a disruption or deletion of the BMT2 gene is further manipulated to have a deletion or disruption of the BMT1 gene. The Δbmt2 Δbmt1 host cell is used to produce the recombinant protein or glycoprotein, which is then evaluated by Western blot or ELISA using an antibody that has been made against a NORF version of the strain. If the recombinant protein or glycoprotein produced by the Δbmt2 Δbmt1 host cell lacks detectable binding to the antibody made against host cell antigens, then the BMT1 and BMT2 deletions or disruptions are sufficient to enable the host cell to produce the recombinant protein or glycoprotein that lacks cross binding activity to the antibodies against host cell antigens.

However, if detectable cross binding activity is detected, then the host cell is further manipulated to have a deletion of the BMT3 or BMT4 genes. For example, the host cell that has a disruption or deletion of the BMT1 and BMT2 gene is further manipulated to have a deletion or disruption of the BMT3 gene. The Δbmt2 Δbmt1 Δbmt3 host cell is used to produce the protein or recombinant glycoprotein, which is then evaluated by Western blot or ELISA using an antibody that has been made against a NORF version of the host cell. If the recombinant protein or glycoprotein produced by the Δbmt2 Δbmt1 Δbmt3 host cell lacks detectable binding to the antibody made against host cell antigens, then the BMT1, BMT2, and BMT3 deletions or disruptions are sufficient to enable the host cell to produce the recombinant protein or glycoprotein that lacks cross binding activity to the antibodies against host cell antigens.

However, if detectable cross binding activity is detected, then the host cell is further manipulated to have a deletion of the BMT4 gene. The Δbmt2 Δbmt1 Δbmt3 Δbmt4 host cell is used to produce the recombinant protein or glycoprotein, which is then evaluated by Western blot or ELISA using an antibody that has been made against a NORF version of the strain to confirm that the recombinant protein or glycoprotein lacks detectable binding to the antibody made against host cell antigens.

The present invention further provides a recombinant methylotrophic yeast host cells such as *Pichia pastoris* host cell in which the host cell does not display a β-mannosyltransferase 2 activity with respect to an N-glycan or O-glycan and does not display at least one of a β-mannosyltransferase 1 activity or a β-mannosyltransferase 3 activity with respect to an N-glycan or O-glycan and which includes a nucleic acid molecule encoding the recombinant protein or glycoprotein. In further embodiments, the host cell does not display β-mannosyltransferase 2 activity, β-mannosyltransferase 1 activity, and β-mannosyltransferase 3 activity with respect to an N-glycan or O-glycan. In a further aspect, the present invention provides a recombinant host cell that does not display a β-mannosyltransferase 2 activity, β-mannosyltransferase 1 activity, β-mannosyltransferase 3 activity, and β-mannosyltransferase 4 activity with respect to an N-glycan or O-glycan and which includes a nucleic acid molecule encoding the recombinant protein or glycoprotein.

The present invention further provides a general method for producing a recombinant protein or glycoprotein that lacks detectable cross binding activity to anti-host cell antigen antibodies comprising providing a recombinant methylotrophic yeast such as *Pichia pastoris* host cell does not display a β-mannosyltransferase 2 activity with respect to an N-glycan or O-glycan and does not display at least one activity selected from β-mannosyltransferase 1 activity and β-mannosyltransferase 3 activity with respect to an N-glycan or O-glycan and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens. In further embodiments, the host cell lacks β-mannosyltransferase 2 activity, β-mannosyltransferase 1 activity, and β-mannosyltransferase 3 activity with respect to an N-glycan or O-glycan.

In a further aspect, the present invention provides a general method for producing a recombinant protein or glycoprotein that lacks detectable cross binding activity to anti-host cell antigen antibodies comprising providing a recombinant methylotrophic yeast such as *Pichia pastoris* host cell that does not display β-mannosyltransferase 2 activity, β-mannosyltransferase 1 activity, β-mannosyltransferase 3 activity, and β-mannosyltransferase 4 activity with respect to an N-glycan or O-glycan and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens.

The present invention further provides a recombinant methylotrophic yeast host cells such as *Pichia pastoris* host cell in which the gene encoding a β-mannosyltransferase 2 activity with respect to an N-glycan or O-glycan has been deleted or disrupted and at least one gene encoding a β-mannosyltransferase 1 activity or β-mannosyltransferase 3 activity with respect to an N-glycan or O-glycan has been deleted or disrupted and which includes a nucleic acid molecule encoding the recombinant protein or glycoprotein. In further embodiments, the genes encoding a β-mannosyltransferase 2 activity, a β-mannosyltransferase 1 activity, and a β-mannosyltransferase 3 activity with respect to an N-glycan or O-glycan have been deleted or disrupted. In a further aspect, the present invention provides a recombinant host cell the genes encoding a β-mannosyltransferase 2 activity, a β-mannosyltransferase 1 activity, a β-mannosyltransferase 3 activity, and β-mannosyltransferase 4 activity with respect to an N-glycan or O-glycan have been deleted or disrupted and which includes a nucleic acid molecule encoding the recombinant protein or glycoprotein.

The present invention further provides a general method for producing a recombinant protein or glycoprotein that lacks detectable cross binding activity to anti-host cell antigen antibodies comprising providing a recombinant methylotrophic yeast such as *Pichia pastoris* host cell in which the gene encoding a β-mannosyltransferase 2 activity with respect to an N-glycan or O-glycan has been deleted or disrupted and at least one gene encoding an activity selected from β-mannosyltransferase 1 activity and β-mannosyltransferase 3 activity with respect to an N-glycan or O-glycan has been deleted or disrupted and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens. In further embodiments, the genes encoding a β-mannosyltransferase 2 activity, a β-mannosyltransferase 1 activity, and a β-mannosyltransferase 3 activity with respect to an N-glycan or O-glycan have been deleted or disrupted.

In a further aspect, the present invention provides a general method for producing a recombinant protein or glycoprotein that lacks detectable cross binding activity to anti-host cell antigen antibodies comprising providing a recombinant methylotrophic yeast such as *Pichia pastoris* host cell in which the genes encoding a β-mannosyltransferase 2 activity, a β-mannosyltransferase 1 activity, a β-mannosyltransferase 3 activity, and a β-mannosyltransferase 4 activity with respect to an N-glycan or O-glycan have been deleted or disrupted and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens.

The present invention further provides a recombinant *Pichia pastoris* host cell in which the BMT2 gene and at least one of BMT1 gene and BMT3 gene have been deleted or disrupted and which includes a nucleic acid molecule encoding the recombinant protein or glycoprotein. In further embodiments, the BMT2 gene, BMT1 gene, and BMT3 gene have been deleted or disrupted. In a further aspect, the present invention provides a recombinant *Pichia pastoris* host cell in which the BMT1 gene, BMT2 gene, BMT3 gene, and BMT4 gene have been deleted or disrupted and which includes a nucleic acid molecule encoding the recombinant protein or glycoprotein.

The present invention further provides a general method for producing a recombinant protein or glycoprotein that lacks detectable cross binding activity to anti-host cell antigen antibodies comprising providing a recombinant *Pichia pastoris* host cell in which the BMT2 gene and at least one of the BMT1 gene and the BMT3 gene have been deleted or disrupted and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens. In further embodiments, the BMT2 gene, BMT1 gene, and BMT3 gene have been deleted or disrupted.

In a further aspect, the present invention provides a general method for producing a recombinant protein or glycoprotein that lack detectable cross binding activity to anti-host cell antigen antibodies comprising providing a recombinant *Pichia pastoris* host cell in which the BMT1 gene, BMT2 gene, BMT3 gene, and BMT4 gene have been deleted or disrupted and which includes a nucleic acid molecule encoding the recombinant protein or glycoprotein; growing the host cell in a medium under conditions effective for expressing the recombinant protein or glycoprotein; and recovering the recombinant protein or glycoprotein from the medium to produce the recombinant protein or glycoprotein that lacks detectable cross binding activity with antibodies made against host cell antigens.

The present invention further provides a recombinant *Pichia pastoris* host cell in which the BMT2 gene and at least one of the BMT1 gene and the BMT3 gene have been deleted or disrupted and which includes a nucleic acid molecule encoding the recombinant protein or glycoprotein. In further embodiments, the BMT2 gene, BMT1 gene, and BMT3 gene have been deleted or disrupted. In a further aspect, the present invention provides a recombinant *Pichia pastoris* host cell in which the BMT1 gene, BMT2 gene, BMT3 gene, and BMT4 gene have been deleted or disrupted and which includes a nucleic acid molecule encoding the recombinant protein or glycoprotein.

In general, the recombinant protein or glycoprotein is a therapeutic glycoprotein. Examples of therapeutic glycoproteins contemplated, include but are not limited to erythropoietin (EPO); cytokines such as interferon α, interferon β, interferon γ, and interferon ω; and granulocyte-colony stimulating factor (GCSF); GM-CSF; coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; and urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4—Ig; transmembrane activator and calcium modulator and cyclophilin ligand; glucagon like protein 1; and IL-2 receptor agonist.

In particular aspects of the invention, the nucleic acid molecule encoding the recombinant protein or glycoprotein is codon-optimized to enhance expression of the recombinant protein or glycoprotein in the host cell. For example, as shown in the examples, the nucleic acid molecule encoding the human mature form of erythropoietin was codon-optimized for enhanced expression of the erythropoietin in a methylotrophic yeast such as Pichia pastoris strain that had been genetically engineered to produce an erythropoietin variant comprising biantennary N-glycans in which the predominant glycoform comprised both antennae terminally sialylated.

The present invention further provides compositions comprising one or more proteins or glycoproteins lacking detectable cross-binding to antibodies against host cell antigens produced using the methods herein and in the host cells described herein. The compositions can further include pharmaceutically acceptable carriers and salts.

Suitable host cells include any host cell that includes homologues of the Pichia pastoris BMT1, BMT2, BMT3, and/or BMT4 genes. Currently, examples of such host cells include Candida albicans and the methylotrophic yeast Pichia pastoris. Thus, in particular aspects of the invention, the host cell is a methylotrophic yeast such as Pichia pastoris and mutants thereof and genetically engineered variants thereof. Methylotrophic yeast such as Pichia pastoris that are contemplated for use in the present invention can be genetically modified so that they express glycoproteins in which the glycosylation pattern is human-like or humanized. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in US 2004/0018590. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition. Such can be achieved by eliminating selected endogenous glycosylation enzymes and/or supplying exogenous enzymes as described by Gerngross et al., U.S. Pat. No. 7,029,872 and U.S. Pat. No. 7,449, 308. For example, a host cell can be selected or engineered to be depleted in 1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. No. 7,029, 872, U.S. Pat. No. 7,449,308, and U.S. Published Patent Application No. 2005/0170452 disclose lower eukaryote host cells capable of producing a glycoprotein comprising a $Man_5GlcNAc_2$ glycoform.

In a further embodiment, the immediately preceding host cell further includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. No. 7,029,872, U.S. Pat. No. 7,449,308, and U.S. Published Patent Application No. 2005/0170452 disclose lower eukaryote host cells capable of producing a glycoprotein comprising a $GlcNAcMan_5GlcNAc_2$ glycoform. The glycoprotein produced in the above cells can be treated in vitro with a hexaminidase to produce a recombinant glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a $GlcNAc_2Man_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform.

U.S. Pat. No. 7,029,872 and U.S. Published Patent Application Nos. 2004/0018590 and 2005/0170452 disclose lower eukaryote host cells capable of producing a glycoprotein comprising a GlcNAc$_2$Man$_3$GlcNAc$_2$ glycoform. The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycoform or mixture thereof. U.S. Pat. No. 7,029,872 and U.S. Published Patent Application No. 2006/0040353 discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc$_2$Man$_3$GlcNAc$_2$ glycoform or NANAGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2004/074458 and 2007/0037248.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target Galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

In further aspects, any one of the aforementioned host cells, the host cell is further modified to include a fucosyltransferase and a pathway for producing fucose and transporting fucose into the ER or Golgi. Examples of methods for modifying *Pichia pastoris* to render it capable of producing glycoproteins in which one or more of the N-glycans thereon are fucosylated are disclosed in PCT International Application No. PCT/US2008/002787. In particular aspects of the invention, the *Pichia pastoris* host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of fucosyltransferase is selected from the group consisting of α1,2-fucosyltransferase, α1,3-fucosyltransferase, α1,4-fucosyltransferase, and α1,6-fucosyltransferase.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include *Pichia pastoris* that are genetically engineered to eliminate glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of Pmtp inhibitors and/or an alpha-mannosidase as disclosed in Published International Application No. WO 2007061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted alpha-1,2-mannosidase.

PMT deletions or disruptions and/or Pmtp inhibitors control O-glycosylation by reducing O-glycosylation occupancy; that is by reducing the total number of O-glycosylation sites on the glycoprotein that are glycosylated. The further addition of an alpha-1,2-mannsodase that is secreted by the cell controls O-glycosylation by reducing the mannose chain length of the O-glycans that are on the glycoprotein. Thus, combining PMT deletions or disruptions and/or Pmtp inhibitors with expression of a secreted alpha-1,2-mannosidase controls O-glycosylation by reducing occupancy and chain length. In particular circumstances, the particular combination of PMT deletions or disruptions, Pmtp inhibitors, and alpha-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and alpha-1,2-mannosidase. In another aspect, genes encoding one or more endogenous mannosyltransferase enzymes are deleted. This deletion(s) can be in combination with providing the secreted alpha-1,2-mannosidase and/or PMT inhibitors or can be in lieu of providing the secreted alpha-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of glycoproteins such as whole antibodies as they traverse the secretory pathway and are transported to the cell surface. Thus, in cells in which O-glycosylation is controlled, the yield of properly assembled glycoproteins such as antibody fragments is increased over the yield obtained in host cells in which O-glycosylation is not controlled.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in PCT International Application No. PCT/US2009/033507. Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

Therefore, the methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans are selected from the group consisting of $Man_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}Man_3GlcNAc_2$; hybrid N-glycans are selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high mannose N-glycans are selected from the group consisting of $Man_6GlcNAc_2$, $Man_7GlcNAc_2$, $Man_8GlcNAc_2$, and $Man_9GlcNAc_2$. Examples of N-glycan structures include but are not limited to $Man_5GlcNAc_2$, $GlcNAcMan_5GlcNAc_2$, $GlcNAcMan_3GlcNAc_2$, $GlcNAc_2Man_3GlcNAc_2$, $GlcNAc_3Man_3GlcNAc_2$, $GlcNAc_4Man_3GlcNAc_2$, $GalGlcNAc_2Man_3GlcNAc_2$, $Gal_2GlcNAc_2Man_3GlcNAc_2$, $Gal_2GlcNAc_3Man_3GlcNAc_2$, $Gal_2GlcNAc_4Man_3GlcNAc_2$, $Gal_3GlcNAc_3Man_3GlcNAc_2$, $Gal_3GlcNAc_4Man_3GlcNAc_2$, $Gal_4GlcNAc_4Man_3GlcNAc_2$, $NANAGal_2GlcNAc_2Man_3GlcNAc_2$, $NANA_2Gal_2GlcNAc_2Man_3GlcNAc_2$, $NANA_3Gal_3GlcNAc_3Man_3GlcNAc_2$, and $NANA_4Gal_4GlcNAc_4Man_3GlcNAc_2$.

Yeast selectable markers that can be used to construct the recombinant host cells include drug resistance markers and genetic functions which allow the yeast host cell to synthesize essential cellular nutrients, e.g. amino acids. Drug resistance markers which are commonly used in yeast include chloramphenicol, kanamycin, methotrexate, G418 (geneticin), Zeocin, and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272:30061-30066

(1997)). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135). Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X56180.

The present invention further provides a method for producing a mature human erythropoietin in methylotrophic yeast such as *Pichia pastoris* comprising predominantly sialic acid-terminated biantennary N-glycans and having no detectable cross binding activity with antibodies made against host cell antigens. The method comprises providing a recombinant *Pichia pastoris* host cell genetically engineered to produce sialic acid-terminated biantennary N-glycans and in which at least the BMT1, BMT2, and BMT3 genes have been deleted or disrupted and which includes two or more nucleic acid molecules, each encoding a fusion protein comprising a mature human erythropoietin EPO fused to a signal peptide that targets the ER or Golgi apparatus and which is removed when the fusion protein is in the ER or Golgi apparatus; growing the host cell in a medium under conditions effective for expressing and processing the first and second fusion proteins; and recovering the mature human erythropoietin from the medium to produce the mature human erythropoietin comprising predominantly sialic acid-terminated biantennary N-glycans and having no detectable cross binding activity with antibodies made against host cell antigens.

In particular aspects, the nucleic acid molecule encoding the mature human erythropoietin is codon-optimized for optimal expression in the methylotrophic yeast such as *Pichia pastoris*. As shown in the examples, the mature human erythropoietin is encoded as a fusion protein in which the EPO is fused at the N-terminus of the mature form of the erythropoietin to the C-terminus of a signal peptide that targets the fusion protein to the secretory pathway for processing, including glycosylation. Examples of signal peptides include but are not limited to the *S. cerevisiae* αMATpre signal peptide or a chicken lysozyme signal peptide. Other signal sequences can be used instead of those disclosed herein, for example, the *Aspergillus niger* α-amylase signal peptide and human serum albumin (HSA) signal peptide. In one embodiment, a first nucleic acid molecule encodes a fusion protein wherein the mature erythropoietin is fused to the *S. cerevisiae* αMATpre signal peptide and second nucleic acid molecule encodes a fusion protein wherein the mature erythropoietin is fused to the *S. cerevisiae* αMATpre signal peptide a chicken lysozyme signal peptide. The signal peptide can be fused to the mature human erythropoietin by a linker peptide that can contain one or more protease cleavage sites.

In further aspects, the host cell includes between two and twelve copies of the expression cassettes encoding the fusion protein comprising the mature human erythropoietin. In some aspects, the host cell includes about eight to eleven copies of the expression cassettes encoding the fusion protein comprising the mature human erythropoietin. In other aspects, the host cell includes about three to four copies of the first nucleic acid and five to seven copies of the second nucleic acid.

The host cell is genetically engineered to produce sialic acid-terminated biantennary N-glycans and in which at least the BMT1, BMT2, and BMT3 genes have been deleted or disrupted. Such a host cell further includes at least a deletion or disruption of the OCH1, PNO1, MNN4, and MNN4L1 genes. The host cell further includes one or more nucleic acid molecules encoding at least the following chimeric glycosylation enzymes: α1,2-mannosidase catalytic domain fused to a cellular targeting peptide that targets the catalytic domain to the ER or Golgi apparatus of the host cell; GlcNAc transferase I catalytic domain fused to a cellular targeting peptide that targets the catalytic domain to the ER or Golgi apparatus of the host cell; mannosidase II catalytic domain fused to a cellular targeting peptide that targets the catalytic domain to the ER or Golgi apparatus of the host cell; GlcNAc transferase II catalytic domain fused to a cellular targeting peptide that targets the catalytic domain to the ER or Golgi apparatus of the host cell; β1,4-galactosyltransferase catalytic domain fused to a cellular targeting peptide that targets the catalytic domain to the ER or Golgi apparatus of the host cell; and α1,2-sialyltransferase catalytic domain fused to a cellular targeting peptide that targets the catalytic domain to the ER or Golgi apparatus of the host cell. These glycosylation enzymes are selected to be active at the location in the ER or Golgi apparatus to which they are targeted. Methods for selecting glycosylation enzymes and targeting the enzymes to particular regions of the ER or Golgi apparatus for optimal activity have been described in U.S. Pat. Nos. 7,029,872 and 7,449,308 and in Published U.S. Application Nos. 2006/0040353 and 2006/0286637. The host cells are further modified to include the enzymes of a pathway as disclosed in Published U.S. Application No. and 2006/0286637 to produce CMP-sialic acid and to include GlcNAc and galactose transporters and a UDP-galactose-4-epimerase. Finally, the host further includes a nucleic acid molecule encoding a fungal α1,2-mannosidase catalytic domain fused to a cellular targeting peptide that targets the catalytic domain to the secretory pathway for secretion and which effects a reduction in O-glycan occupancy and chain length.

Detection of detectable cross binding activity with antibodies made against host cell antigens can be determined in a sandwich ELISA or in a Western blot.

In further aspects, recovering the mature human erythropoietin comprising predominantly sialic acid-terminated biantennary N-glycans and having no detectable cross binding activity with antibodies made against host cell antigens includes a cation exchange chromatography step and/or a hydroxyapatite chromatography step and/or an anion exchange chromatography step. In one embodiment, the recovering the mature human erythropoietin comprising predominantly sialic acid-terminated biantennary N-glycans and having no detectable cross binding activity with antibodies made against host cell antigens comprises a cation exchange chromatography step followed by a hydroxyapatite chromatography step. Optionally, recovery of the mature human erythropoietin comprising predominantly sialic acid-terminated biantennary N-glycans and having no detectable cross binding activity with antibodies made against host cell antigens includes an anion chromatography step.

Further provided is a composition comprising a mature human erythropoietin comprising predominantly sialic acid-terminated bi-antennary N-glycans and having no detectable cross binding activity with antibodies made against host cell antigens obtained as disclosed herein and a pharmaceutically acceptable salt. In particular embodiments, about 50 to 60% of the N-glycans comprise sialic acid residues on both antennae; in further embodiments, greater than 70% of the N-glycans comprise sialic acid residues on both antennae. In further aspects, less than 30% of the N-glycans are neutral N-glycans (i.e., are not sialylated on at least one terminus at the non-reducing end of the N-glycan). In further still aspects, less than 20% of the N-glycans are neutral N-glycans.

In particular aspects, the mature human erythropoietin comprising predominantly sialic acid-terminated biantennary N-glycans and having no detectable cross binding activity with antibodies made against host cell antigens is conjugated to a hydrophilic polymer, which is particular embodiments is a polyethylene glycol polymer. Examples of mature human erythropoietin comprising predominantly sialic acid-terminated biantennary N-glycans conjugated to polyethylene glycol polymers has been described in commonly-owned U.S. Published Application No. 2008/0139470.

The polyethylene glycol polymer (PEG) group may be of any convenient molecular weight and may be linear or branched. The average molecular weight of the PEG will preferably range from about 2 kiloDalton ("kDa") to about 100 kDa, more preferably from about 5 kDa to about 60 kDa, more preferably from about 20 kDa to about 50 kDa; most preferably from about 30 kDa to about 40 kDa. These PEGs can be supplied from any commericial vendors including NOF Corporation (Tokyo, Japan), Dow Pharma (ChiroTech Technology, Cambridge, UK), Nektar (San Carlos, Calif.) and SunBio (Anyang City, South Korea). Suitable PEG moieties include, for example, 40 kDa methoxy poly(ethylene glycol) propionaldehyde; 60 kDa methoxy poly(ethylene glycol) propionaldehyde; 31 kDa alpha-methyl-w-(3-oxopropoxy), polyoxyethylene; 30 kDa PEG: 30 kDa Methoxy poly (ethylene glycol) propionaldehyde and 45 kDa 2,3-Bis (methylpolyoxyethylene-oxy)-1-[(3-oxopropyl) polyoxyethylene-oxy]-propane. The PEG groups will generally be attached to the erythropoietin via acylation or reductive amination through a reactive group on the PEG moiety (e.g., an aldehyde, amino, thiol, or ester group) to a reactive group on the protein or polypeptide of interest (e.g., an aldehyde, amino, or ester group). For example, the PEG moiety may be linked to the N-terminal amino acid residue of erythropoietin, either directly or through a linker.

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis (See, for example, Example 4). The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

The following examples are intended to promote a further understanding of the present invention.

EXAMPLE 1

Genetically engineered *Pichia pastoris* strain YGLY3159 is a strain that produces recombinant human erythropoietin with sialylated N-glycans (rhEPO). Construction of the strain has been described in U.S. Published Application No. 20080139470 and is illustrated schematically in FIG. 1. Briefly, the strain was constructed as follows.

The strain YGLY3159 was constructed from wild-type *Pichia pastoris* strain NRRL-Y 11430 using methods described earlier (See for example, U.S. Pat. No. 7,449,308; U.S. Pat. No. 7,479,389; U.S. Published Application No. 20090124000; Published PCT Application No. WO2009085135; Nett and Gerngross, Yeast 20:1279 (2003); Choi et al., Proc. Natl. Acad. Sci. USA 100:5022 (2003); Hamilton et al., Science 301:1244 (2003)). All plasmids were made in a pUC19 plasmid using standard molecular biology procedures. For nucleotide sequences that were optimized for expression in *P. pastoris*, the native nucleotide sequences were analyzed by the GENEOPTIMIZER software (GeneArt, Regensburg, Germany) and the results used to generate nucleotide sequences in which the codons were optimized for *P. pastoris* expression. Yeast strains were transformed by electroporation (using standard techniques as recommended by the manufacturer of the electroporator BioRad).

Figure 2:
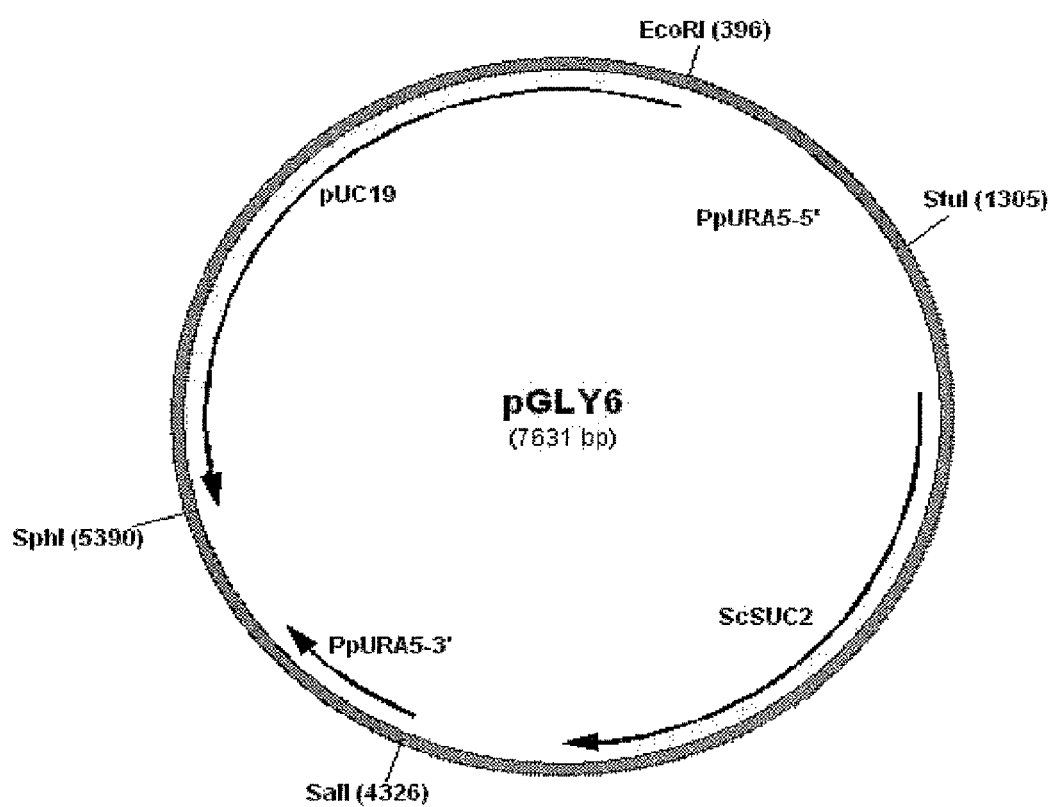
FIG. 2 shows a map of plasmid pGLY6. Plasmid pGLY6 is an integration vector that targets the URA5 locus and contains a nucleic acid molecule comprising the *S. cerevisiae* invertase gene or transcription unit (ScSUC2) flanked on one side by a nucleic acid molecule comprising a nucleotide sequence from the 5' region of the *P. pastoris* URA5 gene (PpURA5-5') and on the other side by a nucleic acid molecule comprising the a nucleotide sequence from the 3' region of the *P. pastoris* URA5 gene (PpURA5-3').

Plasmid pGLY6 (FIG. 2) is an integration vector that targets the URA5 locus contains a nucleic acid molecule comprising the *S. cerevisiae* invertase gene or transcription unit (ScSUC2; SEQ ID NO:1) flanked on one side by a nucleic acid molecule comprising a nucleotide sequence from the 5' region of the *P. pastoris* URA5 gene (SEQ ID NO:59) and on the other side by a nucleic acid molecule comprising the a nucleotide sequence from the 3' region of the *P. pastoris* URA5 gene (SEQ ID NO:60). Plasmid pGLY6 was linearized and the linearized plasmid transformed into wild-type strain NRRL-Y 11430 to produce a number of strains in which the ScSUC2 gene was inserted into the URA5 locus by double-crossover homologous recombination. Strain YGLY1-3 was selected from the strains produced and is auxotrophic for uracil.

Figure 3:
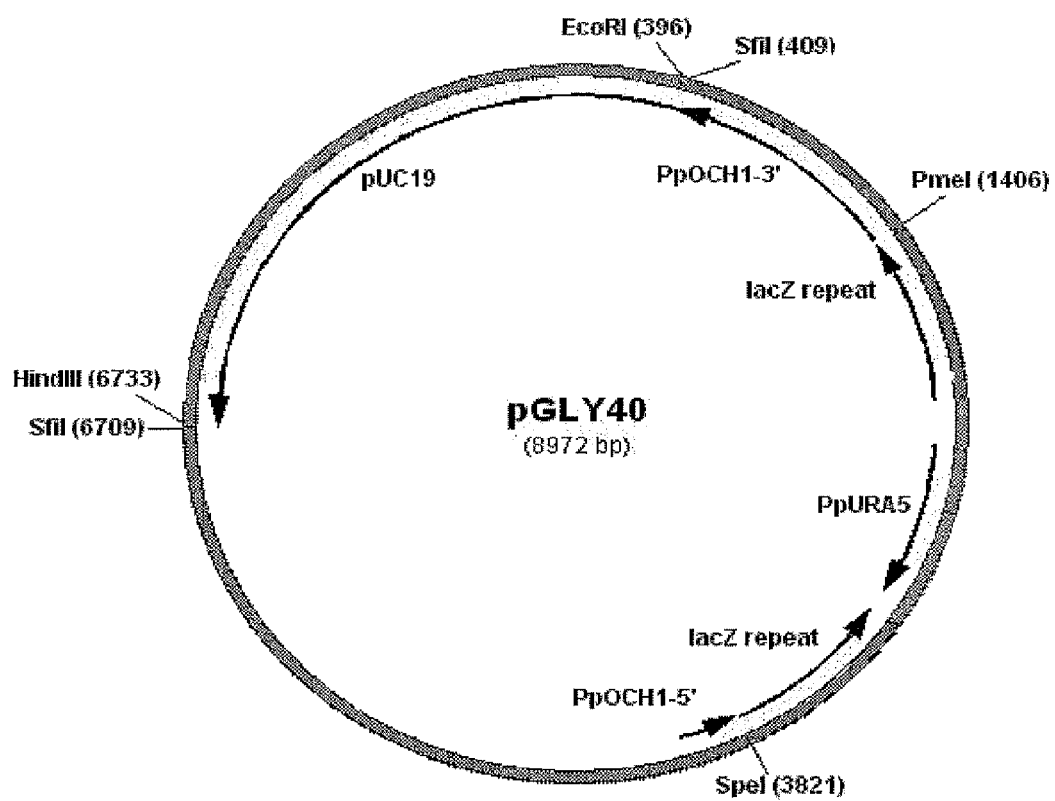
FIG. 3 shows a map of plasmidpGLY40. Plasmid pGLY40 is an integration vector that targets the OCH1 locus and contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the OCH1 gene (PpOCH1-5') and on the other side by a nucleic acid molecule comprising a nucleotide sequence from the 3' region of the OCH1 gene (PpOCH1-3').

Plasmid pGLY40 (FIG. 3) is an integration vector that targets the OCH1 locus and contains a nucleic acid molecule comprising the *P. pastoris* URA5 gene or transcription unit (SEQ ID NO:61) flanked by nucleic acid molecules comprising lacZ repeats (SEQ ID NO:62) which in turn is flanked on one side by a nucleic acid molecule comprising a nucleotide sequence from the 5' region of the OCH1 gene (SEQ ID NO:64) and on the other side by a nucleic acid molecule comprising a nucleotide sequence from the 3' region of the OCH1 gene (SEQ ID NO:65). Plasmid pGLY40 was linearized with SfiI and the linearized plasmid transformed into strain YGLY1-3 to produce a number of strains in which the URA5 gene flanked by the lacZ repeats has been inserted into the OCH1 locus by double-crossover homologous recombination. Strain YGLY2-3 was selected from the strains produced and is prototrophic for URA5. Strain YGLY2-3 was counterselected in the presence of 5-fluoro-orotic acid (5-FOA) to produce a number of strains in which the URA5 gene has been lost and only the lacZ repeats remain in the OCH1 locus. This renders the strain auxotrophic for uracil. Strain YGLY4-3 was selected.

Figure 4:
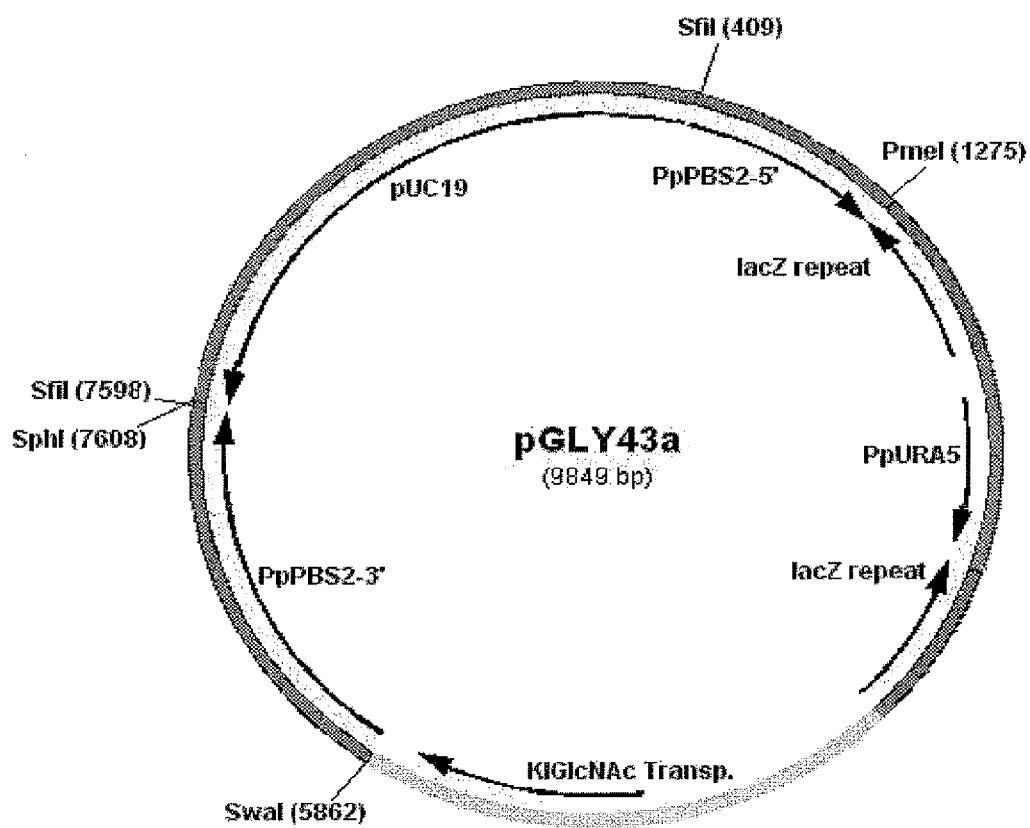
FIG. 4 shows a map of plasmid pGLY43a. Plasmid pGLY43a is an integration vector that targets the BMT2 locus and contains a nucleic acid molecule comprising the *K. lactis* UDP-N-acetylglucosamine (UDP-GlcNAc) transporter gene or transcription unit (KlGlcNAc Transp.) adjacent to a nucleic acid molecule comprising the *P. pastoris* URA5 gene or transcription unit (PpURA5) flanked by nucleic acid molecules comprising lacZ repeats (lacZ repeat). The adjacent genes are flanked on one side by a nucleic acid molecule comprising a nucleotide sequence from the 5' region of the BMT2 gene (PpPBS2-5') and on the other side by a nucleic acid molecule comprising a nucleotide sequence from the 3' region of the BMT2 gene (PpPBS2-3').

Plasmid pGLY43a (FIG. 4) is an integration vector that targets the BMT2 locus and contains a nucleic acid molecule comprising the *K. lactis* UDP-N-acetylglucosamine (UDP-GlcNAc) transporter gene or transcription unit (KlMNN2-2, SEQ ID NO:3) adjacent to a nucleic acid molecule comprising the *P. pastoris* URA5 gene or transcription unit flanked by nucleic acid molecules comprising lacZ repeats. The adjacent genes are flanked on one side by a nucleic acid molecule comprising a nucleotide sequence from the 5' region of the BMT2 gene (SEQ ID NO: 66) and on the other side by a nucleic acid molecule comprising a nucleotide sequence from the 3' region of the BMT2 gene (SEQ ID NO:67). Plasmid pGLY43a was linearized with SfiI and the linearized plasmid transformed into strain YGLY4-3 to produce to produce a number of strains in which the KlMNN2-2 gene and URA5 gene flanked by the lacZ repeats has been inserted into the BMT2 locus by double-crossover homologous recombination. The BMT2 gene has been disclosed in Mille et al., J. Biol. Chem. 283: 9724-9736 (2008) and U.S. Pat. No. 7,465,557. Strain YGLY6-3 was selected from the strains produced and is prototrophic for uracil. Strain YGLY6-3 was counterselected in the presence of 5-FOA to produce strains in which the URA5 gene has been lost and only the lacZ repeats remain. This renders the strain auxotrophic for uracil. Strain YGLY8-3 was selected.

Figure 5:
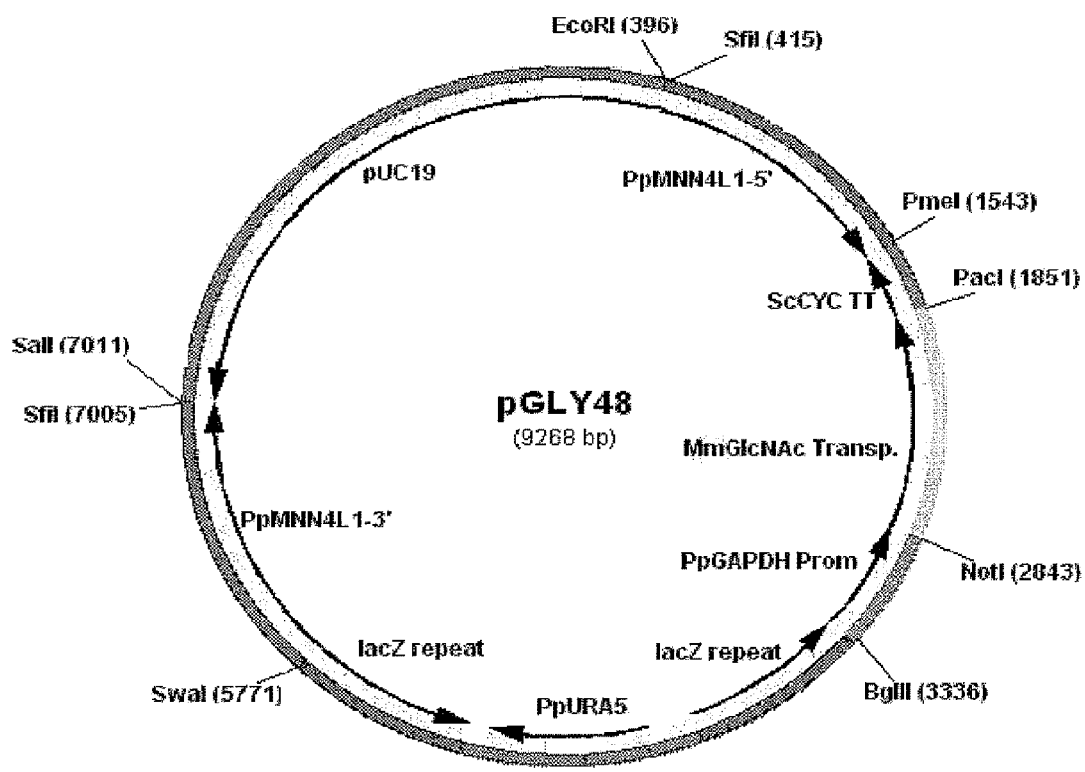
FIG. 5 shows a map of plasmid pGLY48. Plasmid pGLY48 is an integration vector that targets the MNN4L1 locus and contains an expression cassette comprising a nucleic acid molecule encoding the mouse homologue of the UDP-GlcNAc transporter (MmGlcNAc Transp.) open reading frame (ORF) operably linked at the 5' end to a nucleic acid molecule comprising the *P. pastoris* GAPDH promoter (Pp-GAPDH Prom) and at the 3' end to a nucleic acid molecule comprising the *S. cerevisiae* CYC termination sequence (Sc-CYC TT) adjacent to a nucleic acid molecule comprising the *P. pastoris* URA5 gene or transcription unit (PpURA5) flanked by lacZ repeats (lacZ repeat) and in which the expression cassettes together are flanked on one side by a nucleic acid molecule comprising a nucleotide sequence from the 5' region of the *P. Pastoris* MNN4L1 gene (PpMNN4L1-5') and on the other side by a nucleic acid molecule comprising a nucleotide sequence from the 3' region of the MNN4L1 gene (PpMNN4L1-3').

Plasmid pGLY48 (FIG. 5) is an integration vector that targets the MNN4L1 locus and contains an expression cassette comprising a nucleic acid molecule encoding the mouse homologue of the UDP-GlcNAc transporter (SEQ ID NO:17) open reading frame (ORF) operably linked at the 5' end to a nucleic acid molecule comprising the *P. pastoris* GAPDH promoter (SEQ ID NO:53) and at the 3' end to a nucleic acid molecule comprising the *S. cerevisiae* CYC termination sequences (SEQ ID NO:56) adjacent to a nucleic acid molecule comprising the *P. pastoris* URA5 gene flanked by lacZ repeats and in which the expression cassettes together are flanked on one side by a nucleic acid molecule comprising a nucleotide sequence from the 5' region of the *P. Pastoris* MNN4L1 gene (SEQ ID NO:76) and on the other side by a nucleic acid molecule comprising a nucleotide sequence from the 3' region of the MNN4L1 gene (SEQ ID NO:77). Plasmid pGLY48 was linearized with SfiI and the linearized plasmid transformed into strain YGLY8-3 to produce a number of strains in which the expression cassette encoding the mouse UDP-GlcNAc transporter and the URA5 gene have been inserted into the MNN4L1 locus by double-crossover homologous recombination. The MNN4L1 gene (also referred to as MNN4B) has been disclosed in U.S. Pat. No. 7,259,007. Strain YGLY10-3 was selected from the strains produced and then counterselected in the presence of 5-FOA to produce a number of strains in which the URA5 gene has been lost and only the lacZ repeats remain. Strain YGLY12-3 was selected.

Figure 6:
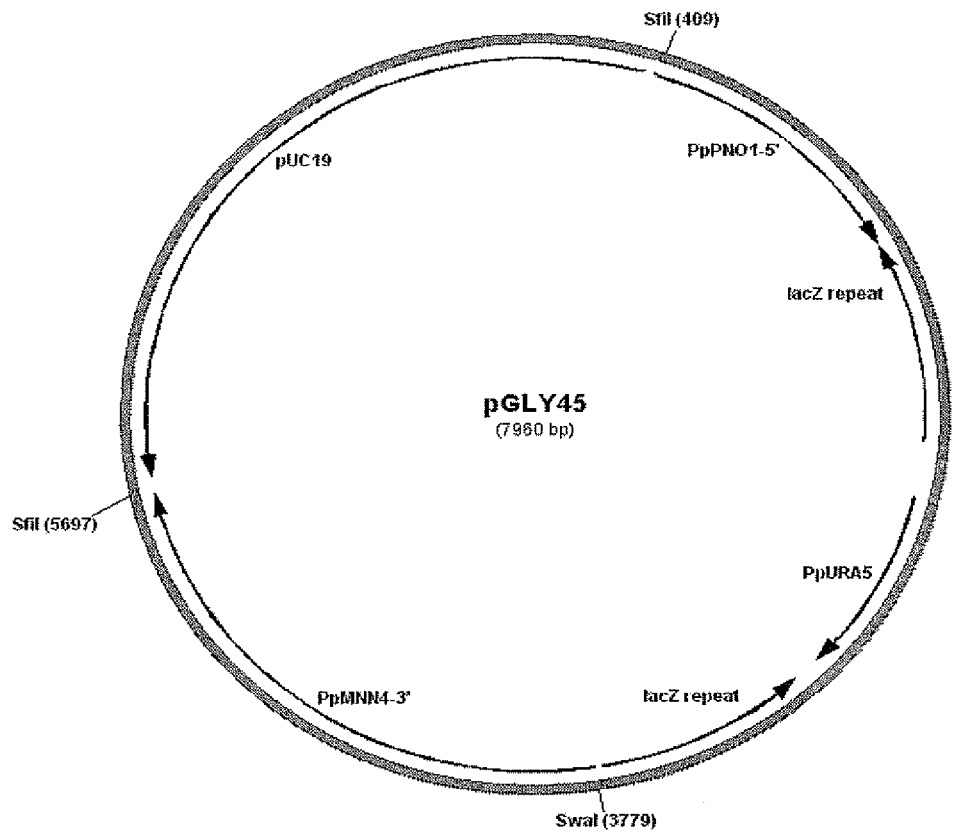
FIG. 6 shows as map of plasmid pGLY45. Plasmid pGLY45 is an integration vector that targets the PNO1/MNN4 loci contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the PNO1 gene (PpPNO1-5') and on the other side by a nucleic acid molecule comprising a nucleotide sequence from the 3' region of the MNN4 gene (PpMNN4-3').

Plasmid pGLY45 (FIG. 6) is an integration vector that targets the PNO1/MNN4 loci contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the PNO1 gene (SEQ ID NO:74) and on the other side by a nucleic acid molecule comprising a nucleotide sequence from the 3' region of the MNN4 gene (SEQ ID NO:75). Plasmid pGLY45 was linearized with SfiI and the linearized plasmid transformed into strain YGLY12-3 to produce to produce a number of strains in which the URA5 gene flanked by the lacZ repeats has been inserted into the MNN4 loci by double-crossover homologous recombination. The PNO1 gene has been disclosed in U.S. Pat. No. 7,198,921 and the MNN4 gene (also referred to as MNN4B) has been disclosed in U.S. Pat. No. 7,259,007. Strain YGLY14-3 was selected from the strains produced and then counterselected in the presence of 5-FOA to produce a number of strains in which the URA5 gene has been lost and only the lacZ repeats remain. Strain YGLY16-3 was selected.

Figure 7:
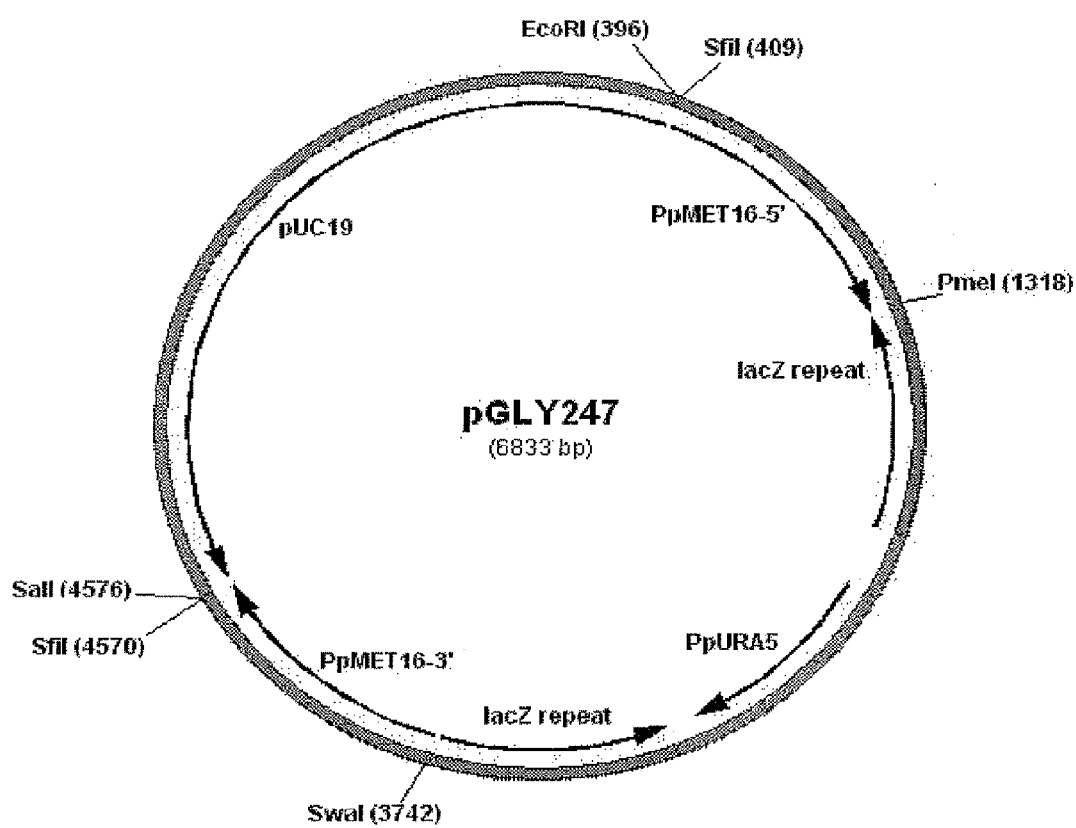
FIG. 7 shows a map of plasmid pGLY247. Plasmid pGLY247 is an integration vector that targets the MET16 locus and contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the MET16 gene (PpMET16-5') and on the other side by a nucleic acid molecule comprising a nucleotide sequence from the 3' region of the MET16 gene (PpMET16-3').

Plasmid pGLY247 (FIG. 7) is an integration vector that targets the MET16 locus and contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the MET16 gene (SEQ ID NO:84) and on the other side by a nucleic acid molecule comprising a nucleotide sequence from the 3' region of the MET16 gene (SEQ ID NO:85). Plasmid pGLY247 was linearized with SfiI and the linearized plasmid transformed into strain YGLY16-3 to produce a number of strains in which the URA5 flanked by the lacZ repeats has been inserted into the MET16 locus by double-crossover homologous recombination. Strain YGLY20-3 was selected.

Figure 8:
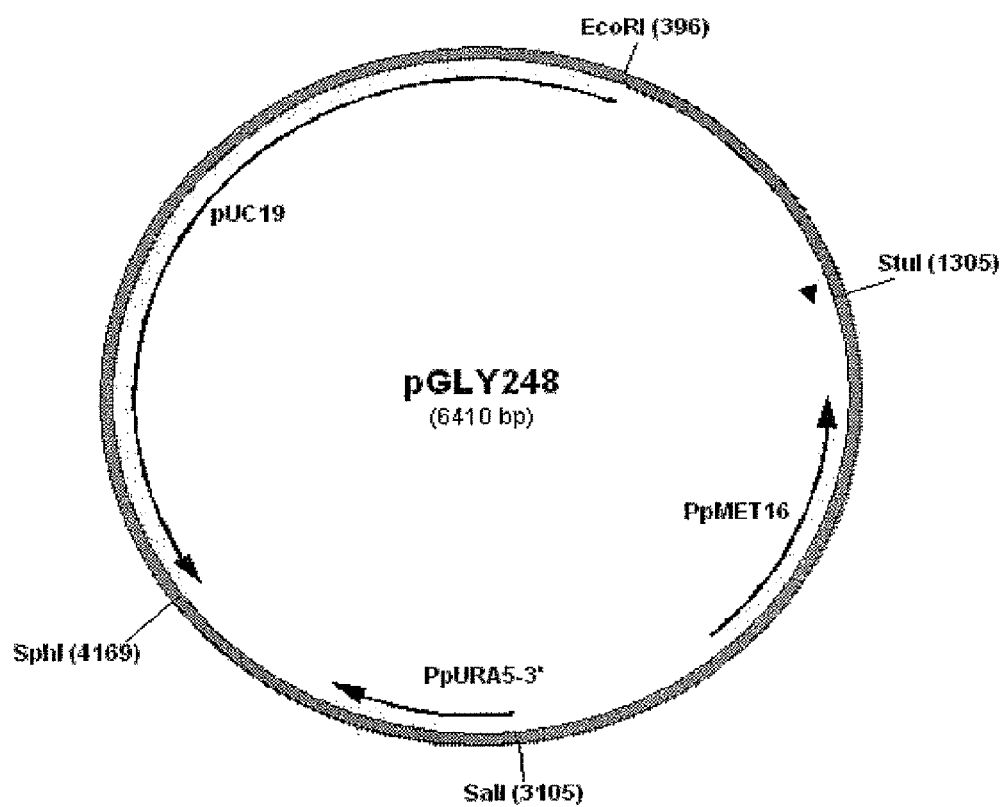
FIG. 8 shows a map of plasmid pGLY248. Plasmid pGLY248 is an integration vector that targets the URA5 locus and contains a nucleic acid molecule comprising the *P. pastoris* MET16 gene or transcription unit (PpMET16) flanked on one side by a nucleic acid molecule comprising a nucleotide sequence from the 5' region of the URA5 gene (PpURA5-5') and on the other side by a nucleic acid molecule comprising a nucleotide sequence from the 3' region of the URA5 gene (PpURA5-3').

Plasmid pGLY248 (FIG. 8) is an integration vector that targets the URA5 locus and contains a nucleic acid molecule comprising the *P. pastoris* MET16 gene (SEQ ID NO:86) flanked on one side by a nucleic acid molecule comprising a nucleotide sequence from the 5' region of the URA5 gene (SEQ ID NO:59) and on the other side by a nucleic acid molecule comprising a nucleotide sequence from the 3' region of the URA5 gene (SEQ ID NO:60). Plasmid pGLY248 was linearized and the linearized plasmid transformed into strain YGLY20-3 to produce a number of strains in which the ScSUC2 gene inserted into the URA5 locus has been replaced with the MET16 gene by double-crossover homologous recombination. Strain YGLY22-3 was selected and then counterselected in the presence of 5-FOA to produce a number of strains in which the URA5 gene inserted into the MET16 locus has been lost and only the lacZ repeats remain. Strain YGLY24-3 was selected.

Figure 9:
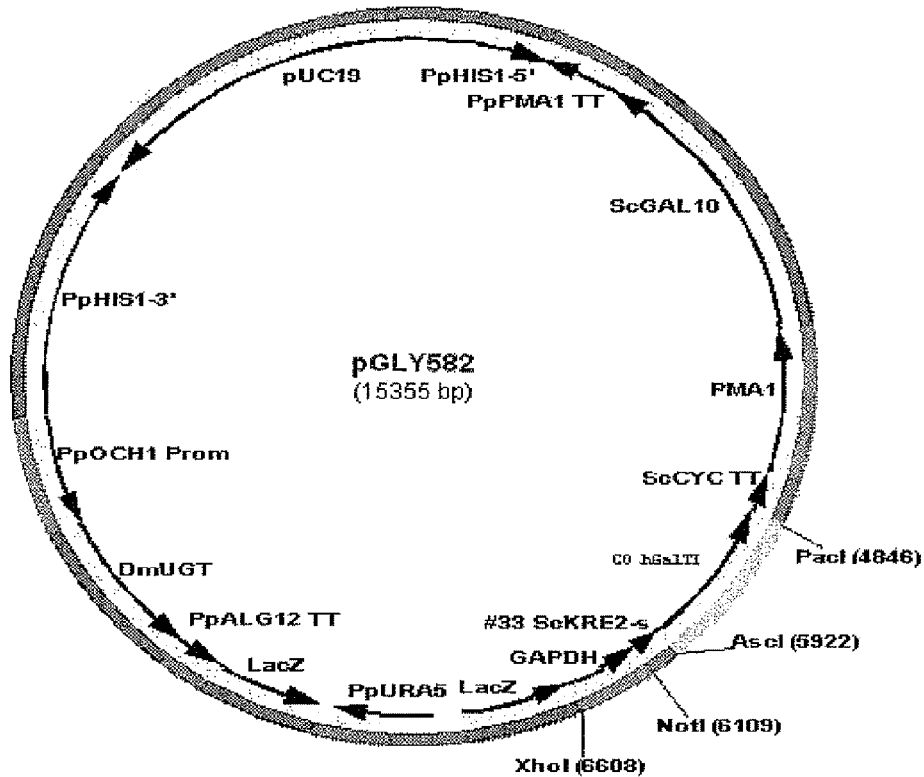
FIG. 9 shows a map of plasmid pGLY582. Plasmid pGLY582 is an integration vector that targets the HIS1 locus and contains in tandem four expression cassettes encoding (1) the *S. cerevisiae* UDP-glucose epimerase (ScGAL10), (2) the human galactosyltransferase I (hGalT) catalytic domain fused at the N-terminus to the *S. cerevisiae* KRE2-s leader peptide (33), (3) the *P. pastoris* URA5 gene or transcription unit (PpURA5) flanked by lacZ repeats (lacZ repeat), and (4) the *D. melanogaster* UDP-galactose transporter (DmUGT).

Plasmid pGLY582 (FIG. 9) is an integration vector that targets the HIS1 locus and contains in tandem four expression cassettes encoding (1) the *S. cerevisiae* UDP-glucose epimerase (ScGAL10), (2) the human galactosyltransferase I (hGalT) catalytic domain fused at the N-terminus to the *S. cerevisiae* KRE2-s leader peptide (33) to target the chimeric enzyme to the ER or Golgi, (3) the *P. pastoris* URA5 gene or transcription unit flanked by lacZ repeats, and (4) the *D. melanogaster* UDP-galactose transporter (DmUGT). The expression cassette encoding the ScGAL10 comprises a nucleic acid molecule encoding the ScGAL10 ORF (SEQ ID NO:21) operably linked at the 5' end to a nucleic acid molecule comprising the *P. pastoris* PMA1 promoter (SEQ ID NO:45) and operably linked at the 3' end to a nucleic acid molecule comprising the *P. pastoris* PMA1 transcription termination sequence (SEQ ID NO:46). The expression cassette encoding the chimeric galactosyltransferase I comprises a nucleic acid molecule encoding the hGalT catalytic domain codon optimized for expression in *P. pastoris* (SEQ ID NO:23) fused at the 5' end to a nucleic acid molecule encoding the KRE2-s leader 33 (SEQ ID NO:13), which is operably linked at the 5' end to a nucleic acid molecule comprising the *P. pastoris* GAPDH promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The expression cassette encoding the DmUGT comprises a nucleic acid molecule encoding the DmUGT ORF (SEQ ID NO:19) operably linked at the 5' end to a nucleic acid molecule comprising the *P. pastoris* OCH1 promoter (SEQ ID NO:47) and operably linked at the 3' end to a nucleic acid molecule comprising the *P. pastoris* ALG12 transcription termination sequence (SEQ ID NO:48). The four tandem cassettes are flanked on one side by a nucleic acid molecule comprising a nucleotide sequence from the 5' region of the HIS1 gene (SEQ ID NO:87) and on the other side by a nucleic acid molecule comprising a nucleotide sequence from the 3' region of the HIS1 gene (SEQ ID NO:88). Plasmid pGLY582 was linearized and the linearized plasmid transformed into strain YGLY24-3 to produce a number of strains in which the four tandem expression cassette have been inserted into the HIS1 locus by homologous recombination. Strain YGLY58 was selected and is auxotrophic for histidine and prototrophic for uridine.

Plasmid pGLY167b (FIG. 10) is an integration vector that targets the ARG1 locus and contains in tandem three expression cassettes encoding (1) the *D. melanogaster* mannosidase II catalytic domain (KD) fused at the N-terminus to *S. cerevisiae* MNN2 leader peptide (53) to target the chimeric enzyme to the ER or Golgi, (2) the *P. pastoris* HIS1 gene or transcription unit, and (3) the rat N-acetylglucosamine (GlcNAc) transferase II catalytic domain (TC) fused at the N-terminus to *S. cerevisiae* MNN2 leader peptide (54) to target the chimeric enzyme to the ER or Golgi. The expression cassette encoding the KD53 comprises a nucleic acid molecule encoding the *D. melanogaster* mannosidase II catalytic domain codon-optimized for expression in *P. pastoris* (SEQ ID NO:33) fused at the 5' end to a nucleic acid molecule encoding the MNN2 leader 53 (SEQ ID NO:5), which is operably linked at the 5' end to a nucleic acid molecule comprising the *P. pastoris* GAPDH promoter and at the 3' end to a nucleic acid molecule comprising the *S. cerevisiae* CYC transcription termination sequence. The HIS1 expression cassette comprises a nucleic acid molecule comprising the *P. pastoris* HIS1 gene or transcription unit (SEQ ID NO:89). The expression cassette encoding the TC54 comprises a nucleic acid molecule encoding the rat GlcNAc transferase II catalytic domain codon-optimized for expression in *P. pastoris* (SEQ ID NO:31) fused at the 5' end to a nucleic acid molecule encoding the MNN2 leader 54 (SEQ ID NO:7), which is operably linked at the 5' end to a nucleic acid molecule comprising the *P. pastoris* PMA1 promoter and at the 3' end to a nucleic acid molecule comprising the *P. pastoris* PMA1 transcription termination sequence. The three tandem cassettes are flanked on one side by a nucleic acid molecule comprising a nucleotide sequence from the 5' region of the ARG1 gene (SEQ ID NO:79) and on the other side by a nucleic acid molecule comprising a nucleotide sequence from the 3' region of the ARG1 gene (SEQ ID NO:80). Plasmid pGLY167b was linearized with SfiI and the linearized plasmid transformed into strain YGLY58 to produce a number of strains (in which the three tandem expression cassette have been inserted into the ARG1 locus by double-crossover homologous recombination. The strain YGLY73 was selected from the strains produced and is auxotrophic for arginine and prototrophic for uridine and histidine. The strain was then counterselected in the presence of 5-FOA to produce a number of strains now auxotrophic for uridine. Strain YGLY1272 was selected.

Plasmid pGLY1430 (FIG. 11) is a KINKO integration vector that targets the ADE1 locus without disrupting expression of the locus and contains in tandem four expression cassettes encoding (1) the human GlcNAc transferase I catalytic domain (NA) fused at the N-terminus to *P. pastoris* SEC12 leader peptide (10) to target the chimeric enzyme to the ER or Golgi, (2) mouse homologue of the UDP-GlcNAc transporter (MmTr), (3) the mouse mannosidase IA catalytic domain (FB) fused at the N-terminus to *S. cerevisiae* SEC12 leader peptide (8) to target the chimeric enzyme to the ER or Golgi, and (4) the *P. pastoris* URA5 gene or transcription unit. KINKO (Knock-In with little or No Knock-Out) integration vectors enable insertion of heterologous DNA into a targeted locus without disrupting expression of the gene at the targeted locus and have been described in U.S. Published Application No. 20090124000. The expression cassette encoding the NA10 comprises a nucleic acid molecule encoding the human GlcNAc transferase I catalytic domain codon-optimized for expression in *P. pastoris* (SEQ ID NO:25) fused at the 5' end to a nucleic acid molecule encoding the SEC12 leader 10 (SEQ ID NO:11), which is operably linked at the 5' end to a nucleic acid molecule comprising the *P. pastoris* PMA1 promoter and at the 3' end to a nucleic acid molecule comprising the *P. pastoris* PMA1 transcription termination sequence. The expression cassette encoding MmTr comprises a nucleic acid molecule encoding the mouse homologue of the UDP-GlcNAc transporter ORF operably linked at the 5' end to a nucleic acid molecule comprising the *P. pastoris* SEC4 promoter (SEQ ID NO:49) and at the 3' end to a nucleic acid molecule comprising the *P. pastoris* OCH1 termination sequences (SEQ ID NO:50). The expression cassette encoding the FB8 comprises a nucleic acid molecule encoding the mouse mannosidase IA catalytic domain (SEQ ID NO:27) fused at the 5' end to a nucleic acid molecule encoding the SEC12-m leader 8 (SEQ ID NO:15), which is operably linked at the 5' end to a nucleic acid molecule comprising the *P. pastoris* GADPH promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The four tandem cassettes are flanked on one side by a nucleic acid molecule comprising a nucleotide sequence from the 5' region and complete ORF of the ADE1 gene (SEQ ID NO:82) followed by a *P. pastoris* ALG3 termination sequence (SEQ ID NO:54) and on the other side by a nucleic acid molecule comprising a nucleotide sequence from the 3' region of the ADE1 gene (SEQ ID NO:83). Plasmid pGLY1430 was linearized with SfiI and the linearized plasmid transformed into strain YGLY1272 to produce a number of strains in which the four tandem expression cassette have been inserted into the ADE1 locus immediately following the ADE1 ORF by double-crossover homologous recombination. The strain YGLY1305 was selected from the strains produced and is auxotrophic for arginine and now prototrophic for uridine, histidine, and adenine. The strain was then counterselected in the presence of 5-FOA to produce a number of strains now auxotrophic for uridine. Strain YGLY1461 was selected and is capable of making glycoproteins that have predominantly galactose terminated N-glcyans.

Plasmid pGFI165 (FIG. 12) is a KINKO integration vector that targets the PRO1 locus without disrupting expression of the locus and contains expression cassettes encoding (1) the *T. reesei* α-1,2-mannosidase catalytic domain fused at the N-terminus to *S. cerevisiae* αMATpre signal peptide (aMAT-TrMan) to target the chimeric protein to the secretory pathway and secretion from the cell and (2) the *P. pastoris* URA5 gene or transcription unit. The expression cassette encoding the aMATTrMan comprises a nucleic acid molecule encoding the *T. reesei* catalytic domain (SEQ ID NO:29) fused at the 5' end to a nucleic acid molecule encoding the *S. cerevisiae* αMATpre signal peptide (SEQ ID NO:9), which is operably linked at the 5' end to a nucleic acid molecule comprising the *P. pastoris* GAPDH promoter and at the 3'end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The two tandem cassettes are flanked on one side by a nucleic acid molecule comprising a nucleotide sequence from the 5' region and complete ORF of the PRO1 gene (SEQ ID NO:90) followed by a *P. pastoris* ALG3 termination sequence and on the other side by a nucleic acid molecule comprising a nucleotide sequence from the 3' region of the PRO1 gene (SEQ ID NO:91). Plasmid pGF1165 was linearized with SfiI and the linearized plasmid transformed into strain YGLY1461 to produce a number of strains in which the two expression cassette have been inserted into the PRO1 locus immediately following the PRO1 ORF by double-crossover homologous recombination. The strain YGLY1703 was selected from the strains produced and is auxotrophic for arginine and prototrophic for uridine, histidine, adenine, and proline. This strain is capable of producing glycoproteins that have reduced O-glycosylation (See Published U.S. Application No. 20090170159).

Plasmid pGLY2088 (FIG. 13) is an integration vector that targets the TRP2 or AOX1 locus and contains expression cassettes encoding (1) mature human erythropoetin (EPO) fused at the N-terminus to a *S. cerevisiae* αMATpre signal peptide (alpha MF-pre) to target the chimeric protein to the secretory pathway and secretion from the cell and (2) the zeocin resistance protein (Sh ble or Zeocin$^R$). The expression cassette encoding the EPO comprises a nucleic acid molecule encoding the mature human EPO codon-optimized for expression in *P. pastoris* (SEQ ID NO:92) fused at the 5' end to a nucleic acid molecule encoding the *S. cerevisiae* αMAT-pre signal peptide, which is operably linked at the 5' end to a nucleic acid molecule comprising the *P. pastoris* AOX1 promoter (SEQ ID NO:55) and at the 3' end to a nucleic acid molecule comprising the *S. cerevisiae* CYC transcription termination sequence. The Zeocin$^R$ expression cassette comprises a nucleic acid molecule encoding the Sh ble ORF (SEQ ID NO:58) operably linked at the 5' end to the *S. cerevisiae* TEF1 promoter (SEQ ID NO:57) and at the 3' end to the *S. cerevisiae* CYC termination sequence. The two tandem cassettes are flanked on one side by a nucleic acid molecule comprising a nucleotide sequence comprising the TRP2 gene (SEQ ID NO:78). Plasmid pGLY2088 was linearized at the PmeI site and transformed into strain YGLY1703 to produce a number of strains in which the two expression cassette have been inserted into the AOX1 locus by roll in single-crossover homologous recombination, which results in multiple copies of the EPO expression cassette inserted into the AOX1 locus without disrupting the AOX1 locus. The strain YGLY2849 was selected from the strains produced and is auxotrophic for arginine and now prototrophic for uridine, histidine, adenine, and proline. The strain contains about three to four copies of the EPO expression cassette as determined by measuring the intensity of sequencing data of DNA isolated from the strain. During processing of the chimeric EPO in the ER and Golgi, the leader peptide is removed. Thus, the rhEPO produced is the mature form of the EPO.

Plasmid pGLY2456 (FIG. 14) is a KINKO integration vector that targets the TRP2 locus without disrupting expression of the locus and contains six expression cassettes encoding (1) the mouse CMP-sialic acid transporter (mCMP-Sia Transp), (2) the human UDP-GlcNAc 2-epimerase/N-acetyl-mannosamine kinase (hGNE), (3) the *Pichia pastoris* ARG1 gene or transcription unit, (4) the human CMP-sialic acid synthase (hCMP-NANA), (5) the human N-acetylneuraminate-9-phosphate synthase (hSIAP S), (6) the mouse α-2,6-sialyltransferase catalytic domain (mST6) fused at the N-terminus to *S. cerevisiae* KRE2 leader peptide (33) to target the chimeric enzyme to the ER or Golgi, and the *P. pastoris* ARG1 gene or transcription unit. The expression cassette encoding the mouse CMP-sialic acid Transporter comprises a nucleic acid molecule encoding the mCMP Sia Transp ORF codon optimized for expression in *P. pastoris* (SEQ ID NO:35), which is operably linked at the 5' end to a nucleic acid molecule comprising the *P. pastoris* PMA1 promoter and at the 3' end to a nucleic acid molecule comprising the *P. pastoris* PMA1 transcription termination sequence. The expression cassette encoding the human UDP-GlcNAc 2-epimerase/N-acetylmannosamine kinase comprises a nucleic acid molecule encoding the hGNE ORF codon optimized for expression in *P. pastoris* (SEQ ID NO:37), which is operably linked at the 5' end to a nucleic acid molecule comprising the *P. pastoris* GAPDH promoter and at the 3' end to a nucleic acid molecule comprising the *S. cerevisiae* CYC transcription termination sequence. The expression cassette encoding the *P. pastoris* ARG1 gene comprises (SEQ ID NO:81). The expression cassette encoding the human CMP-sialic acid synthase comprises a nucleic acid molecule encoding the hCMP-NANA S ORF codon optimized for expression in *P. pastoris* (SEQ ID NO:39), which is operably linked at the 5' end to a nucleic acid molecule comprising the *P. pastoris* GPDAH promoter and at the 3' end to a nucleic acid molecule comprising the *S. cerevisiae* CYC transcription termination sequence. The expression cassette encoding the human N-acetylneuraminate-9-phosphate synthase comprises a nucleic acid molecule encoding the hSIAP S ORF codon optimized for expression in *P. pastoris* (SEQ ID NO:41), which is operably linked at the 5' end to a nucleic acid molecule comprising the *P. pastoris* PMA1 promoter and at the 3' end to a nucleic acid molecule comprising the *P. pastoris* PMA1 transcription termination sequence. The expression cassette encoding the chimeric mouse α-2,6-sialyltransferase comprises a nucleic acid molecule encoding the mST6 catalytic domain codon optimized for expression in *P. pastoris* (SEQ ID NO:43) fused at the 5' end to a nucleic acid molecule encoding the *S. cerevisiae* KRE2 signal peptide, which is operably linked at the 5' end to a nucleic acid molecule comprising the *P. pastoris* TEF promoter (SEQ ID NO:51) and at the 3' end to a nucleic acid molecule comprising the *P. pastoris* TEF transcription termination sequence (SEQ ID NO:52). The six tandem cassettes are flanked on one side by a nucleic acid molecule comprising a nucleotide sequence from the 5' region of the ORF encoding Trp2p ending at the stop codon (SEQ ID NO:98) followed by a *P. pastoris* ALG3 termination sequence and on the other side by a nucleic acid molecule comprising a nucleotide sequence from the 3' region of the TRP2 gene (SEQ ID NO:99). Plasmid pGLY2456 was linearized with SfiI and the linearized plasmid transformed into strain YGLY2849 to produce a number of strains in which the six expression cassette have been inserted into the TRP2 locus immediately following the TRP2 ORF by double-crossover homologous recombination. The strain YGLY3159 was selected from the strains produced and is now prototrophic for uridine, histidine, adenine, proline, arginine, and tryptophan. The strain is resistant to Zeocin and contains about three to four copies of the EPO expression cassette. The strain produced rhEPO; however, using the methods in Example 5, the rhEPO has cross-reactivity binding to antibodies made against HCA (See Example 6).

While the various expression cassettes were integrated into particular loci of the *Pichia pastoris* genome in the examples herein, it is understood that the operation of the invention is independent of the loci used for integration. Loci other than those disclosed herein can be used for integration of the expression cassettes. Suitable integration sites include those enumerated in U.S. Published Application No. 20070072262 and include homologs to loci known for *Saccharomyces cerevisiae* and other yeast or fungi.

EXAMPLE 2

Strain YGLY3159 in Example 1 was further genetically engineered to disrupt the BMT1, BMT3, and BMT4 genes as follows.

Strain YGLY3159 was counterselected in the presence of 5-FOA to produce strain YGLY3225, which is now auxotrophic for uridine.

Plasmid pGLY3411 (pSH1092) (FIG. 15) is an integration vector that contains the expression cassette comprising the *P. pastoris* URA5 gene flanked by lacZ repeats flanked on one side with the 5' nucleotide sequence of the *P. pastoris* BMT4 gene (SEQ ID NO:72) and on the other side with the 3' nucleotide sequence of the *P. pastoris* BMT4 gene (SEQ ID NO:73). Plasmid pGLY3411 was linearized and the linearized plasmid transformed into YGLY3159 to produce a number of strains in which the URA5 expression cassette has been inserted into the BMT4 locus by double-crossover homologous recombination. Strain YGLY4439 was selected from the strains produced and is prototrophic for uracil, adenine, histidine, proline, arginine, and tryptophan. The strain is resistant to Zeocin and contains about three to four copies of the rhEPO expression cassette. The strain has a disruption or deletion of the BMT2 and BMT4 genes.

Plasmid pGLY3430 (pSH1115) (FIG. 16) is an integration vector that contains an expression cassette comprising a nucleic acid molecule encoding the Nourseothricin resistance (NAT$^R$) ORF (originally from pAG25 from EROSCARF, Scientific Research and Development GmbH, Daimlerstrasse 13a, D-61352 Bad Homburg, Germany, See Goldstein et al., Yeast 15: 1541 (1999)) ORF (SEQ ID NO:102) operably linked to the *Ashbya gossypii* TEF1 promoter (SEQ ID NO:105) and *Ashbya gossypii* TEF1 termination sequences (SEQ ID NO:106) flanked one side with the 5' nucleotide sequence of the *P. pastoris* BMT1 gene (SEQ ID NO:68) and on the other side with the 3' nucleotide sequence of the *P. pastoris* BMT1 gene (SEQ ID NO:69). Plasmid pGLY3430 was linearized and the linearized plasmid transformed into strain YGLY4439 to produce a number of strains in which the NAT$^R$ expression cassette has been inserted into the BMT1 locus by double-crossover homologous recombination. The strain YGLY6661 was selected from the strains produced and is prototrophic for uracil, adenine, histidine, proline, arginine, and tryptophan. The strain is resistant to Zeocin and Nourseothricin and contains about three to four copies of the EPO expression cassette. The strain has a disruption or deletion of the BMT1, BMT2, and BMT4 genes. Strain YGLY7013 was selected as well; however, this strain had only a partial disruption of the BMT1 gene. This strain was designated as having a disruption or deletion of the BMT1, BMT2 and BMT4 genes.

Plasmid pGLY4472 (pSH1186) (FIG. 17) is an integration vector that contains an expression cassette comprising a nucleic acid molecule encoding the *E. coli* hygromycin B phosphotransferase gene (Hyg$^R$) ORF (SEQ ID NO:103) operably linked to the *Ashbya gossypii* TEF1 promoter (SEQ ID NO:105) and *Ashbya gossypii* TEF1 termination sequences (SEQ ID NO:106) flanked one side with the 5' nucleotide sequence of the *P. pastoris* BMT3 gene (SEQ ID NO:70) and on the other side with the 3' nucleotide sequence of the *P. pastoris* BMT3 gene (SEQ ID NO:71). Plasmid pGLY3430 was linearized and the linearized plasmid transformed into strain YGLY6661 to produce a number of strains in which the Hyg$^R$ expression cassette has been inserted into the BMT3 locus by double-crossover homologous recombination. Strains YGLY7361 to YGLY7366 and strains YGLY7393 to YGLY7398 were selected from the strains produced and are prototrophic for uracil, adenine, histidine, proline, arginine, and tryptophan. The strains are resistant to Zeocin, Nourseothricin, and Hygromycin and contain about three to four copies of the EPO expression cassette. The strains have disruptions or deletions of the BMT1, BMT2, BMT3, and BMT4 genes and produce rhEPO lacking cross-reactivity binding to antibodies made against host cell antigen (HCA).

EXAMPLE 3

Figure 1A:
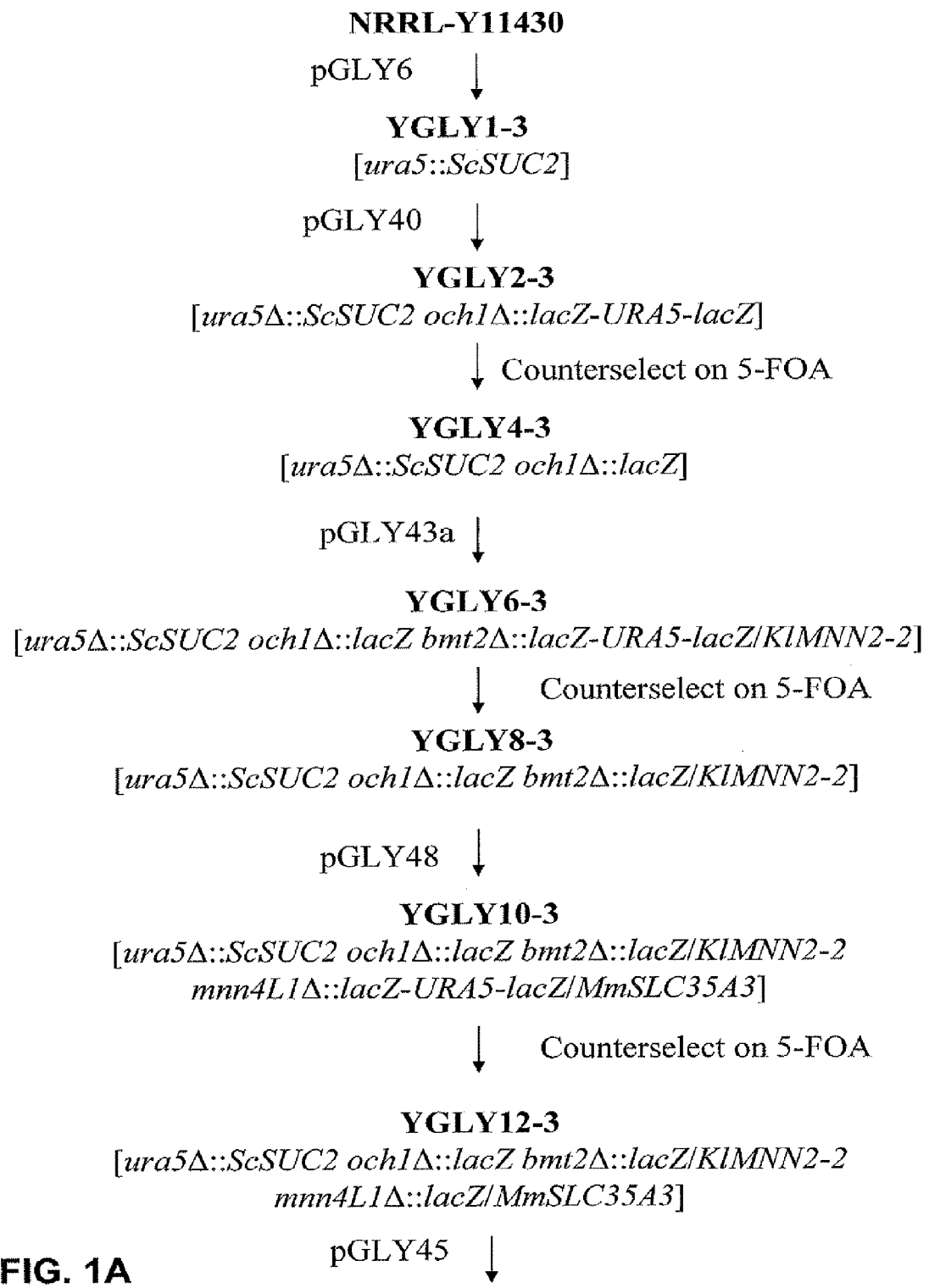
FIG. 1 A-J shows the genealogy of *P. pastoris* strain YGLY3159 (FIG. 1E) and strains YGLY7113 to YGLY7122 (FIG. 1I) beginning from wild-type strain NRRL-Y11430 (FIG. 1A).

Strain YGLY3159 in Example 1 was further genetically engineered to produce strains in which the BMT1, BMT3, and BMT4 genes have been disrupted or deleted and to include several copies of an expression cassette encoding mature human EPO fused to the chicken lysozyme leader peptide. Briefly, construction of these strains from YGLY3159 is shown in FIG. 1 and briefly described as follows.

Strain YGLY3159 was counterselected in the presence of 5-FOA to produce strain YGLY3225, which is now auxotrophic for uridine.

Plasmid pGLY2057 (FIG. 18) is an integration vector that targets the ADE2 locus and contains an expression cassette encoding the *P. pastoris* URA5 gene flanked by lacZ repeats. The expression cassette is flanked on one side by a nucleic acid molecule comprising a nucleotide sequence from the 5' region of the ADE2 gene (SEQ ID NO:100) and on the other side by a nucleic acid molecule comprising a nucleotide sequence from the 3' region of the ADE2 gene (SEQ ID NO:101). Plasmid pGLY2057 was linearized with SfiI and the linearized plasmid transformed into strain YGLY3225 to produce a number of strains in which the URA5 cassette has been inserted into the ADE2 locus by double-crossover homologous recombination. Strain YGLY3229 was selected from the strains produced and is auxotrophic for adenine and prototrophic for uridine, histidine, proline, arginine, and tryptophan. The strain is resistant to Zeocin and contains about three to four copies of the EPO expression cassette.

Plasmid pGLY2680 (FIG. 19) is an integration vector that can target the TRP2 or AOX1 locus and contains expression cassettes encoding (1) a chimeric EPO comprising the human mature erythropoietin (EPO) fused at the N-terminus to chicken lysozyme signal peptide to target the chimeric protein to the secretory pathway and secretion from the cell and (2) the *P. pastoris* ADE2 gene without a promoter. The ADE2 gene is poorly transcribed from a cryptic promoter. Thus, selection of ade2Δ yeast strains transformed with the vector in medium not supplemented with adenine requires multiple copies of the vector to be integrated into the genome to render the recombinant prototrophic for adenine. Since the vector further includes the EPO expression cassette, the recombinant yeast will also include multiple copies of the EPO cassette integrated into the genome. This vector and method has been described in Published PCT Application WO2009085135. The DNA sequence encoding the chicken lysozyme signal peptide is shown in SEQ ID NO:94, the codon-optimized ORF encoding the mature human EPO is shown in SEQ ID NO:92, and the *P. pastoris* ADE2 gene without its promoter but including its termination sequences is shown in SEQ ID NO:96. The chimeric EPO is operably linked to the AOX1 promoter and *S. cerevisiae* CYC termination sequences. The two tandem cassettes are flanked on one side by a nucleic acid molecule comprising a nucleotide sequence comprising the TRP2 gene.

Plasmid pGLY2680 was linearized at the PmeI site and transformed into YGLY3229 to produce a number of strains in which the two expression cassette have been inserted into the AOX1 locus by roll in single-crossover homologous recombination, which results in multiple copies of the EPO expression cassette inserted into the AOX1 locus without disrupting the AOX1 locus. Strain YGLY4209 was selected from the strains produced. This strain there are about 5-7 copies of the EPO expression cassette as determined by measuring the intensity of sequencing data of DNA isolated from the strain inserted into the locus. The strain is prototrophic for adenine, uridine, histidine, proline, arginine, and tryptophan. The strain contains in total about eight to eleven copies of EPO expression cassettes. During processing of the chimeric EPO in the ER and Golgi, the leader peptide is removed. Thus, the rhEPO produced is the mature form of the EPO.

Strain YGLY4209 was counterselected in the presence of 5'-FOA to produce a number of strains that were auxotrophic for uracil. From the transformants produced, strain YGLY4244 was selected.

Plasmid pGLY2713 (FIG. 20), an integration vector that targets the *P. pastoris* PEP4 gene (SEQ ID NO:104), contains the *P. pastoris* PNO1 ORF adjacent to the expression cassette comprising the *P. pastoris* URA5 gene flanked by lacZ repeats and flanked on one side with the 5' nucleotide sequence of the *P. pastoris* PEP4 gene and on the other side with the 3' nucleotide sequence of the *P. pastoris* PEP4 gene. Plasmid pGLY2713 was linearized with SfiI and the linearized plasmid transformed into strain YGLY4244 to produce a number of strains in which the PNO1 ORF and URA5 expression cassette have been inserted into the PEP4 locus by double-crossover homologous recombination. Strain YGLY5053 was selected from the strains produced and counterselected in the presence of 5-FOA to produce a number of strains in which the URA5 has been lost from the genome. Strain YGLY5597 was selected from the strains produced and is prototrophic for adenine, histidine, proline, arginine, and tryptophan. The strain is resistant to Zeocin and contains about eight to eleven copies of the rhEPO expression cassette.

Plasmid pGLY3411 (pSH1092) (FIG. 15) is an integration vector that contains the expression cassette comprising the *P. pastoris* URA5 gene flanked by lacZ repeats flanked on one side with the 5' nucleotide sequence of the *P. pastoris* BMT4 gene (SEQ ID NO:72) and on the other side with the 3' nucleotide sequence of the *P. pastoris* BMT4 gene (SEQ ID NO:73). Plasmid pGLY3411 was linearized and the linearized plasmid transformed into strain YGLY5597 to produce a number of strains in which the URA5 expression cassette has been inserted into the BMT4 locus by double-crossover homologous recombination. The strain YGLY5618 was selected from the strains produced and is prototrophic for uracil, adenine, histidine, proline, arginine, and tryptophan. The strain is resistant to Zeocin and Nourseothricin and contains about eight to eleven copies of the rhEPO expression cassette. The strain has disruptions of the BMT2 and BMT4 genes.

Plasmid pGLY3430 (pSH1115) (FIG. 16) is an integration vector that contains an expression cassette comprising a nucleic acid molecule encoding the Nourseothricin resistance (NAT$^R$) ORF (originally from pAG25 from EROSCARF, Scientific Research and Development GmbH, Daimlerstrasse 13a, D-61352 Bad Homburg, Germany, See Goldstein et al., Yeast 15: 1541 (1999)) ORF (SEQ ID NO:102) operably linked to the *Ashbya gossypii* TEF1 promoter and *Ashbya gossypii* TEF1 termination sequences flanked one side with the 5' nucleotide sequence of the *P. pastoris* BMT1 gene (SEQ ID NO:68) and on the other side with the 3' nucleotide sequence of the *P. pastoris* BMT1 gene (SEQ ID NO:69). Plasmid pGLY3430 was linearized and the linearized plasmid transformed into strain YGLY5618 to produce a number of strains in which the NAT$^R$ expression cassette has been inserted into the BMT1 locus by double-crossover homologous recombination. The strain YGLY7110 was selected from the strains produced and is prototrophic for uracil, adenine, histidine, proline, arginine, and tryptophan. The strain is resistant to Zeocin and Nourseothricin and contains about eight to eleven copies of the rhEPO expression cassette. The strain has disruptions of the BMT1, BMT2, and BMT4 genes.

Plasmid pGLY4472 (pSH1186) (FIG. 17) is an integration vector that contains an expression cassette comprising a nucleic acid molecule encoding the *E. coli* hygromycin B phosphotransferase gene (Hyg$^R$) ORF (SEQ ID NO:103) operably linked to the *Ashbya gossypii* TEF1 promoter and *Ashbya gossypii* TEF1 termination sequences flanked one side with the 5' nucleotide sequence of the *P. pastoris* BMT3 gene (SEQ ID NO:70) and on the other side with the 3' nucleotide sequence of the *P. pastoris* BMT3 gene (SEQ ID NO:71). Plasmid pGLY3430 was linearized and the linearized plasmid transformed into strain YGLY7110 to produce a number of strains in which the Hyg$^R$ expression cassette has been inserted into the BMT3 locus by double-crossover homologous recombination. Strains YGLY7113 to YGLY7122 were selected from the strains produced and are prototrophic for uracil, adenine, histidine, proline, arginine, and tryptophan. The strains are resistant to Zeocin, Nourseothricin, and Hygromycin and contain about eight to eleven copies of the EPO expression cassette. The strains have disruptions of the BMT1, BMT2, BMT3, and BMT4 genes and produce rhEPO lacking detectable cross-reactivity binding to antibodies made against HCA.

EXAMPLE 4

Several of the strains in Examples 1 to 3 were used to produce rhEPO as described below and shown schematically in FIG. 21. Briefly, production begins by inoculating shake flasks containing culture media with cells from the working cell bank and proceeds through a series of inoculations, incubations, and transfers of the expanding cultures into vessels of increasing size until sufficient biomass is available to inoculate the production bioreactor. Glycerol is the primary carbon source during batch phase, then culture growth is maintained through feeding of glycerol and salts. When the glycerol is depleted, cells are induced to express rhEPO protein by switching to a methanol feed. Inhibitors are added at induction to minimize O-glycosylation (e.g., PMTi 3, 5-[[3-(1-Phenylethoxy)-4-(2-phenylethoxy)]phenyl]methylene]-4-oxo-2-thioxo-3-thiazolidineacetic Acid, (See Published PCT Application No. WO 2007061631)) and to minimize proteolysis Inhibitors of proteolysis are added again at the end of the phase to minimize proteolysis. The culture is cooled to about 4° C. and harvested.

Laboratory scale cultivation of the strains was conducted in 500 mL SixFors and 3 L fermentors using in general the following procedures. Bioreactor Screenings (SIXFORS) are done in 0.5 L vessels (Sixfors multi-fermentation system, ATR Biotech, Laurel, Md.) under the following conditions: pH at 6.5, 24° C., 0.3 SLPM, and an initial stirrer speed of 550 rpm with an initial working volume of 350 mL (330 mL BMGY medium and 20 mL inoculum). IRIS multi-fermenter software (ATR Biotech, Laurel, Md.) is used to linearly increase the stirrer speed from 550 rpm to 1200 rpm over 10 hours, one hour after inoculation. Seed cultures (200 mL of BMGY in a 1 L baffled flask) are inoculated directly from agar plates. The seed flasks are incubated for 72 hours at 24° C. to reach optical densities (OD$_{600}$) between 95 and 100. The fermenters are inoculated with 200 mL stationary phase flask cultures that were concentrated to 20 mL by centrifugation. The batch phase ended on completion of the initial charge glycerol (18-24 h) fermentation and are followed by a second batch phase that is initiated by the addition of 17 mL of glycerol feed solution (50% [w/w] glycerol, 5 mg/L Biotin, 12.5 mL/L PMTi salts (65 g/L FeSO$_4$.7H$_2$O, 20 g/L ZnCl$_2$, 9 g/L H$_2$SO$_4$, 6 g/L CuSO$_4$.5H$_2$O, 5 g/L H$_2$SO$_4$, 3 g/L MnSO$_4$.7H$_2$O, 500 mg/L CoCl$_2$.6H$_2$O, 200 mg/L NaMoO$_4$.2H$_2$O, 200 mg/L biotin, 80 mg/L NaI, 20 mg/L H$_3$BO$_4$)). Upon completion of the second batch phase, as signaled by a spike in dissolved oxygen, the induction phase is initiated by feeding a methanol feed solution (100% MeOH 5 mg/L biotin, 12.5 mL/L PMTi) at 0.6 g/h for 32-40 hours. The cultivation is harvested by centrifugation.

Bioreactor cultivations (3 L) are done in 3 L (Applikon, Foster City, Calif.) and 15 L (Applikon, Foster City, Calif.) glass bioreactors and a 40 L (Applikon, Foster City, Calif.) stainless steel, steam in place bioreactor. Seed cultures are prepared by inoculating BMGY media directly with frozen stock vials at a 1% volumetric ratio. Seed flasks are incubated at 24° C. for 48 hours to obtain an optical density ($OD_{600}$) of 20±5 to ensure that cells are growing exponentially upon transfer. The cultivation medium contained 40 g glycerol, 18.2 g sorbitol, 2.3 g $K_2HPO_4$, 11.9 g $KH_2PO_4$, 10 g yeast extract (BD, Franklin Lakes, N.J.), 20 g peptone (BD, Franklin Lakes, N.J.), $4 \times 10^{-3}$ g biotin and 13.4 g Yeast Nitrogen Base (BD, Franklin Lakes, N.J.) per liter. The bioreactor is inoculated with a 10% volumetric ratio of seed to initial media. Cultivations are done in fed-batch mode under the following conditions: temperature set at 24±0.5° C., pH controlled at to 6.5±0.1 with $NH_4OH$, dissolved oxygen was maintained at 1.7±0.1 mg/L by cascading agitation rate on the addition of $O_2$. The airflow rate is maintained at 0.7 vvm. After depletion of the initial charge glycerol (40 g/L), a 50% glycerol solution containing 12.5 mL/L of PTM1 salts is fed exponentially at 50% of the maximum growth rate for eight hours until 250 g/L of wet cell weight was reached. Induction is initiated after a 30 minute starvation phase when methanol was fed exponentially to maintain a specific growth rate of 0.01 $h^{-1}$. When an oxygen uptake rate of 150 mM/L/h is reached the methanol feed rate is kept constant to avoid oxygen limitation. The cultivation is harvested by centrifugation.

After clarification by centrifugation and microfiltration, the filtrate is concentrated 10× by ultrafiltration and the rhEPO protein is purified through a sequence of two chromatography steps using a blue dye-affinity and hydroxyapatite.

Primary clarification is performed by centrifugation. The whole cell broth is transferred into 1000 mL centrifuge bottles and centrifuged at 4° C. for 15 minutes at 13,000×g. An ultrafiltration step can be employed for larger fermentors (10 L to 40 L and larger). This step can be performed utilizing Sartorious flat sheets with a pore size of 10K to a five-fold concentration.

A capture step is performed using Blue SEPHAROSE 6 Fast Flow (Pseudo-Affinity) Chromatography. A Blue SEPHAROSE 6 fast Flow (FF) column (GE Healthcare) is equilibrated with 50 mM MOPS, pH 7.0. The culture supernatant is adjusted to 100 mM NaCl and passed through deadend filter (Whatman, Polycap TC) before loading to the column. The residence time is maintained to about 10 minutes with a 3 column volumes (CV) wash after loading. The elution is step elution of 4 CV with 1 M NaCl in 50 mM MOPS, pH 7.0. EPO elutes at the 1 M NaCl.

An intermediate step is performed using hydroxyapatite (HA) chromatography. A Macro-prep ceramic hydroxyapatite Type I 40 μm (Bio-Rad) is used after the capture step. This column is equilibrated with equilibration solution: 50 mM MOPS, pH 7.0 containing 1 M NaCl and 10 mM $CaCl_2$. About 10 mM $CaCl_2$ is added to the pooled rhEPO from the blue column before loading. The column wash is executed with 3 CV of equilibration solution followed by step elution of 10 CV at 12.5 mM Na phosphate in MPOS, pH 7.0 to provide HA pool 1 containing the rhEPO.

A cation exchange chromatography step can be used to further purify the rhEPO. The pooled sample after hydroxyapatite chromatography step (e.g., HA pool 1) is dialyzed against 50 mM Na acetate, pH 5.0 overnight at 4° C. and a Source 30S column or Poros cation exchange column (GE Healthcare) is equilibrated with the same buffer. The dialyzed sample is applied to the column and a 10 CV linear gradient from 0 to 750 mM NaCl is applied with rhEPO eluting between 350 to 500 mM NaCl to provide the rhEPO.

The N terminus of the purified rhEPO molecule can be conjugated to 40-kDa linear polyethylene glycol (PEG) via reductive amination (PEGylation). The activated PEG is added to the rhEPO sample (conc. about 1 mg/mL) in 50 mM Sodium acetate buffer at pH 5.2 at a protein:PEG ratio of 1:10. The reaction is carried out at room temperature under reducing conditions by adding 10 mM sodium cyanoborohydride to the reaction mixture with overnight stirring. The reaction is stopped by adding 10 mM Tris, pH 6.0.

The mono-PEGylated rhEPO product is purified using a cation-exchange chromatography step before diafiltration into the final formulation buffer (20 mM sodium phosphate, 120 mM sodium chloride, 0.005% Polysorbate 20 (w/v), pH 7.0).

The final product is diluted to a concentration suitable for filling and sterile filtered into the drug substance storage container. The PEGylated rhEPO can be stored at 2-8° C. until filling, at which time it is aseptically filled into glass vials that are then sealed with a rubber stopper and aluminum cap.

Commercial formulations of proteins are known and may be used. Examples include but are not limited to ARANESP®: Polysorbate solution: Each 1 mL contains 0.05 mg polysorbate 80, and is formulated at pH 6.2±0.2 with 2.12 mg sodium phosphate monobasic monohydrate, 0.66 mg sodium phosphate dibasic anhydrous, and 8.18 mg sodium chloride in water for injection, USP (to 1 mL). Albumin solution: Each 1 mL contains 2.5 mg albumin (human), and is formulated at pH 6.0±0.3 with 2.23 mg sodium phosphate monobasic monohydrate, 0.53 mg sodium phosphate dibasic anhydrous, and 8.18 mg sodium chloride in water for injection, USP (to 1 mL). EPOGEN® is formulated as a sterile, colorless liquid in an isotonic sodium chloride/sodium citrate buffered solution or a sodium chloride/sodium phosphate buffered solution for intravenous (IV) or subcutaneous (SC) administration. Single-dose, Preservative-free Vial: Each 1 mL of solution contains 2000, 3000, 4000 or 10,000 Units of Epoetin alfa, 2.5 mg Albumin (Human), 5.8 mg sodium citrate, 5.8 mg sodium chloride, and 0.06 mg citric acid in water for injection, USP (pH 6.9±0.3). This formulation contains no preservative. Preserved vials contain 1% benzyl alcohol.

EXAMPLE 5

Methods used for analyzing the presence or absence of host cell antigen (HCA) included Western blot analysis and sandwich enzyme-linked immunosorbent assay (ELISA).

Host cell Antigen (HCA) antibody was prepared in rabbits using the supernatant from NORF strain cultures. The NORF strain is genetically the same as YGLY3159 except that it lacks the ORF encoding the human mature EPO. NORF strain fermentation supernatant prepared in complete Freund's adjuvant was injected into rabbits, which were then boosted three times with fermentation supernatant prepared in Incomplete Freund's adjuvant. After 45 days, the rabbits were bled and polyclonal antibodies to HCA were prepared using standard methods, for example, rabbit polyclonal IgG 9161 F072208-S, which was SLr Protein A purified, and GiF2 polyclonal rabbit::6316 whole rabbit serum. The GIF2 antibody was not protein A purified.

Western Blots for detecting *P. Pastoris* HCA were performed as follows. Purified PEGylated or non-PEGylated rhEPO-containing samples were reduced in sample loading buffer, of which 1 μL was then applied to the wells of 4-20% polyacrylamide SDS Tris-HCl (4-20% SDS-PAGE) gels (Bio RAD) and electrophoresed at 150V for about 60 minutes. The resolved proteins were electrotransferred to nitrocellulose membranes at 100V for about 60 minutes. After transfer, the membranes were blocked for one hour with 1% Blocking Solution (Roche Diagnostics). After blocking, the membranes were probed with the rabbit anti-HCA polyclonal antibody (primary antibody) diluted 1:3000. Afterwards, the membranes were washed and detection of the rabbit anti-HCA antibody was with the secondary antibody, goat-anti-Rabbit IgG (H+L) (Pierce #31460, Lot #H51015156) conjugated to horseradish peroxidase (HRP), at a 1:5000 dilution. After washing the membranes, detection of bound secondary antibody was using 3,3' Diaminobenzidine (DAB). For detecting EPO protein, the primary antibody was EPO (B-4) HRP-conjugated antibody used at a 1:1000 dilution (SC5290 Lot# A0507, Santa Cruz Biotechnology). A secondary antibody was not used. Routinely, the EPO samples were electrophoresed in parallel with rhEPO samples that had been deglycosylated with PNGaseF treatment. Deglycosylation was performed with 50 uL samples to which 1 μL of PNGaseF enzyme at 500 units/uL was added. After incubation at 37° C. for two hours, the samples were reduced in sample loading buffer and 1 μL aliquots were removed and applied to the SDS gels as above.

Sandwich ELISAs for detecting *P. Pastoris* HCA were performed as follows. The wells of 96 well ELISA plates were coated with 1 μg/well of mouse anti-hEPO monoclonal antibody. The wells were then blocked for 30 minutes with phosphate-buffered saline (PBS). About 100 μL of purified non-PEGylated rhEPO-containing samples concentrated to about 200 ng/mL were added to the wells. Primary detection used the rabbit anti-HCA polyclonal antibody at a 1:800 starting dilution in PBS which was then serially diluted 1:1 in PBS across a row ending with the $11^{th}$ well at a 1:819, 200 dilution. The $12^{th}$ well served as a negative control. The standard for the ELISA was rhEPO purified from YGLY3159. After 60 minutes, the wells were washed with PBS three times. Detection of the rabbit anti-HCA antibody used goat anti-rabbit antibody conjugated to alkaline phosphatase (AP) at a 1:10,000 dilution in PBS. After 60 minutes the wells were washed three times with PBS and detection of bound secondary antibody used 4-Methylumbelliferyl phosphate (4-MUPS). The ELISA plates were read using a Tecan Genios Multidetection Microplate Reader at 340 nm excitation wavelength and 465 nm emission wavelength.

EXAMPLE 6

This example shows that YGLY3159 produces rhEPO with cross binding activity (CBA) with anti-HCA antibody and that the cross-binding activity was due to the presence of β-1,2-mannose residues (α-1,2-mannosidase resistant) on at least a portion of the N-glycans on the rhEPO even though the rhEPO had been produced in strain in which the β-1,2-mannosyltransferase gene BMT2 had been deleted or disrupted.

rhEPO was recovered by a three-step chromatographic separation from the fermentation supernatant of glyco-engineered *P. pastoris* production strain YGLY 3159 showed about 95% protein purity as determined by SDS-PAGE, RP-HPLC, and SEC-HPLC. Mono-PEGylated rhEPO was separated by cation-exchange chromatographic step from its hyper and un-PEGylated conjugates with about 96% purity as determined by SDS-PAGE gel. However, antibody against HCA of the YGLY3159 strain detected a glycoprotein in rhEPO preparations produced from the strain that co-migrated with rhEPO on Western blots. FIG. 22 which shows that anti-HCA antibody identified a protein that co-migrates with rhEPO on 4-20% SDS-PAGE gels. Removal of sialic acid from rhEPO did not abolish the cross-binding activity; however, removal of the entire N-glycan from rhEPO using PNGase F produced a deglycosylated form of rhEPO that was not detectable in Western blots probed with anti-HCA antibody. This is shown in FIG. 23 which shows that only the deglycosylated form of rHEPO lacked cross-binding activity with the anti-HCA antibody.

To determine wither the cross-binding activity was rhEPO specific or could be identified in purified glycoprotein preparations from other recombinant *P. pastoris* strains, an glycoproteins produced in other strains were isolated, resolved by 4-20% SDS-PAGE gels, and the gels transferred to nitrocellulose membranes. In the case of a recombinant human whole antibody (rhIgG) produced in a recombinant *P. pastoris*, cross-binding activity was detected in protein preparations produced in wild-type *P. pastoris* (hypermannosylated from both N and O-glycocylated region) and in a recombinant GS2.0 strain that makes predominantly $Man_5GlcNAc_2$ N-glycans but also contained detectable $Man_9GlcNAc_2$ N-glycans that were α-1,2-mannosidase resistant (FIG. 24, arrow). However, the rhIgG preparations from wild-type *P. pastoris* contained cross-binding activity with an apparent molecular weight greater than that of rhIgG suggesting that the preparations contained contaminating host cell glycoproteins. The cross-binding activity was not removed by PNGase F digestion (circled in FIG. 24).

FIG. 25 shows that glycosylated rhEPO produced in YGLY3159 had cross binding activity to anti-HCA antibody but that human fetuin, human asialofetuin, human scrum albumin (HSA), and LEUKINE (a recombinant human granulocyte macrophage colony stimulating factor (rhu GM-CSF) produced in *S. cerevisiae*) had no cross-binding activity to anti-HCA antibody. Fetuins are heavily glycosylated blood glycoproteins that are made in the liver and secreted into the blood stream. They belong to a large group of binding proteins mediating the transport and availability of a wide variety of cargo substances in the blood stream. The best known representative of these carrier proteins is serum albumin, the most abundant protein in the blood plasma of adult animals. Fetuin is more abundant in fetal blood, hence the name "fetuin" (from Latin, fetus). Fetal calf serum contains more fetuin than albumin while adult serum contains more albumin than fetuin. Asialofetuins are fetuins which the terminal sialic acid from N- and O-glycans are removed by mild hydrolysis or neuraminidase treatment. Currently, there are no reports of β-linked mannoses in *S. cerevisiae*. HSA is not a glycosylated protein.

Lab scale data demonstrated that the intermediate chromatographic step purification of rhEPO from Blue SEPHAROSE 6 FF capture pool using hydroxy apatite (HA) type I 40 μm resin can separate rhEPO that has nearly undetectable cross-binding activity (HA pool 1) from rhEPO that had high-mannose-type N-glycans (HA pools 2 and 3). HA pool 1 contained about 90.40% bisialylated N-glycans (the desired N-glycan form) and less than 3.5% neutral N-glycans. In contrast, linear gradient elution from 0 to 100 mM sodium phosphate showed that later elution fractions (HA pools 2 and 3) contained high mannose-type N-glycans and increased cross binding activity to anti-HCA antibody in Western blots. This can be seen in the HPLC N-glycan analysis and Western blots of 4-20% SDS-PAGE gels shown in FIG. 26

Anion column chromatography using Q SEPHAROSE FF or Source 30Q anion resins were also tested. The HA pools 1-3 were combined and dialyzed against 50 mM Na acetate, pH 5.0 overnight at 4° C. The dialyzed sample was applied to the column and a 10 CV linear gradient from 0 to 750 mM NaCl was applied with rhEPO eluting between 350 to 500 mM NaCl to provide the rhEPO. FIG. 27A shows an example of a Q SEPHAROSE FF purification of rhEPO. Data showed that high mannose type glycans ($Man_{6,7,8,9,>9}$, mostly α1,2 mannosidase resistant) that show corresponding higher cross-binding activity did not bind to the anion exchange resins when bound and unbound material was analyzed in a sandwich ELISA (FIG. 27B). Table 1 shows the results of HPLC analysis of the N-glycan content of the rhEPO in the bound fraction (Q SEPHAROSE FF pool 1) and flow-through fraction (Q SEPHAROSE FF Flow Through). Table 2 shows the N-glycan content of the neutral N-glycans shown in Table 1.

TABLE 1

Q Sepharose FF - Purification of rhEPO
N-Glycan HPLC Analysis

| Sample | % Neutral | % Mono Sialylated | % Bi Sialylated |
|---|---|---|---|
| Input (HA pools) | 11.04 | 13.66 | 75.30 |
| Q SEPHAROSE FF pool 1 | 3.01 | 6.47 | 90.52 |
| Q SEPHAROSE FF Flow Through | 26.71 | 21.19 | 52.10 |

TABLE 2

Q Sepharose FF - Purification of rhEPO
% Neutral N-Glycan Profile

| Sample | % G2 | % $Man_5$ | % $Man_{6-8}$ | % $Man_9$ |
|---|---|---|---|---|
| Input (HA pools) | 3.1 | 2.8 | 2.4 | 2.74 |
| Q SEPHAROSE FF pool 1 | 3.01 | ND | ND | ND |
| Q SEPHAROSE FF Flow Through | 4.2 | 8.0 | 3.9 | 10.61 |

ND—not detected
G2 - N-glycan structure is $Gal_2GlcNAc_2Man_3GlcNAc_2$

The figures and tables show that rhEPO with undetectable cross-binding activity to anti-HCA antibodies and good protein and glycan quality can therefore be bound/eluted from anion exchange resins. These data also suggested that the family of fungal genes involved in biosynthesis of β-1,2-linked oligomannosides (BMT1, BMT2, BMT3, BMT4) was responsible for the low level cross-binding impurities in the rhEPO preparations.

Therefore, when viewed as a whole, the results suggested that the cross-binding activity to anti-HCA antibodies was not specific to rhEPO but was due to α-1,2-mannosidase resistant N-glycans on the glycoproteins. YGLY 3159 had been generated by knocking out five endogenous glycosylation genes and introducing 15 heterologous genes. YGLY3159 is bmt2Δ knockout strain. NMR spectroscopy studies suggest that bmt2Δ knockout strains can produce glycoproteins with varying amounts of residual β-1,2-mannose N-glycans. Since YGLY 3159 is bmt2Δ, it was postulated that BMT1 and BMT3 were responsible for the residual low level β-1,2-mannose transfer on core N-glycans.

While a combination of chromatography steps to purify the rhEPO can produce rhEPO preparations free of detectable cross-binding activity to anti-HCA antibodies, it would be particularly desirable to genetically modify the P. pastoris host strains to reduce or eliminate detectable cross-binding activity to anti-HCA antibodies in the strains. This minimizes the risk of possible contamination of the rhEPO preparations with cross-binding activity due to variability during the purification. In addition, because each purification step can result in a loss of rhEPO, the genetically modified P. pastoris strains can reduce the number of purification steps and thus reduce the amount of rhEPO lost during the steps eliminated. Therefore, expression of the four BMT genes were serially deleted or disrupted to identify strains that did not produce detectable cross-binding activity to anti-HCA antibodies.

EXAMPLE 7

In order to reduce the presence of β-linked mannose type N-glycans to undetectable levels, the BMT1 and BMT4 genes were disrupted and the rhEPO analyzed for the presence of α-1,2-mannosidase resistant N-glycans.

Strains YGLY6661 and YGLY7013 were constructed as described Example 2 and analyzed for the presence of α-1,2-mannosidase resistant N-glycans using anti-HCA antibodies. Strain YGLY7013 was bmt2Δ and bmt4Δ and strain YGLY6661 was bmt2Δ, bmt4Δ, and bmt1Δ. rhEPO produced from the strains were subjected Blue SEPHAROSE 6FF chromatography and aliquots of the Blue SEPHAROSE 6FF capture pool were treated with PNGase F vel non. The treated and untreated aliquots were electrophoresed on SDS-PAGE, the gels transferred to nitrocellulose membranes, and the membranes probed with anti-EPO antibody or anti-HCA antibodies. FIG. 28 shows in Western blots of 4-20% SDS-PAGE gels of aliquots of Blue SEPHAROSE 6 FF capture pools that rhEPO produced in either strain still had α-1,2-mannosidase resistant N-glycans which cross-reacted with anti-HCA antibodies. Tables 3 and 4 show the distribution of N-glycan species in rhEPO in Blue Sepaharose 6 FF capture pools from both fermentation and SixFors cultures. As shown in the tables, both strains produced a substantial amount of neutral N-glycans of which a portion was resistant to in vitro α1,2-mannosidase digestion.

TABLE 3

Week 44 - rhEPO - Blue SEPHAROSE 6 FF Capture Pool - Fermentation

| Pools | % Bi-Sialylated | % Mono Sialylated | % Neutral | % Neutral | | | |
|---|---|---|---|---|---|---|---|
| | | | | % G2 | % M5 | % M6-M8 | % M9+ |
| F074411 (YGLY 6661) | 52.98 | 34.08 | 12.94 | 1.7 | 2.63 | 3.65 | 4.96 |
| F074411 (YGLY 6661) α1,2 Mannosidase | 53.42 | 34.32 | 12.26 | 1.9 | 5.05 | 3.4 | 1.91 |
| F074410 (YGLY 7013) | 25.10 | 47.00 | 27.90 | 12.99 | 2.22 | 5.67 | 7.02 |

TABLE 3-continued

Week 44 - rhEPO - Blue SEPHAROSE 6 FF Capture Pool - Fermentation

| Pools | % Bi-Sialylated | % Mono Sialylated | % Neutral | % Neutral |  |  |  |
|---|---|---|---|---|---|---|---|
|  |  |  |  | % G2 | % M5 | % M6-M8 | % M9+ |
| F074410 (YGLY 7013) α1,2 Mannosidase | 26.34 | 49.03 | 26.34 | 13.14 | 5.39 | 4.68 | 1.42 |

G2 - Gal$_2$GlcNAc$_2$Man$_3$GlcNAc$_2$ N-glycans
M6-M8 - Man$_6$GlcNAc$_2$ to Man$_8$GlcNAc$_2$ N-glycans
M9+ - Man$_9$GlcNAc$_2$ and lager N-glycans

TABLE 4

Week 41 - rhEPO - Blue SEPHAROSE 6 FF Capture Pool - SixFors

| Pools | % Bi-Sialylated | % Mono Sialylated | % Neutral | % Neutral |  |  |  |  |
|---|---|---|---|---|---|---|---|---|
|  |  |  |  | % G2 | % M5 | % M6-M8 | % M9 | % M9+ |
| X074128 (YGLY 6661) | 43.49 | 39.24 | 17.27 | 1.7 | 7.8 | 6.69 | 0.45 | 0.63 |
| X074128 (YGLY 6661) α1,2 Mannosidase | 42.52 | 39.26 | 18.22 | 1.2 | 11.84 | 5.02 | 0.1 | 0.06 |
| X074131 (YGLY 7013) | 66.90 | 18.83 | 14.27 | 1.84 | 8.36 | 2.82 | 0.66 | 0.59 |
| X074131 (YGLY 7013) α1,2 Mannosidase | 64.81 | 19.70 | 15.49 | 1.06 | 13.1 | 0.77 | 0.56 | 0 |

G2 - Gal$_2$GlcNAc$_2$Man$_3$GlcNAc$_2$ N-glycans
M6-M8 - Man$_6$GlcNAc$_2$ to Man$_8$GlcNAc$_2$ N-glycans
M9 - Man$_9$GlcNAc$_2$ N-glycans
M9+ - Man$_9$GlcNAc$_2$ and lager N-glycans A sandwich ELISA of rhEPO in the Blue SEPHAROSE 6 FF capture pools made from both strains compared to YGLY3159 showed that both strains had cross-binding activity to anti-HCA antibody (FIG. 29). Further purifying the rhEPO by hydroxyapatite (HA) chromatography and analyzing the samples by sandwich ELISA showed that the HA pool 1 containing rhEPO produced from YGLY6661 (bmt2Δ, bmt4Δ, and bmt1Δ) appeared to lack detectable cross-binding activity to anti-HCA antibody but that rhEPO produced in YGLY7013 (bmt2Δ and bmt4Δ) still had detectable cross-binding activity to anti-HCA antibody (FIG. 30). The results suggested that deleting the BMT2 and BMT1 genes was not sufficient to remove all detectable cross-binding activity. The results also show that hydroxyapatite chromatography can remove detectable cross-binding activity in the HA pool 1. FIG. 31 is a Western blot of 4-20% SDS-PAGE gels showing that rhEPO in another Blue SEPHAROSE 6 FF capture pool prepared from strain YGLY6661 continued to have cross-binding activity to anti-HCA antibody and that the cross-binding activity could be still be rendered undetectable by deglycosylating the rhEPO. The result indicated that to produce rhEPO that had no detectable cross-binding activity to anti-HCA antibodies, expression of the BMT3 gene needed to be abrogated by disruption or deletion.

EXAMPLE 8

In order to more effectively achieve the elimination of detectable β-linked mannose type glycans, all four BMT genes involved in -mannosyltransferase pathway were disrupted. Strains YGLY7361-7366 and YGLY7393-7398 (Example 2) were evaluated for ability to produce rhEPO lacking detectable cross-binding activity to anti-HCA antibody.

Various YGLY7361-7366 and YGLY7393-7398 strains in which all four BMT genes involved in the β-mannosyltransferase pathway were disrupted were grown in 500 mL Six-Fors fermentors and then processed for rhEPO through Blue SEPHAROSE 6 FF pools (Blue pools). Aliquots from the Blue pools were analyzed by 4-20% SDS-PAGE. FIG. 32 shows Commassie blue stained 4-20% SDS-PAGE gels of the Blue pools from the various strains with and without PNGase F treatment. The gels show that all of the tested strains produced glycosylated rhEPO. Several of the strains were evaluated for cross-binding activity to anti-HCA antibody by sandwich ELISA. FIG. 33 shows that most of the strains lacked detectable cross-binding activity to anti-HCA antibody. However, strains YGLY7363 and YGLY7365 had detectable cross-binding activity to anti-HCA antibody. Reconfirmation of YGLY7365 by PCR indicated that this strain was not a complete knock-out of the BMT3 gene, explaining the relatively high binding observed with the anti-HCA antibody present in the ELISA (FIG. 33). HPLC N-glycan analysis of strains YGLY7361-7366 is shown in Table 5 and strains YGLY7393-7398 are shown in Table 6. The data in the tables are graphically presented in FIG. 34.

TABLE 5

| | Week 46a - SixFors - Δbmt1-4 strains - Blue pools | | | | | | |
|---|---|---|---|---|---|---|---|
| | % Bi- | % Mono | % | | % Neutral | | |
| Pools | Sialylated | Sialylated | Neutral | % G2 | % M5 | % M6-M8 | % M9+ |
| X074613 (YGLY 7361) | 22.10 | 47.83 | 30.07 | 13.85 | 2.53 | 6.77 | 6.92 |
| X074613 (YGLY 7361) α1,2 Mannosidase | 21.55 | 48.18 | 30.27 | 13.68 | 4.53 | 5.47 | 6.59 |
| X074614 (YGLY 7362) | 67.36 | 24.69 | 7.95 | 0.6 | 4.36 | 2.8 | 0.19 |
| X074614 (YGLY 7362) α1,2 Mannosidase | 66.21 | 25.25 | 8.54 | 1.1 | 6.7 | 0.68 | 0.06 |
| *X074615 (YGLY 7363) | 49.40 | 39.17 | 11.43 | 0.8 | 4.42 | 5.91 | 0.3 |
| X074615 (YGLY 7363) α1,2 Mannosidasc | 48.52 | 39.20 | 12.28 | 0.4 | 7.2 | 4.68 | ND |
| X074616 (YGLY 7366) | 55.99 | 33.85 | 10.16 | 0.8 | 3.73 | 4.94 | 0.69 |
| X074616 (YGLY 7366) α1,2 Mannosidase | 55.44 | 34.24 | 10.32 | 1.9 | 7.2 | 1.02 | 0.2 |
| *X074617 (YGLY 7365) | 43.22 | 42.10 | 14.68 | 5.37 | 5.88 | 3.03 | 0.4 |
| X074617 (YGLY 7365) α1,2 Mannosidase | 42.70 | 42.40 | 14.90 | 4.5 | 8.4 | 2.0 | ND |
| X074618 (YGLY 7364) | 48.18 | 38.44 | 13.38 | 0.7 | 6.56 | 5.76 | 0.36 |
| X074618 (YGLY 7364) α1,2 Mannosidase | 47.52 | 39.75 | 12.73 | 0.4 | 6.74 | 5.09 | 0.5 |

G2 - Gal$_2$GlcNAc$_2$Man$_3$GlcNAc$_2$ N-glycans
M6-M8 - Man$_6$GlcNAc$_2$ to Man$_8$GlcNAc$_2$ N-glycans
M9+ - Man$_9$GlcNAc$_2$ and lager N-glycans
*Showed cross-binding activity to anti-HCA antibody

TABLE 6

| | Week 46a - SixFors - Δbmt1-4 strains - Blue pools | | | | | | | |
|---|---|---|---|---|---|---|---|---|
| | % Bi- | % Mono | % | | % Neutral | | | |
| Pools | Sialylated | Sialylated | Neutral | % G2 | % M5 | % M6-M8 | % M9 | % Hyb |
| X074637 (YGLY 7393) | 51.04 | 35.45 | 13.51 | 2.3 | 6.4 | 1.41 | 1.2 | 2.2 |
| X074637 (YGLY 7393) α1,2 Mannosidase | 50.33 | 35.44 | 14.23 | 2.5 | 9.14 | ND | ND | 2.54 |
| X074638 (YGLY 7394) | 63.56 | 25.65 | 10.79 | 1.1 | 6.6 | 1.9 | 0.4 | 0.79 |
| X074638 (YGLY 7394) α1,2 Mannosidase | 62.88 | 25.75 | 11.37 | 1.2 | 8.96 | ND | ND | 1.21 |
| X074639 (YGLY 7395) | 56.05 | 31.43 | 12.52 | 1.9 | 5.1 | 2.2 | 1.9 | 1.4 |
| X074639 (YGLY 7395) α1,2 Mannosidase | 56.27 | 31.81 | 11.92 | 1.9 | 8.43 | ND | ND | 1.59 |
| X074640 (YGLY 7396) | 50.42 | 36.71 | 12.87 | 3.2 | 6.7 | 1.27 | 0.3 | 1.4 |
| X074640 (YGLY 7396) α1,2 Mannosidase | 49.94 | 36.86 | 13.20 | 3.2 | 8.12 | ND | ND | 1.88 |
| X074641 (YGLY 7397) | 49.32 | 36.07 | 14.61 | 2.6 | 7.0 | 2.4 | 0.5 | 2.11 |

TABLE 6-continued

Week 46a - SixFors - Δbmt1-4 strains - Blue pools

| Pools | % Bi-Sialylated | % Mono Sialylated | % Neutral | % G2 | % M5 | % M6-M8 | % M9 | % Hyb |
|---|---|---|---|---|---|---|---|---|
| X074641 (YGLY 7397) | 48.72 | 35.86 | 15.42 | 2.7 | 10.24 | ND | ND | 2.48 |
| α1,2 Mannosidase | | | | | | | | |
| X074642 (YGLY 7398) | 65.74 | 22.61 | 11.65 | 0.8 | 7.7 | 1.97 | 0.43 | 3.71 |
| X074642 (YGLY 7398) α1,2 Mannosidase | 64.99 | 22.87 | 12.14 | 1.0 | 10.02 | ND | ND | 1.12 |

G2 - $Gal_2GlcNAc_2Man_3GlcNAc_2$ N-glycans
M6-M8 - $Man_6GlcNAc_2$ to $Man_8GlcNAc_2$ N-glycans
M9 - $Man_9GlcNAc_2$ N-glycans
M9+ - $Man_9GlcNAc_2$ and lager N-glycans
Hyb - hybrid N-glycans Strains YGLY7362, 7366, 7396, and 7398 were cultivated in 3 L fermentors and processed through Blue SEPHAROSE 6 FF chromatography followed by hydroxyapatite (HA) chromatography. Aliquots from both the Blue pools and the HA pools were reduced and analyzed by 4-20% SDS-PAGE. Corresponding pools for YGLY3159 were included as positive controls. FIG. 35A shows a Commassie blue stained 4-20% SDS-PAGE showing that both the Blue pools (left half of gel) and HA pools (right half of gel) produced rhEPO. FIG. 35B shows a Western blot of the same samples probed with anti-HCA antibodies. None of the tested strains had any detectable cross-binding activity to anti-HCA antibodies in either the Blue pool or the HA pool 1.

FIG. 36 analyzes the Blue pool and HA pool 1 for rhEPO isolated from 500 mL SixFors cultures of YGLY7398 for cross-binding activity to anti-HCA antibodies. The rightmost panel shows a Western blot probed with another anti-HCA preparation: GiF2 polyclonal rabbit::6316. This antibody produced the same results as produced using the F072208-S antibody, which had been used to produce the ELISAs and Western blots shown herein. The 6316 antibody shows that the cross-binding activity is not antibody specific.

These results show that deleting or disrupting all four BMT genes can result in strains that do not produce detectable cross-binding activity to anti-HCA antibodies in either the rhEPO after the preliminary Blue SEPHAROSE 6 FF capture step or the intermediate hydroxyapatite step using Type I 40 µM hydroxyapatite. These strains minimize the risk that rhEPO preparations will be made that contain cross-binding activity to anti-HCA antibodies. This enables the production of rhEPO with less risk of inducing an adverse immune response in the individual receiving the rhEPO.

EXAMPLE 9

A comparison of the pharmacokinetics of the rhEPO produced in the strains produced in Example 2 with all four BMT genes disrupted or deleted and PEGylated was compared to PEGylated rhEPO produced from strain YGLY3159. The comparison showed that the PEGylated EPO had a reduced in vivo half-life and lower in vivo potency (See Tables 7 and 8). The rhEPO produced in the strains produced in Example 2 with no detectable cross-binding activity to anti-HCA antibodies had pharmacokinetics generally similar to that of EPOGEN and not the higher pharmacokinetics of ARANESP. The reduced pharmacokinetics was found to be a function of the amount of bi-sialylated biantennary N-glycans. Higher levels of bi-sialylated biantennary N-glycan on the rhEPO was correlated with higher pharmacokinetics. These results are consistent with published data showing that longer half life is correlated with greater sialic acid content in recombinant human erythropoietin produced in CHO cells (Egrie et al, Exp. Hematol. 31: 290-299 (2003)).

TABLE 7

| PK of rhEPO from YGLY3159 (CBA) vs YGLY7398 (no CBA) | | |
|---|---|---|
| | YGLY3159 | YGLY7398 |
| T½ (hr) | 20.9 ± 2 | 13 ± 2 |

CBA—cross-binding activity

TABLE 8

| rhEPO source | Relative Potency (Reticulocyte Production) | 95% Confidence Interval |
|---|---|---|
| YGLY3159 vs YGLY7398 | 0.82 | (0.68, 1.00) |

EXAMPLE 10

In order to effectively achieve the elimination of detectable β-linked mannose type glycans and produce a strain that produces rhEPO with higher pharmacokinetics, strains YGLY7113-7122 described in Example 3 were made and evaluated for ability to produce rhEPO lacking detectable cross-binding activity to anti-HCA antibody. These strains were modified to also express human mature EPO as a fusion protein fused to the chicken lysozyme leader sequence. Thus, these strains express both human mature EPO fused to the *S. cerevisiae* αMATpre signal peptide and the human mature EPO as a fusion protein fused to the chicken lysozyme leader sequence.

Various YGLY7113-YGLY7122 strains in which all four BMT genes involved in the β-mannosyltransferase pathway were disrupted and expressing the were grown in 500 mL SixFors fermentors and then processed for rhEPO through Blue SEPHAROSE 6 FF pools (Blue pools). Aliquots of the Blue pools for several strains were analyzed by sandwich ELISA using anti-HCA antibodies. FIG. 37 shows that YGLY7118 had very low cross-binding activity to anti-HCA antibody but all of the other strains showed no detectable cross-binding activity to anti-HCA antibodies. HPLC N-glycan analysis of strains YGLY7113-7117 is shown in Table 9 and strains YGLY7118-7122 are shown in Table 10. The tables are graphically presented in FIG. 38.

TABLE 9

Week 48 - SixFors - Δbmt1-4 strains - Blue pools

| Pools | % Bi-Sialylated | % Mono Sialylated | % Neutral | % Neutral | | | | |
|---|---|---|---|---|---|---|---|---|
| | | | | % G2 | % M5 | % M6-M8 | % M9 | % Hyb |
| X074814 (YGLY 7113) | 70.23 | 9.97 | 19.80 | 0.2 | 9.2 | 6.85 | 2.05 | 1.5 |
| X074814 (YGLY 7113) α1,2 Mannosidase | 68.96 | 10.56 | 20.48 | 0.3 | 18.4 | ND | ND | 1.78 |
| X074815 (YGLY 7115) | 62.61 | 14.01 | 23.38 | 0.5 | 7.15 | 10.37 | 3.96 | 1.4 |
| X074815 (YGLY 7115) α1,2 Mannosidase | 61.77 | 13.95 | 24.28 | 0.1 | 22.22 | ND | ND | 1.96 |
| X074816 (YGLY 7114) | 67.64 | 8.22 | 24.14 | 0.2 | 4.2 | 11.41 | 6.33 | 2.0 |
| X074816 (YGLY 7114) α1,2 Mannosidase | 65.92 | 8.32 | 25.76 | 0.2 | 23.35 | ND | ND | 2.21 |
| X074817 (YGLY 7116) | 66.46 | 8.06 | 25.48 | 4.73 | 5.38 | 6.94 | 7.23 | 1.2 |
| X074817 (YGLY 7116) α1,2 Mannosidase | 65.54 | 8.69 | 25.77 | 0.5 | 23.8 | ND | ND | 1.47 |
| X074818 (YGLY 7117) | 70.06 | 11.09 | 18.85 | 0.6 | 8.59 | 6.0 | 2.21 | 1.45 |
| X074818 (YGLY 7117) α1,2 Mannosidase | 68.67 | 11.42 | 19.91 | 0.4 | 17.5 | ND | ND | 2.01 |

G2 - Gal$_2$GlcNAc$_2$Man$_3$GlcNAc$_2$ N-glycans
M6-M8 - Man$_6$GlcNAc$_2$ to Man$_8$GlcNAc$_2$ N-glycans
M9 - Man$_9$GlcNAc$_2$ N-glycans
M9+ - Man$_9$GlcNAc$_2$ and larger N-glycans
Hyb - hybrid N-glycans

TABLE 10

Week 48 - SixFors - Δbmt1-4 strains - Blue pools

| Pools | % Bi-Sialylated | % Mono Sialylated | % Neutral | % Neutral | | | | |
|---|---|---|---|---|---|---|---|---|
| | | | | % G2 | % M5 | % M6-M8 | % M9 | % Hyb |
| X074819 (YGLY 7119) | 58.12 | 27.10 | 14.78 | 0.7 | 6.83 | 4.98 | 1.17 | 1.1 |
| X074819 (YGLY 7119) α1,2 Mannosidase | 57.03 | 26.87 | 16.10 | 0.45 | 14.55 | ND | ND | 1.1 |
| X074820 (YGLY 7120) | 73.60 | 10.84 | 15.56 | 0.89 | 8.6 | 3.75 | 1.64 | 0.68 |
| X074820 (YGLY 7120) α1,2 Mannosidase | 72.43 | 11.13 | 16.44 | 0.7 | 15.63 | ND | ND | 0.11 |
| X074821 (YGLY 7121) | 59.41 | 19.85 | 20.74 | 0.8 | 3.04 | 10.7 | 5.55 | 0.65 |
| X074821 (YGLY 7121) α1,2 Mannosidase | 58.39 | 20.00 | 21.6 | 0.4 | 20.17 | ND | ND | 1.04 |
| X074822 (YGLY 7122) | 57.43 | 24.16 | 18.41 | 1.37 | 10.89 | 4.95 | 0.4 | 0.8 |

TABLE 10-continued

Week 48 - SixFors - Δbmt1-4 strains - Blue pools

| Pools | % Bi-Sialylated | % Mono Sialylated | % Neutral | % Neutral | | | | |
|---|---|---|---|---|---|---|---|---|
| | | | | % G2 | % M5 | % M6-M8 | % M9 | % Hyb |
| X074822 (YGLY 7122) α1,2 Mannosidase | 55.77 | 24.44 | 19.79 | 1.8 | 17.28 | ND | ND | 0.71 |
| X074824 (YGLY 7118) | 55.56 | 21.47 | 22.97 | 0.33 | 2.98 | 11.85 | 6.59 | 1.22 |
| X074824 (YGLY 7118) α1,2 Mannosidase | 54.68 | 21.67 | 23.65 | 0.4 | 22.5 | ND | ND | 0.75 |

G2 - $Gal_2GlcNAc_2Man_3GlcNAc_2$ N-glycans
M6-M8 - $Man_6GlcNAc_2$ to $Man_8GlcNAc_2$ N-glycans
M9 - $Man_9GlcNAc_2$ N-glycans
M9+ - $Man_9GlcNAc_2$ and larger N-glycans
Hyb - hybrid N-glycans Strains YGLY7115, 7117, and 7120 were cultivated in 3 L fermentors and processed through Blue SEPHAROSE 6 FF chromatography followed by hydroxyapatite (HA) chromatography. Aliquots from both the Blue pools and the HA pools were reduced and analyzed by 4-20% SDS-PAGE. Corresponding pools for YGLY3159 were included as positive controls. Corresponding pools for YGLY7395 were included as negative controls. FIG. 39A shows a Commassie blue stained 4-20% SDS-PAGE showing that both the Blue pools (left half of gel) and HA pools (right half of gel) produced rhEPO. FIG. 39B shows a Western blot of the same samples probed with anti-HCA antibodies. None of the tested strains had any detectable cross-binding activity to anti-HCA antibodies in either the Blue pool or the HA pool 1.

These results also show that deleting or disrupting all four BMT genes can result in strains that do not produce detectable cross-binding activity to anti-HCA antibodies in either the rhEPO after the preliminary Blue SEPHAROSE 6 FF capture step or the intermediate hydroxyapatite step using Type I 40 μM hydroxyapatite. These strains minimize the risk that rhEPO preparations will be made that contain cross-binding activity to anti-HCA antibodies. This enables the production of rhEPO with less risk of inducing an adverse immune response in the individual receiving the rhEPO.

EXAMPLE 11

The blue pools containing rhEPO produced by YGLY7117 were further subjected to hydroxyapatite column chromatography and the rhEPO in the HA pools were analyzed for sialylation content. FIG. 40A and FIG. 40B show HPLC traces of the N-glycans from rhEPO produced in YGLY3159 compared to the N-glycans from rhEPO produced in YGLY7117, respectively. The figures also show that the hydroxyapatite column removed additional contaminants; thus, in this analysis the sialylation content of the rhEPO produced by YGLY7117 was about 99% (neutral N-glycans were about 1%) of which about 89% was A2 or bisialylated and about 10% was A1 or monosialylated.

Sialylation analysis of rhEPO produced in YGLY7117 following PEGylation according to the process in Example 3 was similar to the amount of sialylation prior to PEGylation; however, the amount of sialylation can vary to a limited extent depending for example, on what modifications were made to the growing conditions, e.g., medium compositions, feeding rate, etc (See Table 11). Thus, the methods herein produce rhEPO compositions having at least about 75% A2 sialylation or between about 75 and 89% A2 sialylation. Thus, the total sialic acid content is at least 4.5 moles sialic acid per mole of rhEPO, more specifically, from about 4.6 to 5.7 mole of sialic acid per mole of rhEPO.

TABLE 11

| | BPP (2000L) (n = 3) | FPP (800L) (n = 2) | Avecia (15L) (n = 2) | Avecia (100L) (n = 1) |
|---|---|---|---|---|
| Purity by SDS PAGE (EPO related) (≥95.0%) | 99.5 ± 0.4% | 99.4 ± 0.0% | 99.4 ± 0.1% | 99.4% |
| Integrity by SDS PAGE (Mono-PEG) (≥80.0%) | 96.8 ± 0.7% | 96.0 ± 2.2% | 95.2 ± 2.0% | 97.7% |
| Total sialic acid (≥4.5 mol SA/mol protein) | 5.0-5.7 | 4.6-4.7 | 5.1-5.2 | 5.2 |
| N-Linked glycan by CE (70-85% A2) | 75.2-80.2% | 74.2-77.8% | 80.9-88.7% | 83.9% |

A2—bi-sialylated
CE—capillary electrophoresis
SA—sialic acid
BPP—Biologics Pilot Plant
FPP—Fermentation Pilot Plant A comparison of the pharmacokinetics of the rhEPO produced in the YGLY7117 produced in Example 3 with all four BMT genes disrupted or deleted and PEGylated was compared to PEGylated rhEPO produced from strain YGLY3159. The comparison showed that the PEGylated rhEPO produced in strain YGLY7117 had in viva half-life and in viva potency similar to that of YGLY3159 and ARANESP (See Tables 12 and 13).

TABLE 12

PK of rhEPO from YGLY3159 (CBA) vs YGLY7117 (no CBA)

| | YGLY3159 | YGLY7117 |
|---|---|---|
| T½ (hr) | 20.9 ± 2 | 20.6 ± 4 |

CBA—cross-binding activity

TABLE 13

| rhEPO source | Relative Potency (Reticulocyte Production) | 95% Confidence Interval |
|---|---|---|
| YGLY3159 vs YGLY7117 | 0.94 | (0.77, 1.14) |

SEQUENCES

Sequences that were used to produce some of the strains disclosed in Examples 1-11 are provided in Table 14.

TABLE 14

| SEQ ID NO: | Description | Sequence |
|---|---|---|
| 1 | S. cerevisiae invertase gene (ScSUC2) | AGGCCTCGCAACAACCTATAATTGAGTTAAGTGCCTTTCCAAGCT AAAAAGTTTGAGGTTATAGGGGCTTAGCATCCACACGTCACAAT CTCGGGTATCGAGTATAGTATGTAGAATTACGGCAGGAGGTTTC CCAATGAACAAAGGACAGGGGCACGGTGAGCTGTCGAAGGTATC CATTTTATCATGTTTCGTTTGTACAAGCACGACATACTAAGACAT TTACCGTATGGGAGTTGTTGTCCTAGCGTAGTTCTCGCTCCCCCA GCAAAGCTCAAAAAAGTACGTCATTTAGAATAGTTTGTGAGCAA ATTACCAGTCGGTATGCTACGTTAGAAAGGCCCACAGTATTCTTC TACCAAAGGCGTGCCTTTGTTGAACTCGATCCATTATGAGGGCTT CCATTATTCCCCGCATTTTTATTACTCTGAACAGGAATAAAAAGA AAAAACCCAGTTTAGGAAATTATCCGGGGGCGAAGAAATACGCG TAGCGTTAATCGACCCCACGTCCAGGGTTTTTCCATGGAGGTTTC TGGAAAAACTGACGAGGAATGTGATTATAAATCCCTTTATGTGA TGTCTAAGACTTTTAAGGTACGCCCGATGTTTGCCTATTACCATC ATAGAGACGTTTCTTTTCGAGGAATGCTTAAACGACTTTGTTTGA CAAAAATGTTGCCTAAGGGCTCTATAGTAAACCATTTGGAAGAA AGATTTGACGACTTTTTTTTTTGGATTTCGATCCTATAATCCTTC CTCCTGAAAAGAAACATATAAATAGATATGTATTATTCTTCAAAA CATTCTCTTGTTCTTGTGCTTTTTTTTTACCATATATCTTACTTTTT TTTTTCTCTCAGAGAAACAAGCAAAACAAAAAGCTTTTCTTTTCA CTAACGTATATGATGCTTTTGCAAGCTTTCCTTTTCCTTTTGGCTG GTTTTGCAGCCAAAATATCTGCATCAATGACAAACGAAACTAGC GATAGACCTTTGGTCCACTTCACACCCAACAAGGGCTGGATGAA TGACCCAAATGGGTTGTGGTACGATGAAAAAGATGCCAAATGGC ATCTGTACTTTCAATACAACCCAAATGACACCGTATGGGGTACGC CATTGTTTTGGGGCATGCTACTTCCGATGATTTGACTAATTGGG AAGATCAACCCATTGCTATCGCTCCCAAGCGTAACGATTCAGGT GCTTTCTCTGGCTCCATGGTGGTTGATTACAACAACACGAGTGGG TTTTTCAATGATACTATTGATCCAAGACAAAGATGCGTTGCGATT TGGACTTATAACACTCCTGAAAGTGAAGAGCAATACATTAGCTA TTCTCTTGATGGTGGTTACACTTTTACTGAATACCAAAAGAACCC TGTTTTAGCTGCCAACTCCACTCAATTCAGAGATCCAAAGGTGTT CTGGTATGAACCTTCTCAAAAATGGATTATGACGGCTGCCAAATC ACAAGACTACAAAATTGAAATTTACTCCTCTGATGACTTGAAGTC CTGGAAGCTAGAATCTGCATTTGCCAATGAAGGTTTCTTAGGCTA CCAATACGAATGTCCAGGTTTGATTGAAGTCCCAACTGAGCAAG ATCCTTCCAAATCTTATTGGGTCATGTTTATTTCTATCAACCCAGG TGCACCTGCTGGCGGTTCCTTCAACCAATATTTTGTTGGATCCTTC AATGGTACTCATTTTGAAGCGTTTGACAATCAATCTAGAGTGGTA GATTTGGTAAGGACTACTATGCCTTGCAAACTTTCTTCAACACT GACCCAACCTACGGTTCAGCATTAGGTATTGCCTGGGCTTCAAAC TGGGAGTACAGTGCCTTTGTCCCAACTAACCCATGGAGATCATCC ATGTCTTTGGTCCGCAAGTTTTCTTTGAACACTGAATATCAAGCT AATCCAGAGACTGAATTGATCAATTTGAAAGCCGAACCAATATT GAACATTAGTAATGCTGGTCCCTGGTCTCGTTTTGCTACTAACAC AACTCTAACTAAGGCCAATTCTTACAATGTCGATTTGAGCAACTC GACTGGTACCCTAGAGTTTGAGTTGGTTTACGCTGTTAACACCAC ACAAACCATATCCAAATCCGTCTTTGCCGACTTATCACTTTGGTT CAAGGGTTTAGAAGATCCTGAAGAATATTTGAGAATGGGTTTTG AAGTCAGTGCTTCTTCCTTCTTTTTGGACCGTGGTAACTCTAAGG TCAAGTTTGTCAAGGAGAACCCATATTTCACAAACAGAATGTCT GTCAACAACCAACCATTCAAGTCTGAGAACGACCTAAGTTACTA TAAAGTGTACGGCCTACTGGATCAAAACATCTTGGAATTGTACTT CAACGATGGAGATGTGGTTTCTACAAATACCTACTTCATGACCAC CGGTAACGCTCTAGGATCTGTGAACATGACCACTGGTGTCGATA ATTTGTTCTACATTGACAAGTTCCAAGTAAGGGAAGTAAAATAG AGGTTATAAAACTTATTGTCTTTTTTATTTTTTCAAAAGCCATTC TAAAGGGCTTTAGCTAACGAGTGACGAATGTAAAACTTTATGAT TCAAAGAATACCTCCAAACCATTGAAAATGTATTTTTATTTTTA TTTTCTCCCGACCCCAGTTACCTGGAATTTGTTCTTTATGTACTTT ATATAAGTATAATTCTCTTAAAAATTTTTACTACTTTGCAATAGA CATCATTTTTTCACGTAATAAACCCACAATCGTAATGTAGTTGCC |

TABLE 14-continued

| SEQ ID NO: | Description | Sequence |
|---|---|---|
| | | TTACACTACTAGGATGGACCTTTTTGCCTTTATCTGTTTTGTTACT GACACAATGAAACCGGGTAAAGTATTAGTTATGTGAAAATTTAA AAGCATTAAGTAGAAGTATACCATATTGTAAAAAAAAAAAGCGT TGTCTTCTACGTAAAAGTGTTCTCAAAAAGAAGTAGTGAGGGAA ATGGATACCAAGCTATCTGTAACAGGAGCTAAAAAATCTCAGGG AAAAGCTTCTGGTTTGGGAAACGGTCGAC |
| 2 | S. cerevisiae invertase (ScSUC2) | MLLQAFLFLLAGFAAKISASMTNETSDRPLVHFTPNKGWMNDPNGL WYDEKDAKWHLYFQYNPNDTVWGTPLFWGHATSDDLTNWEDQPI AIAPKRNDSGAFSGSMVVDYNNTSGFFNDTIDPRQRCVAIWTYNTP ESEEQYISYSLDGGYTFTEYQKNPVLAANSTQFRDPKVFWYEPSQK WIMTAAKSQDYKIEIYSSDDLKSWKLESAFANEGFLGYQYECPGLIE VPTEQDPSKSYWVMFISINPGAPAGGSFNQYFVGSFNGTHFEAFDNQ SRVVDFGKDYYALQTFFNTDPTYGSALGIAWASNWEYSAFVPTNP WRSSMSLVRKFSLNTEYQANPETELINLKAEPILNISNAGPWSRFAT NTTLTKANSYNVDLSNSTGTLEFELVYAVNTTQTISKSVFADLSLWF KGLEDPEEYLRMGFEVSASSFFLDRGNSKVKFVKENPYFTNRMSVN NQPFKSENDLSYYKVYGLLDQNILELYFNDGDVVSTNTYFMTTGNA LGSVNMTTGVDNLFYIDKFQVREVK |
| 3 | K. lactis UDP-GlcNAc transporter gene (KlMNN2-2) | AAACGTAACGCCTGGCACTCTATTTTCTCAAACTTCTGGGACGGA AGAGCTAAATATTGTGTTGCTTGAACAAACCCAAAAAAACAAAA AAATGAACAAACTAAAACTACACCTAAATAAACCGTGTGTAAAA CGTAGTACCATATTACTAGAAAAGATCACAAGTGTATCACACAT GTGCATCTCATATTACATCTTTTATCCAATCCATTCTCTCTATCCC GTCTGTTCCTGTCAGATTCTTTTTCCATAAAAAGAAGAAGACCCC GAATCTCACCGGTACAATGCAAAACTGCTGAAAAAAAAAGAAA GTTCACTGGATACGGGAACAGTGCCAGTAGGCTTCACCACATGG ACAAAACAATTGACGATAAAATAAGCAGGTGAGCTTCTTTTTCA AGTCACGATCCCTTTATGTCTCAGAAACAATATATACAAGCTAAA CCCTTTTGAACCAGTTCTCTCTTCATAGTTATGTTCACATAAATTG CGGGAACAAGACTCCGCTGGCTGTCAGGTACACGTTGTAACGTT TTCGTCCGCCCAATTATTAGCACAACATTGGCAAAAGAAAAAC TGCTCGTTTTCTCTACAGGTAAATTACAATTTTTTTCAGTAATTTT CGCTGAAAAATTTAAAGGGCAGGAAAAAAAGACGATCTCGACTT TGCATAGATGCAAGAACTGTGGTCAAAACTTGAAATAGTAATTT TGCTGTGCGTGAACTAATAAATATATATATATATATATATATATA TTTGTGTATTTTGTATATGTAATTGTGCACGTCTTGGCTATTGGAT ATAAGATTTTCGCGGGTTGATGACATAGAGCGTGTACTACTGTAA TAGTTGTATATTCAAAAGCTGCTGCGTGGAGAAAGACTAAAATA GATAAAAAGCACACATTTTGACTTCGGTACCGTCAACTTAGTGG GACAGTCTTTTATATTGGTGTAAGCTCATTTCTGGTACTATTCGA AACGAACAGTGTTTTCTGTATTACCGTCCAATCGTTTGTCATGA GTTTTGTATTGATTTTGTCGTTAGTGTTCGGAGGATGTTGTTCCAA TGTGATTAGTTTCGAGCACATGGTGCAAGGCAGCAATATAAATTT GGGAAATATTGTTACATTCACTCAATTCGTGTCTGTGACGCTAAT TCAGTTGCCCAATGCTTTGGACTTCTCTCACTTTCCGTTTAGGTTG CGACCTAGACACATTCCTCTTAAGATCCATATGTTAGCTGTGTTT TTGTTCTTTACCAGTTCAGTCGCCAATAACAGTGTGTTTAAATTT GACATTTCCGTTCCGATTCATATTATCATTAGATTTTCAGGTACC ACTTTGACGATGATAATAGGTTGGGCTGTTTGTAATAAGAGGTAC TCCAAACTTCAGGTGCAATCTGCCATCATTATGACGCTTGGTGCG ATTGTCGCATCATTATACCGTGACAAAGAATTTTCAATGGACAGT TTAAAGTTGAATACGGATTCAGTGGGTATGACCCAAAAATCTAT GTTTGGTATCTTTGTTGTGCTAGTGGCCACTGCCTTGATGTCATTG TTGTCGTTGCTCAACGAATGGACGTATAACAAGTACGGGAAACA TTGGAAAGAAACTTTGTTCTATTCGCATTTCTTGGCTCTACCGTTG TTTATGTTGGGGTACACAAGGCTCAGAGACGAATTCAGAGACCT CTTAATTTCCTCAGACTCAATGGATATTCCTATTGTTAAATTACC AATTGCTACGAAACTTTTCATGCTAATAGCAAATAACGTGACCCA GTTCATTTGTATCAAAGGTGTTAACATGCTAGCTAGTAACACGGA TGCTTTGACACTTTCTGTCGTGCTTCTAGTGCGTAAATTTGTTAGT CTTTTACTCAGTGTCTACATCTACAAGAACGTCCTATCCGTGACT GCATACCTAGGGACCATCACCGTGTTCCTGGGAGCTGGTTTGTAT TCATATGGTTCGGTCAAAACTGCACTGCCTCGCTGAAACAATCC ACGTCTGTATGGATACTCGTTTCAGAATTTTTTGATTTTCTGCCGG ATATGGTTTCTCATCTTTACAATCGCATTCTTAATTATACCAGAA CGTAATTCAATGATCCCAGTGACTCGTAACTCTTATATGTCAATT TAAGC |
| 4 | K. lactis UDP-GlcNAc transporter (KlMNN2-2) | MSFVLILSLVFGGCCSNVISFEHMVQGSNINLGNIVTFTQFVSVTLIQ LPNALDFSHPFPFRLRPRHIPLKIHMLAVFLFFTSSVANNSVFKFDISVP IHIIIRFSGTTLTMIIGWAVCNKRYSKLQVQSAIIMTLGAIVASLYRDK EFSMDSLKLNTDSVGMTQKSMFGIFVVLVATALMSLLSLLNEWTY NKYGKHWKETLFYSHFLALPLFMLGYTRLRDEFRDLLISSDSMDIPI VKLPIATKLFMLIANNVTQFICIKGVNMLASNTDALTLSVVLLVRKF VSLLLSVYIYKNVLSVTAYLGTITVFLGAGLYSYGSVKTALPR |

TABLE 14-continued

| SEQ ID NO: | Description | Sequence |
|---|---|---|
| 5 | DNA encodes Mnn2 leader (53) | ATGCTGCTTACCAAAAGGTTTTCAAAGCTGTTCAAGCTGACGTTC ATAGTTTTGATATTGTGCGGGCTGTTCGTCATTACAAACAAATAC ATGGATGAGAACACGTCG |
| 6 | Mnn2 leader (53) | MLLTKRFSKLFKLTFIVLILCGLFVITNKYMDENTS |
| 7 | DNA encodes Mnn2 leader (54) The last 9 nucleotides are the linker containing the AscI restriction site) | ATGCTGCTTACCAAAAGGTTTTCAAAGCTGTTCAAGCTGACGTTC ATAGTTTTGATATTGTGCGGGCTGTTCGTCATTACAAACAAATAC ATGGATGAGAACACGTCGGTCAAGGAGTACAAGGAGTACTTAGA CAGATATGTCCAGAGTTACTCCAATAAGTATTCATCTTCCTCAGA CGCCGCCAGCGCTGACGATTCAACCCCATTGAGGGACAATGATG AGGCAGGCAATGAAAAGTTGAAAAGCTTCTACAACAACGTTTTC AACTTTCTAATGGTTGATTCGCCCGGGCGCGCC |
| 8 | Mnn2 leader (54) | MLLTKRFSKLFKLTFIVLILCGLFVITNKYMDENTSVKEYKEYLDRY VQSYSNKYSSSSD AASADDSTPLRDNDEAGNEKLKSFYNNVFNFLMVDSPGRA |
| 9 | DNA encodes *S. cerevisiae* Mating Factor pre signal sequence | ATG AGA TTC CCA TCC ATC TTC ACT GCT GTT TTG TTC GCT GCT TCT TCT GCT TTG GCT |
| 10 | *S. cerevisiae* Mating Factor pre signal sequence | MRFPSIFTAVLFAASSALA |
| 11 | DNA encodes Pp SEC12 (10) The last 9 nucleotides are the linker containing the AscI restriction site used for fusion to proteins of interest. | ATGCCCAGAAAAATATTTAACTACTTCATTTTGACTGTATTCATG GCAATTCTTGCTATTGTTTTACAATGGTCTATAGAGAATGGACAT GGGCGCGCC |
| 12 | Pp SEC12 (10) | MPRKIFNYFILTVFMAILAIVLQWSIENGHGRA |
| 13 | DNA encodes ScMnt1 (Kre2) (33) | ATGGCCCTCTTTCTCAGTAAGAGACTGTTGAGATTTACCGTCATT GCAGGTGCGGTTATTGTTCTCCTCCTAACATTGAATTCCAACAGT AGAACTCAGCAATATATTCCGAGTTCCATCTCCGCTGCATTTGAT TTTACCTCAGGATCTATATCCCCTGAACAACAAGTCATCGGGCGC GCC |
| 14 | ScMnt1 (Kre2) (33) | MALFLSKRLLRFTVIAGAVIVLLLTLNSNSRTQQYIPSSISAAFDFTSG SISPEQQVIGRA |

TABLE 14-continued

| SEQ ID NO: | Description | Sequence |
|---|---|---|
| 15 | DNA encodes ScSEC12 (8) The last 9 nucleotides are the linker containing the AscI restriction site used for fusion to proteins of interest | ATGAACACTATCCACATAATAAAATTACCGCTTAACTACGCCAA CTACACCTCAATGAAACAAAAAATCTCTAAATTTTTCACCAACTT CATCCTTATTGTGCTGCTTTCTTACATTTTACAGTTCTCCTATAAG CACAATTTGCATTCCATGCTTTTCAATTACGCGAAGGACAATTTT CTAACGAAAAGAGACACCATCTCTTCGCCCTACGTAGTTGATGA AGACTTACATCAAACAACTTTGTTTGGCAACCACGGTACAAAAA CATCTGTACCTAGCGTAGATTCCATAAAAGTGCATGGCGTGGGG CGCGCC |
| 16 | ScSEC12 (8) | MNTIHIIKLPLNYANYTSMKQKISKFFTNFILIVLLSYILQFSYKHNLH SMLFNYAKDNFLTKRDTISSPYVVDEDLHQTTLFGNHGTKTSVPSV DSIKVHGVGRA |
| 17 | DNA encodes MmSLC35 A3 UDP-GlcNAc transporter | ATGTCTGCCAACCTAAAATATCTTTCCTTGGGAATTTTGGTGTTTC AGACTACCAGTCTGGTTCTAACGATGCGGTATTCTAGGACTTTAA AAGAGGAGGGGCCTCGTTATCTGTCTTCTACAGCAGTGGTTGTGG CTGAATTTTTGAAGATAATGGCCTGCATCTTTTTAGTCTACAAAG ACAGTAAGTGTAGTGTGAGAGCACTGAATAGAGTACTGCATGAT GAAATTCTTAATAAGCCCATGGAAACCCTGAAGCTCGCTATCCC GTCAGGGATATATACTCTTCAGAACAACTTACTCTATGTGGCACT GTCAAACCTAGATGCAGCCACTTACCAGGTTACATATCAGTTGA AAATACTTACAACAGCATTATTTTCTGTGTCTATGCTTGGTAAAA AATTAGGTGTGTACCAGTGGCTCTCCCTAGTAATTCTGATGGCAG GAGTTGCTTTTGTACAGTGGCCTTCAGATTCTCAAGAGCTGAACT CTAAGGACCTTTCAACAGGCTCACAGTTTGTAGGCCTCATGGCAG TTCTCACAGCCTGTTTTTCAAGTGGCTTTGCTGGAGTTTATTTTGA GAAAATCTTAAAAGAAACAAAACAGTCAGTATGGATAAGGAAC ATTCAACTTGGTTTCTTTGGAAGTATATTTGGATTAATGGGTGTA TACGTTTATGATGGAGAATTGGTCTCAAAGAATGGATTTTTTCAG GGATATAATCAACTGACGTGGATAGTTGTTGCTCTGCAGGCACTT GGAGGCCTTGTAATAGCTGCTGTCATCAAATATGCAGATAACATT TTAAAAGGATTTGCGACCTCCTTATCCATAATTATTGTCAACAATA ATATCTTATTTTTGGTTCAAGATTTTGTGCCAACCAGTGTCTTTTT TCCTTGGAGCCATCCTTGTAATAGCAGCTACTTTCTTGTATGGTT ACGATCCCAAACCTGCAGGAAATCCCACTAAAGCATAG |
| 18 | MmSLC35 A3 UDP-GlcNAc transporter | MSANLKYLSLGILVFQTTSLVLTMRYSRTLKEEGPRYLSSTAVVVAE FLKIMACIFLVYKDSKCSVRALNRVLHDEILNKPMETLKLAIPSGIYT LQNNLLYVALSNLDAATYQVTYQLKILTTALFSVSMLGKKLGVYQ WLSLVILMAGVAFVQWPSDSQELNSKDLSTGSQFVGLMAVLTACFS SGFAGVYFEKILKETKQSVWIRNIQLGFFGSIFGLMGVYVYDGELVS KNGFFQGYNQLTWIVVALQALGGLVIAAVIKYADNILKGFATSLSII LSTIISYFWLQDFVPTSVFFLGAILVIAATFLYGYDPKPAGNPTKA |
| 19 | DNA encodes DmUGT | ATGAATAGCATACACATGAACGCCAATACGCTGAAGTACATCAG CCTGCTGACGCTGACCCTGCAGAATGCCATCCTGGGCCTCAGCAT GCGCTACGCCCGCACCCGGCCAGGCGACATCTTCCTCAGCTCCAC GGCCGTACTCATGGCAGAGTTCGCCAAACTGATCACGTGCCTGTT CCTGGTCTTCAACGAGGAGGGCAAGGATGCCCAGAAGTTTGTAC GCTCGCTGCACAAGACCATCATTGCGAATCCCATGGACACGCTG AAGGTGTGCGTCCCCTCGCTGGTCTATATCGTTCAAAACAATCTG CTGTACGTCTCTGCCTCCCATTTGGATGCGGCCACCTACCAGGTG ACGTACCAGCTGAAGATTCTCACCACGGCCATGTTCGCGGTTGTC ATTCTGCGCCGCAAGCTGCTGAACACGCAGTGGGGTGCGCTGCT GCTCCTGGTGATGGGCATCGTCCTGGTGCAGTTGGCCCAAACGG AGGGTCCGACGAGTGGCTCAGCCGGTGGTGCCGCAGCTGCAGCC ACGGCCGCCTCCTCTGGCGGTGCTCCCGAGCAGAACAGGATGCT CGGACTGTGGGCCGCACTGGGCGCCTGCTTCCTCCTCCGGATTCGC GGGCATCTACTTTGAGAAGATCCTCAAGGGTGCCGAGATCTCCG TGTGGATGCGGAATGTGCAGTTGAGTCTGCTCAGCATTCCCTTCG GCCTGCTCACCTGTTTCGTTAACGACGGCAGTAGGATCTTCGACC AGGGATTCTTCAAGGGCTACGATCTGTTTGTCTGGTACCTGGTCC TGCTGCAGGCCGGCGGTGGATTGATCGTTGCCGTGGTGGTCAAG TACGCGGATAACATTCTCAAGGGCTTCGCCACCTCGCTGGCCATC ATCATCTCGTGCGTGGCCTCCATATACATCTTCGACTTCAATCTC ACGCTGCAGTTCAGCTTCGGAGCTGGCCTGGTCATCGCCTCCATA TTTCTCTACGGCTACGATCCGGCCAGGTCGGCGCCGAAGCCAACT ATGCATGGTCCTGGCGGCGATGAGGAGAAGCTGCTGCCGCGCGT CTAG |

TABLE 14-continued

| SEQ ID NO: | Description | Sequence |
|---|---|---|
| 20 | DmUGT | MNSIHMNANTLKYISLLTLTLQNAILGLSMRYARTRPGDIFLSSTAV LMAEFAKLITCLFLVFNEEGKDAQKFVRSLHKTIIANPMDTLKVCVP SLVYIVQNNLLYVSASHLDAATYQVTYQLKILTTAMFAVVILRRKL LNTQWGALLLLVMGIVLVQLAQTEGPTSGSAGGAAAAATAASSGG APEQNRMLGLWAALGACFLSGFAGIYFEKILKGAEISVWMRNVQLS LLSIPFGLLTCFVNDGSRIFDQGFFKGYDLFVWYLVLLQAGGGLIVA VVVKYADNILKGFATSLAIIISCVASIYIFDFNLTLQFSFGAGLVIASIF LYGYDPARSAPKPTMHGPGGDEEKLLPRV |
| 21 | DNA encodes ScGAL10 | ATGACAGCTCAGTTACAAAGTGAAAGTACTTCTAAAATTGTTTTG GTTACAGGTGGTGCTGGATACATTGGTTCACACACTGTGGTAGA GCTAATTGAGAATGGATATGACTGTGTTGTTGCTGATAACCTGTC GAATTCAACTTATGATTCTGTAGCCAGGTTAGAGGTCTTGACCAA GCATCACATTCCCTTCTATGAGGTTGATTTGTGTGACCGAAAAGG TCTGGAAAAGGTTTTCAAAGAATATAAAATTGATTCGGTAATTCA CTTTGCTGGTTTAAAGGCTGTAGGTGAATCTACACAAATCCCGCT GAGATACTATCACAATAACATTTTGGGAACTGTCGTTTTATTAGA GTTAATGCAACAATACAACGTTTCCAAATTTGTTTTTTCATCTTCT GCTACTGTCTATGGTGATGCTACGAGATTCCCAAATATGATTCCT ATCCCAGAAGAATGTCCCTTAGGGCCTACTAATCCGTATGGTCAT ACGAAATACGCCATTGAGAATATCTTGAATGATCTTTACAATAGC GACAAAAAAGTTGGAAGTTTGCTATCTTGCGTTATTTTAACCCA ATTGGCGCACATCCCTCTGGATTAATCGGAGAAGATCCGCTAGG TATACCAAACAATTTGTTGCCATATATGGCTCAAGTAGCTGTTGG TAGGCGCGAGAAGCTTTACATCTTCGGAGACGATTATGATTCCA GAGATGGTACCCCGATCAGGGATTATATCCACGTAGTTGATCTA GCAAAAGGTCATATTGCAGCCCTGCAATACCTAGAGGCCTACAA TGAAAATGAAGGTTTGTGTCGTGAGTGGAACTTGGGTTCCGGTA AAGGTTCTACAGTTTTTGAAGTTTATCATGCATTCTGCAAAGCTT CTGGTATTGATCTTCCATACAAAGTTACGGGCAGAAGAGCAGGT GATGTTTTGAACTTGACGGCTAAACCAGATAGGGCCAAACGCGA ACTGAAATGGCAGACCGAGTTGCAGGTTGAAGACTCCTGCAAGG ATTTATGGAAATGGACTACTGAGAATCCTTTTGGTTACCAGTTAA GGGGTGTCGAGGCCAGATTTTCCGCTGAAGATATGCGTTATGAC GCAAGATTTGTGACTATTGGTGCCGGCACCAGATTTCAAGCCAC GTTTGCCAATTTGGGCGCCAGCATTGTTGACCTGAAAGTGAACG GACAATCAGTTGTTCTTGGCTATGAAAATGAGGAAGGTATTTG AATCCTGATAGTGCTTATATAGGCGCCACGATCGGCAGGTATGCT AATCGTATTTCGAAGGGTAAGTTTAGTTTATGCAACAAAGACTAT CAGTTAACCGTTAATAACGGCGTTAATGCGAATCATAGTAGTATC GGTTCTTTCCACAGAAAAAGATTTTTGGGACCCATCATTCAAAAT CCTTCAAAGGATGTTTTTACCGCCGAGTACATGCTGATAGATAAT GAGAAGGACACCGAATTTCCAGGTGATCTATTGGTAACCATACA GTATACTGTGAACGTTGCCCAAAAAAGTTTGGAAATGGTATATA AAGGTAAATTGACTGCTGGTGAAGCGACGCCAATAAATTTAACA AATCATAGTTATTTCAATCTGAACAAGCCATATGGAGACACTATT GAGGGTACGGAGATTATGGTGCGTTCAAAAAAATCTGTTGATGT CGACAAAAACATGATTCCTACGGGTAATATCGTCGATAGAGAAA TTGCTACCTTTAACTCTACAAAGCCAACGGTCTTAGGCCCCAAAA ATCCCCAGTTTGATTGTTGTTTTGTGGTGGATGAAAATGCTAAGC CAAGTCAAATCAATACTCTAAACAATGAATTGACGCTTATTGTCA AGGCTTTTCATCCCGATTCCAATATTACATTAGAAGTTTTAAGTA CAGAGCCAACTTATCAATTTTATACCGGTGATTTCTTGTCTGCTG GTTACGAAGCAAGACAAGGTTTTGCAATTGAGCCTGGTAGATAC ATTGATGCTATCAATCAAGAGAACTGGAAAGATTGTGTAACCTT GAAAAACGGTGAAACTTACGGGTCCAAGATTGTCTACAGATTTT CCTGA |
| 22 | ScGal10 | MTAQLQSESTSKIVLVTGGAGYIGSHTVVELIENGYDCVVADNLSN STYDSVARLEVLTKHHIPFYEVDLCDRKGLEKVFKEYKIDSVIHFAG LKAVGESTQIPLRYYHNNILGTVVLLELMQQYNVSKFVFSSSATVY GDATRFPNMIPIPEECPLGPTNPYGHTKYAIENILNDLYNSDKKSWK FAILRYFNPIGAHPSGLIGEDPLGIPNNLLPYMAQVAVGRREKLYIFG DDYDSRDGTPIRDYIHVVDLAKGHIAALQYLEAYNENEGLCREWNL GSGKGSTVFEVYHAFCKASGIDLPYKVTGRRAGDVLNLTAKPDRA KRELKWQTELQVEDSCKDLWKWTTENPFGYQLRGVEARFSAEDM RYDARFVTIGAGTRFQATFANLG ASIVDLKVNGQSVVLGYENEEGYLNPDSAYIGATIGRYANRISKGKF SLCNKDYQLTVNNGVNANHSSIGSFHRKRFLGPIIQNPSKDVFTAEY MLIDNEKDTEFPGDLLVTIQYTVNVAQKSLEMVYKGKLTAGEATPI NLTNHSYFNLNKPYGDTIEGTEIMVRSKKSVDVDKNMIPTGNIVDRE IATFNSTKPTVLGPKNPQFDCCFVVDENAKPSQINTLNNELTLIVKAF HPDSNITLEVLSTEPTYQFYTGDFLSAGYEARQGFAIEPGRYIDAINQ ENWKDCVTLKNGETYGSKIVYRFS |

| SEQ ID NO: | Description | Sequence |
|---|---|---|
| 23 | hGalT codon optimized (XB) | GGTAGAGATTTGTCTAGATTGCCACAGTTGGTTGGTGTTTCCACT CCATTGCAAGGAGGTTCTAACTCTGCTGCTGCTATTGGTCAATCT TCCGGTGAGTTGAGAACTGGTGGAGCTAGACCACCTCCACCATT GGGAGCTTCCTCTCAACCAAGACCAGGTGGTGATTCTTCTCCAGT TGTTGACTCTGGTCCAGGTCCAGCTTCTAACTTGACTTCCGTTCC AGTTCCACACACTACTGCTTTGTCCTTGCCAGCTTGTCCAGAAGA ATCCCCATTGTTGGTTGGTCCAATGTTGATCGAGTTCAACATGCC AGTTGACTTGGAGTTGGTTGCTAAGCAGAACCCAAACGTTAAGA TGGGTGGTAGATACGCTCCAAGAGACTGTGTTTCCCCACACAAA GTTGCTATCATCATCCCATTCAGAAACAGACAGGAGCACTTGAA GTACTGGTTGTACTACTTGCACCCAGTTTTGCAAAGACAGCAGTT GGACTACGGTATCTACGTTATCAACCAGGCTGGTGACACTATTTT CAACAGAGCTAAGTTGTTGAATGTTGGTTTCCAGGAGGCTTTGAA GGATTACGACTACACTTGTTTCGTTTTCTCCGACGTTGACTTGATT CCAATGAACGACCACAACGCTTACAGATGTTTCTCCCAGCCAAG ACACATTTCTGTTGCTATGGACAAGTTCGGTTTCTCCTTGCCATA CGTTCAATACTTCGGTGGTGTTTCCGCTTTGTCCAAGCAGCAGTT CTTGACTATCAACGGTTTCCCAAACAATTACTGGGGATGGGGTG GTGAAGATGACGACATCTTTAACAGATTGGTTTTCAGAGGAATG TCCATCTCTAGACCAAACGCTGTTGTTGGTAGATGTAGAATGATC AGACACTCCAGAGACAAGAAGAACGAGCCAAACCCACACAAGAT TCGACAGAATCGCTCACACTAAGGAAACTATGTTGTCCGACGGA TTGAACTCCTTGACTTACCAGGTTTTGGACGTTCAGAGATACCCA TTGTACACTCAGATCACTGTTGACATCGGTACTCCATCCTAG |
| 24 | hGalT I catalytic doman (XB) | GRDLSRLPQLVGVSTPLQGGSNSAAAIGQSSGELRTGGARPPPPLGA SSQPRPGGDSSPVVDSGPGPASNLTSVPVPHTTALSLPACPEESPLLV GPMLIEFNMPVDLELVAKQNPNVKMGGRYAPRDCVSPHKVAIIIPFR NRQEHLKYWLYYLHPVLQRQQLDYGIYVINQAGDTIFNRAKLLNV GFQEALKDYDYTCFVFSDVDLIPMNDHNAYRCFSQPRHISVAMDKF GFSLPYVQYFGGVSALSKQQFLTINGFPNNYWGWGGEDDDIFNRLV FRGMSISRPNAVVGRCRMIRHSRDKKNEPNPQRFDRIAHTKETMLS DGLNSLTYQVLDVQRYPLYTQITVDIGTPS |
| 25 | DNA encodes human GnTI catalytic doman (NA) Codon-optimized | TCAGTCAGTGCTCTTGATGGTGACCCAGCAAGTTTGACCAGAGA AGTGATTAGATTGGCCCAAGACGCAGAGGTGGAGTTGGAGAGAC AACGTGGACTGCTGCAGCAAATCGGAGATGCATTGTCTAGTCAA AGAGGTAGGGTGCCTACCGCAGCTCCTCCAGCACAGCCTAGAGT GCATGTGACCCCTGCACCAGCTGTGATTCCTATCTTGGTCATCGC CTGTGACAGATCTACTGTTAGAAGATGTCTGGACAAGCTGTTGCA TTACAGACCATCTGCTGAGTTGTTCCCTATCATCGTTAGTCAAGA CTGTGGTCACGAGGAGACTGCCCAAGCCATCGCTCCTACGGAT CTGCTGTCACTCACATCAGACAGCCTGACCTGTCATCTATTGCTG TGCCACCAGACCACAGAAAGTTCCAAGGTTACTACAAGATCGCT AGACACTACGATGGGCATTGGGTCAAGTCTTCAGACAGTTTAG ATTCCCTGCTGCTGTGGTGGTGGAGGATGACTTGGAGGTGGCTCC TGACTTCTTTGAGTACTTTAGAGCAACCTATCCATTGCTGAAGGC AGACCCATCCCTGTGGTGTGTCTCTGCCTGGAATGACAACGGTAA GGAGCAAATGGTGGACGCTTCTAGGCCTGAGCTGTTGTACAGAA CCGACTTCTTTCCTGGTCTGGGATGGTTGCTGTTGGCTGAGTTGT GGGCTGAGTTGGAGCCTAAGTGGCCAAAGGCATTCTGGGACGAC TGGATGAGAAGACCTGAGCAAAGACAGGGTAGAGCCTGTATCAG ACCTGAGATCTCAAGAACCATGACCTTTGGTAGAAAGGGAGTGT CTCACGGTCAATTCTTTGACCAACACTTGAAGTTTATCAAGCTGA ACCAGCAATTTGTGCACTTCACCCAACTGGACCTGTCTTACTTGC AGAGAGAGGCCTATGACAGAGATTTCCTAGCTAGAGTCTACGGA GCTCCTCAACTGCAAGTGGAGAAAGTGAGGACCAATGACAGAAA GGAGTTGGGAGAGGTGAGAGTGCAGTACACTGGTAGGGACTCCT TTAAGGCTTTCGCTAAGGCTCTGGGTGTCATGGATGACCTTAAGT CTGGAGTTCCTAGAGCTGGTTACAGAGGTATTGTCACCTTTCAAT TCAGAGGTAGAAGAGTCCACTTGGCTCCTCCACCTACTTGGGAG GGTTATGATCCTTCTTGGAATTAG |
| 26 | Human GnT I catalytic doman (NA) | SVSALDGDPASLTREVIRLAQDAEVELERQRGLLQQIGDALSSQRGR VPTAAPPAQPRVHVTPAPAVIPILVIACDRSTVRRCLDKLLHYRPSAE LFPIIVSQDCGHEETAQAIASYGSAVTHIRQPDLSSIAVPPDHRKFQG YYKIARHYRWALGQVFRQFRFPAAVVVEDDLEVAPDFFEYFRATYP LLKADPSLWCVSAWNDNGKEQMVDASRPELLYRTDFFPGLWLLL AELWAELEPKWPKAFWDDWMRRPEQRQGRACIRPEISRTMTFGRK GVSHGQFFDQHLKFIKLNQQFVHFTQLDLSYLQREAYDRDFLARVY GAPQLQVEKVRTNDRKELGEVRVQYTGRDSFKAFAKALGVMDDL KSGVPRAGYRGIVTFQFRGRRVHLAPPPTWEGYDPSWN |

TABLE 14-continued

| SEQ ID NO: | Description | Sequence |
|---|---|---|
| 27 | DNA encodes Mm ManI catalytic doman (FB) | GAGCCCGCTGACGCCACCATCCGTGAGAAGAGGGCAAAGATCAA<br>AGAGATGATGACCCATGCTTGGAATAATTATAAACGCTATGCGT<br>GGGGCTTGAACGAACTGAAACCTATATCAAAAGAAGGCCATTCA<br>AGCAGTTTGTTTGGCAACATCAAAGGAGCTACAATAGTAGATGC<br>CCTGGATACCCTTTTCATTATGGGCATGAAGACTGAATTTCAAGA<br>AGCTAAATCGTGGATTAAAAAATATTTAGATTTTAATGTGAATGC<br>TGAAGTTTCTGTTTTTGAAGTCAACATACGCTTCGTCGGTGGACT<br>GCTGTCAGCCTACTATTTGTCCGGAGAGGAGATATTTCGAAAGA<br>AAGCAGTGGAACTTGGGGTAAAATTGCTACCTGCATTTCATACTC<br>CCTCTGGAATACCTTGGGCATTGCTGAATATGAAAAGTGGGATC<br>GGGCGGAACTGGCCCTGGGCCTCTGGAGGCAGCAGTATCCTGGC<br>CGAATTTGGAACTCTGCATTTAGAGTTTATGCACTTGTCCCACTT<br>ATCAGGAGACCCAGTCTTTGCCGAAAAGGTTATGAAAATTCGAA<br>CAGTGTTGAACAAACTGGACAAACCAGAAGGCCTTTATCCTAAC<br>TATCTGAACCCCAGTAGTGGACAGTGGGGTCAACATCATGTGTC<br>GGTTGGAGGACTTGGAGACAGCTTTTATGAATATTTGCTTAAGGC<br>GTGGTTAATGTCTGACAAGACAGATCTCGAAGCCAAGAAGATGT<br>ATTTTGATGCTGTTCAGGCCATCGAGACTCACTTGATCCGCAAGT<br>CAAGTGGGGGACTAACGTACATCGCAGAGTGGAAGGGGGGCCTC<br>CTGGAACACAAGATGGGCCACCTGACGTGCTTTGCAGGAGGCAT<br>GTTTGCACTTGGGGCAGATGGAGCTCCGGAAGCCCGGGCCCAAC<br>ACTACCTTGAACTCGGAGCTGAAATTGCCCGCACTTGTCATGAAT<br>CTTATAATCGTACATATGTGAAGTTGGGACCGGAAGCGTTTCGAT<br>TTGATGGCGGTGTGGAAGCTATTGCCACGAGGCAAAATGAAAAG<br>TATTACATCTTACGGCCCGAGGTCATCGAGACATACATGTACATG<br>TGGCGACTGACTCACGACCCCAAGTACAGGACCTGGGCCTGGGA<br>AGCCGTGGAGGCTCTAGAAAGTCACTGCAGAGTGAACGGAGGCT<br>ACTCAGGCTTACGGGATGTTTACATTGCCCGTGAGAGTTATGACG<br>ATGTCCAGCAAAGTTTCTTCCTGGCAGAGACACTGAAGTATTTGT<br>ACTTGATATTTTCCGATGATGACCTTCTTCCACTAGAACACTGGA<br>TCTTCAACACCGAGGCTCATCCTTTCCCTATACTCCGTGAACAGA<br>AGAAGGAAATTGATGGCAAAGAGAAATGA |
| 28 | Mm ManI catalytic doman (FB) | EPADATIREKRAKIKEMMTHAWNNYKRYAWGLNELKPISKEGHSS<br>SLFGNIKGATIVDALDTLFIMGMKTEFQEAKSWIKKYLDFNVNAEV<br>SVFEVNIRFVGGLLSAYYLSGEEIFRKKAVELGVKLLPAFHTPSGIPW<br>ALLNMKSGIGRNWPWASGGSSILAEFGTLHLEFMHLSHLSGDPVFA<br>EKVMKIRTVLNKLDKPEGLYPNYLNPSSGQWGQHHVSVGGLGDSF<br>YEYLLKAWLMSDKTDLEAKKMYFDAVQAIETHLIRKSSGGLTYIAE<br>WKGGLLEHKMGHLTCFAGGMFALGADGAPEARAQHYLELGAEIA<br>RTCHESYNRTYVKLGPEAFRFDGGVEAIATRQNEKYYILRPEVIETY<br>MYMWRLTHDPKYRTWAWEAVEALESHCRVNGGYSGLRDVYIARE<br>SYDDVQQSFFLAETLKYLYLIFSDDDLLPLEHWIFNTEAHPFPILREQ<br>KKEIDGKEK |
| 29 | DNA encodes Tr ManI catalytic doman | CGCGCCGGATCTCCCAACCCTACGAGGGCGGCAGCAGTCAAGGC<br>CGCATTCCAGACGTCGTGGAACGCTTACCACCATTTTGCCTTTCC<br>CCATGACGACCTCCACCCGGTCAGCAACAGCTTTGATGATGAGA<br>GAAACGGCTGGGGCTCGTCGGCAATCGATGGCTTGGACACGGCT<br>ATCCTCATGGGGGATGCCGACATTGTGAACACGATCCTTCAGTAT<br>GTACCGCAGATCAACTTCACCACGACTGCGGTTGCCAACCAAGG<br>CATCTCCGTGTTCGAGACCAACATTCGGTACCTCGGTGGCCTGCT<br>TTCTGCCTATGACCTGTTGCGAGGTCCTTTCAGCTCCTTGGCGAC<br>AAACCAGACCCTGGTAAACAGCCTTCTGAGGCAGGCTCAAACAC<br>TGGCCAACGGCCTCAAGGTTGCGTTCACCACTCCCAGCGGTGTCC<br>CGGACCCTACCGTCTTCTTCAACCCTACTGTCCGGAGAAGTGGTG<br>CATCTAGCAACAACGTCGCTGAAATTGGAAGCCTGGTGCTCGAG<br>TGGACACGGTTGAGCGACCTGACGGGAAACCCGCAGTATGCCCA<br>GCTTGCGCAGAAGGGCGAGTCGTATCTCCTGAATCCAAAGGGAA<br>GCCCGGAGGCATGGCCTGGCCTGATTGGAACGTTTGTCAGCACG<br>AGCAACGGTACCTTTCAGGATAGCAGCGGCAGCTGGTCCGGCCT<br>CATGGACAGCTTCTACGAGTACCTGATCAAGATGTACCTGTACG<br>ACCCGGTTGCGTTTGCACACTACAAGGATCGCTGGGTCCTTGCTG<br>CCGACTCGACCATTGCGCATCTCGCCTCTCACCCGTCGACGCA<br>AGGACTTGACCTTTTTGTCTTCGTACAACGGACAGTCTACGTCGC<br>CAAACTCAGGACATTTGGCCAGTTTTGCCGGTGGCAACTTCATCT<br>TGGGAGGCATTCTCCTGAACGAGCAAAGTACATTGACTTTGGA<br>ATCAAGCTTGCCAGCTCGTACTTTGCCACGTACAACCAGACGGCT<br>TCTGGAATCGGCCCCGAAGGCTTCGCGTGGGTGGACAGCGTGAC<br>GGGCGCCGGCGGCTCGCCGCCCTCGTCCCAGTCCGGGTTCTACTC<br>GTCGGCAGGATTCTGGGTGACGGCACCGTATTACATCCTGCGGC<br>CGGAGACGCTGGAGAGCTTGTACTACGCATACCGCGTCACGGGC<br>GACTCCAAGTGGCAGGACCTGGCGTGGGAAGCGTTCAGTGCCAT<br>TGAGGACGCATGCCGCGCCGGCAGCGCGTACTCGTCCATCAACG<br>ACGTGACGCAGGCCAACGGCGGGGGTGCCTCTGACGATATGGAG |

TABLE 14-continued

| SEQ ID NO: | Description | Sequence |
|---|---|---|
| | | AGCTTCTGGTTTGCCGAGGCGCTCAAGTATGCGTACCTGATCTTT<br>GCGGAGGAGTCGGATGTGCAGGTGCAGGCCAACGGCGGGAACA<br>AATTTGTCTTTAACACGGAGGCGCACCCCTTTAGCATCCGTTCAT<br>CATCACGACGGGGCGGCCACCTTGCTTAA |
| 30 | Tr Man I catalytic doman | RAGSPNPTRAAAVKAAFQTSWNAYHHFAFPHDDLHPVSNSFDDER<br>NGWGSSAIDGLDTAILMGDADIVNTILQYVPQINFTTTAVANQGISV<br>FETNIRYLGGLLSAYDLLRGPFSSLATNQTLVNSLLRQAQTLANGLK<br>VAFTTPSGVPDPTVFFNPTVRRSGASSNNVAEIGSLVLEWTRLSDLT<br>GNPQYAQLAQKGESYLLNPKGSPEAWPGLIGTFVSTSNGTFQDSSGS<br>WSGLMDSFYEYLIKMYLYDPVAFAHYKDRWVLAADSTIAHLASHP<br>STRKDLTFLSSYNGQSTSPNSGHLASFAGGNFILGGILLNEQKYIDFG<br>IKLASSYFATYNQTASGIGPEGFAWVDSVTGAGGSPPSSQSGFYSSA<br>GFWVTAPYYILRPETLESLYYAYRVTGDSKWQDLAWEAFSAIEDAC<br>RAGSAYSSINDVTQANGGGASDDMESFWFAEALKYAYLIFAEESDV<br>QVQANGGNKFVFNTEAHPFSIRSSSRRGGHLA |
| 31 | DNA encodes Rat GnT II (TC) Codon-optimized | TCCTTGGTTTACCAATTGAACTTCGACCAGATGTTGAGAAACGTT<br>GACAAGGACGGTACTTGGTCTCCTGGTGAGTTGGTTTTGGTTGTT<br>CAGGTTCACAACAGACCAGAGTACTTGAGATTGTTGATCGACTC<br>CTTGAGAAAGGCTCAAGGTATCAGAGAGGTTTTGGTTATCTTCTC<br>CCACGATTTCTGGTCTGCTGAGATCAACTCCTTGATCTCCTCCGTT<br>GACTTCTGTCCAGTTTTGCAGGTTTTCTTCCCATTCTCCATCCAAT<br>TGTACCCATCGAGTTCCCAGGTTCTGATCCAAGAGACTGTCCAA<br>GAGACTTGAAGAAGAACGCTGCTTTGAAGTTGGGTTGTATCAAC<br>GCTGAATACCCAGATTCTTTCGGTCACTACAGAGAGGCTAAGTTC<br>TCCCAAACTAAGCATCATTGGTGGTGGAAGTTGCACTTTGTTTGG<br>GAGAGAGTTAAGGTTTTGCAGGACTACACTGGATTGATCTTGTTC<br>TTGGAGGAGGATCATTACTTGGCTCCAGACTTCTACCACGTTTTC<br>AAGAAGATGTGGAAGTTGAAGCAACAAGAGTGTCCAGGTTGTGA<br>CGTTTTGTCCTTGGGAACTTACACTACTATCAGATCCTTCTACGG<br>TATCGCTGACAAGGTTGACGTTAAGACTTGGAAGTCCACTGAAC<br>ACAACATGGGATTGGCTTTGACTAGAGATGCTTACCAGAAGTTG<br>ATCGAGTGTACTGACACTTTCTGTACTTACGACGACTACAACTGG<br>GACTGGACTTTGCAGTACTTGACTTTGGCTTGTTTGCCAAAAGTT<br>TGGAAGGTTTTGGTTCCACAGGCTCCAAGAATTTTCCACGCTGGT<br>GACTGTGGAATGCACCACAAGAAAACTTGTAGACCATCCACTCA<br>GTCCGCTCAAATTGAGTCCTTGTTGAACAACAACAAGCAGTACTT<br>GTTCCCAGAGACTTTGGTTATCGGAGAGAAGTTTCCAATGGCTGC<br>TATTTCCCCACCAAGAAAGAATGGTGGATGGGGTGATATTAGAG<br>ACCACGAGTTGTGTAAATCCTACAGAAGATTGCAGTAG |
| 32 | Rat GnTII (TC) | SLVYQLNFDQMLRNVDKDGTWSPGELVLVVQVHNRPEYLRLLIDS<br>LRKAQGIREVLVIFSHDFWSAEINSLISSVDFCPVLQVFFPFSIQLYPS<br>EFPGSDPRDCPRDLKKNAALKLGCINAEYPDSFGHYREAKFSQTKH<br>HWWWKLHFVWERVKVLQDYTGLILFLEEDHYLAPDFYHVFKKMW<br>KLKQQECPGCDVLSLGTYTTIRSFYGIADKVDVKTWKSTEHNMGLA<br>LTRDAYQKLIECTDTFCTYDDYNWDWTLQYLTLACLPKVWKVLVP<br>QAPRIFHAGDCGMHHKKTCRPSTQSAQIESLLNNNKQYLFPETLVIG<br>EKFPMAAISPPRKNGGWGDIRDHELCKSYRRLQ |
| 33 | DNA encodes *Drosophila melanogaster* ManII codon-optimized (KD) | AGAGACGATCCAATTGAGACCTCCATTGAAGGTTGCTAGATCCCC<br>AAGACCAGGTCAATGTCAAGATGTTGTTCAGGACGTCCCAAACG<br>TTGATGTCCAGATGTTGGAGTTGTACGATAGAATGTCCTTCAAGG<br>ACATTGATGGTGGTGTTTGCAGCAGGGTTGGAACATTAAGTAC<br>GATCCATTGAAGTACAACGCTCATCACAAGTTGAAGGTCTTCGTT<br>GTCCCACACTCCCACAACGATCCTGGTTGGATTCAGACCTTCGAG<br>GAATACTACCAGCACGACACCAAGCACATCTTGTCCAACGCTTTT<br>GAGACATTTGCACGACAACCCAGAGATGAAGTTCATCTGGGCTG<br>AAATCTCCTACTTCGCTAGATTCTACCACGATTTGGGTGAGAACA<br>AGAAGTTGCAGATGAAGTCCATCGTCAAGAACGGTCAGTTGGAA<br>TTCGTCACTGGTGGATGGGTCATGCCAGACGAGGCTAACTCCCA<br>CTGGAGAAACGTTTTGTTGCAGTTGACCGAAGGTCAAACTTGGTT<br>GAAGCAATTCATGAACGTCACTCCAACTGCTTCCTGGGCTATCGA<br>TCCATTCGGACACTCTCCAACTATGCCATACATTTTGCAGAAGTC<br>TGGTTTCAAGAATATGTTGATCCAGAGAACCCACTACTCCGTTAA<br>GAAGGAGTTGGCTAACAGAGACAGTTGGAGTTCTTGTGGAGAC<br>AGATCTGGGACAACAAAGGTGACACTGCTTTGTTCACCCACATG<br>ATGCCATTCTACTCTTACGACATTCCTCATACCTGTGGTCCAGAT<br>CCAAAGGTTTGTTGTCAGTTCGATTTCAAAAGAATGGGTTCCTTC<br>GGTTTGTCTTGTCCATGGAAGGTTCCACCTAGAACTATCTCTGAT<br>CAAAATGTTGCTGCTAGATCCAGATTTGTTGGTTGATCAGTGGAA<br>AAGAAGGCTGAGTTGTACAGAACCAACGTCTTGTTGATTCCATTG<br>GGTGACGACTTCAGATTCAAGCAGAACACCGAGTGGGATGTTCA<br>GAGAGTCAACTACGAAAGATTGTTCGAACACATCAACTCTCAGG<br>CTCACTTCAATGTCCAGGCTCAGTTCGGTACTTTGCAGGAATACT<br>TCGATGCTGTTCACCAGGCTGAAAGAGCTGGACAAGCTGAGTTC |

TABLE 14-continued

| SEQ ID NO: | Description | Sequence |
|---|---|---|
| | | CCAACCTTGTCTGGTGACTTCTTCACTTACGCTGATAGATCTGAT<br>AACTACTGGTCTGGTTACTACACTTCCAGACCATACCATAAGAGA<br>ATGGACAGAGTCTTGATGCACTACGTTAGAGCTGCTGAAATGTT<br>GTCCGCTTGGCACTCCTGGGACGGTATGGCTAGAATCGAGGAAA<br>GATTGGAGCAGGCTAGAAGAGAGTTGTCCTTGTTCCAGCACCAC<br>GACGGTATTACTGGTACTGCTAAAACTCACGTTGTCGTCGACTAC<br>GAGCAAAGAATGCAGGAAGCTTTGAAAGCTTGTCAAATGGTCAT<br>GCAACAGTCTGTCTACAGATTGTTGACTAAGCCATCCATCTACTC<br>TCCAGACTTCTCCTTCTCCTACTTCACTTTGGACGACTCCAGATG<br>GCCAGGTTCTGGTGTTGAGGACTCTAGAACTACCATCATCTTGGG<br>TGAGGATATCTTGCCATCCAAGCATGTTGTCATGCACAACACCTT<br>GCCACACTGGAGAGAGCAGTTGGTTGACTTCTACGTCTCCTCTCC<br>ATTCGTTTCTGTTACCGACTTGGCTAACAATCCAGTTGAGGCTCA<br>GGTTTCTCCAGTTTGGTCTTGGCACCACGACACTTTGACTAAGAC<br>TATCCACCCACAAGGTTCCACCACCAAGTACAGAATCATCTTCAA<br>GGCTAGAGTTCCACCAATGGGTTTGGCTACCTACGTTTTGACCAT<br>CTCCGATTCCAAGCCAGAGCACACCTCCTACGCTTCCAATTTGTT<br>GCTTAGAAAGAACCCAACTTCCTTGCCATTGGGTCAATACCCAG<br>AGGATGTCAAGTTCGGTGATCCAAGAGAGATCTCCTTGAGAGTT<br>GGTAACGGTCCAACCTTGGCTTTCTCTGAGCAGGGTTTGTTGAAG<br>TCCATTCAGTTGACTCAGGATTCTCCACATGTTCCAGTTCACTTC<br>AAGTTCTTGAAGTACGGTGTTAGATCTCATGGTGATAGATCTGGT<br>GCTTACTTGTTCTTGCCAAATGGTCCAGCTTCTCCAGTCGAGTTG<br>GGTCAGCCAGTTGTCTTGGTCACTAAGGGTAAATTGGAGTCTTCC<br>GTTTCTGTTGGTTTGCCATCTGTCGTTCACCAGACCATCATGAGA<br>GGTGGTGCTCCAGAGATTAGAAATTTGGTCGATATTGGTTCTTTG<br>GACAACACTGAGATCGTCATGAGATTGGAGACTCATATCGACTC<br>TGGTGATATCTTCTACACTGATTTGAATGGATTGCAATTCATCAA<br>GAGGAGAAGATTGGACAAGTTGCCATTGCAGGCTAACTACTACC<br>CAATTCCATCTGGTATGTTCATTGAGGATGCTAATACCAGATTGA<br>CTTTGTTGACCGGTCAACCATTGGGTGGATCTTCTTTGGCTTCTG<br>GTGAGTTGGAGATTATGCAAGATAGAAGATTGGCTTCTGATGAT<br>GAAAGAGGTTTGGGTCAGGGTGTTTTGGACAACAAGCCAGTTTT<br>GCATATTTACAGATTGGTCTTGGAGAAGGTTAACAACTGTGTCAG<br>ACCATCTAAGTTGCATCCAGCTGGTTACTTGACTTCTGCTGCTCA<br>CAAAGCTTCTCAGTCTTTGTTGGATCCATTGGACAAGTTCATCTT<br>CGCTGAAAATGAGTGGATCGGTGCTCAGGGTCAATTCGGTGGTG<br>ATCATCCATCTGCTAGAGAGGATTGGATGTCTCTGTCATGAGAA<br>GATTGACCAAGTCTTCTGCTAAAACCCAGAGAGTTGGTTACGTTT<br>TGCACAGAACCAATTTGATGCAATGTGGTACTCCAGAGGAGCAT<br>ACTCAGAAGTTGGATGTCTGTCACTTGTTGCCAAATGTTGCTAGA<br>TGTGAGAGAACTACCTTGACTTTCTTGCAGAATTTGGAGCACTTG<br>GATGGTATGGTTGCTCCAGAAGTTTGTCCAATGGAAACCGCTGCT<br>TACGTCTCTTCTCACTCTTCTTGA |
| 34 | Drosophila melanogaster ManII catalytic doman (KD) | RDDPIRPPLKVARSPRPGQCQDVVQDVPNVDVQMLELYDRMSFKDI<br>DGGVWKQGWNIKYDPLKYNAHHKLKVFVVPHSHNDPGWIQTFEE<br>YYQHDTKHILSNALRHLHDNPEMKFIWAEISYFARFYHDLGENKKL<br>QMKSIVKNGQLEFVTGGWVMPDEANSHWRNVLLQLTEGQTWLKQ<br>FMNVTPTASWAIDPFGHSPTMPYILQKSGFKNMLIQRTHYSVKKEL<br>AQQRQLEFLWRQIWDNKGDTALFTHMMPFYSYDIPHTCGPDPKVC<br>CQFDFKRMGSFGLSCPWKVPPRTISDQNVAARSDLLVDQWKKKAE<br>LYRTNVLLIPLGDDFRFKQNTEWDVQRVNYERLFEHINSQAHFNVQ<br>AQFGTLQEYFDAVHQAERAGQAEFPTLSGDFFTYADRSDNYWSGY<br>YTSRPYHKRMDRVLMHYVRAAEMLSAWHSWDGMARIEERLEQAR<br>RELSLFQHHDGITGTAKTHVVVDYEQRMQEALKACQMVMQQSVY<br>RLLTKPSIYSPDFSFSYFTLDDSRWPGSGVEDSRTTIILGEDILPSKHV<br>VMHNTLPHWREQLVDFYVSSPFVSVTDLANNPVEAQVSPVWSWH<br>HDTLTKTIHPQGSTTKYRIIFKARVPPMGLATYVLTISDSKPEHTSYA<br>SNLLLRKNPTSLPLGQYPEDVKFGDPREISLRVGNGPTLAFSEQGLL<br>KSIQLTQDSPHVPVHFKFLKYGVRSHGDRSGAYLFLPNGPASPVELG<br>QPVVLVTKGKLESSVSVGLPSVVHQTIMRGGAPEIRNLVDIGSLDNT<br>EIVMRLETHIDSGDIFYTDLNGLQFIKRRRLDKLPLQANYYPIPSGMF<br>IEDANTRLTLLTGQPLGGSSLASGELEIMQDRRLASDDERGLGQGVL<br>DNKPVLHIYRLVLEKVNNCVRPSKLHPAGYLTSAAHKASQSLLDPL<br>DKFIFAENEWIGAQGQFGGDHPSAREDLDVSVMRRLTKSSAKTQRV<br>GYVLHRTNLMQCGTPEEHTQKLDVCHLLPNVARCERTTLTFLQNLE<br>HLDGMVAPEVCPMETAAYVSSHSS |
| 35 | Mouse CMP-sialic acid transporter (MmCST) Codon optimized | ATGGCTCCAGCTAGAGAAAACGTTTCCTTGTTCTTCAAGTTGTAC<br>TGTTTGGCTGTTATGACTTTGGTTGCTGCTGCTTACACTGTTGCTT<br>TGAGATACACTAGAACTACTGCTGAGGAGTTGTACTTCTCCACTA<br>CTGCTGTTTGTATCACTGAGGTTATCAAGTTGTTGATCTCCGTTG<br>GTTTGTTGGCTAAGGAGACTGGTTCTTTGGGAAGATTCAAGGCTT<br>CCTTGTCCGAAAACGTTTTGGGTTCCCCAAAGGAGTTGGCTAAGT<br>TGTCTGTTCCATCCTTGGTTTACGCTGTTCAGAACAACATGGCTTT<br>CTTGGCTTTGTCTAACTTGGACGCTGCTGTTTACCAAGTTACTTAC |

TABLE 14-continued

| SEQ ID NO: | Description | Sequence |
|---|---|---|
| | | CAGTTGAAGATCCCATGTACTGCTTTGTGTACTGTTTTGATGTTG<br>AACAGAACATTGTCCAAGTTGCAGTGGATCTCCGTTTTCATGTTG<br>TGTGGTGGTGTTACTTTGGTTCAGTGGAAGCCAGCTCAAGCTTCC<br>AAAGTTGTTGTTGCTCAGAACCCATTGTTGGGTTTCGGTGCTATT<br>GCTATCGCTGTTTTGTGTTCCGGTTTCGCTGGTGTTTACTTCGAGA<br>AGGTTTTGAAGTCCTCCGACACTTCTTTGTGGGTTAGAAACATCC<br>AGATGTACTTGTCCGGTATCGTTGTTACTTTGGCTGGTACTTACTT<br>GTCTGACGGTGCTGAGATTCAAGAGAAGGGATTCTTCTACGGTT<br>ACACTTACTATGTTTGGTTCGTTATCTTCTTGGCTTCCGTTGGTGG<br>TTTGTACACTTCCGTTGTTGTTAAGTACACTGACAACATCATGAA<br>GGGATTCTCTGCTGCTGCTGCTATTGTTTTGTCCACTATCGCTTCC<br>GTTTTGTTGTTCGGATTGCAGATCACATTGTCCTTTGCTTTGGGAG<br>CTTTGTTGGTTTGTGTTTCCATCTACTTGTACGGATTGCCAAGACA<br>AGACACTACTTCCATTCAGCAAGAGGCTACTTCCAAGGAGAGAA<br>TCATCGGTGTTTAGTAG |
| 36 | Mouse CMP-sialic acid transporter (MmCST) | MAPARENVSLFFKLYCLAVMTLVAAAYTVALRYTRTTAEELYFSTT<br>AVCITEVIKLLISVGLLAKETGSLGRFKASLSENVLGSPKELAKLSVP<br>SLVYAVQNNMAFLALSNLDAAVYQVTYQLKIPCTALCTVLMLNRT<br>LSKLQWISVFMLCGGVTLVQWKPAQASKVVVAQNPLLGFGAIAIA<br>VLCSGFAGVYFEKVLKSSDTSLWVRNIQMYLSGIVVTLAGTYLSDG<br>AEIQEKGFFYGYTYYVWFVIFLASVGGLYTSVVVKYTDNIMKGFSA<br>AAAIVLSTIASVLLFGLQITLSFALGALLVCVSIYLYGLPRQDTTSIQQ<br>EATSKERIIGV |
| 37 | Human UDP-GlcNAc 2-epimerase/N-acetylmannosamine kinase (HsGNE) codon opitimized | ATGGAAAGAACGGTAACAACAGAAAGTTGAGAGTTTGTGTTGC<br>TACTTGTAACAGAGCTGACTACTCCAAGTTGGCTCCAATCATGTT<br>CGGTATCAAGACTGAGCCAGAGTTCTTCGAGTTGGACGTTGTTGT<br>TTTGGGTTCCCACTTGATTGATGACTACGGTAACACTTACAGAAT<br>GATCGAGCAGGACGACTTCGACATCAACACTAGATTGCACACTA<br>TTGTTAGAGGAGAGGACGAAGCTGCTATGGTTGAATCTGTTGGA<br>TTGGCTTTGGTTAAGTTGCCAGACGTTTTGAACAGATTGAAGCCA<br>GACATCATGATTGTTCACGGTGACAGATTCGATGCTTTGGCTTTG<br>GCTACTTCCGCTGCTTTGATGAACATTAGAATCTTGCACATCGAG<br>GGTGGTGAAGTTTCTGGTACTATCGACGACTCCATCAGACACGCT<br>ATCACTAAGTTGGCTCACTACCATGTTTGTTGTACTAGATCCGCT<br>GAGCAACACTTGATTTCCATGTGTGAGGACCACGACAGAATTTT<br>GTTGGCTGGTTGTCCATCTTACGACAAGTTGTTGTCCGCTAAGAA<br>CAAGGACTACATGTCCATCATCAGAATGTGGTTGGGTGACGACG<br>TTAAGTCTAAGGACTACATCGTTGCTTTGCAGCACCCAGTTACTA<br>CTGACATCAAGCACTCCATCAAGATGTTCGAGTTGACTTTGGACG<br>CTTTGATCTCCTTCAACAAGAGAACTTTGGTTTTGTTCCCAAACA<br>TTGACGCTGGTTCCAAAGAGATGGTTAGAGTTATGAGAAAGAAG<br>GGTATCGAACACCACCCAAACTTCAGAGCTGTTAAGCACGTTCC<br>ATTCGACCAATTCATCCAGTTGGTTGCTCATGCTGGTTGTATGAT<br>CGGTAACTCCTCCTGTGGTGTTAGAGAAGTTGGTGCTTTCGGTAC<br>TCCAGTTATCAACTTGGGTACTAGACAGATCGGTAGAGAGACTG<br>GAGAAAACGTTTTGCATGTTAGAGATGCTGACACTCAGGACAAG<br>ATTTTGCAGGCTTTGCACTTGCAATTCGGAAAGCAGTACCCATGT<br>TCCAAAATCTACGGTGACGGTAACGCTGTTCCAAGAATCTTGAA<br>GTTTTTGAAGTCCATCGACTTGCAAGAGCCATTGCAGAAGAAGTT<br>CTGTTTCCCACCAGTTAAGGAGAACATCTCCCAGGACATTGACCA<br>CATCTTGGAGACATTGTCCGCTTTGGCTGTTGATTTGGGTGGAAC<br>TAACTTGAGAGTTGCTATCGTTTCCATGAAGGGAGAGATCGTTAA<br>GAAGTACACTCAGTTCAACCCAAAGACTTACGAGGAGAGAATCA<br>ACTTGATCTTGCAGATGTGTGTTGAAGCTGCTGCTGAGGCTGTTA<br>AGTTGAACTGTAGAATCTTGGGTGTTGGTATCTCTACTGGTGGTA<br>GAGTTAATCCAAGAGAGGGTATCGTTTTGCACTCCACTAAGTTGA<br>TTCAGGAGTGGAACTCCGTTGATTTGAGAACTCCATTGTCCGACA<br>CATTGCACTTGCCAGTTTGGGTTGACAACGACGGTAATTGTGCTG<br>CTTTGGCTGAGAGAAAGTTCGGTCAAGGAAAGGGATTGGAGAAC<br>TTCGTTACTTTGATCACTGGTACTGGTATTGGTGGTGGTATCATTC<br>ACCAGCACGAGTTGATTCACGGTTCTTCCTTCTGTGCTGCTGAAT<br>TGGGACACTTGGTTGTTTCTTTGGACGGTCCAGACTGTTCTTGTG<br>GTTCCCACGGTTGTATTGAAGCTTACGCATCAGGAATGGCATTGC<br>AGAGAGAGGCTAAGAAGTTGCACGACGAGGACTTGTTGTTGGTT<br>GAGGGAATGTCTGTTCCAAAGGACGAGGCTGTTGGTGCTTTGCA<br>TTTGATCCAGGCTGCTAAGTTGGGTAATGCTAAGGCTCAGTCCAT<br>CTTGAGAACTGCTGGTACTGCTTTGGGATTGGGTGTTGTTAATAT<br>CTTGCACACTATGAACCCATCCTTGGTTATCTTGTCCGGTGTTTTG<br>GCTTCTCACTACATCCACATCGTTAAGGACGTTATCAGACAGCAA<br>GCTTTGTCCTCCGTTCAAGACGTTGATGTTGTTGTTTCCGACTTGG<br>TTGACCCAGCTTTGTTGGGTGCTGCTTCCATGGTTTTGGACTACA<br>CTACTAGAAGAATCTACTAATAG |

TABLE 14-continued

| SEQ ID NO: | Description | Sequence |
|---|---|---|
| 38 | Human UDP-GlcNAc 2-epimerase/N-acetylmannosamine kinase (HsGNE) | MEKNGNNRKLRVCVATCNRADYSKLAPIMFGIKTEPEFFELDVVVL GSHLIDDYGNTYRMIEQDDFDINTRLHTIVRGEDEAAMVESVGLAL VKLPDVLNRLKPDIMIVHGDRFDALALATSAALMNIRILHIEGGEVS GTIDDSIRHAITKLAHYHVCCTRSAEQHLISMCEDHDRILLAGCPSY DKLLSAKNKDYMSIIRMWLGDDVKSKDYIVALQHPVTTDIKHSIKM FELTLDALISFNKRTLVLFPNIDAGSKEMVRVMRKKGIEHHPNFRAV KHVPFDQFIQLVAHAGCMIGNSSCGVREVGAFGTPVINLGTRQIGRE TGENVLHVRDADTQDKILQALHLQFGKQYPCSKIYGDGNAVPRILK FLKSIDLQEPLQKKFCFPPVKENISQDIDHILETLSALAVDLGGTNLR VAIVSMKGEIVKKYTQFNPKTYEERINLILQMCVEAAAEAVKLNCRI LGVGISTGGRVNPREGIVLHSTKLIQEWNSVDLRTPLSDTLHLPVWV DNDGNCAALAERKFGQGKGLENFVTLITGTGIGGGIIHQHELIHGSS FCAAELGHLVVSLDGPDCSCGSHGCIEAYASGMALQREAKKLHDE DLLLVEGMSVPKDEAVGALHLIQAAKLGNAKAQSILRTAGTALGLG VVNILHTMNPSLVILSGVLASHYIHIVKDVIRQQALSSVQDVDVVVS DLVDPALLGAASMVLDYTTRRIY |
| 39 | Human CMP-sialic acid synthase (HsCSS) codon optimized | ATGGACTCTGTTGAAAAGGGTGCTGCTACTTCTGTTTCCAACCCA AGAGGTAGACCATCCAGAGGTAGACCTCCTAAGTTGCAGAGAAA CTCCAGAGGTGGTCAAGGTAGAGGTGTTGAAAAGCCACCACACT TGGCTGCTTTGATCTTGGCTAGAGGAGGTTCAAGGGTATCCCAT TGAAGAACATCAAGCACTTGGCTGGTGTTCCATTGATTGGATGG GTTTTGAGAGCTGCTTTGGACTCTGGTGCTTTCCAATCTGTTTGG GTTTCCACTGACCACGACGAGATTGAGAACGTTGCTAAGCAATT CGGTGCTCAGGTTCACAGAAGATCCTCTGAGGTTTCCAAGGACTC TTCTACTTCCTTGGACGCTATCATCGAGTTCTTGAACTACCACAA CGAGGTTGACATCGTTGGTAACATCCAAGCTACTTCCCCATGTTT GCACCCAACTGACTTGCAAAAAGTTGCTGAGATGATCAGAGAAG AGGGTTACGACTCCGTTTTCTCCGTTGTTAGAAGGCACCAGTTCA GATGGTCCGAGATTCAGAAGGGTGTTAGAGAGGTTACAGAGCCA TTGAACTTGAACCCAGCTAAAAGACCAAGAAGGCAGGATTGGGA CGGTGAATTGTACGAAAACGGTTCCTTCTACTTCGCTAAGAGACA CTTGATCGAGATGGGATACTTGCAAGGTGGAAAGATGGCTTACT ACGAGATGAGAGCTGAACACTCCGTTGACATCGACGTTGATATC GACTGGCCAATTGCTGAGCAGAGAGTTTTGAGATACGGTTACTTC GGAAAGGAGAAGTTGAAGGAGATCAAGTTGTTGGTTTGTAACAT CGACGGTTGTTTGACTAACGGTCACATCTACGTTTCGGTGACCA GAAGGAGATTATCTCCTACGACGTTAAGGACGCTATTGGTATCTC CTTGTTGAAGAAGTCCGGTATCGAAGTTAGATTGATCTCCGAGA GAGCTTGTTCCAAGCAAACATTGTCCTCTTTGAAGTTGGACTGTA AGATGGAGGTTTCCGTTTCTGACAAGTTGGCTGTTGTTGACGAAT GGAGAAAGGAGATGGGTTTGTGTTGGAAGGAAGTTGCTTACTTG GGTAACGAAGTTTCTGACGAGGAGTGTTTGAAGAGAGTTGGTTT GTCTGGTGCTCCAGCTGATGCTTGTTCCACTGCTCAAAAGGCTGT TGGTTACATCTGTAAGTGTAACGGTGGTAGAGGTGCTATTAGAG AGTTCGCTGAGCACATCTGTTTGTTGATGGAGAAAGTTAATAACT CCTGTCAGAAGTAGTAG |
| 40 | Human CMP-sialic acid synthase (HsCSS) | MDSVEKGAATSVSNPRGRPSRGRPPKLQRNSRGGQGRGVEKPPHLA ALILARGGSKGIPLKNIKHLAGVPLIGWVLRAALDSGAFQSVWVST DHDEIENVAKQFGAQVHRRSSEVSKDSSTSLDAIIEFLNYHNEVDIV GNIQATSPCLHPTDLQKVAEMIREEGYDSVFSVVRRHQFRWSEIQK GVREVTEPLNLNPAKRPRRQDWDGELYENGSFYFAKRHLIEMGYL QGGKMAYYEMRAEHSVDIDVDIDWPIAEQRVLRYGYFGKEKLKEI KLLVCNIDGCLTNGHIYVSGDQKEIISYDVKDAIGISLLKKSGIEVRLI SERACSKQTLSSLKLDCKMEVSVSDKLAVVDEWRKEMGLCWKEV AYLGNEVSDEECLKRVGLSGAPADACSTAQKAVGYICKCNGGRGA IREFAEHICLLMEKVNNSCQK |
| 41 | Human N-acetylneuraminate-9-phosphate synthase (HsSPS) codon optimized | ATGCCATTGGAATTGGAGTTGTGTCCTGGTAGATGGGTTGGTGGT CAACACCCATGTTTCATCATCGCTGAGATCGGTCAAAACCACCA AGGAGACTTGGACGTTGCTAAGAGAATGATCAGAATGGCTAAGG AATGTGGTGCTGACTGTGCTAAGTTCCAGAAGTCCGAGTTGGAG TTCAAGTTCAACAGAAAGGCTTTGGAAAGACCATACACTTCCAA GCACTCTTGGGGAAAGACTTACGAGAACACAAGAGACACTTGG AGTTCTCTCACGACCAATACAGAGAGTTGCAGAGATACGCTGAG GAAGTTGGTATCTTCTTCACTGCTTCTGGAATGGACGAAATGGCT GTTGAGTTCTTGCACGAGTTGAACGTTCCATTCTTCAAAGTTGGT TCCGGTGACACTAACAACTTCCCATACTTGGAAAAGACTGCTAA GAAAGGTAGACCAATGGTTATCTCCTCTGGAATGCAGTCTATGG ACACTATGAAGCAGGTTTACCAGATCGTTAAGCCATTGAACCCA AACTTTTGTTTCTTGCAGTGTACTTCCGCTTACCCATTGCAACCAG AGGACGTTAATTTGAGAGTTATCTCCGAGTACCAGAAGTTGTTCC CAGACATCCCAATTGGTTACTCTGGTCACGAGACTGGTATTGCTA TTTCCGTTGCTGCTGTTGCTTTGGGTGCTAAGGTTTTGGAGAGAC ACATCACTTTGGACAAGACTTGGAAGGGTTCTGATCACTCTGCTT CTTTGGAACCTGGTGAGTTGGCTGAACTTGTTAGATCAGTTAGAT |

TABLE 14-continued

| SEQ ID NO: | Description | Sequence |
|---|---|---|
| | | TGGTTGAGAGAGCTTTGGGTTCCCCAACTAAGCAATTGTTGCCAT GTGAGATGGCTTGTAACGAGAAGTTGGGAAAGTCCGTTGTTGCT AAGGTTAAGATCCCAGAGGGTACTATCTTGACTATGGACATGTT GACTGTTAAAGTTGGAGAGCCAAAGGGTTACCCACCAGAGGACA TCTTTAACTTGGTTGGTAAAAAGGTTTTGGTTACTGTTGAGGAGG ACGACACTATTATGGAGGAGTTGGTTGACAACCACGGAAAGAAG ATCAAGTCCTAG |
| 42 | Human N-acetylneuraminate-9-phosphate synthase (HsSPS) | MPLELELCPGRWVGGQHPCFIIAEIGQNHQGDLDVAKRMIRMAKEC GADCAKFQKSELEFKFNRKALERPYTSKHSWGKTYGEHKRHLEFSH DQYRELQRYAEEVGIFFTASGMDEMAVEFLHELNVPFFKVGSGDTN NFPYLEKTAKKGRPMVISSGMQSMDTMKQVYQIVKPLNPNFCFLQC TSAYPLQPEDVNLRVISEYQKLFPDIPIGYSGHETGIAISVAAVALGA KVLERHITLDKTWKGSDHSASLEPGELAELVRSVRLVERALGSPTK QLLPCEMACNEKLGKSVVAKVKIPEGTILTMDMLTVKVGEPKGYPP EDIFNLVGKKVLVTVEEDDTIMEELVDNHGKKIKS |
| 43 | Mouse alpha-2,6-sialyl transferase catalytic domain (MmmST6) codon optimized | GTTTTTCAAATGCCAAAGTCCCAGGAGAAAGTTGCTGTTGGTCCA GCTCCACAAGCTGTTTTCTCCAACTCCAAGCAAGATCCAAAGGA GGGTGTTCAAATCTTGTCCTACCCAAGAGTTACTGCTAAGGTTAA GCCACAACCATCCTTGCAAGTTTGGGACAAGGACTCCACTTACTC CAAGTTGAACCCAAGATTGTTGAAGATTTGGAGAAACTACTTGA ACATGAACAAGTACAAGGTTTCCTACAAGGGTCCAGGTCCAGGT GTTAAGTTCTCCGTTGAGGCTTTGAGATGTCACTTGAGAGACCAC GTTAACGTTTCCATGATCGAGGCTACTGACTTCCCATTCAACACT ACTGAATGGGAGGGATACTTGCCAAAGGAGAACTTCAGAACTAA GGCTGGTCCATGGCATAAGTGTGCTGTTGTTTCTTCTGCTGGTTC CTTGAAGAACTCCCAGTTGGGTAGAGAAATTGACAACCACGACG CTGTTTTGAGATTCAACGGTGCTCCAACTGACAACTTCCAGCAGG ATGTTGGTACTAAGACTACTATCAGATTGGTTAACTCCCAATTGG TTACTACTGAGAAGAGATTCTTGAAGGACTCCTTGTACACTGAGG GAATCTTGATTTTGTGGGACCCATCTGTTTACCACGCTGACATTC CACAATGGTATCAGAAGCCAGACTACAACTTCTTCGAGACTTAC AAGTCCTACAGAAGATTGCACCCATCCCAGCCATTCTACATCTTG AAGCCACAAATGCCATGGGAATTGTGGGACATCATCCAGGAAAT TTCCCCAGACTTGATCCAACCAAACCCACCATCTTCTGGAATGTT GGGTATCATCATCATGATGACTTTGTGTGACCAGGTTGACATCTA CGAGTTCTTGCCATCCAAGAGAAAGACTGATGTTTGTTACTACCA CCAGAAGTTCTTCGACTCCGCTTGTACTATGGGAGCTTACCACCC ATTGTTGTTCGAGAAGAACATGGTTAAGCACTTGAACGAAGGTA CTGACGAGGACATCTACTTGTTCGGAAAGGCTACTTTGTCCGGTT TCAGAAACAACAGATGTTAG |
| 44 | Mouse alpha-2,6-sialyl transferase catalytic domain (MmmST6) | VFQMPKSQEKVAVGPAPQAVFSNSKQDPKEGVQILSYPRVTAKVKP QPSLQVWDKDSTYSKLNPRLLKIWRNYLNMNKYKVSYKGPGPGVK FSVEALRCHLRDHVNVSMIEATDFPPFNTTEWEGYLPKENFRTKAGP WHKCAVVSSAGSLKNSQLGREIDNHDAVLRFNGAPTDNFQQDVGT KTTIRLVNSQLVTTEKRFLKDSLYTEGILILWDPSVYHADIPQWYQK PDYNFFETYKS YRRLHPSQPFYILKPQMPWELWDIIQEISPDLIQPNPPSSGMLGIIMM TLCDQVDIYEFLPSKRKTDVCYYHQKFFDSACTMGAYHPLLFEKNM VKHLNEGTDEDIYLFGKATLSGFRNNRC |
| 45 | Sequence of the PpPMA1 promoter: | AAATGCGTACCTCTTCTACGAGATTCAAGCGAATGAGAATAATG TAATATGCAAGATCAGAAAGAATGAAAGGAGTTGAAAAAAAAA ACCGTTGCGTTTTGACCTTGAATGGGGTGGAGGTTTCCATTCAAA GTAAAGCCTGTGTCTTGGTATTTTCGGCGGCACAAGAAATCGTAA TTTTCATCTTCTAAACGATGAAGATCGCAGCCCAACCTGTATGTA GTTAACCGGTCGGAATTATAAGAAAGATTTTCGATCAACAAACC CTAGCAAATAGAAAGCAGGGTTACAACTTTAAACCGAAGTCACA AACGATAAACCACTCAGCTCCCACCCAAATTCATTCCCACTAGCA GAAAGGAATTATTTAATCCCTCAGGAAACCTCGATGATTCTCCCG TTCTTCCATGGGCGGGTATCGCAAAATGAGGAATTTTTCAAATTT CTCTATTGTCAAGACTGTTTATTATCTAAGAAATAGCCCAATCCG AAGCTCAGTTTTGAAAAAATCACTTCCGCGTTTCTTTTTTACAGC CCGATGAATATCCAAATTTGGAATATGGATTACTCTATCGGGACT GCAGATAATATGACAACAACGCAGATTACATTTTAGGTAAGGCA TAAACACCAGCCAGAAATGAAACGCCCACTAGCCATGGTCGAAT AGTCCAATGAATTCAGATAGCTATGGTCTAAAAGCTGATGTTTTT TATTGGGTAATGGCGAAGAGTCCAGTACGACTTCCAGCAGAGCT GAGATGGCCATTTTTGGGGGTATTAGTAACTTTTTGAGCTCTTTT CACTTCGATGAAGTGTCCCATTCGGGATATAATCGGATCGTCTCG TTTTTCTCGAAAATACAGCTTAGCGTCGTCCGCTTGTTGTAAAAGC AGCACCACATTCCTAATCTCTTATATAAACAAAACAACCCAAATT ATCAGTGCTGTTTTCCCACCAGATATAAGTTTCTTTTCTCTTCCGC TTTTTGATTTTTTATCTCTTTCCTTTAAAAACTTCTTTACCTTAAAG GGCGGCC |

TABLE 14-continued

| SEQ ID NO: | Description | Sequence |
|---|---|---|
| 46 | Sequence of the PpPMA1 terminator: | TAAGCTTCACGATTTGTGTTCCAGTTTATCCCCCCTTTATATACCG<br>TTAACCCTTTCCCTGTTGAGCTGACTGTTGTTGTATTACCGCAATT<br>TTTCCAAGTTTGCCATGCTTTTCGTGTTATTTGACCGATGTCTTTT<br>TTCCCAAATCAAACTATATTTGTTACCATTTAAACCAAGTTATCT<br>TTTGTATTAAGAGTCTAAGTTTGTTCCCAGGCTTCATGTGAGAGT<br>GATAACCATCCAGACTATGATTCTTGTTTTTTATTGGGTTTGTTTG<br>TGTGATACATCTGAGTTGTGATTCGTAAAGTATGTCAGTCTATCT<br>AGATTTTTAATAGTTAATTGGTAATCAATGACTTGTTTGTTTTAAC<br>TTTTAAATTGTGGGTCGTATCCACGCGTTTAGTATAGCTGTTCAT<br>GGCTGTTAGAGGAGGGCGATGTTTATATACAGAGGACAAGAATG<br>AGGAGGCGGCGTGTATTTTTAAAATGGAGACGCGACTCCTGTAC<br>ACCTTATCGGTTGG |
| 47 | Sequence of the PpOCH1 promoter: | TGGACACAGGAGACTCAGAAACAGACACAGAGCGTTCTGAGTCC<br>TGGTGCTCCTGACGTAGGCCTAGAACAGGAATTATTGGCTTTATT<br>TGTTTGTCCATTTCATAGGCTTGGGGTAATAGATAGATGACAGAG<br>AAATAGAGAAGACCTAATATTTTTGTTCATGGCAAATCGCGGGT<br>TCGCGGTCGGGTCACACACGGAGAAGTAATGAGAAGAGCTGGTA<br>ATCTGGGGTAAAAGGGTTCAAAAGAAGGTCGCCTGGTAGGGATG<br>CAATACAAGGTTGTCTTGGAGTTTACATTGACCAGATGATTTGGC<br>TTTTTCTCTGTTCAATTCACATTTTTCAGCGAGAATCGGATTGACG<br>GAGAAATGGCGGGGTGTGGGGTGGATAGATGGCAGAAATGCTC<br>GCAATCACCGCGAAAGAAAGACTTTATGGAATAGAACTACTGGG<br>TGGTGTAAGGATTACATAGCTAGTCCAATGGAGTCCGTTGGAAA<br>GGTAAGAAGAAGCTAAAACCGGCTAAGTAACTAGGGAAGAATG<br>ATCAGACTTTGATTTGATGAGGTCTGAAAATACTCTGCTGCTTTT<br>TCAGTTGCTTTTTCCCTGCAACCTATCATTTTCCTTTTCATAAGCC<br>TGCCTTTTCTGTTTTCACTTATATGAGTTCCGCCGAGACTTCCCCA<br>AATTCTCTCCTGGAACATTCTCTATCGCTCTCCTTCCAAGTTGCGC<br>CCCCTGGCACTGCCTAGTAATATTACCACGCGACTTATATTCAGT<br>TCCACAATTTCCAGTGTTCGTAGCAAATATCATCAGCC |
| 48 | Sequence of the PpALG12 terminator: | AATATATACCTCATTTGTTCAATTTGGTGTAAAGAGTGTGGCGGA<br>TAGACTTCTTGTAAATCAGGAAAGCTACAATTCCAATTGCTGCAA<br>AAAATACCAATGCCCATAAACCAGTATGAGCGGTGCCTTCGACG<br>GATTGCTTACTTTCCGACCCTTTGTCGTTTGATTCTTCTGCCTTTG<br>GTGAGTCAGTTTGTTTCGACTTTATATCTGACTCATCAACTTCCTT<br>TACGGTTGCGTTTTTAATCATAATTTTAGCCGTTGGCTTATTATCC<br>CTTGAGTTGGTAGGAGTTTTGATGATGCTG |
| 49 | Sequence of the PpSEC4 promoter: | GAAGTAAAGTTGGCGAAACTTTGGGAACCTTTGGTTAAAACTTT<br>GTAATTTTTGTCGCTACCCATTAGGCAGAATCTGCATCTTGGGAG<br>GGGGATGTGGTGGCGTTCTGAGATGTACGCGAAGAATGAAGAGC<br>CAGTGGTAACAACAGGCCTAGAGAGATACGGGCATAATGGGTAT<br>AACCTACAAGTTAAGAATGTAGCAGCCCTGGAAACCAGATTGAA<br>ACGAAAAACGAAATCATTTAAACTGTAGGATGTTTTGGCTCATTG<br>TCTGGAAGGCTGGCTGTTTATTGCCCTGTTCTTTGCATGGGAATA<br>AGCTATTATATCCCTCACATAATCCCAGAAAATAGATTGAAGCA<br>ACGCGAAATCCTTACGTATCGAAGTAGCCTTCTTACACATTCACG<br>TTGTACGGATAAGAAAACTACTCAAACGAACAATC |
| 50 | Sequence of the PpOCH1 terminator: | AATAGATATAGCGAGATTAGAGAATGAATACCTTCTTCTAAGCG<br>ATCGTCCGTCATCATAGAATATCATGGACTGTATAGTTTTTTTTT<br>GTACATATAATGATTAAACGGTCATCCAACATCTCGTTGACAGAT<br>CTCTCAGTACGCGAAATCCCTGACTATCAAAGCAAGAACCGATG<br>AAGAAAAAAACAACAGTAACCCAAACACCACAACAAACACTTT<br>ATCTTCTCCCCCCCAACACCAATCATCAAAGAGATGTCGGAACA<br>CAAACACCAAGAAGCAAAAACTAACCCCATATAAAAACATCCTG<br>GTAGATAATGCTGGTAACCCGCTCTCCTTCCATATTCTGGGCTAC<br>TTCACGAAGTCTGACCGGTCTCAGTTGATCAACATGATCCTCGAA<br>ATGG |
| 51 | Sequence of the PpTEF1 promoter | TTAAGGTTTGGAACAACACTAAACTACCTTGCGGTACTACCATTG<br>ACACTACACATCCTTAATTCCAATCCTGTCTGGCCTCCTTCACCTT<br>TTAACCATCTTGCCCATTCCAACTCGTGTCAGATTGCGTATCAAG<br>TGAAAAAAAAAAATTTTAAATCTTTAACCCAATCAGGTAATAA<br>CTGTCGCCTCTTTTATCTGCCGCACTGCATGAGGTGTCCCCTTAGT<br>GGGAAAGAGTACTGAGCCAACCCTGGAGGACAGCAAGGGAAAA<br>ATACCTACAACTTGCTTCATAATGGTCGTAAAACAATCCTTGTC<br>GGATATAAGTGTTGTAGACTGTCCCTTATCCTCTGCGATGTTCTT<br>CCTCTCAAAGTTTGCGATTTCTCTCTATCAGAATTGCCATCAAGA<br>GACTCAGGACTAATTTCGCAGTCCCACACGCACTCGTACATGATT<br>GGCTGAAATTTCCCTAAAGAATTTCTTTTTCACGAAAATTTTTTTT<br>TTACACAAGATTTTCAGCAGATATAAAATGGAGAGCAGGACCTC<br>CGCTGTGACTCTTCTTTTTTTCTTTTATTCTCACTACATACATTTT<br>AGTTATTCGCCAAC |

TABLE 14-continued

| SEQ ID NO: | Description | Sequence |
|---|---|---|
| 52 | Sequence of the PpTEF1 terminator: | ATTGCTTGAAGCTTTAATTTATTTTATTAACATAATAATAATACA<br>AGCATGATATATTTGTATTTTGTTCGTTAACATTGATGTTTTCTTC<br>ATTTACTGTTATTGTTTGTAACTTTGATCGATTTATCTTTTCTACTT<br>TACTGTAATATGGCTGGCGGGTGAGCCTTGAACTCCCTGTATTAC<br>TTTACCTTGCTATTACTTAATCTATTGACTAGCAGCGACCTCTTCA<br>ACCGAAGGGCAAGTACACAGCAAGTTCATGTCTCCGTAAGTGTC<br>ATCAACCCTGGAAACAGTGGGCCATGTC |
| 53 | Sequence of the PpGAPDH promoter: | TTTTTGTAGAAATGTCTTGGTGTCCTCGTCCAATCAGGTAGCCAT<br>CTCTGAAATATCTGGCTCCGTTGCAACTCCGAACGACCTGCTGGC<br>AACGTAAAATTCTCCGGGGTAAAACTTAAATGTGGAGTAATGGA<br>ACCAGAAACGTCTCTTCCCTTCTCTCTCCTTCCACCGCCCGTTACC<br>GTCCCTAGGAAATTTTACTCTGCTGGAGAGCTTCTTCTACGGCCC<br>CCTTGCAGCAATGCTCTTCCCAGCATTACGTTGCGGGTAAAACGG<br>AGGTCGTGTACCCGACCTAGCAGCCCAGGGATGGAAAAGTCCCG<br>GCCGTCGCTGGCAATAATAGCGGGCGGACGCATGTCATGAGATT<br>ATTGGAAACCACCAGAATCGAATATAAAAGGCGAACACCTTTCC<br>CAATTTTGGTTTCTCCTGACCCAAAGACTTTAAATTTAATTTATTT<br>GTCCCTATTTCAATCAATTGAACAACTATCAAAACACA |
| 54 | Sequence of the PpALG3 terminator: | ATTTACAATTAGTAATATTAAGGTGGTAAAAACATTCGTAGAATT<br>GAAATGAATTAATATAGTATGACAATGGTTCATGTCTATAAATCT<br>CCGGCTTCGGTACCTTCTCCCCAATTGAATACATTGTCAAAATGA<br>ATGGTTGAACTATTAGGTTCGCCAGTTTCGTTATTAAGAAAACTG<br>TTAAAATCAAATTCCATATCATCGGTTCCAGTGGGAGGACCAGTT<br>CCATCGCCAAAATCCTGTAAGAATCCATTGTCAGAACCTGTAAA<br>GTCAGTTTGAGATGAAATTTTCCGGTCTTTGTTGACTTGGAAGC<br>TTCGTTAAGGTTAGGTGAAACAGTTTGATCAACCAGCGGCTCCCG<br>TTTTCGTCGCTTAGTAG |
| 55 | Sequence of the PpAOX1 promoter and integration locus: | AACATCCAAAGACGAAAGGTTGAATGAAACCTTTTTGCCATCCG<br>ACATCCACAGGTCCATTCTCACACATAAGTGCCAAACGCAACAG<br>GAGGGGATACACTAGCAGCAGACCGTTGCAAACGCAGGACCTCC<br>ACTCCTCTTCTCCTCAACACCCACTTTTGCCATCGAAAAACCAGC<br>CCAGTTATTGGGCTTGATTGGAGCTCGCTCATTCCAATTCCTTCT<br>ATTAGGCTACTAACACCATGACTTTATTAGCCTGTCTATCCTGGC<br>CCCCCTGGCGAGGTTCATGTTTGTTTATTTCCGAATGCAACAAGC<br>TCCGCATTACACCCGAACATCACTCCAGATGAGGGCTTTCTGAGT<br>GTGGGGTCAAATAGTTTCATGTTCCCCAAATGGCCCAAAACTGA<br>CAGTTTAAACGCTGTCTTGGAACCTAATATGACAAAAGCGTGAT<br>CTCATCCAAGATGAACTAAGTTTGGTTCGTTGAAATGCTAACGGC<br>CAGTTGGTCAAAAAGAAACTTCCAAAAGTCGGCATACCGTTTGT<br>CTTGTTTGGTATTGATTGACGAATGCTCAAAAATAATCTCATTAA<br>TGCTTAGCGCAGTCTCTCTATCGCTTCTGAACCCCGGTGCACCTG<br>TGCCGAAACGCAAATGGGGAAACACCCGCTTTTTGGATGATTAT<br>GCATTGTCTCCACATTGTATGCTTCCAAGATTCTGGTGGGAATAC<br>TGCTGATAGCCTAACGTTCATGATCAAAATTTAACTGTTCTAACC<br>CCTACTTGACAGCAATATATAAACAGAAGGAAGCTGCCCTGTCT<br>TAAACCTTTTTTTTTATCATCATTATTAGCTTACTTTCATAATTGC<br>GACTGGTTCCAATTGACAAGCTTTTGATTTTAACGACTTTTAACG<br>ACAACTTGAGAAGATCAAAAAACAACTAATTATTCGAAACG |
| 56 | Sequence of the ScCYC1 terminator: | ACAGGCCCCTTTTCCTTTGTCGATATCATGTAATTAGTTATGTCAC<br>GCTTACATTCACGCCCTCCTCCCACATCCGCTCTAACCGAAAGG<br>AAGGAGTTAGACAACCTGAAGTCTAGGTCCCTATTTATTTTTTT<br>AATAGTTATGTTAGTATTAAGAACGTTATTTATATTTCAAATTTTT<br>CTTTTTTTTCTGTACAAACGCGTGTACGCATGTAACATTATACTG<br>AAAACCTTGCTTGAGAAGGTTTTGGGACGCTCGAAGGCTTTAATT<br>TGCAAGCTGCCGGCTCTTAAG |
| 57 | Sequence of the ScTEF1 promoter: | GATCCCCCACACACCATAGCTTCAAAATGTTTCTACTCCTTTTTA<br>CTCTTCCAGATTTTCTCGGACTCCGCGCATCGCCGTACCACTTCA<br>AAACACCCAAGCACAGCATACTAAATTTCCCCTCTTTCTTCCTCT<br>AGGGTGTCGTTAATTACCCGTACTAAAGGTTTGGAAAAGAAAAA<br>AGAGACCGCCTCGTTTCTTTTTCTTCGTCGAAAAAGGCAATAAAA<br>ATTTTTATCACGTTTCTTTTTCTTGAAAATTTTTTTTTTGATTTTT<br>TTCTCTTTCGATGACCTCCCATTGATATTTAAGTTAATAAACGGT<br>CTTCAATTTCTCAAGTTTCAGTTTCATTTTCTTGTTCTATTACAA<br>CTTTTTTTACTTCTTGCTCATTAGAAAGAAAGCATAGCAATCTAA<br>TCTAAGTTTTAATTACAAA |

TABLE 14-continued

| SEQ ID NO: | Description | Sequence |
|---|---|---|
| 58 | Sequence of the Shble ORF (Zeocin resistance marker): | ATGGCCAAGTTGACCAGTGCCGTTCCGGTGCTCACCGCGCGCGA<br>CGTCGCCGGAGCGGTCGAGTTCTGGACCGACCGGCTCGGGTTCT<br>CCCGGGACTTCGTGGAGGACGACTTCGCCGGTGTGGTCCGGGAC<br>GACGTGACCCTGTTCATCAGCGCGGTCCAGGACCAGGTGGTGCC<br>GGACAACACCCTGGCCTGGGTGTGGGTGCGCGGCCTGGACGAGC<br>TGTACGCCGAGTGGTCGGAGTCGTGTCCACGAACTTCCGGGAC<br>GCCTCCGGGCCGGCCATGACCGAGATCGGCGAGCAGCCGTGGGG<br>GCGGGAGTTCGCCCTGCGCGACCCGGCCGGCAACTGCGTGCACT<br>TCGTGGCCGAGGAGCAGGACTGA |
| 59 | Sequence of the 5'-Region used for knock out of PpURA5: | ATCGGCCTTTGTTGATGCAAGTTTTACGTGGATCATGGACTAAGG<br>AGTTTTATTTGGACCAAGTTCATCGTCCTAGACATTACGGAAAGG<br>GTTCTGCTCCTCTTTTTGGAAACTTTTTGGAACCTCTGAGTATGAC<br>AGCTTGGTGGATTGTACCCATGGTATGGCTTCCTGTGAATTTCTA<br>TTTTTTTCTACATTGGATTCACCAATCAAAACAAATTAGTCGCCAT<br>GGCTTTTTGGCTTTTGGGTCTATTTGTTTGGACCTTCTTGGAATAT<br>GCTTTGCATAGATTTTTGTTCCACTTGGACTACTATCTTCCAGAG<br>AATCAAATTGCATTTACCATTCATTTCTTATTGCATGGGATACAC<br>CACTATTTACCAATGGATAAATACAGATTGGTGATGCCACCTACA<br>CTTTTCATTGTACTTTGCTACCCAATCAAGACGCTCGTCTTTTCTG<br>TTCTACCATATTACATGGCTTGTTCTGGATTTGCAGGTGGATTCCT<br>GGGCTATATCATGTATGATGTCACTCATTACGTTCTGCATCACTC<br>CAAGCTGCCTCGTTATTTCCAAGAGTTGAAGAAATATCATTTGGA<br>ACATCACTACAAGAATTACGAGTTAGGCTTTGGTGTCACTTCCAA<br>ATTCTGGGACAAAGTCTTTGGGACTTATCTGGGTCCAGACGATGT<br>GTATCAAAAGACAAATTAGAGTATTTATAAAGTTATGTAAGCAA<br>ATAGGGGCTAATAGGGAAAGAAAAATTTTGGTTCTTTATCAGAG<br>CTGGCTCGCGCGCAGTGTTTTTCGTGCTCCTTTGTAATAGTCATTT<br>TTGACTACTGTTCAGATTGAAATCACATTGAAGATGTCACTCGAG<br>GGGTACCAAAAAAGGTTTTTGGATGCTGCAGTGGCTTCGC |
| 60 | Sequence of the 3'-Region used for knock out of PpURA5: | GGTCTTTTCAACAAAGCTCCATTAGTGAGTCAGCTGGCTGAATCT<br>TATGCACAGGCCATCATTAACAGCAACCTGGAGATAGACGTTGT<br>ATTTGGACCAGCTTATAAAGGTATTCCTTTGGCTGCTATTACCGT<br>GTTGAAGTTGTACGAGCTCGGCGGCAAAAAATACGAAAATGTCG<br>GATATGCGTTCAATAGAAAAGAAAAGAAAGACCACGGAGAAGG<br>TGGAAGCATCGTTGGAGAAAGTCTAAAGAATAAAAGAGTACTGA<br>TTATCGATGATGTGATGACTGCAGGTACTGCTATCAACGAAGCAT<br>TTGCTATAATTGGAGCTGAAGGTGGGAGAGTTGAAGGTAGTATT<br>ATTGCCCTAGATAGAATGGAGACTACAGGAGATGACTCAAATAC<br>CAGTGCTACCCAGGCTGTTAGTCAGAGATATGGTACCCCTGTCTT<br>GAGTATAGTGACATTGGACCATATTGTGGCCCATTTGGGCGAAA<br>CTTTCACAGCAGACGAGAAATCTCAAATGGAAACGTATAGAAAA<br>AAGTATTTGCCCAAATAAGTATGAATCTGCTTCGAATGAATGAAT<br>TAATCCAATTATCTTCTCACCATTATTTTCTTCTGTTTCGGAGCTT<br>TGGGCACGGCGGCGGGTGGTGCGGGCTCAGGTTCCCTTTCATAA<br>ACAGATTTAGTACTTGGATGCTTAATAGTGAATGGCGAATGCAA<br>AGGAACAATTTCGTTCATCTTTAACCCTTTCACTCGGGGTACACG<br>TTCTGGAATGTACCCGCCCTGTTGCAACTCAGGTGGACCGGGCA<br>ATTCTTGAACTTTCTGTAACGTTGTTGGATGTTCAACCAGAAATT<br>GTCCTACCAACTGTATTAGTTTCCTTTTGGTCTTATATTGTTCATC<br>GAGATACTTCCCACTCTCCTTGATAGCCACTCTCACTCTTCCTGG<br>ATTACCAAAATCTTGAGGATGAGTCTTTTCAGGCTCCAGGATGCA<br>AGGTATATCCAAGTACCTGCAAGCATCTAATATTGTCTTTGCCAG<br>GGGGTTCTCCACACCATACTCCTTTTGGCGCATGC |
| 61 | Sequence of the PpURA5 auxotrophic marker: | TCTAGAGGGACTTATCTGGGTCCAGACGATGTGTATCAAAAGAC<br>AAATTAGAGTATTTATAAAGTTATGTAAGCAAATAGGGGCTAAT<br>AGGGAAAGAAAAATTTTGGTTCTTTATCAGAGCTGGCTCGCGCG<br>CAGTGTTTTTCGTGCTCCTTTGTAATAGTCATTTTTGACTACTGTT<br>CAGATTGAAATCACATTGAAGATGTCACTGGAGGGGTACCAAAA<br>AAGGTTTTTGGATGCTGCAGTGGCTTCGCAGGCCTTGAAGTTTGG<br>AACTTTCACCTTGAAAAGTGGAAGACAGTCTCCATACTTCTTTAA<br>CATGGGTCTTTTCAACAAAGCTCCATTAGTGAGTCAGCTGGCTGA<br>ATCTTATGCTCAGGCCATCATTAACAGCAACCTGGAGATAGACG<br>TTGTATTTGGACCAGCTTATAAAGGTATTCCTTTGGCTGCTATTA<br>CCGTGTTGAAGTTGTACGAGCTGGGCGGCAAAAAATACGAAAAT<br>GTCGGATATGCGTTCAATAGAAAAGAAAAGAAAGACCACGGAG<br>AAGGTGGAAGCATCGTTGGAGAAAGTCTAAAGAATAAAAGAGT<br>ACTGATTATCGATGATGTGATGACTGCAGGTACTGCTATCAACGA<br>AGCATTTGCTATAATTGGAGCTGAAGGTGGGAGAGTTGAAGGTT<br>GTATTATTGCCCTAGATAGAATGGAGACTACAGGAGATGACTCA<br>AATACCAGTGCTACCCAGGCTGTTAGTCAGAGATATGGTACCCCT<br>GTCTTGAGTATAGTGACATTGGACCATATTGTGGCCCATTTGGGC |

TABLE 14-continued

| SEQ ID NO: | Description | Sequence |
|---|---|---|
| | | GAAACTTTCACAGCAGACGAGAAATCTCAAATGGAAACGTATAG AAAAAAGTATTTGCCCAAATAAGTATGAATCTGCTTCGAATGAA TGAATTAATCCAATTATCTTCTCACCATTATTTTCTTCTGTTTCGG AGCTTTGGGCACGGCGGCGGATCC |
| 62 | Sequence of the part of the Ec lacZ gene that was used to construct the PpURA5 blaster (recyelable auxotrophic marker) | CCTGCACTGGATGGTGGCGCTGGATGGTAAGCCGCTGGCAAGCG GTGAAGTGCCTCTGGATGTCGCTCCACAAGGTAAACAGTTGATT GAACTGCCTGAACTACCGCAGCCGGAGAGCGCCGGGCAACTCTG GCTCACAGTACGCGTAGTGCAACCGAACGCGACCGCATGGTCAG AAGCCGGGCACATCAGCGCCTGGCAGCAGTGGCGTCTGGCGGAA AACCTCAGTGTGACGCTCCCCGCCGCGTCCCACGCCATCCCGCAT CTGACCACCAGCGAAATGGATTTTTGCATCGAGCTGGGTAATAA GCGTTGGCAATTTAACCGCCAGTCAGGCTTTCTTTCACAGATGTG GATTGGCGATAAAAAACAACTGCTGACGCCGCTGCGCGATCAGT TCACCCGTGCACCGCTGGATAACGACATTGGCGTAAGTGAAGCG ACCCGCATTGACCCTAACGCCTGGGTCGAACGCTGGAAGGCGGC GGGCCATTACCAGGCCGAAGCAGCGTTGTTGCAGTGCACGGCAG ATACACTTGCTGATGCGGTGCTGATTACGACCGCTCACGCGTGGC AGCATCAGGGGAAAACCTTATTTATCAGCCGGAAAACCTACCGG ATTGATGGTAGTGGTCAAATGGCGATTACCGTTGATGTTGAAGTG GCGAGCGATACACCGCATCCGGCGCGGATTGGCCTGAACTGCCAG |
| 63 | PpURA5 amino acid sequence | MSLEGYQKRFLDAAVASQALKFGTFTLKSGRQSPYFFNMGLFNKAP LVSQLAESYAQAIINSNLEIDVVFGPAYKGIPLAAITVLKLYELGGKK YENVGYAFNRKEKKDHGEGGSIVGESLKNKRVLIIDDVMTAGTAIN EAFAIIGAEGGRVEGCIIALDRMETTGDDSNTSATQAVSQRYGTPVL SIVTLDHIVAHLGETFTADEKSQMETYRKKYLPKZ |
| 64 | Sequence of the 5'-Region used for knock out of PpOCH1: | AAAACCTTTTTTCCTATTCAAACACAAGGCATTGCTTCAACACGT GTGCGTATCCTTAACACAGATACTCCATACTTCTAATAATGTGAT AGACGAATACAAAGATGTTCACTCTGTGTTGTGTCTACAAGCATT TCTTATTCTGATTGGGGATATTCTAGTTACAGCACTAAACAACTG GCGATACAAACTTAAATTAAATAATCCGAATCTAGAAAATGAAC TTTTTGGATGGTCCGCCTGTTGGTTGGATAAATCAATACCGATTAA ATGGATTCTATTCCAATGAGACACTCTGATGT CAATAATCATTTGCTTGCAACAACAAACCCGTCATCTAATCAAAG GGTTTGATGAGGCTTACCTTCAATTGCAGATAAACTCATTGCTGT CCACTGCTGTATTATGTGAGAATATGGGTGATGAATCTGGTCTTC TCCACTCAGCTAACATGGCTGTTTGGGCAAAGGTGGTACAATTAT ACGGAGATCAGGCAATAGTGAAATTGTTGAATATGGCTACTGGA CGATGCTTCAAGGATGTACGTCTAGTAGGAGCCGTGGGAAGATT GCTGGCAGAACCAGTTGGCACGTCGCAACAATCCCCAAGAAATG AAATAAGTGAAAACGTAACGTCAAAGACAGCAATGGAGTCAAT ATTGATAACACCACTGGCAGAGCGGTTCGTACGTCGTTTTGGAGC CGATATGAGGCTCAGCGTGCTAACAGCACGATTGACAAGAAGAC TCTCGAGTGACAGTAGGTTGAGTAAAGTATTCGCTTAGATTCCCA ACCTTCGTTTTATTCTTTCGTAGACAAAGAAGCTGCATGCGAACA TAGGGACAACTTTTATAAATCCAATTGTCAAACCAACGTAAAAC CCTCTGGCACCATTTTCAACATATATTTGTGAAGCAGTACGCAAT ATCGATAAATACTCACCGTTGTTTGTAACAGCCCCAACTTGCATA CGCCTTCTAATGACCTCAAATGGATAAGCCGCAGCTTGTGCTAAC ATACCAGCAGCACCGCCCGCGGTCAGCTGCGCCCACACATATAA AGGCAATCTACGATCATGGGAGGAATTAGTTTTGACCGTCAGGT CTTCAAGAGTTTTGAACTCTTCTTCTTGAACTGTGTAACCTTTTAA ATGACGGGATCTAAATACGTCATGGATGAGATCATGTGTGTAAA AACTGACTCCAGCATATGGAATCATTCCAAAGATTGTAGGAGCG AACCCACGATAAAAGTTTCCCAACCTTGCCAAAGTGTCTAATGCT GTGACTTGAAATCTGGGTTCCTCGTTGAAGACCCTGCGTACTATG CCCAAAAACTTTCCTCCACGAGCCCTATTAACTTCTCTATGAGTT TCAAATGCCAAACGGACACGGATTAGGTCCAATGGGTAAGTGAA AAACACAGAGCAAACCCCAGCTAATGAGCCGGCCAGTAACCGTC TTGGAGCTGTTTCATAAGAGTCATTAGGGATCAATAACGTTCTAA TCTGTTCATAACATACAAATTTTATGGCTGCATAGGGAAAAATTC TCAACAGGGTAGCCGAATGACCCTGATATAGACCTGCGACACCA TCATACCCATAGATCTGCCTGACAGCCTTAAAGAGCCCGCTAAA AGACCCGGAAAACCGAGAGAACTCTGGATTAGCAGTCTGAAAAA GAATCTTCACTCTGTCTAGTGGAGCAATTAATGTCTTAGCGGCAC TTCCTGCTACTCCGCCAGCTACTCCTGAATAGATCACATACTGCA AAGACTGCTTGTCGATGACCTTGGGGTTATTTAGCTTCAAGGGCA ATTTTTGGGACATTTTGGACACAGGAGACTCAGAAACAGACACA GAGCGTTCTGAGTCCTGGTGCTCCTGACGTAGGCCTAGAACAGG AATTATTGGCTTTATTTGTTTGTCCATTTCATGAGCTTGGGGTAAT AGATAGATGACAGAGAAATAGAGAAGACCTAATATTTTTGTTC ATGGCAAATCGCGGGTTCGCGGTCGGGTCACACACGGAGAAGTA ATGAGAAGAGCTGGTAATCTGGGGTAAAAGGGTTCAAAAGAAG GTCGCCTGGTAGGGATGCAATACAAGGTTGTCTTGGAGTTTACAT TGACCAGATGATTTGGCTTTTTCTCTGTTCAATTCACATTTTTCAG |

TABLE 14-continued

| SEQ ID NO: | Description | Sequence |
|---|---|---|
| | | CGAGAATCGGATTGACGGAGAAATGGCGGGGTGTGGGGTGGAT
AGATGGCAGAAATGCTCGCAATCACCGCGAAAGAAAGACTTTAT
GGAATAGAACTACTGGGTGGTGTAAGGATTACATAGCTAGTCCA
ATGGAGTCCGTTGGAAAGGTAAGAAGAAGCTAAAACCGGCTAA
GTAACTAGGGAAGAATGATCAGACTTTGATTTGATGAGGTCTGA
AAATACTCTGCTGCTTTTTCAGTTGCTTTTTCCCTGCAACCTATCA
TTTTCCTTTTCATAAGCCTGCCTTTTCTGTTTTCACTTATATGAGTT
CCGCCGAGACTTCCCCAAATTCTCTCCTGGAACATTCTCTATCGC
TCTCCTTCCAAGTTGCGCCCCCTGGCACTGCCTAGTAATATTACC
ACGCGACTTATATTCAGTTCCACAATTTCCAGTGTTCGTAGCAAA
TATCATCAGCCATGGCGAAGGCAGATGGCAGTTTGCTCTACTATA
ATCCTCACAATCCACCCAGAAGGTATTACTTCTACATGGCTATAT
TCGCCGTTTCTGTCATTTGCGTTTTGTACGGACCCTCACAACAATT
ATCATCTCCAAAAATAGACTATGATCCATTGACGCTCCGATCACT
TGATTTGAAGACTTTGGAAGCTCCTTCACAGTTGAGTCCAGGCAC
CGTAGAAGATAATCTTCG |
| 65 | Sequence of the 3'- Region used for knock out of PpOCH1: | AAAGCTAGAGTAAAATAGATATAGCGAGATTAGAGAATGAATAC
CTTCTTCTAAGCGATCGTCCGTCATCATAGAATATCATGGACTGT
ATAGTTTTTTTTTTGTACATATAATGATTAAACGGTCATCCAACA
TCTCGTTGACAGATCTCTCAGTACGCGAAATCCCTGACTATCAAA
GCAAGAACCGATGAAGAAAAAACAACAGTAACCCAAACACCA
CAACAAACACTTTATCTTCTCCCCCCCAACACCAATCATCAAAGA
GATGTCGGAACCAAACACCAAGAAGCAAAAACTAACCCCATATA
AAAACATCCTGGTAGATAATGCTGGTAACCCGCTCTCCTTCCATA
TTCTGGGCTACTTCACGAAGTCTGACCGGTCTCAGTTGATCAACA
TGATCCTCGAAATGGGTGGCAAGATCGTTCCAGACCTGCCTCCTC
TGGTAGATGGAGTGTTGTTTTTGACAGGGGATTACAAGTCTATTG
ATGAAGATACCCTAAAGCAACTGGGGGACGTTCCAATATACAGA
GACTCCTTCATCTACCAGTGTTTTGTGCACAAGACATCTCTTCCC
ATTGACACTTTCCGAATTGACAAGAACGTCGACTTGGCTCAAGAT
TTGATCAATAGGGCCCTTCAAGAGTCTGTGGATCATGTCACTTCT
GCCAGCACAGCTGCAGCTGCTGCTGTTGTTGTCGCTACCAACGGC
CTGTCTTCTAAACCAGACGCTCGTACTAGCAAAATACAGTTCACT
CCCGAAGAAGATCGTTTTATTCTTGACTTTGTTAGGAGAAATCCT
AAACGAAGAAACACACATCAACTGTACACTGAGCTCGCTCAGCA
CATGAAAAACCATACGAATCATTCTATCCGCCACAGATTTCGTCG
TAATCTTTCCGCTCAACTTGATTGGGTTTATGATATCGATCCATTG
ACCAACCAACCTCGAAAAGATGAAAACGGGAACTACATCAAGGT
ACAAGGCCTTCCA |
| 66 | Sequence of the 5'- Region used for knock out of PpBMT2: | GGCCGAGCGGGCCTAGATTTTCACTACAAATTTCAAAACTACGC
GGATTTATTGTCTCAGAGAGCAATTTGGCATTTCTGAGCGTAGCA
GGAGGCTTCATAAGATTGTATAGGACCGTACCAACAAATTGCCG
AGGCACAACACGGTATGCTGTGCACTTATGTGGCTACTTCCCTAC
AACGGAATGAAACCTTCCTCTTTCCGCTTAAACGAGAAAGTGTGT
CGCAATTGAATGCAGGTGCCTGTGCGCCTTGGTGTATTGTTTTTG
AGGGCCCAATTTATCAGGCGCCTTTTTTCTTGGTTGTTTTCCCTTA
GCCTCAAGCAAGGTTGGTCTATTTCATCTCCGCTTCTATACCGTG
CCTGATACTGTTGGATGAGAACACGACTCAACTTCCTGCTGCTCT
GTATTGCCAGTGTTTTGTCTGTGATTTGGATCGGAGTCCTCCTTAC
TTGGAATGATAATAATCTTGGCGGAATCTCCCTAAACGGAGGCA
AGGATTCTGCCTATGATGATCTGCTATCATTGGGAAGCTTCAACG
ACATGGAGGTCGACTCCTATGTCACCAACATCTACGACAATGCTC
CAGTGCTAGGATGTACGGATTTGTCTTATCATGGATTGTTGAAAG
TCACCCCAAAGCATGACTTAGCTTGCGATTTGGAGTTCATAAGAG
CTCAGATTTTGGACATTGACGTTTACTCCGCCATAAAAGACTTAG
AAGATAAAGCCTTGACTGTAAAACAAAAGGTTGAAAAACACTGG
TTTACGTTTTATGGTAGTTCAGTCTTTCTGCCCGAACACGATGTG
CATTACCTGGTTAGACGAGTCATCTTTTCGGCTGAAGGAAAGGC
GAACTCTCCAGTAACATC |
| 67 | Sequence of the 3'- Region used for knock out of PpBMT2: | CCATATGATGGGTGTTTGCTCACTCGTATGGATCAAAATTCCATG
GTTTCTTCTGTACAACTTGTACATTATTTGGACTTTTCTAACGGT
TTTTCTGGTGATTTGAGAAGTCCTTATTTTGGTGTTCGCAGCTTAT
CCGTGATTGAACCATCAGAAATACTGCAGCTCGTTATCTAGTTTC
AGAATGTGTTGTAGAATACAATCAATTCTGAGTCTAGTTTGGGTG
GGTCTTGGCGACGGGACCGTTATATGCATCTATGCAGTGTTAAGG
TACATAGAATGAAAATGTAGGGGTTAATCGAAAGCATCGTTAAT
TTCAGTAGAACGTAGTTCTATTCCCTACCCAAATAATTTGCCAAG
AATGCTTCGTATCCACATACGCAGTGGACGTAGCAAATTTCACTT
TGGACTGTGACCTCAAGTCGTTATCTTCTACTTGGACATTGATGG
TCATTACGTAATCCACAAAGAATTGGATAGCCTCTCGTTTTATCT
AGTGCACAGCCTAATAGCACTTAAGTAAGAGCAATGGACAAATT
TGCATAGACATTGAGCTAGATACGTAACTCAGATCTTGTTCACTC
ATGGTGTACTCGAAGTACTGCTGGAACCGTTACCTCTTATCATTT
CGCTACTGGCTCGTGAAACTACTGGATGAAAAAAAAAAAAGAGC |

TABLE 14-continued

| SEQ ID NO: | Description | Sequence |
|---|---|---|
| | | TGAAAGCGAGATCATCCCATTTTGTCATCATACAAATTCACGCTT<br>GCAGTTTTGCTTCGTTAACAAGACAAGATGTCTTTATCAAAGACC<br>CGTTTTTTCTTCTTGAAGAATACTTCCCTGTTGAGCACATGCAAA<br>CCATATTTATCTCAGATTTCACTCAACTTGGGTGCTTCCAAGAGA<br>AGTAAAATTCTTCCCACTGCATCAACTTCCAAGAAACCCGTAGAC<br>CAGTTTCTCTTCAGCCAAAAGAAGTTGCTCGCCGATCACCGCGGT<br>AACAGAGGAGTCAGAAGGTTTCACACCCTTCCATCCCGATTTCA<br>AAGTCAAAGTGCTGCGTTGAACCAAGGTTTTCAGGTTGCCAAAG<br>CCCAGTCTGCAAAAACTAGTTCCAAATGGCCTATTAATTCCCATA<br>AAAGTGTTGGCTACGTATGTATCGGTACCTCCATTCTGGTATTTG<br>CTATTGTTGTCGTTGGTGGGTTGACTAGACTGACCGAATCCGGTC<br>TTTCCATAACGGAGTGGAAACCTATCACTGGTTCGGTTCCCCCAC<br>TGACTGAGGAAGACTGGAAGTTGGAATTTGAAAAATACAAACAA<br>AGCCCTGAGTTTCAGGAACTAAATTCTCACATAACATTGGAAGA<br>GTTCAAGTTTATATTTTCCATGGAATGGGGACATAGATTGTTGGG<br>AAGGGTCATCGGCCTGTCGTTTGTTCTTCCCACGTTTTACTTCATT<br>GCCCGTCGAAAGTGTTCCAAAGATGTTGCATTGAAACTGCTTGCA<br>ATATGCTCTATGATAGGATTCCAAGGTTTCATCGGCTGGTGGATG<br>GTGTATTCCGGATTGGACAAACAGCAATTGGCTGAACGTAACTC<br>CAAACCAACTGTGTCTCCATATCGCTTAACTACCCATCTTGGAAC<br>TGCATTTGTTATTTACTGTTACATGATTTACACAGGGCTTCAAGTT<br>TTGAAGAACTATAAGATCATGAAACAGCCTGAAGCGTATGTTCA<br>AATTTTCAAGCAAATTGCGTCTCCAAAATTGAAAACTTTCAAGAG<br>ACTCTCTTCAGTTCTATTAGGCCTGGTG |
| 68 | Sequence of the 5'-Region used for knock out of BMT1 | CATATGGTGAGAGCCGTTCTGCACAACTAGATGTTTTCGAGCTTC<br>GCATTGTTTCCTGCAGCTCGACTATTGAATTAAGATTTCCGGATA<br>TCTCCAATCTCACAAAAACTTATGTTGACCACGTGCTTTCCTGAG<br>GCGAGGTGTTTTATATGCAAGCTGCCAAAAATGGAAAACGAATG<br>GCCATTTTTCGCCCAGGCAAATTATTCGATTACTGCTGTCATAAA<br>GACAGTGTTGCAAGGCTCACATTTTTTTTAGGATCCGAGATAAA<br>GTGAATACAGGACAGCTTATCTCTATATCTTGTACCATTCGTGAA<br>TCTTAAGAGTTCGGTTAGGGGGACTCTAGTTGAGGGTTGGCACTC<br>ACGTATGGCTGGGCGCAGAAATAAAATTCAGGCGCAGCAGCACT<br>TATCGATG |
| 69 | Sequence of the 3'-Region used for knock out of BMT1 | GAATTCACAGTTATAAATAAAAACAAAAACTCAAAAAGTTTGGG<br>CTCCACAAAATAACTTAATTTAAATTTTTGTCTAATAAATGAATG<br>TAATTCCAAGATTATGTGATGCAAGCACAGTATGCTTCAGCCCTA<br>TGCAGCTACTAATGTCAATCTCGCCTGCGAGCGGGCCTAGATTTT<br>CACTACAAATTTCAAAACTACGCGGATTTATTGTCTCAGAGAGCA<br>ATTTGGCATTTCTGAGCGTAGCAGGAGGCTTCATAAGATTGTATA<br>GGACCGTACCAACAAATTGCCGAGGCACAACACGGTATGCTGTG<br>CACTTATGTGGCTACTTCCCTACAACGGAATGAAACCTTCCTCTT<br>TCCGCTTAAACGAGAAGTGTGTCGCAATTGAATGCAGGTGCCT<br>GTGCGCTTGGTGTATTGTTTTTGAGGGCCCAATTTATCAGGCGC<br>CTTTTTTCTTGGTTGTTTTCCCTTAGCCTCAAGCAAGGTTGGTCTA<br>TTTCATCTCCGCTTCTATACCGTGCCTGATACTGTTGGATGAGAA<br>CACGACTCAACTTCCTGCTGCTCTGTATTGCCAGTGTTTTGTCTGT<br>GATTTGGATCGGAGTCCTCCTTACTTGGAATGATAATAATCTTGG<br>CGGAATCTCCCTAAACGGAGGCAAGGATTCTGCCTATGATGATC<br>TGCTATCATTGGGAAGCTT |
| 70 | Sequence of the 5'-Region used for knock out of BMT3 | GATATCTCCCTGGGGACAATATGTGTTGCAACTGTTCGTTGTTGG<br>TGCCCCAGTCCCCCAACCGGTACTAATCGGTCTATGTTCCCGTAA<br>CTCATATTCGGTTAGAACTAGAACAATAAGTGCATCATTGTTCAA<br>CATTGTGGTTCAATTGTCGAACATTGCTGGTGCTTATATCTACAG<br>GGAAGACGATAAGCCTTTGTACAAGAGAGGTAACAGACAGTTAA<br>TTGGTATTTCTTTGGGAGTCGTTGCCCTCTACGTTGTCTCCAAGAC<br>ATACTACATTCTGAGAAACAGATGGAAGACTCAAAAATGGAGA<br>AGCTTAGTGAAGAAGAGAAAGTTGCCTACTTGGACAGAGCTGAG<br>AAGGAGAACCTGGGTTCTAAGAGGCTGGACTTTTTGTTCGAGAG<br>TTAAACTGCATAATTTTTTCTAAGTAAATTTCATAGTTATGAAAT<br>TTCTGCAGCTTAGTGTTTACTGCATCGTTTACTGCATCACCCTGTA<br>AATAATGTGAGCTTTTTTCCTTCCATTGCTTGGTATCTTCCTTGCT<br>GCTGTTT |
| 71 | Sequence of the 3'-Region used for knock out of BMT3 | ACAAAACAGTCATGTACAGAACTAACGCCTTTAAGATGCAGACC<br>ACTGAAAAGAATTGGGTCCCATTTTTCTTGAAAGACGACCAGGA<br>ATCTGTCCATTTTGTTTACTCGTTCAATCCTCTGAGAGTACTCAAC<br>TGCAGTCTTGATAACGGTGCATGTGATGTTCTATTTGAGTTACCA<br>CATGATTTGGCATGTCTTCCGAGCTACGTGGTGCCACTCCTATG<br>CTCAATCTTCCTCAGGCAATCCCGATGGCAGACGACAAAGAAAT<br>TTGGGTTTCATTCCCAAGAACGAGAATATCAGATTGCGGGTGTTC<br>TGAAACAATGTACAGGCCAATGTTAATGCTTTTTGTTAGAGAAG<br>GAACAAACTTTTTTGCTGAGC |

TABLE 14-continued

| SEQ ID NO: | Description | Sequence |
| --- | --- | --- |
| 72 | Sequence of the 5'-Region used for knock out of BMT4 | AAGCTTGTTCACCGTTGGGACTTTTCCGTGGACAATGTTGACTAC<br>TCCAGGAGGGATTCCAGCTTTCTCTACTAGCTCAGCAATAATCAA<br>TGCAGCCCCAGGCGCCCGTTCTGATGGCTTGATGACCGTTGTATT<br>GCCTGTCACTATAGCCAGGGGTAGGGTCCATAAAGGAATCATAG<br>CAGGGAAATTAAAAGGGCATATTGATGCAATCACTCCCAATGGC<br>TCTCTTGCCATTGAAGTCTCCATATCAGCACTAACTTCCAAGAAG<br>GACCCCTTCAAGTCTGACGTGATAGAGCACGCTTGCTCTGCCACC<br>TGTAGTCCTCTCAAAACGTCACCTTGTGCATCAGCAAAGACTTTA<br>CCTTGCTCCAATACTATGACGGAGGCAATTCTGTCAAAATTCTCT<br>CTCAGCAATTCAACCAACTTGAAAGCAAATTGCTGTCTCTTGATG<br>ATGGAGACTTTTTTCCAAGATTGAAATGCAATGTGGGACGACTC<br>AATTGCTTCTTCCAGCTCCTCTTCGGTTGATTGAGGAACTTTTGA<br>AACCACAAAATTGGTCGTTGGGTCATGTACATCAAACCATTCTGT<br>AGATTTAGATTCGACGAAAGCGTTGTTGATGAAGGAAAAGGTTG<br>GATACGGTTTGTCGGTCTCTTTGGTATGGCCGGTGGGGTATGCAA<br>TTGCAGTAGAAGATAATTGGACAGCCATTGTTGAAGGTAGAGAA<br>AAGGTCAGGGAACTTGGGGGTTATTTATACCATTTTACCCCACAA<br>ATAACAACTGAAAAGTACCCATTCCATAGTGAGAGGTAACCGAC<br>GGAAAAAGACGGGCCCATGTTCTGGGACCAATAGAACTGTGTAA<br>TCCATTGGGACTAATCAACAGACGATTGGCAATATAATGAAATA<br>GTTCGTTGAAAAGCCACGTCAGCTGTCTTTTCATTAACTTTGGTC<br>GGACACAACATTTTCTACTGTTGTATCTGTCCTACTTTGCTTATCA<br>TCTGCCACAGGGCAAGTGGATTTCCTTCTCGCGCGGCTGGGTGAA<br>AACGGTTAACGTGAA |
| 73 | Sequence of the 3'-Region used for knock out of BMT4 | GCCTTGGGGGACTTCAAGTCTTTGCTAGAAACTAGATGAGGTCA<br>GGCCCTCTTATGGTTGTGTCCCAATTGGGCAATTTCACTCACCTA<br>AAAAGCATGACAATTATTTAGCGAAATAGGTAGTATATTTTCCCT<br>CATCTCCCAAGCAGTTTCGTTTTTGCATCCATATCTCTCAAATGA<br>GCAGCTACGACTCATTAGAACCAGAGTCAAGTAGGGGTGAGCTC<br>AGTCATCAGCCTTCGTTTCTAAAACGATTGAGTTCTTTTGTTGCTA<br>CAGGAAGCGCCCTAGGGAACTTTCGCACTTTGGAAATAGATTTT<br>GATGACCAAGAGCGGGAGTTGATATTAGAGAGGCTGTCCAAAGT<br>ACATGGGATCAGGCCGGCCAAATTGATTGGTGTGACTAAACCAT<br>TGTGTACTTGGACACTCTATTACAAAAGCGAAGATGATTTGAAGT<br>ATTACAAGTCCCGAAGTGTTAGAGGATTCTATCGAGCCCAGAAT<br>GAAATCATCAACCGTTATCAGCAGATTGATAAACTCTTGGAAAG<br>CGGTATCCCATTTTCATTATTGAAGAACTACGATAATGAAGATGT<br>GAGAGACGGCGACCCTCTGAACGTAGACGAAGAAACAAATCTAC<br>TTTTGGGGTACAATAGAGAAAGTGAATCAAGGGAGGTATTTGTG<br>GCCATAATACTCAACTCTATCATTAATG |
| 74 | Sequence of the 5'-Region used for knock out of PpPNO1 and PpMNN4: | TCATTCTATATGTTCAAGAAAAGGGTAGTGAAAGGAAAGAAAAG<br>GCATATAGGCGAGGGAGAGTTAGCTAGCATACAAGATAATGAAG<br>GATCAATAGCGGTAGTTAAAGTGCACAAGAAAAGAGCACCTGTT<br>GAGGCTGATGATAAAGCTCCAATTACATTGCCACAGAGAAACAC<br>AGTAACAGAAATAGGAGGGGATGCACCACGAGAAGGAGCATTCA<br>GTGAACAACTTTGCCAAATTCATAACCCCAAGCGCTAATAAGCC<br>AATGTCAAAGTCGGCTACTAACATTAATAGTACAACAACTATCG<br>ATTTTCAACCAGATGTTTGCAAGGACTACAAACAGACAGGTTAC<br>TGCCGGATATGGTGACACTTGTAAGTTTTTGCACCTGAGGGATGAT<br>TTCAAACAGGGATGGAAATTAGATAGGGAGTGGGAAAATGTCCA<br>AAAGAAGAAGCATAATACTCTCAAAGGGGTTAAGGAGATCCAA<br>ATGTTTAATGAAGATGAGCTCAAAGATATCCCGTTTAAATGCATT<br>ATATGCAAAGGAGATTACAAATCACCCGTGAAAACTTCTTGCAA<br>TCATTATTTTTGCGAACAATGTTTCCTGCAACGGTCAAGAAGAAA<br>ACCAAATTGTATTATATGTGGCAGAGACACTTTAGGAGTTGCTTT<br>ACCAGCAAAGAAGTTGTCCCAATTTCTGGCTAAGATACATAATA<br>ATGAAAGTAATAAAGTTTAGTAATTGCATTGCGTTGACTATTGAT<br>TGCATTGATGTCGTGTGATACTTTCACCGAAAAAAAACACGAAG<br>CGCAATAGGAGCGGTTGCATATTAGTCCCCAAAGCTATTTAATTG<br>TGCCTGAAACTGTTTTTTAAGCTCATCAAGCATAATTGTATGCAT<br>TGCGACGTAACCAACGTTTAGGCGCAGTTTAATCATAGCCCACTG<br>CTAAGCC |
| 75 | Sequence of the 3'-Region used for knock out of PpPNO1 and PpMNN4: | CGGAGGAATGCAAATAATAATCTCCTTAATTACCCACTGATAAG<br>CTCAAGAGACGCGGTTTGAAAACGATATAATGAATCATTTGGAT<br>TTTATAATAAACCCTGACAGTTTTTCCACTGTATTGTTTTAACACT<br>CATTGGAAGCTGTATTGATTCTAAGAAGCTAGAAATCAATACGG<br>CCATACAAAAGATGACATTGAATAAGCACCGGCTTTTTTGATTAG<br>CATATACCTTAAAGCATGCATTCATGGCTACATAGTTGTTAAAGG<br>GCTTCTTCCATTATCAGTATAATGAATTACATAATCATGCACTTA<br>TATTTGCCCATCTCTGTTCTCTCACTCTTGCCTGGGTATATTCTAT<br>GAAATTGCGTATAGCGTGTCTCCAGTTGAACCCCAAGCTTGGCG<br>AGTTTGAAGAGAATGCTAACCTTGCGTATTCCTTGCTTCAGGAAA<br>CATTCAAGGAGAAACAGGTCAAGAAGCCAAACATTTTGATCCTT<br>CCCGAGTTAGCATTGACTGGCTACAATTTTCAAAGCCAGCAGCG |

TABLE 14-continued

| SEQ ID NO: | Description | Sequence |
|---|---|---|
| | | GATAGAGCCTTTTTTGGAGGAAACAACCAAGGGAGCTAGTACCC
AATGGGCTCAAAAAGTATCCAAGACGTGGGATTGCTTTACTTTA
ATAGGATACCCAGAAAAAAGTTTAGAGAGCCCTCCCCGTATTTA
CAACAGTGCGGTACTTGTATCGCCTCAGGGAAAAGTAATGAACA
ACTACAGAAAGTCCTTCTTGTATGAAGCTGATGAACATTGGGGA
TGTTCGGAATCTTCTGATGGGTTTCAAACAGTAGATTTATTAATT
GAAGGAAAGACTGTAAAGACATCATTTGGAATTTGCATGGATTT
GAATCCTTATAAATTTGAAGCTCCATTCACAGACTTCGAGTTCAG
TGGCCATTGCTTGAAAACCGGTACAAGACTCATTTTGTGCCCAAT
GGCCTGGTTGTCCCCTCTATCGCCTTCCATTAAAAAGGATCTTAG
TGATATAGAGAAAAGCAGACTTCAAAAGTTCTACCTTGAAAAAA
TAGATACCCCGGAATTTGACGTTAATTACGAATTGAAAAAAGAT
GAAGTATTGCCCACCCGTATGAATGAAACGTTGGAAACAATTGA
CTTTGAGCCTTCAAAACCGGACTACTCTAATATAAATTATTGGAT
ACTAAGGTTTTTTCCCTTTCTGACTCATGTCTATAAACGAGATGT
GCTCAAAGAGAATGCAGTTGCAGTCTTATGCAACCGAGTTGGCA
TTGAGAGTGATGTCTTGTACGGAGGATCAACCACGATTCTAAACT
TCAATGGTAAGTTAGCATCGACACAAGAGGAGCTGGAGTTGTAC
GGGCAGACTAATAGTCTCAACCCCAGTGTGGAAGTATTGGGGGC
CCTTGGCATGGGTCAACAGGGAATTCTAGTACGAGACATTGAAT
TAACATAATATACAATATACAATAAACACAAATAAAGAATACAA
GCCTGACAAAAATTCACAAATTATTGCCTAGACTTGTCGTTATCA
GCAGCGACCTTTTTCCAATGCTCAATTTCACGATATGCCTTTTCTA
GCTCTGCTTTAAGCTTCTCATTGGAATTGCTAACTCGTTGACTG
CTTGGTCAGTGATGAGTTTCTCCAAGGTCCATTTCTCGATGTTGTT
GTTTTCGTTTTCCTTTAATCTCTTGATATAATCAACAGCCTTCTTT
AATATCTGAGCCTTGTTCGAGTCCCCTGTTGGCAACAGAGCGGCC
AGTTCCTTTATTCCGTGGTTTATATTTTCTCTTCTACGCCTTTCTAC
TTCTTTGTGATTCTCTTTACGCATCTTATGCCATTCTTCAGAACCA
GTGGCTGGCTTAACCGAATAGCCAGAGCCTGAAGAAGCCGCACT
AGAAGAAGCAGTGGCATTGTTGACTATGG |
| 76 | Sequence of the 5'-Region used for knock out of PpMNN4L1: | GATCTGGCCATTGTGAAACTTGACACTAAAGACAAAACTCTTAG
AGTTTCCAATCACTTAGGAGACGATGTTTCCTACAACGAGTACGA
TCCCTCATTGATCATGAGCAATTTGTATGTGAAAAAAGTCATCGA
CCTTGACACCTTGGATAAAAGGGCTGGAGGAGGTGGAACCACCT
GTGCAGGCGGTCTGAAAGTGTTCAAGTACGGATCTACTACCAAA
TATACATCTGGTAACCTGAACGGCGTCAGGTTAGTATACTGGAA
CGAAGGAAAGTTGCAAAGCTCCAAATTTGTGGTTCGATCCTCTA
ATTACTCTCAAAAGCTTGGAGGAAACAGCAACGCCGAATCAATT
GACAACAATGGTGTGGGTTTTGCCTCAGCTGGAGACTCAGGCGC
ATGGATTCTTTCCAAGCTACAAGATGTTAGGGAGTACCAGTCATT
CACTGAAAAGCTAGGTGAAGCTACGATGAGCATTTTCGATTTCC
ACGGTCTTAAACAGGAGACTTCTACTACAGGGCTTGGGGTAGTT
GGTATGATTCATTCTTACGACGGTGAGTTCAAACAGTTTGGTTTG
TTCACTCCAATGACATCTATTCTACAAAGACTTCAACGAGTGACC
AATGTAGAATGGTGTGTAGCGGGTTGCGAAGATGGGGATGTGGA
CACTGAAGGAGAACACGAATTGAGTGATTTGGAACAACTGCATA
TGCATAGTGATTCCGACTAGTCAGGCAAGAGAGAGCCCTCAAAT
TTACCTCTCTGCCCCTCCTCACTCCTTTTGGTACGCATAATTGCAG
TATAAAGAACTTGCTGCCAGCCAGTAATCTTATTTCATACGCAGT
TCTATATAGCACATAATCTTGCTTGTATGTATGAAATTTACCGCG
TTTTAGTTGAAATTGTTTATGTTGTGTGCCTTGCATGAAATCTCTC
GTTAGCCCTATCCTTACATTTAACTGGTCTCAAAACCTCTACCAA
TTCCATTGCTGTACAACAATATGAGGCGGCATTACTGTAGGGTTG
GAAAAAAATTGTCATTCCAGCTAGAGATCACACGACTTCATCAC
GCTTATTGCTCCTCATTGCTAAATCATTTACTCTTGACTTCGACCC
AGAAAAGTTCGCC |
| 77 | Sequence of the 3'-Region used for knock out of PpMNN4L1: | GCATGTCAAACTTGAACACAACGACTAGATAGTTGTTTTTTCTAT
ATAAAACGAAACGTTATCATCTTTAATAATCATTGAGGTTTACCC
TTATAGTTCCGTATTTTCGTTTCCAAACTTAGTAATCTTTTGGAAA
TATCATCAAAGCTGGTGCCAATCTTCTTGTTGAAGTTTCAAACT
GCTCCACCAAGCTACTTAGAGACTGTTCTAGGTCTGAAGCAACTT
CGAACACAGAGACAGCTGCCGCCGATTGTTCTTTTTTGTGTTTTT
CTTCTGGAAGAGGGGCATCATCTTGTATGTCCAATGCCCGTATCC
TTTCTGAGTTGTCCGACACATTGTCCTTCGAAGAGTTTCCTGACA
TTGGGCTTCTTCTATCCGTGTATTAATTTTGGGTTAAGTTCCTCGT
TTGCATAGCAGTTGGATACCTCGATTTTTTTGGCTCCTATTTACCTG
ACATAATATTCTACTATAATCCAACTTGGACGCGTCATCTATGAT
AACTAGGCTCTCCTTTGTTCAAAGGGGACGTCTTCATAATCCACT
GGCACGAAGTAAGTCTGCAACGAGGCGGCTTTTGCAACAGAACG
ATAGTGTCGTTTCGTACTTGGACTATGCTAAACAAAAGGATCTGT
CAAACATTTCAACCGTGTTTCAAGGCACTCTTTACGAATTATCGA
CCAAGACCTTCCTAGACGAACATTTCAACATATCCAGGCTACTGC
TTCAAGGTGGTGCAAATGATAAAGGTATAGATATTAGATGTGTTT
GGGACCTAAAACAGTTCTTGCCTGAAGATTCCCTTGAGCAACAG |

TABLE 14-continued

| SEQ ID NO: | Description | Sequence |
|---|---|---|
| | | GCTTCAATAGCCAAGTTAGAGAAGCAGTACCAAATCGGTAACAA
AAGGGGGAAGCATATAAAACCTTTACTATTGCGACAAAATCCAT
CCTTGAAAGTAAAGCTGTTTGTTCAATGTAAAGCATACGAAACG
AAGGAGGTAGATCCTAAGATGGTTAGAGAACTTAACGGGACATA
CTCCAGCTGCATCCCATATTACGATCGCTGGAAGACTTTTTTCAT
GTACGTATCGCCCACCAACCTTTCAAAGCAAGCTAGGTATGATTT
TGACAGTTCTCACAATCCATTGGTTTTCATGCAACTTGAAAAAAC
CCAACTCAAACTTCATGGGGATCCATACAATGTAAATCATTACG
AGAGGGCGAGGTTGAAAAGTTTCCATTGCAATCACGTCGCATCA
TGGCTACTGAAAGGCCTTAAC |
| 78 | Sequence of the PpTRP2 gene integration locus: | TAATGGCCAAACGGTTTCTCAATTACTATATACTACTAACCATTT
ACCTGTAGCGTATTTCTTTTCCCTCTTCGCGAAAGCTCAAGGGCA
TCTTCTTGACTCATGAAAAATATCTGGATTTCTTCTGACAGATCA
TCACCCTTGAGCCCAACTCTCTAGCCTATGAGTGTAAGTGATAGT
CATCTTGCAACAGATTATTTTGGAACGCAACTAACAAAGCAGAT
ACACCCTTCAGCAGAATCCTTTCTGGATATTGTGAAGAATGATCG
CCAAAGTCACAGTCCTGAGACAGTTCCTAATCTTTACCCCATTTA
CAAGTTCATCCAATCAGACTTCTTAACGCCTCATCTGGCTTATAT
CAAGCTTACCAACAGTTCAGAAACTCCCAGTCCAAGTTTCTTGCT
TGAAAGTGCGAAGAATGGTGACACCGTTGACAGGTACACCTTTA
TGGGACATTCCCCCAGAAAAATAATCAAGACTGGGCCTTTAGAG
GGTGCTGAAGTTGACCCCTTGGTGCTTCTGGAAAAAGAACTGAA
GGGCACCAGACAAGCGCAACTTCCTGGTATTCCTCGTCTAAGTG
GTGGTGCCATAGGATACATCTCGTACGATTGTATTAAGTACTTTG
AACCAAAAACTGAAAGAAAACTGAAAGATGTTTTGCAACTTCCG
GAAGCAGCTTTGATGTTGTTCGACACGATCGTGGCTTTTGACAAT
GTTTATCAAAGATTCCAGGTAATTGGAAACGTTTCTCTATCCGTT
GATGACTCGGACGAAGCTATTCTTGAGAAATATTATAAGACAAG
AGAAGAAGTGGAAAAGATCAGTAAAGTGGTATTTGACAATAAA
ACTGTTCCCTACTATGAACAGAAAGATATTATTCAAGGCCAAAC
GTTCACCTCTAATATTGGTCAGGAAGGGTATGAAAACCATGTTCG
CAAGCTGAAAGAACATATTCTGAAAGGAGACATCTTCCAAGCTG
TTCCCTCTCAAAGGGTAGCCAGGCCGACCTCATTGCACCCTTTCA
ACATCTATCGTCATTTGAGAACTGTCAATCCTTCTCCATACATGT
TCTATATTGACTATCTAGACTTCCAAGTTGTTGGTGCTTCACCTG
AATTACTAGTTAAATCCGACAACAACAACAAAATCATCACACAT
CCTATTGCTGGAACTCTTCCCAGAGGTAAAACTATCGAAGAGGA
CGACAATTATGCTAAGCAATTGAAGTCGTCTTTGAAAGACAGGG
CCGAGCACGTCATGCTGGTAGATTTGGCCAGAAATGATATTAAC
CGTGTGTGTGAGCCCACCAGTACCACGGTTGATCGTTTATTGACT
GTGGAGAGATTTTCTCATGTGATGCATCTTGTGTCAGAAGTCAGT
GGAACATTGAGACCAAACAAGACTCGCTTCGATGCTTTCAGATC
CATTTTCCCAGCAGGAACCGTCTCCGGTGCTCCGAAGGTAAGAG
CAATGCAACTCATAGGAGAATTGGAAGGAGAAAAGAGAGGTGT
TTATGCGGGGGCCGTAGGACACTGGTCGTACGATGGAAAATCGA
TGGACACATGTATTGCCTTAAGAACAATGGTCGTCAAGGACGGT
GTCGCTTACCTTCAAGCCGGAGGTGGAATTGTCTACGATTCTGAC
CCCTATGACGAGTACATCGAAACCATGAACAAAATGAGATCCAA
CAATAACACCATCTTGGAGGCTGAGAAAATCTGGACCGATAGGT
TGGCCAGAGACGAGAATCAAAGTGAATCCGAAGAAAACGATCA
ATGAACGGAGGACGTAAGTAGGAATTTATGGTTTGGCCAT |
| 79 | Sequence of the 5'-Region used for knock out of PpARG1: | GATCTGGCCTTCCCTGAATTTTTACGTCCAGCTATACGATCCGTT
GTGACTGTATTTCCTGAAATGAAGTTTCAACCTAAAGTTTTGGTT
GTACTTGCTCCACCTACCACGGAAACTAATATCGAAACCAATGA
AAAAGTAGAACTGGAATCGTCAATCGAAATTCGCAACCAAGTGG
AACCCAAAGACTTGAATCTTTCTAAAGTCTATTCTAGTGACACTA
ATGGCAACAGAAGATTTGAGCTGACTTTTCAAATGAATCTCAAT
AATGCAATATCAACATCAGACAATCAATGGGCTTTGTCTAGTGA
CACAGGATCAATTATAGTAGTGTCTTCTGCAGGAAGAATAACTTC
CCCGATCCTAGAAGTCGGGGCATCCGTCTGTGTCTTAAGATCGTA
CAACGAACACCTTTTGGCAATAACTTGTGAAGGAACATGCTTTTC
ATGGAATTTAAAGAAGCAAGAATGTGTTCTAAACAGCATTTCAT
TAGCACCTATAGTCAATTCACACATGCTAGTTAAGAAAGTTGGA
GATGCAAGGAACTATTCTATTGTATCTGCCGAAGGAGACAACAA
TCCGTTACCCCAGATTCTAGACTGCGAACTTCCAAAAATGGCGC
TCCAATTGTGGCTCTTAGCACGAAAGACATCTACTCTTATTCAA
GAAAATGAAAGTCTGGATCCATTTGATTGATTCGAAATACTTTGA
ATTGTTGGGTGCTGACAATGCACTGTTTGAGTGTGTGGAAGCGCT
AGAAGGTCCAATTGGAATGCTAATTCATAGATTGGTAGATGAGT
TCTTCCATGAAAAACACTGCCGGTAAAAAACTCAAACTTTACAAC
AAGCGAGTACTGGAGGACCTTTCAAATTCACTTGAAGAACTAGG
TGAAAATGCGTCTCAATTAAGAGAGAAACTTGACAAACTCTATG
GTGATGAGGTTGAGGCTTCTTGACCTCTTCTCTCTATCTGCGTTTC
TTTTTTTTTTTTTTTTTTTTTTTTTCAGTTGAGCCAGACCGCGCT
AAACGCATACCAATTGCCAAATCAGGCAATTGTGAGACAGTGGT |

TABLE 14-continued

| SEQ ID NO: | Description | Sequence |
|---|---|---|
| | | AAAAAAGATGCCTGCAAAGTTAGATTCACACAGTAAGAGAGATC<br>CTACTCATAAATGAGGCGCTTATTTAGTAGCTAGTGATAGCCACT<br>GCGGTTCTGCTTTATGCTATTTGTTGTATGCCTTACTATCTTTGTT<br>TGGCTCCTTTTCTTGACGTTTTCCGTTGGAGGGACTCCCTATTCT<br>GAGTCATGAGCCGCACAGATTATCGCCCAAAATTGACAAAATCT<br>TCTGGCGAAAAAAGTATAAAAGGAGAAAAAAGCTCACCCTTTTC<br>CAGCGTAGAAAGTATATATCAGTCATTGAAGAC |
| 80 | Sequence of the 3'-Region used for knock out of PpARG1: | GGGACTTTAACTCAAGTAAAAGGATAGTTGTACAATTATATATA<br>CGAAGAATAAATCATTACAAAAGTATTCGTTTCTTTGATTCTTA<br>ACAGGATTCATTTTCTGGGTGTCATCAGGTACAGCGCTGAATATC<br>TTGAAGTTAACATCGAGCTCATCATCGACGTTCATCACACTAGCC<br>ACGTTTCCGCAACGGTAGCAATAATTAGGAGCGGACCACACAGT<br>GACGACATCTTTCTCTTTGAAATGGTATCTGAAGCCTTCCATGAC<br>CAATTGATGGGCTCTAGCGATGAGTTGCAAGTTATTAATGTGGTT<br>GAACTCACGTGCTACTCGAGCACCGAATAACCAGCCAGCTCCAC<br>GAGGAGAAACAGCCCAACTGTCGACTTCATCTGGGTCAGACCAA<br>ACCAAGTCACAAAATCCTCCTTCATGAGGGACCTCTTGCGCTCGG<br>CTGAGAACTCTGATTTGATCTAACATGCGAATATCGGGAGAGAG<br>ACCACCATGGATACATAATATTTTACCATCAATGATGGCACTAAG<br>GGTTAAAAAGTCGAACACCTGGCAACAGTACTTCCAGACAGTGG<br>TGGAACCATATTTATTGAGACATTCCTCATAAAATCCATAAACCT<br>GAGTGATCTGTCTGGATTCATGATTTCCCCTTACCAATGTGATAT<br>GTTGAGGAAACTTAATTTTTAAAATCATGAGTAACGTGAACGTCT<br>CCAACGAGAAATAGCCTCTATCCACATAGTCTCCTAGGAAGATA<br>TAGTTCTGTTTTATTCCATTAGAGGAGGATCCGGGAAACCCACCA<br>CTAATCTTGAAAAGTTCCAGTAGATCGTGAAATTGGCCGTGAAT<br>ATCTCCGCATACTGTCACTGGACTCTGCACTGGCTGTATATTGGA<br>TTCCTCCATCAGCAAATCCTTCACCCGTTCGCAAAGATGCTTCAT<br>ATCATTTTCACTTAAAGCCTTGCAGCTTTTGACTTCTTCAAACCAC<br>TGATCTGGTCCTCTTTCTGGCATGATTAAGGTCTATAATATTTCTG<br>AGCTGAGATGTAAAAAAAAATAATAAAAATGGGGAGTGAAAAA<br>GTGTGTAGCTTTTAGGAGTTTGGGATTGATACCCCAAAATGATCT<br>TTATGAGAATTAAAAGGTAGATACGCTTTTAATAAGAACACCTA<br>TCTATAGTACTTTGTGGTCTTGAGTAATTGAGATGTTCAGCTTCT<br>GAGGTTTGCCGTTATTCTGGGATAGTAGTGCGCGACCAAACAAC<br>CCGCCAGGCAAAGTGTGTTGTGCTCGAAGACGATTGCCAGAAGA<br>GTAAGTCCGTCCTGCCTCAGATGTTACACACTTTCTTCCCTAGAC<br>AGTCGATGCATCATCGGATTTAAACCTGAAACTTTGATGCCATGA<br>TACGCCTAGTCACGTCGACTGAGATTTTAGATAAGCCCCGATCCC<br>TTTAGTACATTCCTGTTATCCATGGATGGAATGGCCTGATA |
| 81 | Sequence of the PpARG1 auxotrophic marker: | CAGTTGAGCCAGACCGCGCTAAACGCATACCAATTGCCAAATCA<br>GGCAATTGTGAGACAGTGGTAAAAAAGATGCCTGCAAAGTTAGA<br>TTCACACAGTAAGAGAGATCCTACTCATAAATGAGGCGCTTATTT<br>AGTAGCTAGTGATAGCCACTGCGGTTCTGCTTTATGCTATTTGTT<br>GTATGCCTTACTATCTTTGTTGGCTCCTTTTCTTGACGTTTTCC<br>GTTGGAGGGACTCCCTATTCTGAGTCATGAGCCGCACAGATTATC<br>GCCCAAAATTGACAAAATCTTCTGGCGAAAAAGTATAAAAGGA<br>GAAAAAAGCTCACCCTTTTCCAGCGTAGAAAGTATATATCAGTC<br>ATTGAAGACTATTATTTAAATAACACAATGTCTAAAGGAAAAGT<br>TTGTTTGGCCTACTCCGGTGGTTTGGATACCTCCATCATCCTAGCT<br>TGGTTGTTGGAGCAGGGATACGAAGTCGTTGCCTTTTTAGCCAAC<br>ATTGGTCAAGAGGAAGACTTTGAGGCTGCTAGAGAGAAAGCTCT<br>GAAGATCGGTGCTACCAAGTTTATCGTCAGTGACGTTAGGAAGG<br>AATTTGTTGAGGAAGTTTTGTTCCCAGCAGTCCAAGTTAACGCTA<br>TCTACGAGAACGTCTACTTACTGGGTACCTCTTTGGCCAGACCAG<br>TCATTGCCAAGGCCCAAATAGAGGTTGCTGAACAAGAAGGTTGT<br>TTTGCTGTTGCCCACGGTTGTACCGGAAAGGGTAACGATCAGGTT<br>AGATTTGAGCTTTCCTTTTATGCTCTGAAGCCTGACGTTGTCTGTA<br>TCGCCCCATGGAGAGACCCAGAATTCTTCGAAAGATTCGCTGGT<br>AGAAATGACTTGCTGAATTACGCTGCTGAGAAGGATATTCCAGT<br>TGCTCAGACTAAAGCCAAGCCATGGTCTACTGATGAGAACATGG<br>CTCACATCTCCTTCGAGGCTGGTATTCTAGAAGATCCAAACACTA<br>CTCCTCCAAAGGACATGTGGAAGCTCACTGTTGACCCAGAAGAT<br>GCACCAGACAAGCCAGAGTTCTTTGACGTCCACTTTGAGAAGGG<br>TAAGCCAGTTAAATTAGTTCTCGAGAACAAAACTGAGGTCACCG<br>ATCCGGTTGAGATCTTTTTGACTGCTAACGCCATTGCTAGAAGAA<br>ACGGTGTTGGTAGAATTGACATTGTCGAGAACAGATTCATCGGA<br>ATCAAGTCCAGAGGTTGTTATGAAACTCCAGGTTTGACTCTACTG<br>AGAACCACTCACATCGACTTGGAAGGTCTTACCGTTGACCGTGA<br>AGTTAGATCGATCAGAGACACTTTTGTTACCCCAACCTACTCTAA<br>GTTGTTATACAACGGGTTGTACTTTACCCCAGAAGGTGAGTACGT<br>CAGAACTATGATTCAGCCTTCTCAAAACACCGTCAACGGTGTTGT<br>TAGAGCCAAGGCCTACAAAGGTAATGTGTATAACCTAGGAAGAT<br>ACTCTGAAACCGAGAAATTGTACGATGCTACCGAATCTTCCATG<br>GATGAGTTGACCGGATTCCACCCTCAAGAAGCTGGAGGATTTAT |

TABLE 14-continued

| SEQ ID NO: | Description | Sequence |
|---|---|---|
| | | CACAACACAAGCCATCAGAATCAAGAAGTACGGAGAAAGTGTC<br>AGAGAGAAGGGAAAGTTTTTGGGACTTTAACTCAAGTAAAAGGA<br>TAGTTGTACAATTATATATACGAAGAATAAATCATTACAAAAAG<br>TATTCGTTTCTTTGATTCTTAACAGGATTCATTTTCTGGGTGTCAT<br>CAGGTACAGCGCTGAATATCTTGAAGTTAACATCGAGCTCATCAT<br>CGACGTTCATCACACTAGCCACGTTTCCGCAACGGTAGCAATAAT<br>TAGGAGCGGACCACACAGTGACGACATC |
| 82 | Sequence of the 5'-region that was used to knock into the PpADE1 locus: | GAGTCGGCCAAGAGATGATAACTGTTACTAAGCTTCTCCGTAATT<br>AGTGGTATTTTGTAACTTTTACCAATAATCGTTTATGAATACGGA<br>TATTTTTCGACCTTATCCAGTGCCAAATCACGTAACTTAATCATG<br>GTTTAAATACTCCACTTGAACGATTCATTATTCAGAAAAAAGTCA<br>GGTTGGCAGAAACACTTGGGCGCTTTGAAGAGTATAAGAGTATT<br>AAGCATTAAACATCTGAACTTTCACCGCCCCAATATACTACTCTA<br>GGAAACTCGAAAAATTCCTTTCCATGTGTCATCGCTTCCAACACA<br>CTTTGCTGTATCCTTCCAAGTATGTCCATTGTGAACACTGATCTG<br>GACGGAATCCTACCTTTAATCGCCAAAGGAAAGGTTAGAGACAT<br>TTATGCAGTCGATGAGAACAACTTGCTGTTCGTCGCAACTGACCG<br>TATCTCCGCTTACGATGTGATTATGACAAACGGTATTCCTGATAA<br>GGGAAAGATTTTGACTCAGCTCTCAGTTTTCTGGTTTGATTTTTTG<br>GCACCCTACATAAAGAATCATTTGGTTGCTTCTAATGACAAGGA<br>AGTCTTTGCTTTACTACCATCAAAACTGTCTGAAGAAAaTACAA<br>ATCTCAATTAGAGGGACGATCCTTGATAGTAAAAAAGCACAGAC<br>TGATACCTTTGGAAGCCATTGTCAGAGGTTACATCACTGGAAGTG<br>CATGGAAAGAGTACAAGAACTCAAAAACTGTCCATGGAGTCAAG<br>GTTGAAAACGAGAACCTTCAAGAGAGCGACGCCTTTCCAACTCC<br>GATTTTCACACCTTCAACGAAAGCTGAACAGGGTGAACACGATG<br>AAAACATCTCTATTGAACAAGCTGCTGAGATTGTAGGTAAAGAC<br>ATTTGTGAGAAGGTCGCTGTCAAGGCGGTCGAGTTGTATTCTGCT<br>GCAAAAAACCTCGCCCTTTTGAAGGGGATCATTATTGCTGATACG<br>AAATTCGAATTTGGACTGGACGAAAACAATGAATTGGTACTAGT<br>AGATGAAGTTTTAACTCCAGATTCTTCTAGATTTTGGAATCAAAA<br>GACTTACCAAGTGGGTAAATCGCAAGAGAGTTACGATAAGCAGT<br>TTCTCAGAGATTGGTTGACGGCCAACGGATTGAATGGCAAAGAG<br>GGCGTAGCCATGGATGCAGAAATTGCTATCAAGAGTAAAGAAAA<br>GTATATTGAAGCTTATGAAGCAATTACTGGCAAGAAATGGGCTT<br>GA |
| 83 | Sequence of the 3'-region that was used to knock into the PpADE1 locus: | ATGATTAGTACCCTCCTCGCCTTTTTCAGACATCTGAAATTTCCCT<br>TATTCTTCCAATTCCATATAAAATCCTATTTAGGTAATTAGTAAA<br>CAATGATCATAAAGTGAAATCATTCAAGTAACCATTCCGTTTATC<br>GTTGATTTAAAATCAATAACGAATGAATGTCGGTCTGAGTAGTC<br>AATTTGTTGCCTTTGGAGCTCATTGGCAGGGGGTCTTTGGCTCAG<br>TATGGAAGGTTGAAAGGAAAACAGATGGAAAGTGGTTCGTCAGA<br>AAAGAGGGTATCCTACATGAAGATGAATGCCAAAGAGATATCTCA<br>AGTGATAGCTGAGTTCAGAATTCTTAGTGAGTTAAGCCATCCCAA<br>CATTGTGAAGTACCTTCATCACGAACATATTTCTGAGAATAAAAC<br>TGTCAATTTATACATGGAATACTGTGATGGTGGAGATCTCTCCAA<br>GCTGATTCGAACACATAGAAGGAACAAAGAGTACATTTCAGAAG<br>AAAAAATATGGAGTATTTTTACGCAGGTTTTATTAGCATTGTATC<br>GTTGTCATTATGGAACTGATTTCACGGCTTCAAAGGAGTTTGAAT<br>CGCTCAATAAAGGTAATAGACGAACCCAGAATCCTTCGTGGGTA<br>GACTCGACAAGAGTTATTATTCACAGGGATATAAAACCCGACAA<br>CATCTTTCTGATGAACAATTCAAACCTTGTCAAACTGGGAGATTT<br>TGGATTAGCAAAAATTCTGGACCAAGAAAACGATTTTGCCAAAA<br>CATACGTCGGTACGCCGTATTACATGTCTCCTGAAGTGCTGTTGG<br>ACCAACCCTACTCACCATTATGTGATATATGGTCTCTTGGGTGCG<br>TCATGTATGAGCTATGTGCATTGAGGCCTCCTT |
| 84 | MET16 5' | GGGTGGGCCTGGTAATGTTCACTCCTAGGAACTACTAGAAAAAC<br>TGTGCTAAACGGATTACGTAATTATTATACAAATTCTCTATGGTC<br>TATGGTACATATGGGCTGGTTCAATAATGAATCTATGAAGAATTT<br>GTGCCCATGGGGACCGTTTCTATAAACGTTCTCTTCTTTATGTTTT<br>CCACCTGCTCTTTGAGTTCCGGAAATTCGTTGACAATCTTTTGTCC<br>CAATGTCGATTGGGCGTATTTAAAGCCCAGCTGTTTTCCTCTGAG<br>AAATTGATTCAACTTCCTCACCACCTCCACAAACTCACGCGTGTA<br>TATATCAGGGTTTCTACCGTCTTCGATATAATTGACTACGTCCAC<br>GGGGATGGGAATGTTCAAATCTGTGTTGTGGAGCTTTTGCAAGTG<br>CTCTACAACCTTGTTAATGTTGTTGGAAAGACCCAATTGACTTTC<br>CGCTGTACCGGCGTAATCGTGCACCTGAACACCCAAATGGATGA<br>GGGTTTCGATGAGTTGACTTAGTTCATTTTCAACTTGATCTAATG<br>TTGTCGCAGGTGCACTCATACTTGTCATGGAGAATGAAAGTAAG<br>TTGATAGAGCAGACTTCGAGGATGGGATGAACTTGATTAGGT<br>AATCTTTGACAATGTCTTAGAGGTAGGCAGAGGATGCTGGAAAA<br>AAAAAATTGAAAACGCCCAAGCTTCCAGCTTTGCAAGGAAAGAA<br>GAAAAGGGAGTTGCCAGCACGAAATCGGCTTCCTCCGAAAGGTT |

TABLE 14-continued

| SEQ ID NO: | Description | Sequence |
|---|---|---|
| | | CACAATTGCAGAATTGTCACCATTCAAATGCCTTTACCCTTCATC<br>TGTGGTACCTCAGGCTAAGAACGGGTCACGTGATATTTCGACACT<br>CATCGCCACAATATGTACTAGCAAGAACTTTTCAGATTTAGTAAT<br>CCGTTCGAAACGGG |
| 85 | MET16 3' | CTAGATTTGCACAATATTTGAAAGCTCAGCAAAACATATGAATA<br>TAATTTTTTTTTCTCTACACTATTTATCCTGTAAGTTTCTGTTTCC<br>CCATGTAGGATCTTTTTCTCCTTCTCTGTCTCCCATTTTTTTGTTC<br>CCTGTAGTCTTGCCTTGCCTGAGATGCGAGCTCGTCCGCCCATCC<br>AGTCGTGTGAAGGGCCTAGCTTTTCAAAAAGAAAATACCTCCCG<br>CTAAAGGAGGCGTTGCCCCTTCTATCAGTAGTGTCGTAACCAATT<br>TTCACAAACAATAAAAAAAGGACACCAACAACGAAATCAACTAT<br>TTACACACATCCAGATCCGTCCCCCTCCCCATCCAAGAGTTAAAG<br>ACAAATATGGCTGTTAATAATCCGTCTGAATTTAGAAAGAAGTT<br>GGTCGTAGTAGGAGATGGTGCTTGCGGTAAAACTTGTCTATTGAT<br>GGTGTTTGCCGAGGGCGAGTTCCCTCCATCTTATGTTCCAACTGT<br>TTTTGAGAACTATGCCACCCCAGTAGAGGTTGACAACAGAATAG<br>TACAACTCACTCTATGGGATACTGCCGGACAGGAAGATTATGAT<br>AGACTGAGACCTCTTTCCTATCCCGATGCCAATGTGGTCTTGATT<br>TGTTTTGCTATTGACATTCCTGACACCTTAGATAACGTTCAAGAG<br>AAGTGGATTAGTGAGGTGTTGCATTTCTGTCCTGGAGTCCCTATC<br>ATTTTAGTTGGTTGTAAACTTGACTTGAGAAACGATCCAGAGGTT<br>ATCCGTGAATTACAAGCTGTTGGAAAGCAACCAGTCTCCACCAG<br>TGAGGGTCAGGCCGTTGC |
| 86 | Sequence of the PpMET16 auxotrophic marker: | CAACTTCCTCACCACCTCCACAAACTCACGCGTGTATATATCAGG<br>GTTTCTACCGTCTTCGATATAATTGACTACGTCCACGGGGATGGG<br>AATGTTCAAATCTGTGTTGTGGAGCTTTTGCAAGTGCTCTACAAC<br>CTTGTTAATGTTGTTGGAAAGACCCAATTGACTTTCCGCTGTACC<br>GGCGTAATCGTGCACCTGAACACCCAAATGGATGAGGGTTTCGA<br>TGAGTTGACTTAGTTCATTTTCAACTTGATCTAATGTTGTCGCAG<br>GTGCACTCATACTTGTCATGGAGAATGAAAGTAAGTTGATAGAG<br>AGCAGACTTCGAGGATGGGATGAACTTGATTAGGTAATCTTTGA<br>CAATGTCTTAGAGGTAGGCAGAGGATGCTGGAAAAAAAAAATTG<br>AAAACGCCCAAGCTTCCAGCTTTGCAAGGAAAGAAGAAAAGGG<br>AGTTGCCAGCACGAAATCGGCTTCCTCCGAAAGGTTCACAATTG<br>CAGAATTGTCACCATTCAAATGCCTTTACCCTTCATCTGTGGTAC<br>CTCAGGCTAAGAACGGGTCACGTGATATTTCGACACTCATCGCC<br>ACAATATGTACTAGCAAGAACTTTTCAGATTTAGTAATCCGTTCG<br>AAACGGGAAAAAATGTTTTTACCCTTCTATCAACTGCTAATCTTT<br>CTAGGTTTATACTGCCAGCAGCCCGTTCCAGATACCAACATGCCA<br>TTCACTATAGGCCAGTCAAAAACCAGTTTGAACCTCTCCAAGGTC<br>CAAGTGGACCACCTTAACCTTTCTCTTCAGAATCTCAGTCCAGAA<br>GAAATCATACAATGGTCTATCATTACCTTCCCACACCTGTATCAA<br>ACTACGGCATTCGGATTGACTGGGTTGTGTATAACTGACATGGTT<br>CACAAAATAACAGCCAAAAGAGGCAAAAAGCATGCTATTGACTT<br>GATTTTCATAGACACCTTACATCATTTTCCACAGACTTTAGATCT<br>CGTTGAACGAGTCAAAGATAAATACCACTGCAATGTTCATGTCTT<br>CAAACCACAGAATGCCACTACTGAGCTCGAGTTTGGGGCGCAAT<br>ATGGCGAAAACTTATGGGAAACAGATGATAACAAGTATGACTAC<br>CTCGTAAAAGTTGAACCCTCACAACGTGCCTACCATGCATTAGAC<br>GTCTGCGCCGTCTTCACAGGAAGAAGACGGTCTCAAGGTGGTAA<br>AAGGGGAGAATTGCCCGTGATTGAAATTGATGAAATTTCTCAGG<br>TGGTCAAGATTAATCCGTTAGCATCCTGGGGGTTTGAACAAGTTC<br>AAAACTATATCCAAGCTAATAGCGTTCCATACAACGAATTGCTG<br>GATTTGGGATACAAGTCAGTTGGAGATTACCATTCCACACAACC<br>CACTAAAAATGGTGAAGATGAAAGAGCAGGCAGGTGGAGAGGT<br>AAACAAAAGAGTGAGTGTGGTATCCACGAAGCTTCTAGATTTGC<br>ACAATATTTGAAAGCTCAGCAAAACATATGAATATAATTTTTTTT<br>TTCTCTACACTATTTATCCTGTAAGTTTCTGTTTCCCCATGTAGGA<br>TCTTTTTCTCCTTCTCTGTCTCCCATTTTTTTGTTCCCTGTAGTCT<br>TGCCTTGCCTGAGATGCGAGCTCGTCCGCCCATCCAGTCGTGTGA<br>AGGGCCTAGCTTTTCAAAAGAAAATACCTCCCGCTAAAGGAGG<br>CGTTGCCCCTTCTATCAGTAGTGTCGTAACCAATTTTCACAAACA<br>ATAAAAAAAGGACACCAACAACGAAATCAACTATTTACACACAT<br>CCAGATCCGTCCC |

TABLE 14-continued

| SEQ ID NO: | Description | Sequence |
|---|---|---|
| 87 | Sequence of the 5'- Region used for knock out of PpHIS1: | TAACTGGCCCTTTGACGTTTCTGACAATAGTTCTAGAGGAGTCGT CCAAAAACTCAACTCTGACTTGGGTGACACCACCACGGGATCCG GTTCTTCCGAGGACCTTGATGACCTTGGCTAATGTAACTGGAGTT TTAGTATCCATTTTAAGATGTGTGTTTCTGTAGGTTCTGGGTTGG AAAAAAATTTTAGACACCAGAAGAGAGGAGTGAACTGGTTTGCG TGGGTTTAGACTGTGTAAGGCACTACTCTGTCGAAGTTTTAGATA GGGGTTACCCGCTCCGATGCATGGGAAGCGATTAGCCCGGCTGT TGCCCGTTTGGTTTTTGAAGGGTAATTTTCAATATCTCTGTTTGAG TCATCAATTTCATATTCAAAGATTCAAAAACAAAATCTGGTCCAA GGAGCGCATTTAGGATTATGGAGTTGGCGAATCACTTGAACGAT AGACTATTATTTGC |
| 88 | Sequence of the 3'- Region used for knock out of PpHIS1: | GTGACATTCTTGTCTTTGAGATCAGTAATTGTAGAGCATAGATAG AATAATATTCAAGACCAACGGCTTCTCTTCGGAAGCTCCAAGTA GCTTATAGTGATGAGTACCGGCATATATTTATAGGCTTAAAATTT CGAGGGTTCACTATATTCGTTTAGTGGGAAGAGTTCCTTTCACTC TTGTTATCTATATTGTCAGCGTGGACTGTTTATAACTGTACCAAC TTAGTTTCTTTCAACTCCAGGTTAAGAGACATAAATGTCCTTTGA TGCTGACAATAATCAGTGGAATTCAAGGAAGGACAATCCCGACC TCAATCTGTTCATTAATGAAGAGTTCGAATCGTCCTTAAATCAAG CGCTAGACTCAATTGTCAATGAGAACCCTTTCTTTGACCAAGAAA CTATAAATAGATCGAATGACAAAGTTGGAAATGAGTCCATTAGC TTACATGATATTGAGCAGGCAGACCAAAATAAACCGTCCTTTGA GAGCGATATTGATGGTTCGGCGCCGTTGATAAGAGACGACAAAT TGCCAAAGAAACAAAGCTGGGGGCTGAGCAATTTTTTTTCAAGA AGAAATAGCATATGTTTACCACTACATGAAAATGATTCAAGTGTT GTTAAGACCGAAAGATCTATTGCAGTGGGAACACCCCATCTTCA ATACTGCTTCAATGGAATCTCCAATGCCAAGTACAATGCATTTAC CTTTTTCCCAGTCATCCTATACGAGCAATTCAAATTTTTTTCAAT TTATACTTTACTTTAGTGGCTCTCTCTCAAGCGATACCGCAACTTC GCATTGGATATCTTTCTTCGTATGTCGTCCCACTTTTGTTTGTACT CATAGTGACCATGTCAAAAGAGGCGATGGATGATATTCAACGCC GAAGAAGGGATAGAGAACAGAACAATGAACCATATGAGGTTCT GTCCAGCCCATCACCAGTTTTGTCCAAAAACTTAAAATGTGGTCA CTTGGTTCGATTGCATAAGGGAATGAGAGTGCCCGCAGATATGG TTCTTGTCCAGTCAAGCGAATCCACCGGAGAGTCATTTATCAAGA CAGATCAGCTGGATGGTGAGACTGATTGGAAGCTTCGGATTGTTT CTCCAGTTACACAATCGTTACCAATGACTGAACTTCAAAATGTCG CCATCACTGCAAGCGCACCCTCAAAATCAATTCACTCCTTTCTTG GAAGATTGACCTACAATGGGCAATCATATGGTCTTACGATAGAC AACACAATGTGGTGTAATACTGTATTAGCTTCTGGTTCAGCAATT GGTTGTATAATTTACACAGGTAAAGATACTCGACAATCGATGAA CACAACTCAGCCCAAACTGAAAACGGGCTTGTTAGAACTGGAAA TCAATAGTTTGTCCAAGATCTTATGTGTTTGTGTGTTTGCATTATC TGTCATCTTAGTGCTATTCCAAGGAATAGCTGATGATTGGTACGT CGATATCATGCGGTTTCTCATTCTATTCTCCACTATTATCCCAGTG TCTCTGAGAGTTAACCTTGATCTTGGAAAGTCAGTCCATGCTCAT CAAATAGAAACTGATAGCTCAATACCTGAAACCGTTGTTAGAAC TAGTACAATACCGGAAGACCTGGGAAGAATTGAATACCTATTAA GTGACAAAACTGGAACTCTTACTCAAAATGATATGGAAATGAAA AAACTACACCTAGGAACAGTCTCTTATGCTGGTGATACCATGGAT ATTATTTCTGATCATGTTAAAGGTCTTAATAACGCTAAAACATCG AGGAAAGATCTTGGTATGAGAATAAGAGATTTGGTTACAACTCT GGCCATCTG |
| 89 | Sequence of the PpHIS1 auxotrophic marker: | CAAGTTGCGTCCGGTATACGTAACGTCTCACGATGATCAAAGAT AATACTTAATCTTCATGGTCTACTGAATAACTCATTTAAACAATT GACTAATTGTACATTATATTGAACTTATGCATCCTATTAACGTAA TCTTCTGGCTTCTCTCTCAGACTCCATCAGACACAGAATATCGTT CTCTCTAACTGGTCCTTTGACGTTTCTGACAATAGTTCTAGAGGA GTCGTCCAAAAACTCAACTCTGACTTGGGTGACACCACCACGGG ATCCGGTTCTTCCGAGGACCTTGATGACCTTGGCTAATGTAACTG GAGTTTTAGTATCCATTTTAAGATGTGTGTTTCTGTAGGTTCTGG GTTGGAAAAAAATTTTAGACACCAGAAGAGAGGAGTGAACTGGT TTGCGTGGGTTTAGACTGTGTAAGGCACTACTCTGTCGAAGTTTT AGATAGGGGTTACCCGCTCCGATGCATGGGAAGCGATTAGCCCG GCTGTTGCCCGTTTGGTTTTTGAAGGGTAATTTTCAATATCTCTGT TTGAGTCATCAATTTCATATTCAAAGATTCAAAAACAAAATCTGG TCCAAGGAGCGCATTTAGGATTATGGAGTTGGCGAATCACTTGA ACGATAGACTATTATTTGCTGTTCCTAAAGAGGGCAGATTGTATG AGAAATGCGTTGAATTACTTAGGGGATCAGATATTCAGTTTCGA AGATCCAGTAGATTGGATATAGCTTTGTGCACTAACCTGCCCCTG GCATTGGTTTTCCTTCCAGCTGCTGACATTCCCACGTTTGTAGGA GAGGGTAAATGTGATTTGGGTATAACTGGTATTGACCAGGTTCA GGAAAGTGACGTAGATGTCATACCTTTATTAGACTTGAATTTCGG TAAGTGCAAGTTGCAGATTCAAGTTCCCGAGAATGGTGACTTGA AAGAACCTAAACAGCTAATTGGTAAAGAAATTGTTTCCTCCTTTA |

TABLE 14-continued

| SEQ ID NO: | Description | Sequence |
|---|---|---|
| | | CTAGCTTAACCACCAGGTACTTTGAACAACTGGAAGGAGTTAAG<br>CCTGGTGAGCCACTAAAGACAAAAATCAAATATGTTGGAGGGTC<br>TGTTGAGGCCTCTTGTGCCCTAGGAGTTGCCGATGCTATTGTGGA<br>TCTTGTTGAGAGTGGAGAAACCATGAAAGCGGCAGGGCTGATCG<br>ATATTGAAACTGTTCTTTCTACTTCCGCTTACCTGATCTCTTCGAA<br>GCATCCTCAACACCCAGAACTGATGGATACTATCAAGGAGAGAA<br>TTGAAGGTGTACTGACTGCTCAGAAGTATGTCTTGTGTAATTACA<br>ACGCACCTAGAGGTAACCTTCCTCAGCTGCTAAAACTGACTCCA<br>GGCAAGAGAGCTGCTACCGTTTCTCCATTAGATGAAGAAGATTG<br>GGTGGGAGTGTCCTCGATGGTAGAGAAGAAAGATGTTGGAAGAA<br>TCATGGACGAATTAAAGAAACAAGGTGCCAGTGACATTCTTGTC<br>TTTGAGATCAGTAATTGTAGAGCATAGATAGAATAATATTCAAG<br>ACCAACGGCTTCTCTTCGGAAGCTCCAAGTAGCTTATAGTGATGA<br>GTACCGGCATATATTTATAGGCTTAAAATTTCGAGGGTTCACTAT<br>ATTCGTTTAGTGGGAAGAGTTCCTTTCACTCTTGTTATCTATATTG<br>TCAGCGTGGACTGTTTATAACTGTACCAACTTAGTTTCTTTCAAC<br>TCCAGGTTAAGAGACATAAATGTCCTTTGATGC |
| 90 | Sequence of the 5'-region that was used to knock into the PpPRO1 locus: | GAAGGGCCATCGAATTGTCATCGTCTCCTCAGGTGCCATCGCTGT<br>GGGCATGAAGAGAGTCAACATGAAGCGGAAACCAAAAAAGTTA<br>CAGCAAGTGCAGGCATTGGCTGCTATAGGACAAGGCCGTTTGAT<br>AGGACTTTGGGACGACCTTTTCCGTCAGTTGAATCAGCCTATTGC<br>GCAGATTTTACTGACTAGAACGGATTTGGTCGATTACACCCAGTT<br>TAAGAACGCTGAAAATACATTGGAACAGCTTATTAAAATGGGTA<br>TTATTCCTATTGTCAATGAGAATGACACCCTATCCATTCAAGAAA<br>TCAAATTTGGTGACAATGACACCTTATCCGCCATAACAGCTGGTA<br>TGTGTCATGCAGACTACCTGTTTTTGGTGACTGATGTGGACTGTC<br>TTTACACGGATAACCCTCGTACGAATCCGGACGCTGAGCCAATC<br>GTGTTAGTTAGAAATATGAGGAATCTAAACGTCAATACCGAAAG<br>TGGAGGTTCCGCCGTAGGAACAGGAGGAATGACAACTAAATTGA<br>TCGCAGCTGATTTGGGTGTATCTGCAGGTGTTACAACGATTATTT<br>GCAAAAGTGAACATCCCGAGCAGATTTTGGACATTGTAGAGTAC<br>AGTATCCGTGCTGATAGAGTCGAAATGAGGCTAAATATCTGGT<br>CATCAACGAAGAGGAAACTGTGGAACAATTTCAAGAGATCAATC<br>GGTCAGAACTGAGGGAGTTGAACAAGCTGGACATTCCTTTGCAT<br>ACACGTTTCGTTGGCCACAGTTTTAATGCTGTTAATAACAAAGAG<br>TTTTGGTTACTCCATGGACTAAAGGCCAACGGAGCCATTATCATT<br>GATCCAGGTTGTTATAAGGCTATCACTAGAAAAAACAAAGCTGG<br>TATTCTTCCAGCTGGAATTATTTCCGTAGAGGGTAATTTCCATGA<br>ATACGAGTGTGTTGATGTTAAGGTAGGACTAAGAGATCCAGATG<br>ACCCACATTCACTAGACCCCAATGAAGAACTTTACGTCGTTGGCC<br>GTGCCCGTTGTAATTACCCCAGCAATCAAATCAACAAAATTAAG<br>GGTCTACAAAGCTCGCAGATCGAGCAGGTTCTAGGTTACGCTGA<br>CGGTGAGTATGTTGTTCACAGGGACAACTTGGCTTTCCCAGTATT<br>TGCCGATCCAGAACTGTTGGATGTTGTTGAGAGTACCCTGTCTGA<br>ACAGGAGAGAATCCAAACCAAATAAATAG |
| 91 | Sequence of the 3'-region that was used to knock into the PpPRO1 locus: | AATTTCACATATGCTGCTTGATTATGTAATTATACCTTGCGTTCG<br>ATGGCATCGATTTCCTCTTCTGTCAATGCGCATCGCATTAAAAG<br>TATACTTTTTTTTTTTCCTATAGTACTATTCGCCTTATTATAAACT<br>TTGCTAGTATGAGTTCTACCCCCAAGAAAGAGCCTGATTTGACTC<br>CTAAGAAGAGTCAGCCTCCAAAGAATAGTCTCGGTGGGGGTAAA<br>GGCTTTAGTGAGGAGGGTTTCTCCCAAGGGGACTTCAGCGCTAA<br>GCATATACTAAATCGTCGCCCTAACACCGAAGGCTCTTCTGTGGC<br>TTCGAACGTCATCAGTTCGTCATCATTGCAAAGGTTACCATCCTC<br>TGGATCTGGAAGCGTTGCTGTGGGAAGTGTGTTGGGATCTTCGCC<br>ATTAACTCTTTCTGGAGGGTTCCACGGGCTTGATCCAACCAAGAA<br>TAAAATAGACGTTCCAAAGTCGAAACAGTCAAGGAGACAAAGTG<br>TTCTTTCTGACATGATTTCCACTTCTCATGCAGCTAGAAATGATC<br>ACTCAGAGCAGCAGTTACAAACTGGACAACAATCAGAACAAAA<br>AGAAGAAGATGGTAGTCGATCTTCTTTTTCTGTTTCTTCCCCCGC<br>AAGAGATATCCGGCACCCAGATGTACTGAAAACTGTCGAGAAAC<br>ATCTTGCCAATGACAGCGAGATCGACTCATCTTTACAACTTCAAG<br>GTGGAGATGTCACTAGAGGCATTTATCAATGGGTAACTGGAGAA<br>AGTAGTCAAAAGATAACCCGCCTTTGAAACGAGCAAATAGTTT<br>TAATGATTTTCTTCTGTGCATGGTGACGAGGTAGGCAAGGCAGA<br>TGCTGACCACGATCGTGAAAGCGTATTCGACGAGGATGATATCT<br>CCATTGATGATATCAAAGTTCCGGGAGGGATGCGTCGAAGTTTTT<br>TATTACAAAAGCATAGAGACCAACAACTTTCTGGACTGAATAAA<br>ACGGCTCACCAACCAAAACAACTTACTAAACCTAATTTCTTCACG<br>AACAACTTTATAGAGTTTTTGGCATTGTATGGGCATTTTGCAGGT<br>GAAGATTTGGAGGAAGACGAAGATGAAGATTTAGACAGTGGTTC<br>CGAATCAGTCGCAGTCAGTGATAGTGAGGGAGAATTCAGTGAGG<br>CTGACAACAATTTGTTGTATGATGAAGAGTCTCTCCTATTAGCAC<br>CTAGTACCTCCAACTATGCGAGATCAAGAATAGGAAGTATTCGT |

TABLE 14-continued

| SEQ ID NO: | Description | Sequence |
|---|---|---|
| | | ACTCCTACTTATGGATCTTTCAGTTCAAATGTTGGTTCTTCGTCTA<br>TTCATCAGCAGTTAATGAAAAGTCAAATCCCGAAGCTGAAGAAA<br>CGTGGACAGCACAAGCATAAAACACAATCAAAAATACGCTCGAA<br>GAAGCAAACTACCACCGTAAAAGCAGTGTTGCTGCTATTAAA |
| 92 | Truncated hEPO DNA (codon optimized) | GCTCCACCAAGATTGATTTGTGACTCCAGAGTTTTGGAGAGATAC<br>TTGTTGGAGGCTAAAGAGGCTGAGAACATCACTACTGGTTGTGC<br>TGAACACTGTTCCTTGAACGAGAACATCACAGTTCCAGACACTA<br>AGGTTAACTTCTACGCTTGGAAGAGAATGGAAGTTGGACAACAG<br>GCTGTTGAAGTTTGGCAAGGATTGGCTTTGTTGTCCGAGGCTGTT<br>TTGAGAGGTCAAGCTTTGTTGGTTAACTCCTCCCAACCATGGGAA<br>CCATTGCAATTGCACGTTGACAAGGCTGTTTCTGGATTGAGATCC<br>TTGACTACTTTGTTGAGAGCTTTGGGTGCTCAGAAAGAGGCTATT<br>TCTCCACCAGATGCTGCTTCAGCTGCTCCATTGAGAACTATCACT<br>GCTGACACTTTCAGAAAGTTGTTCAGAGTTTACTCCAACTTCTTG<br>AGAGGAAAGTTGAAGTTGTACACTGGTGAAGCTTGTAGAACTGG<br>TGACTAGTAA |
| 93 | Truncated hEPO protein | APPRLICDSR VLERYLLEAK EAENITTGCA EHCSLNENIT VPDTKVNFYA<br>WKRMEVGQQA VEVWQGLALL SEAVLRGQAL LVNSSQPWEP<br>LQLHVDKAVS GRSLTTLLR ALGAQKEAIS PPDAASAAPL RTITADTFRK<br>LFRVYSNFLR GKLKLYTGEA CRTGD |
| 94 | Chicken lysosome signal DNA (CLSP) | ATGCTGGGTAAGAACGACCCAATGTGTCTTGTTTTGGTCTTGTTG<br>GGATTGACTGCTTTGTTGGGTATCTGTCAAGGT |
| 95 | Chicken lysosome signal peptide (CLSP) | MLGKNDPMCLVLVLLGLTALLGICQG |
| 96 | Sequence of the PpAde2 gene without its promoter but including its termination sequences | ATGGATTCTCAGGTAATAGGTATTCTAGGAGGAGGCCAGCTAGG<br>CCGAATGATTGTTGAGGCCGCTAGCAGGCTCAATATCAAGACCG<br>TGATTCTTGATGATGGTTTTTCACCTGCTAAGCACATTAATGCTG<br>CGCAAGACCACATCGACGGATCATTCAAAGATGAGGAGGCTATC<br>GCCAAGTTAGCTGCCAAATGTGATGTTCTCACTGTAGAGATTGAG<br>CATGTCAACACAGATGCTCTAAAGAGAGTTCAAGACAGAACTGG<br>AATCAAGATATATCCTTTACCAGAGACAATCGAACTAATCAAGG<br>ATAAGTACTTGCAAAAGGAACATTTGATCAAGCACAACATTTCG<br>GTGACAAAGTCTCAGGGTATAGAATCTAATGAAAAGGCGCTGCT<br>TTTGTTTGGAGAAGAGAATGGATTTCCATATCTGTTGAAGTCCCG<br>GACTATGGCTTATGATGGAAGAGGCAATTTTGTAGTGGAGTCTA<br>AAGAGGACATCAGTAAGGCATTAGAATTCTTGAAAGATCGTCCA<br>TTGTATGCCGAGAAGTTTGCTCCTTTTGTTAAAGAATTAGCGGTA<br>ATGGTTGTGAGATCACTGGAAGGCGAAGTATTCTCCTACCCAAC<br>CGTAGAAACTGTGCACAAGGACAATATCTGTCATATTGTGTATGC<br>TCCGGCCAGAGTTAATGACACCATCCAAAAGAAAGCTCAAATAT<br>TAGCTGAAAACACTGTGAAGACTTTCCCAGGCGCTGGAATCTTC<br>GGAGTTGAGATGTTCCTATTGTCTGATGGAGAACTTCTTGTAAAT<br>GAGATTGCTCCAAGGCCCCACAATTCTGGTCACTATACAATCGAT<br>GCATGTGTAACATCTCAGTTCGAAGCACATGTAAGAGCCATAAC<br>TGGTCTGCCAATGCCACTAGATTTCACCAAACTATCTACTTCCAA<br>CACCAACGCTATTATGCTCAATGTTTTGGGTGCTGAAAAATCTCA<br>CGGGGAATTAGAGTTTTGTAGAAGAGCCTTAGAAACACCCGGTG<br>CTTCTGTATATCTGTACGGAAAGACCACCCGATTGGCTCGTAAGA<br>TGGGTCATATCAACATAATAGGATCTTCCATGTTGGAAGCAGAA<br>CAAAAGTTAGAGTACATTCTAGAAGAATCAACCCACTTACCATC<br>CAGTACTGTATCAGCTGACACTAAACCGTTGGTTGGAGTTATCAT<br>GGGTTCAGACTCTGATCTACCTGTGATTTCGAAAGGTTGCGATAT<br>TTTAAAACAGTTTGGTGTTCCATTCGAAGTTACTATTGTCTCTGCT<br>CATAGAACACCACAGAGAATGACCAGATATGCCTTTGAAGCCGC<br>TAGTAGAGGTATCAAGGCTATCATTGCAGGTGCTGGTGGTGCTG<br>CTCATCTTCCAGGAATGGTTGCTGCCATGACTCCGTTGCCAGTCA<br>TTGGTGTTCCTGTCAAGGGCTCTACGTTGGATGTGTAGACTCGC<br>TACACTCGATTGTCCAAATGCCTAGAGGTGTTCCTGTGGCTACGG<br>TTGCTATCAACAACGCCACCAATGCCGCTCTGTTGGCCATCAGGA<br>TTTTAGGTACAATTGACCACACAAATGGCAAAAGGAAATGTCCAAG<br>TATATGAATGCAATGGAGACCGAAGTGTTGGGGAAGGCATCCAA<br>CTTGGAATCTGAAGGGTATGAATCCTATTTGAAGAATCGTCTT*TG<br>AATTTAGTATTGTTTTTTAATAGATGTATATATAATAGTACACGTAACTT* |

TABLE 14-continued

| SEQ ID NO: | Description | Sequence |
|---|---|---|
| | | ATCTATTCCATTCATAATTTTATTTTAAAGGTTCGGTAGAAATTTGTCCT
CCAAAAAGTTGGTTAGAGCCTGGCAGTTTTGATAGGCATTATTATAGA
TTGGGTAATATTTACCCTGCACCTGGAGGAACTTTGCAAAGAGCCTCA
TGTGC |
| 97 | PpADE2 | MDSQVIGILGGGQLGRMIVEAASRLNIKTVILDDGFSPAKHINAAQD
HIDGSFKDEEAIAKLAAKCDVLTVEIEHVNTDALKRVQDRTGIKIYP
LPETIELIKDKYLQKEHLIKHNISVTKSQGIESNEKALLLFGEENGFPY
LLKSRTMAYDGRGNFVVESKEDISKALEFLKDRPLYAEKFAPFVKE
LAVMVVRSLEGEVFSYPTVETVHKDNICHIVYAPARVNDTIQKKAQ
ILAENTVKTFPGAGIFGVEMFLLSDGELLVNEIAPRPHNSGHYTIDAC
VTSQFEAHVRAITGLPMPLDFTKLSTSNTNAIMLNVLGAEKSHGELE
FCRRALETPGASVYLYGKTTRLARKMGHINIIGSSMLEAEQKLEYIL
EESTHLPSSTVSADTKPLVGVIMGSDSDLPVISKGCDILKQFGVPFEV
TIVSAHRTPQRMTRYAFEAASRGIKAIIAGAGGAAHLPGMVAAMTP
LPVIGVPVKGSTLDGVDSLHSIVQMPRGVPVATVAINNATNAALLAI
RILGTIDHKWQKEMSKYMNAMETEVLGKASNLESEGYESYLKNRL |
| 98 | Pp TRP2: 5' and ORF | ACTGGGCCTTTAGAGGGTGCTGAAGTTGACCCCTTGGTGCTTCTG
GAAAAAGAACTGAAGGGCACCAGACAAGCGCAACTTCCTGGTAT
TCCTCGTCTAAGTGGTGGTGCCATAGGATACATCTCGTACGATTG
TATTAAGTACTTTGAACCAAAAACTGAAAGAAAACTGAAAGATG
TTTTGCAACTTCCGGAAGCAGCTTTGATGTTGTTCGACACGATCG
TGGCTTTTGACAATGTTTATCAAAGATTCCAGGTAATTGGAAACG
TTTCTCTATCCGTTGATGACTCGGACGAAGCTATTCTTGAGAAAT
ATTATAAGACAAGAGAAGAAGTGGAAAAGATCAGTAAAGTGGT
ATTTGACAATAAAACTGTTCCCTACTATGAACAGAAAGATATTAT
TCAAGGCCAAACGTTCACCTCTAATATTGGTCAGGAAGGGTATG
AAAACCATGTTCGCAAGCTGAAAGAACATATTCTGAAAGGAGAC
ATCTTCCAAGCTGTTCCCTCTCAAAGGGTAGCCAGGCCGACCTCA
TTGCACCCTTTCAACATCTATCGTCATTTGAGAACTGTCAATCCTT
CTCCATACATGTTCTATATTGACTATCTAGACTTCCAAGTTGTTG
GTGCTTCACCTGAATTACTAGTTAAATCCGACAACAACAACAAA
ATCATCACACATCCTATTGCTGGAACTCTTCCCAGAGGTAAAACT
ATCGAAGAGGACGACAATTATGCTAAGCAATTGAAGTCGTCTTT
GAAAGACAGGGCCGAGCACGTCATGCTGGTAGATTTGGCCAGAA
ATGATATTAACCGTGTGTGTGAGCCCACCAGTACCACGGTTGATC
GTTTATTGACTGTGGAGAGATTTTCTCATGTGATGCATCTTGTGT
CAGAAGTCAGTGGAACATTGAGACCAAACAAGACTCGCTTCGAT
GCTTTCAGATCCATTTTCCCAGCAGGTACCGTCTCCGGTGCTCCG
AAGGTAAGAGCAATGCAACTCATAGGAGAATTGGAAGGAGAAA
AGAGAGGTGTTTATGCGGGGGCCGTAGGACACTGGTCGTACGAT
GGAAAATCGATGGACACATGTATTGCCTTAAGAACAATGGTCGT
CAAGGACGGTGTCGCTTACCTTCAAGCCGGAGGTGGAATTGTCT
ACGATTCTGACCCCTATGACGAGTACATCGAAACCATGAACAAA
ATGAGATCCAACAATAACACCATCTTGGAGGCTGAGAAAATCTG
GACCGATAGGTTGGCCAGAGACGAG
AATCAAAGTGAATCCGAAGAAAACGATCAATGA |
| 99 | PpTRP2 3' region | ACGGAGGACGTAAGTAGGAATTTATGTAATCATGCCAATACATC
TTTAGATTTCTTCCTCTTCTTTTTAACGAAAGACCTCCAGTTTTGC
ACTCTCGACTCTCTAGTATCTTCCCATTTCTGTTGCTGCAACCTCT
TGCCTTCTGTTTCCTTCAATTGTTCTTCTTTCTTCTGTTGCACTTGG
CCTTCTTCCTCCATCTTTCGTTTTTTTTCAAGCCTTTTCAGCAGTTC
TTCTTCCAAGAGCAGTTCTTTGATTTTCTCTCTCCAATCCACCAAA
AAACTGGATGAATTCAACCGGGCATCATCAATGTTCCACTTTCTT
TCTCTTATCAATAATCTACGTGCTTCGGCATACGAGGAATCCAGT
TGCTCCCTAATCGAGTCATCCACAAGGTTAGCATGGGCCTTTTTC
AGGGTGTCAAAAGCATCTGGAGCTCGTTATTCGGAGTCTTGTCT
GGATGGATCAGCAAAGACTTTTTGCGGAAAGTCTTTCTTATATCT
TCCGGAGAACAACCTGGTTTCAAATCCAAGATGGCATAGCTGTC
CAATTTGAAAGTGGAAAGAATCCTGCCAATTTCCTTCTCTCGTGT
CAGCTCGTTCTCCTCCTTTTGCAACAGGTCCACTTCATCTGGCATT
TTTCTTTATGTTAACTTTAATTATTATTAATTATAAAGTTGATTAT
CGTTATCAAAATAATCATATTCGAGAAATAATCCGTCCATGCAAT
ATATAAATAAGAATTCATAATAATGTAATGATAACAGTACCTCT
GATGACCTTTGATGAACCGCAATTTTCTTTCCAATGACAAGACAT
CCCTATAATCAATTATACAGTTTATATATCACAAATAATCACCT
TTTTATAAGAAAACCGTCCTCTCCGTAACAGAACTTATTATCCGC
ACGTTATGGTTAACACACTACTAATACCGATATAGTGTATGAAGT
CGCTACGAGATAGCCATCCAGGAAACTTACCAATTCATCAGCAC
TTTCATGATCCGATTGTTGGCTTTATTCTTTGCGAGACAGATACTT
GCCAATGAAATAACTGATCCCACAGATGAGAATCCGGTGCTCGT |

TABLE 14-continued

| SEQ ID NO: | Description | Sequence |
|---|---|---|
| 100 | Pp ADE2 5' region | CTTAAAATCATCTGCCTCACCCCACCGACCAATGGGAATTCTAGA<br>AACAATTTCATTGCTCTTCTTCTCGTTACCATAAGAATCGGCTGT<br>CATGTTTGACTTAACGAACCCTGGAACAAGGGAATTCACGGTAA<br>TACCTTTTGGAGCAAGTTCAACCGATAGAGCCTTCATTAATGAGT<br>TGATTGCACCTTTGGTGGTCGCATATACCGATTGATTCGGGTAGG<br>TCACTTCGAAACTGTACAGGGAGGCAGTAAAGATGATCCTACCC<br>TTAATCTGGTTCTTAATAAAGTGTTTAGTGACTAGCTGTGTCAAT<br>CTAAATGGAAAATCGACATTTACCTTTTGGATAGCCGCGTAATCT<br>TTCTCCGTAAAACTTGTAAACTCAGATTTAATGGCAATGGCAGCG<br>TTGTTGATTAAAATGTCAATCTTTCCAGTGGAACTCTTCTCCACC<br>GCAGGACTCGTTACGGTCTCTTCCAGCTTTTGCAAGATCGGCATCC<br>ACTAGATCCAACTCAATTGTATGTATGGAGGCACCATCGGCATTT<br>GACATTCTCACCTCTTCAATGAAAGCCGTTGGGTCTGTAGAAGGT<br>CTATGGATAAGAATAAGTTCTGCACCTGCTTCATAAAGTCCTCGA<br>ACTATTCCTTGGCCTAATCCGCTGGTACCACCGGTGATCAAGGCG<br>ACCTTACCATTCAAAGAAAACAAATCAGCGGACATTAGCGACTT<br>GAATAGGGAATGGGTTAGACAAATGAAAGCCGACGAGCCAGCA<br>CTTTATAGTAAGTGCAGGTGAGTCAATAAGAATAAATGTATGGC<br>TTGCTGTCCCTATCGCGTAAGAAGCTTACTAAGATCGCCTAAATT<br>GAAAAGTTGAACAAATCAGTTCTAGCTGGCCTCCATCAGCATTTC<br>GTTCTCCTCTGATCATCTTTGCCAATCGCTAGCATGCCCTCAGCG<br>TGCAAGGAAAAGCACGCTTCTTTCTTATCGACGTATTTTCAACTA<br>TGGCAGAGCCAGGTTAGCAAGTC |
| 101 | Pp ADE2 3' region | ATTTAGTATTGTTTTTTAATAGATGTATATATAATAGTACACGTA<br>ACTTATCTATTCCATTCATAATTTTATTTTAAAGGTTCGGTAGAA<br>ATTTGTCCTCCAAAAAGTTGGTTAGAGCCTGGCAGTTTTGATAGG<br>CATTATTATAGATTGGGTAATATTTACCCTGCACCTGGAGGAACT<br>TTGCAAAGAGCCTCATGTGCTCTAAAAGGATGTCAGAATTCCAA<br>CATTTCAAAATTATATCTGCATGCGTCTGTAATACTGGAACTGTT<br>ATTTTTCTGGTCAGGATTTCACCGCTCTTGTCGTCATGTTTCTCGT<br>CGTCTGAAAGTAAACTGACTTTCCTCTTTCCATAAACACAAAAAT<br>CGATTGCAACTTGGTTATTCTTGAGATTGAAATTTGCTGTGTCTTC<br>AGTGCTTAGCTGAATATCAACAAACTTACTTAGTACTAATAACGA<br>AGCACTATGTAAGTGGCATAACATAGTGGTATTGAAGCGAACA<br>GTGGATATTGAACCCAAGCATTGGCAACATCTGGCTCTGTTGATA<br>CTGATCCGGATCGTTTGGCACCAATTCCTGAAACGGCGTAGTGCC<br>ACCAAGGTTTCGATTTGAGAACAGGTTCATCATCAGAGTCAACC<br>ACCCCAATGTCAATGGCAGGCTCCAACGAAGTAGGTCCAACAAC<br>AACAGGAAGTATTTGACCTTGAAGATCTGTTCCTTTATGATCCAC<br>CACACCCTTGCCCCAATTCCAATAACTTTACCAGTCCCGATGCAGA<br>CATGATAACTGGTACTAATGATCTCCATTGATTTTCGTCGGCACT<br>ACGTAAAGCCTCCAAAAATGAATTCAGAATATCTTCTGAAACTA<br>GATTCTGCTTCTGTGATTCAAGCATTGCTTTATGTAGACATCTCTT<br>GAATAAAAGCAATTCTCCACATATTGGTGTGTGTAAGATAGATCT<br>GGAAAGATGTATCTGGAATAGTCCAGTCAACGTTGTGCAATTGA<br>TTAGCATTACCTTACTGTGAACATCTCTATCTACAACAACAGACT<br>CAATTCGATAGACGTTCCGGGAAAGTTTTTCAAGCGCATTCAGTT<br>TGCTGTTGAACAAAGTGACTTTGCTTTCCAATGTGCAAATACCCC<br>TGTATATCAAGTCCATCACATCACTCAAGACCTTGGTGGAAAAG<br>AATGAAACAGCTGGAGCATAATTTTCGAATGAATTAGGTAAGGT<br>CACTTCATCCTTATCTGTTGTAATGCTATAATCAATAGCGGAACT<br>AACATCTTCCCATGTAACAGGTTTCTTGATCTCTGAATCTGAATC<br>TTTATTTGAAAAAGAATTGAAAAAAGACTCATCACTCATTGGGA<br>ATTCAAGGTCATTAGGGTATTCCATTGTTAGTTCGTGGTCTAGGTT<br>TAAAGGGATCACCTTCGTTAAGACGATGGAAAATAGCTAATCTG<br>TACAATAACCAGATACTTCTAACGAAGCTCTCTCTATCCATCAGT<br>TGACGTGTTGAGGATATCTGAACTAGCTCTTTCCACTGCAATCA<br>GGCATGCTCGTATAGCTGGCAAGCATGTTATTCAGCTTTACCAAG<br>TTAGAAGCCCTTTGGAAACCATCTATAGATTCCCGAAAAAACTTA<br>TACCCACTGAGGGTTTCACTGAGCATAGTCAGTGACATCAAAGA<br>GCATTTCAAATCCATCTCA |
| 102 | NATR ORF | ATGGGTACCACTCTTGACGACACGGCTTACCGGTACCGCACCAG<br>TGTCCCGGGGGACGCCGAGGCCATCGAGGCACTGGATGGGTCCT<br>TCACCACCGACACCGTCTTCCGCGTCACCGCCACCGGGGACGGC<br>TTCACCCTGCGGGAGGTGCCGGTGGACCCGCCCCTGACCAAGGT<br>GTTCCCCGACGACGAATCGGACGACGAATCGGACGACGGGGAG<br>GACGGCGACCCGGACTCCCGGACGTTCGTCGCGTACGGGGACGA<br>CGGCGACCTGGCGGGCTTCGTGGTCGTCTCGTACTCCGGCTGGAA<br>CCGCCGGCTGACCGTCGAGGACATCGAGGTCGCCCCGGAGCACC<br>GGGGGCACGGGGTCGGGCGCGCGTTGATGGGGCTCGCGACGGA<br>GTTCGCCCGCGAGCGGGGCGCCGGGCACCTCTGGCTGGAGGTCA<br>CCAACGTCAACGCACCGGCGATCCACGCGTACCGGCGGATGGGG<br>TTCACCCCTCTGCGGCCTGGACACCGCCCTGTACGACGGCACCGCC<br>TCGGACGGCGAGCAGGCGCTCTACATGAGCATGCCCTGCCCCTA<br>ATCAGTACTG |

| SEQ ID NO: | Description | Sequence |
|---|---|---|
| 103 | HygR ORF | ATGAAAAAGCCTGAACTCACCGCGACGTCTGTCGAGAAGTTTCT GATCGAAAAGTTCGACAGCGTCTCCGACCTGATGCAGCTCTCGG AGGGCGAAGAATCTCGTGCTTTCAGCTTCGATGTAGGAGGGCGT GGATATGTCCTGCGGGTAAATAGCTGCGCCGATGGTTTCTACAA AGATCGTTATGTTTATCGGCACTTTGCATCGGCCGCGCTCCCGAT TCCGGAAGTGCTTGACATTGGGGAATTCAGCGAGAGCCTGACCT ATTGCATCTCCCGCCGTGCACAGGGTGTCACGTTGCAAGACCTGC CTGAAACCGAACTGCCCGCTGTTCTGCAGCCGGTCGCGGAGGCC ATGGATGCGATCGCTGCGGCCGATCTTAGCCAGACGAGCGGGTT CGGCCCATTCGGACCGCAAGGAATCGGTCAATACACTACATGGC GTGATTTCATATGCGCGATTGCTGATCCCCATGTGTATCACTGGC AAACTGTGATGGACGACACCGTCAGTGCGTCCGTCGCGCAGGCT CTCGATGAGCTGATGCTTTGGGCCGAGGACTGCCCCGAAGTCCG GCACCTCGTGCACGCGGATTTCGGCTCCAACAATGTCCTGACGG ACAATGGCCGCATAACAGCGGTCATTGACTGGAGCGAGGCGATG TTCGGGGATTCCCAATACGAGGTCGCCAACATCTTCTTCTGGAGG CCGTGGTTGGCTTGTATGGAGCAGCAGACGCGCTACTTCGAGCG GAGGCATCCGGAGCTTGCAGGATCGCCGCGGCTCCGGGCGTATA TGCTCCGCATTGGTCTTGACCAACTCTATCAGAGCTTGGTTGACG GCAATTTCGATGATGCAGCTTGGGCGCAGGGTCGATGCGACGCA ATCGTCCGATCCGGAGCCGGGACTGTCGGGCGTACACAAATCGC CCGCAGAAGCGCGGCCGTCTGGACCGATGGCTGTGTAGAAGTAC TCGCCGATAGTGGAAACCGACGCCCCAGCACTCGTCCGAGGGCA AAGGAATAG |
| 104 | PpPEP4 region (including upstream knock-out fragment, promoter, open reading frame, and downstream knock-out fragment) | ATTTGAGTCACCTGCTTTAGGGCTGGAAGATATTTGGTTACTAGA TTTTAGTACAAACTCTTGCTTTGTCAATGACATTAAAATAGGCAA GAATCGCAAAACTCAAATATTTCATGGAGATGAGATATGCTTGTT CAAAGATGCCCAGAAAAAGAGCAACTCGTTTATAGGGTTCATA TTGATGATGGAACAGGCCTTTTCCAGGGAGGTAGAAGAACCCAA GCCAATTCTGATGACATTCTGGATATTGATGAGGTTGATGAAAA GTTAAGAGAACTATTGACAAGAGCCTCAAGGAAACGGCATATCA CCCCTGCATTGGAAACTCCTGATAAACGTGTAAAAAGAGCTTATT TGAACAGTATTACTGATAACTCTTGATGGACCTTAAAGATGTATA ATAGTAGACAGAATTCATAATGGTGAGATTAGGTAATCGTCCGG AATAGGAATAGTGGTTTGGGGCGATTAATCGCACCTGCCTTATAT GGTAAGTACCTTGACCGATAAGGTGGCAACTATTTAGAACAAAG CAAGCCACCTTTCTTTATCTGTAACTCTGTCGAAGCAAGCATCTT TACTAGAGAACATCTAAACCATTTTACATTCTAGAGTTCCATTTC TCAATTACTGATAATCAATTTAAAGATGATATTTGACGGTACTAC GATGTCAATTGCCATTGGTTTGCTCTCTACTCTAGGTATTGGTGCT GAAGCCAAAGTTCATTCTGCTAAGATACACAAGCATCCAGTCTC AGAAACTTTAAAAGAGGCCAATTTTGGGCAGTATGTCTCTGCTCT GGAACATAAATATGTTTCTCTGTTCAACGAACAAAATGCTTTGTC CAAGTCGAATTTTATGTCTCAGCAAGATGGTTTTGCCGTTGAAGC TTCGCATGATGCTCCACTTACAAACTATCTTAACGCTCAGTATTT TACTGAGGTATCATTAGGTACCCCTCCACAATCGTTCAAGGTGAT TCTTGACACAGGATCCTCCAATTTATGGGTTCCTAGCAAAGATTG TGGATCATTAGCTTGCTTCTTGCATGCTAAGTATGACCATGATGA GTCTTCTACTTATAAGAAGAATGGTAGTAGCTTTGAAATTAGGTA TGGATCCGGTTCCATGGAAGGGTATGTTTCTCAGGATGTGTTGCA AATTGGGGATTTGACCATTCCCAAAGTTGATTTTGCTGAGGCCAC ATCGGAGCCGGGGTTGGCCTTCGCTTTTGGCAAATTTGACGGAAT TTTGGGGCTTGCTTATGATTCAATATCAGTAAATAAGATTGTTCC TCCAATTTACAAGGCTTTGGAATTAGATCTCCTTGACGAACCAAA ATTTGCCTTCTACTTGGGGGATACGGACAAAGATGAATCCGATG GCGGTTTGGCCACATTTGGTGGTGTGGACAAATCTAAGTATGAA GGAAAGATCACCTGGTTGCCTGTCAGAAGAAAGGCTTACTGGGA GGTCTCTTTTGATGGTGTAGGTTTGGGATCCGAATATGCTGAATT GCAAAAAACTGGTGCAGCCATCGACACTGGAACCTCATTGATTG CTTTGCCCAGTGGCCTAGCTGAAATTCTCAATGCAGAAATTGGTG CTACCAAGGGTTGGTCTGGTCAATACGCTGTGGACTGTGACACTA GAGACTCTTTGCCAGACTTAACTTTAACCTTCGCCGGTTACAACT TTACCATTACTCCATATGACTATACTTTGGAGGTTTCTGGGTCAT GTATTAGTGCTTTCACCCCCATGGACTTTCCTGAACCAATAGGTC CTTTGGCAATCATTGGTGACTCGTTCTTGAGAAAATATTACTCAG TTTATGACCTAGGCAAAGATGCAGTAGGTTTAGCCAAGTCTATTT AGGCAAGAATAAAAGTTGCTCAGCTGAACTTATTTGGTTACTTAT CAGGTAGTGAAGATGTAGAGAATATATGTTTAGGTATTTTTTTTT AGTTTTTCTCCTATAACTCATCTTCAGTACGTGATTGCTTGTCAGC TACCTTGACAGGGCGCATAAGTGATATCGTGTACTGCTCAATCA AGATTTGCCTGCTCCATTGATAAGGGTATAAGAGACCCACCTGCT CCTCTTTAAAATTCTCTCTTAACTGTTGTGAAAATCATCTTCGAA GCAAATTCGAGTTTAAATCTATGCGGTTGGTAACTAAAGGTATGT CATGGTGGTATATAGTTTTTCATTTTACCTTTTACTAATCAGTTTT ACAGAAGAGGAACGTCTTTCTCAAGATCGAAATAGGACTAAATA CTGGAGACGATGGGGTCCTTATTTGGGTGAAAGGCAGTGGGCTA |

TABLE 14-continued

| SEQ ID NO: | Description | Sequence |
|---|---|---|
| | | CAGTAAGGGAAGACTATTCCGATGATGGAGATGCTTGGTCTGCT<br>TTTCCTTTTGAGCAATCTCATTTGAGAACTTATCGCTGGGGAGAG<br>GATGGACTAGCTGGAGTCTCAGACAATCATCAACTAATTTGTTTC<br>TCAATGGCACTGTGGAATGAGAATGATGATATTTTGAAGGAGCG<br>ATTATTTGGGGTCACTGGAGAGGCTGCAAATCATGGAGAGGATG<br>TTAAGGAGCTTTATTATTATCTTGATAATACACCTTCTCACTCTTA<br>TATGAAATACCTTTACAAATATCCACAATCGAAATTTCCTTACGA<br>AGAATTGATTTCAGAGAACCGTAAACGTTCCAGATTAGAAAGAG<br>AGTACGAGATTACTGACTCTGAAGTACTGAAGGATAACAGATAT<br>TTTGATGTGATCTTTGAAATGGCAAAGGACGATGAAGATGAGAA<br>TGAACTTTACTTTAGAATTACCGCTTACAACCGAGGTCCCACCCC<br>TGCCCCTTTACATGTCGCTCCACAGGTAACCTTTAGAAATACCTG<br>GTCCTGGGGTATAGATGAGGAAAAGGATCACGACAAACCTATAG<br>CTTGCAAGGAATACCAAGACAACAACTATTCTATTCGGTTAGAT<br>AGTT |
| 105 | Ashbya gossypii TEF1 promoter | GATCTGTTTAGCTTGCCTCGTCCCCGCCGGGTCACCCGGCCAGCG<br>ACATGGAGGCCCAGAATACCCTCCTTGACAGTCTTGACGTGCGC<br>AGCTCAGGGGCATGATGTGACTGTCGCCCGTACATTTAGCCCATA<br>CATCCCCATGTATAATCATTTGCATCCATACATTTTGATGGCCGC<br>ACGGCGCGAAGCAAAAATTACGGCTCCTCGCTGCAGACCTGCGA<br>GCAGGGAAACGCTCCCCTCACAGACGCGTTGAATTGTCCCCACG<br>CCGCGCCCCTGTAGAGAAATATAAAAGGTTAGGATTTGCCACTG<br>AGGTTCTTCTTTCATATACTTCCTTTTAAAATCTTGCTAGGATACA<br>GTTCTCACATCACATCCGAACATAAACAACC |
| 106 | Ashbya gossypii TEF1 termination sequence | TAATCAGTACTGACAATAAAAAGATTCTTGTTTTCAAGAACTTGT<br>CATTTGTATAGTTTTTTTATATTGTAGTTGTTCTATTTTAATCAAA<br>TGTTAGCGTGATTTATATTTTTTTCGCCTCGACATCATCTGCCCA<br>GATGCGAAGTTAAGTGCGCAGAAAGTAATATCATGCGTCAATCG<br>TATGTGAATGCTGGTCGCTATACTGCTGTCGATTCGATACTAACG<br>CCGCCATCCAGTGTCGAAAAC |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for producing a recombinant glycoprotein in Pichia pastoris host cells that lacks detectable cross binding activity with antibodies that bind immunogenic B-linked mannose residues, comprising:

(a) providing a recombinant Pichia pastoris host cell which does not display β-mannosyltransferase 2 activity with respect to an N-glycan or O-glycan and does not display at least one activity selected from β-mannosyltransferase 1 activity and β-mannosyltransferase 3 activity with respect to an N-glycan or O-glycan and which includes a nucleic acid molecule encoding the recombinant glycoprotein;

(b) growing the host cell in a medium under conditions effective for expressing the recombinant glycoprotein; and (c) recovering the recombinant glycoprotein from the medium to produce the recombinant glycoprotein that lacks detectable cross binding activity with antibodies that bind B-linked mannose residues.

2. The method of claim 1, wherein the host cell does not display β-mannosyltransferase 2 activity, β-mannosyltransferase 1 activity, and β-mannosyltransferase 3 activity with respect to an N-glycan or O-glycan.

3. The method of claim 1, wherein the host cell further does not display β-mannosyltransferase 4 activity with respect to an N-glycan or O-glycan.

4. The method of claim 1, wherein the detectable antibody cross binding activity is determined in a sandwich ELISA.

5. The method of claim 1, wherein the detectable antibody cross binding activity is determined in a Western blot.

6. The method of claim 1, wherein the recombinant glycoprotein is a therapeutic glycoprotein.

7. The method of claim 6, wherein the therapeutic glycoprotein is selected from the group consisting erythropoietin (EPO); cytokines such as interferon α, interferon β, interferon γ, and interferon ω; and granulocyte-colony stimulating factor (GCSF); GM-CSF; coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; and urea trypsin inhibitor; IGF-binding protein; epidermal growth factor; growth hormone-releasing factor; annexin V fusion protein; angiostatin; vascular endothelial growth factor-2; myeloid progenitor inhibitory factor-I; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4—Ig; transmembrane activator and calcium modulator and cyclophilin ligand; glucagon like protein 1; and IL-2 receptor agonist.

8. The method of claim 1, wherein the host cell is genetically engineered to produce glycoproteins that have human-like N-glycans.

9. The method of claim 1, wherein the host cell is genetically engineered to produce glycoproteins that have predominantly an N-glycan selected from $Man_5GlcNAc_2$, $Man_3GlcNAc_2$, $GlcNAcMan_5GlcNAc_2$, $GalGlcNAcMan_5GlcNAc_2$, $NANAGalGlcNAcMan_5GlcNAc_2$, $GlcNAcMan_3GlcNAc_2$, $GlcNAc_{(1-4)}Man_3GlcNAc_2$, $Gal_{(1-4)}GlcNAc_{(1-4)}Man_3GlcNAc_2$, and $NANA_{(1-4)}Gal_{(1-4)}GlcNAc_{(1-4)}Man_3GlcNAc_2$.

10. A composition comprising one or more recombinant glycoproteins obtained by the method of claim 1.

\* \* \* \* \*